(12) United States Patent
Kurose et al.

(10) Patent No.: US 9,156,830 B2
(45) Date of Patent: Oct. 13, 2015

(54) HETEROCYCLIC COMPOUNDS

(75) Inventors: Noriyuki Kurose, Osaka (JP);
Yasuyoshi Iso, Osaka (JP); Naoko Yamaguchi, Osaka (JP); Bin Shao, Richboro, PA (US); Laykea Tafesse, Robbinsville, NJ (US); Xiaoming Zhou, Plainsboro, NJ (US); Jianming Yu, Plainsboro, NJ (US)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 14/118,113

(22) PCT Filed: May 16, 2012

(86) PCT No.: PCT/US2012/038215
§ 371 (c)(1),
(2), (4) Date: Mar. 14, 2014

(87) PCT Pub. No.: WO2012/158844
PCT Pub. Date: Nov. 22, 2012

(65) Prior Publication Data
US 2014/0249159 A1    Sep. 4, 2014

Related U.S. Application Data

(60) Provisional application No. 61/487,224, filed on May 17, 2011.

(51) Int. Cl.
| | |
|---|---|
| A61K 31/497 | (2006.01) |
| C07D 413/14 | (2006.01) |
| C07D 401/14 | (2006.01) |
| C07D 401/04 | (2006.01) |
| C07D 413/04 | (2006.01) |
| C07D 413/12 | (2006.01) |
| C07D 417/14 | (2006.01) |
| C07D 271/10 | (2006.01) |
| C07D 271/06 | (2006.01) |
| C07D 405/14 | (2006.01) |

(52) U.S. Cl.
CPC ........... *C07D 413/14* (2013.01); *C07D 271/06* (2013.01); *C07D 271/10* (2013.01); *C07D 401/04* (2013.01); *C07D 401/14* (2013.01); *C07D 405/14* (2013.01); *C07D 413/04* (2013.01); *C07D 413/12* (2013.01); *C07D 417/14* (2013.01)

(58) Field of Classification Search
None
See application file for complete search history.

(56) References Cited

U.S. PATENT DOCUMENTS

| | | |
|---|---|---|
| 2004/0006091 A1 | 1/2004 | Kyle et al. |
| 2004/0044003 A1 | 3/2004 | Kyle et al. |
| 2004/0106625 A1 | 6/2004 | Kyle et al. |
| 2005/0059671 A1 | 3/2005 | Sun et al. |
| 2005/0245500 A1 | 11/2005 | Roth et al. |
| 2005/0267093 A1 | 12/2005 | Lehmann-Lintz et al. |
| 2006/0128717 A1 | 6/2006 | Sun et al. |
| 2006/0199824 A1 | 9/2006 | Sun et al. |
| 2006/0258669 A1 | 11/2006 | Kyle et al. |
| 2008/0262039 A1 | 10/2008 | Frank et al. |
| 2009/0170867 A1 | 7/2009 | Kurose |
| 2009/0170868 A1 | 7/2009 | Tafesse |
| 2009/0176796 A1 | 7/2009 | Tafesse |
| 2010/0120862 A1 | 5/2010 | Tafesse |
| 2010/0130499 A1 | 5/2010 | Tafesse |
| 2010/0137306 A1 | 6/2010 | Tafesse |
| 2011/0053950 A1 | 3/2011 | Meyers et al. |

FOREIGN PATENT DOCUMENTS

| | | |
|---|---|---|
| EP | 173516 A2 | 3/1986 |
| EP | 173516 A3 | 12/1986 |
| EP | 0837052 A1 | 4/1998 |
| EP | 1757591 A1 | 2/2007 |
| EP | 2261218 A2 | 12/2010 |
| EP | 2261218 A3 | 6/2011 |
| WO | WO 96/01820 | 1/1996 |
| WO | WO 96/11210 | 4/1996 |
| WO | WO 01/66551 A2 | 9/2001 |
| WO | WO 02/08221 A2 | 1/2002 |
| WO | WO 01/66551 A3 | 3/2002 |
| WO | WO 02/008221 A3 | 7/2002 |
| WO | WO 02/083134 A1 | 10/2002 |
| WO | WO 03/045313 A2 | 6/2003 |
| WO | WO 03/066595 A2 | 8/2003 |
| WO | WO 03/045313 A3 | 9/2003 |
| WO | WO 03/074520 A1 | 9/2003 |
| WO | WO 2004/002983 A2 | 1/2004 |
| WO | WO 2004/011441 A1 | 2/2004 |
| WO | WO 03/066595 A3 | 3/2004 |
| WO | WO 2004/002983 A3 | 3/2004 |
| WO | WO 2004/029031 A2 | 4/2004 |
| WO | WO 2004/035549 A1 | 4/2004 |
| WO | WO 2004/058754 A1 | 7/2004 |
| WO | WO 2004/029031 A3 | 8/2004 |
| WO | WO 2005/004866 A1 | 1/2005 |
| WO | WO 2005/009987 A1 | 2/2005 |
| WO | WO 2005/009988 A1 | 2/2005 |
| WO | WO 2005/012287 A1 | 2/2005 |
| WO | WO 2005/030753 A2 | 4/2005 |

(Continued)

*Primary Examiner* — Heidi Reese

(74) *Attorney, Agent, or Firm* — Finnegan, Henderson, Farabow, Garrett & Dunner, LLP

(57) ABSTRACT

The invention relates to compounds of Formula I: wherein $Ar_1$, $Ar_2$, $Ar_3$, $L_1$, $L_2$, Y, Z and v are defined in the specification, and pharmaceutically acceptable derivatives thereof, compositions comprising an effective amount of a compound of Formula I or a pharmaceutically acceptable derivative thereof, and methods for treating or preventing a condition such as pain, UI, an ulcer, IBD and IBS, comprising administering to an animal in need thereof an effective amount of a compound of Formula I or a pharmaceutically acceptable derivative thereof.

31 Claims, 3 Drawing Sheets

(56) References Cited

FOREIGN PATENT DOCUMENTS

| | | |
|---|---|---|
| WO | WO 2005/030766 A1 | 4/2005 |
| WO | WO 2005/030753 A3 | 5/2005 |
| WO | WO 2005/066130 A1 | 7/2005 |
| WO | WO 2007/069773 A1 | 6/2007 |
| WO | WO 2008/132600 A2 | 11/2008 |
| WO | WO 2008/133973 A1 | 11/2008 |
| WO | WO 2008/132600 A3 | 3/2009 |
| WO | WO 2009/147170 A2 | 12/2009 |
| WO | WO 2009/147170 A3 | 6/2010 |
| WO | WO 2010/064597 | 6/2010 |
| WO | WO 2010/092342 A1 | 8/2010 |
| WO | WO 2011/162409 A1 | 12/2011 |

| Agonist Plate | 1 | 2 | 3 | 4 | 5 | 6 | 7 | 8 | 9 | 10 | 11 | 12 |
|---|---|---|---|---|---|---|---|---|---|---|---|---|
| A | Buffer | | | | | | | | | | | |
| B | H₂SO₄ 15.0 mM (final 3.0 mM) | | | | | | | | | | | |
| C | H₂SO₄ 15.5 mM (final 3.1 mM) | | | | | | | | | | | |
| D | H₂SO₄ 16.0 mM (final 3.2 mM) | | | | | | | | | | | |
| E | H₂SO₄ 16.5 mM (final 3.3 mM) | | | | | | | | | | | |
| F | H₂SO₄ 17.0 mM (final 3.4 mM) | | | | | | | | | | | |
| G | H₂SO₄ 17.5 mM (final 3.5 mM) | | | | | | | | | | | |
| H | H₂SO₄ 18.0 mM (final 3.6 mM) | | | | | | | | | | | |

FIG. 1

(A) Agonist Plate

| | 1 | 2 | 3 | 4 | 5 | 6 | 7 | 8 | 9 | 10 | 11 | 12 |
|---|---|---|---|---|---|---|---|---|---|---|---|---|
| A | | | | | | | | | | | | |
| B | | | | | | | | | | | | |
| C | | | $H_2SO_4$ X mM | | | | | $H_2SO_4$ (X + 0.5) mM | | | | |
| D | | | | | | | | | | | | |
| E | | | | | | | | | | | | |
| F | | | | | | | | | | | | |
| G | | | | | | | | | | | | |
| H | | | | | | | | | | | | |

(B) Antagonist Plate — final antagonist concentration [nM]

| | 1 | 2 | 3 | 4 | 5 | 6 | 7 | 8 | 9 | 10 | 11 | 12 |
|---|---|---|---|---|---|---|---|---|---|---|---|---|
| A | | | | | | | | | | | | |
| B | 0.977 | 3.906 | 15.63 | 62.5 | 250 | 1000 | 0.977 | 3.906 | 15.63 | 62.5 | 250 | 1000 |
| C | | | No Antagonists | | | | | | No Antagonists | | | |
| D | | | | | | | | | | | | |
| E | | | | | | | | | | | | |
| F | 0.977 | 3.906 | 15.63 | 62.5 | 250 | 1000 | 0.977 | 3.906 | 15.63 | 62.5 | 250 | 1000 |
| G | | | No Antagonists | | | | | | No Antagonists | | | |
| H | | | | | | | | | | | | |

*FIG. 3*

HETEROCYCLIC COMPOUNDS

CROSS REFERENCE TO RELATED APPLICATIONS

This application is a national phase application based on PCT/US2012/038215, filed May 16, 2012, which claims the benefit of U.S. Provisional Application No. 61/487,224, filed May 17, 2011; the content of all of which is incorporated herein by reference.

FIELD OF THE INVENTION

The invention relates to compounds of Formula I, and pharmaceutically acceptable derivatives thereof, compositions comprising an effective amount of a compound of Formula I or a pharmaceutically acceptable derivative thereof and methods for treating or preventing a condition such as pain, UI, an ulcer, IBD, and IBS, comprising administering to an animal in need thereof an effective amount of a compound of Formula I or a pharmaceutically acceptable derivative thereof.

BACKGROUND

Pain is the most common symptom for which patients seek medical advice and treatment. Pain can be acute or chronic. While acute pain is usually self-limited, chronic pain persists for 3 months or longer and can lead to significant changes in a patient's personality, lifestyle, functional ability and overall quality of life (K. M. Foley, *Pain, in Cecil Textbook of Medicine* pp. 100-107 (J. C. Bennett and F. Plum eds., 20th ed. 1996)).

Moreover, chronic pain can be classified as either nociceptive or neuropathic. Nociceptive pain includes tissue injury-induced pain and inflammatory pain such as that associated with arthritis. Neuropathic pain is caused by damage to the peripheral or central nervous system and is maintained by aberrant somatosensory processing. There is a large body of evidence relating activity at vanilloid receptors (V. Di Marzo et al., *Current Opinion in Neurobiology* 12:372-379 (2002)) to pain processing.

Nociceptive pain has been traditionally managed by administering non-opioid analgesics, such as acetylsalicylic acid, choline magnesium trisalicylate, acetaminophen, ibuprofen, fenoprofen, diflusinal, and naproxen; or opioid analgesics, including morphine, hydromorphone, methadone, levorphanol, fentanyl, oxycodone, and oxymorphone. Id. In addition to the above-listed treatments, neuropathic pain, which can be difficult to treat, has also been treated with anti-epileptics (e.g., gabapentin, carbamazepine, valproic acid, topiramate, phenyloin), NMDA antagonists (e.g., ketamine, dextromethorphan), topical lidocaine (for post-herpetic neuralgia), and tricyclic antidepressants (e.g., fluoxetine, sertraline and amitriptyline).

Urinary incontinence ("UI") is uncontrollable urination, generally caused by bladder-detrusor-muscle instability. UI affects people of all ages and levels of physical health, both in health care settings and in the community at large. Physiologic bladder contraction results in large part from acetylcholine-induced stimulation of post-ganglionic muscarinic-receptor sites on bladder smooth muscle. Treatments for UI include the administration of drugs having bladder-relaxant properties, which help to control bladder-detrusor-muscle overactivity.

None of the existing commercial drug treatments for UI has achieved complete success in all classes of UI patients, nor has treatment occurred without significant adverse side effects.

Treatment of ulcers typically involves reducing or inhibiting the aggressive factors. For example, antacids such as aluminum hydroxide, magnesium hydroxide, sodium bicarbonate, and calcium bicarbonate can be used to neutralize stomach acids. Antacids, however, can cause alkalosis, leading to nausea, headache, and weakness. Antacids can also interfere with the absorption of other drugs into the blood stream and cause diarrhea.

$H_2$ antagonists, such as cimetidine, ranitidine, famotidine, and nizatidine, are also used to treat ulcers. $H_2$ antagonists promote ulcer healing by reducing gastric acid and digestive-enzyme secretion elicited by histamine and other $H_2$ agonists in the stomach and duodenum. $H_2$ antagonists, however, can cause breast enlargement and impotence in men, mental changes (especially in the elderly), headache, dizziness, nausea, myalgia, diarrhea, rash, and fever.

$H^+$, $K^+$-ATPase inhibitors such as omeprazole and lansoprazole are also used to treat ulcers. $H^+$, $K^+$-ATPase inhibitors inhibit the production of enzymes used by the stomach to secrete acid. Side effects associated with $H^+$, $K^+$-ATPase inhibitors include nausea, diarrhea, abdominal colic, headache, dizziness, somnolence, skin rashes, and transient elevations of plasma activities of aminotransferases.

Inflammatory-bowel disease ("IBD") is a chronic disorder in which the bowel becomes inflamed, often causing recurring abdominal cramps and diarrhea. The two types of IBD are Crohn's disease and ulcerative colitis.

Crohn's disease, which can include regional enteritis, granulomatous ileitis, and ileocolitis, is a chronic inflammation of the intestinal wall. Crohn's disease occurs equally in both sexes and is more common in Jews of eastern-European ancestry. Most cases of Crohn's disease begin before age 30 and the majority start between the ages of 14 and 24. The disease typically affects the full thickness of the intestinal wall. Generally the disease affects the lowest portion of the small intestine (ileum) and the large intestine, but can occur in any part of the digestive tract.

Cramps and diarrhea, side effects associated with Crohn's disease, can be relieved by anticholinergic drugs, diphenoxylate, loperamide, deodorized opium tincture, or codeine.

When Crohn's disease causes the intestine to be obstructed or when abscesses or fistulas do not heal, surgery can be necessary to remove diseased sections of the intestine. Surgery, however, does not cure the disease, and inflammation tends to recur where the intestine is rejoined. In almost half of the cases a second operation is needed. Berkow et al., "Crohn's Disease," *The Merck Manual of Medical Information*, pp. 528-530 (1997).

Ulcerative colitis is a chronic disease in which the large intestine becomes inflamed and ulcerated, leading to episodes of bloody diarrhea, abdominal cramps, and fever. Ulcerative colitis usually begins between ages 15 and 30; however, a small group of people have their first attack between ages 50 and 70. Unlike Crohn's disease, ulcerative colitis never affects the small intestine and does not affect the full thickness of the intestine. The disease usually begins in the rectum and the sigmoid colon and eventually spreads partially or completely throughout the large intestine. The cause of ulcerative colitis is unknown.

Treatment of ulcerative colitis is directed to controlling inflammation, reducing symptoms, and replacing lost fluids and nutrients. Anticholinergic drugs and low doses of diphenoxylate or loperamide are administered for treating mild diarrhea. For more intense diarrhea higher doses of diphenoxylate or loperamide, or deodorized opium tincture or codeine are administered.

Irritable-bowel syndrome ("IBS") is a disorder of motility of the entire gastrointestinal tract, causing abdominal pain, constipation, and/or diarrhea. IBS affects three-times more women than men. In IBS, stimuli such as stress, diet, drugs, hormones, or irritants can cause the gastrointestinal tract to contract abnormally. During an episode of IBS, contractions of the gastrointestinal tract become stronger and more frequent, resulting in the rapid transit of food and feces through the small intestine, often leading to diarrhea. Cramps result from the strong contractions of the large intestine and increased sensitivity of pain receptors in the large intestine.

Treatment of IBS typically involves modification of an IBS-patient's diet. Often it is recommended that an IBS patient avoid beans, cabbage, sorbitol, and fructose. A low-fat, high-fiber diet can also help some IBS patients. Regular physical activity can also help keep the gastrointestinal tract functioning properly. Drugs such as propantheline that slow the function of the gastrointestinal tract are generally not effective for treating IBS. Antidiarrheal drugs, such as diphenoxylate and loperamide, help with diarrhea. Berkow et al., "Irritable Bowel Syndrome," *The Merck Manual of Medical Information*, pp. 525-526 (1997).

International publication No. WO 02/08221 describes aryl piperazine compounds useful for treating chronic and acute pain conditions, itch, and urinary incontinence.

International publication No. WO2009147170 and International publication No. WO2008148840 describe piperidine/piperazine derivatives as DGAT inhibitors.

International publication No. WO2005115990 describes amide compounds as amyloid β production inhibitors U.S. Patent Application Publication No. US20050245500 and No. US20050267093 describe amide compounds as MCH receptor antagonists.

International publication No. WO2003045313 and WO2002083134 describe piperidyl amide compounds as MCH receptor antagonists.

International publication No. WO9700853 describes amide compounds as PDG2 angatonists.

International publication No. WO9611210 describes biphenylpropiolamide compounds as antibiotics.

European Patent Application Publication No. EP173516 describes phenyl propinamide compounds as leukotriene antagonists, phospholipase inhibitors or the like.

International publication No. WO9601820 describes piperazinyl amide compounds as anti-Helicobacter agents.

International publication No. WO2001066551 describes piperazine compounds as antifungal agents.

U.S. Patent Application Publication No. US 2004/0044003, International publication No. WO 2003/066595, U.S. Patent Application Publication No. US 2004/0006091, International publication No. WO 2003/074520, U.S. Patent Application Publication No. US 2004/0106625, International publication No. WO 2004/002983, U.S. Patent Application Publication No. US 2004/0235853, International publication No. WO 2004/011441, U.S. Patent Application Publication No. US 2005/0059671, International publication No. WO 2004/029031, U.S. Patent Application Publication No. US 2004/0186111, International publication No. WO 2004/058754, U.S. Patent Application Publication No. US 2006/0199824, International publication No. WO 2005/009987, U.S. Patent Application Publication Nos. US 2006/0128717 and US 20060258669, International publication Nos. WO 2005/009988, WO 2005/004866, WO 2005/012287, WO 2005/030766, WO 2005/030753, WO 2005/066130, and WO2007/069773, U.S. Patent Application Publication Nos. US 2009/0170868, US 2009/0170867, US2009/0176796, US2010/0120862, US2010/0130499 and U52010/0137306, International publication Nos. WO 2008/132600, WO2008/133973, and WO 2004/035549 each describe classes of compounds that are useful for treating pain.

There remains, however, a clear need in the art for new drugs useful for treating or preventing pain, UI, an ulcer, IBD, and IBS. Citation of any reference in this application is not to be construed as an admission that such reference is prior art to the present application.

SUMMARY OF THE INVENTION

The invention provides:

1) A compound of Formula I:

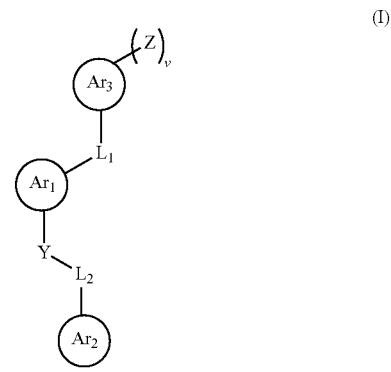

or a pharmaceutically acceptable derivative thereof, wherein $Ar_1$ is

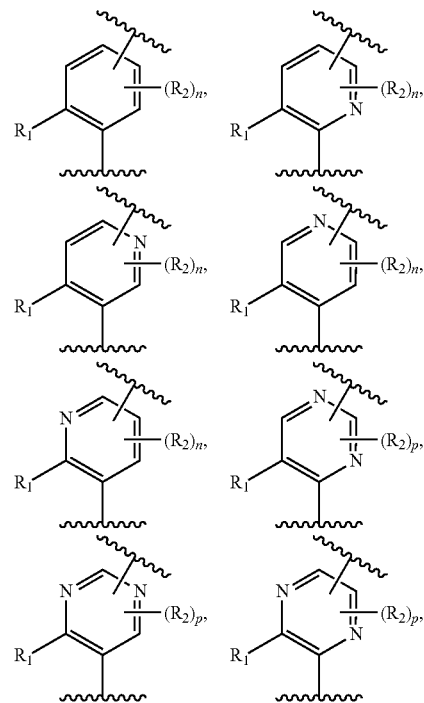

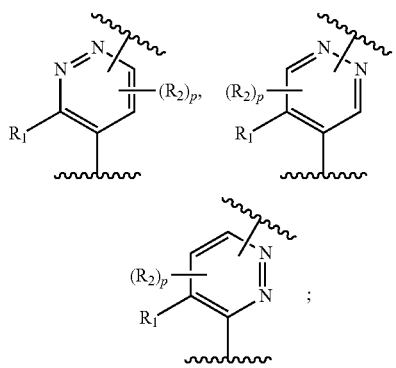

Y is

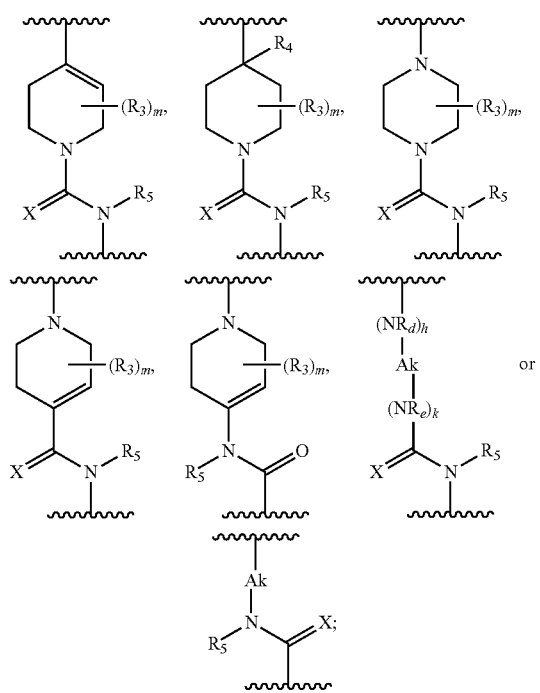

Ar$_2$ is

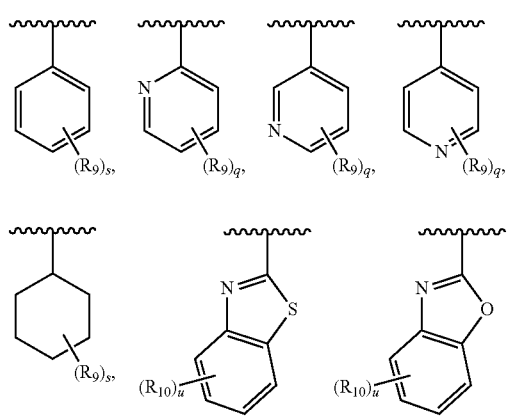

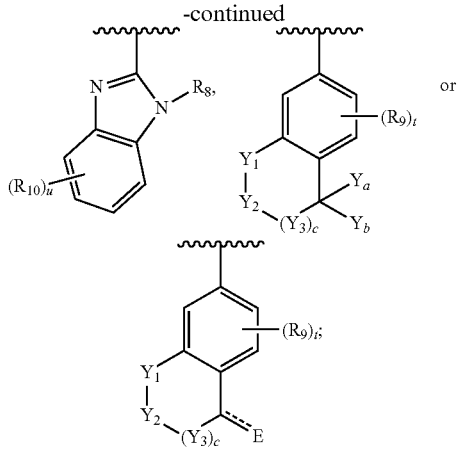

Ar$_3$ is -(3- to 7-membered)heterocycle which is unsubstituted or substituted with 1 or 2 independently selected R$_6$ groups;

Z is
(a) —(C$_1$-C$_6$)alkyl which is unsubstituted or substituted with 1 or 2 —OR$_{12}$ groups,
(b) —(C$_2$-C$_6$)alkenyl which is unsubstituted or substituted with 1 or 2 —OR$_1$, groups,
(c) —OR$_{12}$, or
(d) —C(O)OR$_7$;

L$_1$ and L$_2$ are each independently a bond, (C$_1$-C$_6$)alkylene, (C$_2$-C$_6$)alkenylene, or —(C$_2$-C$_6$)alkynylene, each of which (C$_1$-C$_6$)alkylene, (C$_2$-C$_6$)alkenylene, or (C$_2$-C$_6$)alkynylene is unsubstituted or substituted with 1 or 2 —OR$_7$ groups;

R$_1$ is —H, -halo, —NO$_2$, —CN, —OR$_7$, —N(R$_7$)$_2$, —(C$_1$-C$_4$)alkyl, —C(halo)$_3$, —CH(halo)$_2$, —CH$_2$(halo), —OC(halo)$_3$, —OCH(halo)$_2$, or —OCH$_2$(halo);

each R$_2$ is independently -halo, —OR$_7$, —CN, —NO$_2$, —N(R$_7$)$_2$, —(C$_1$-C$_{10}$)alkyl, —(C$_2$-C$_{10}$)alkenyl, —(C$_2$-C$_{10}$)alkynyl, or -phenyl;

X is O, S, N—CN, or N—OR$_7$;

each R$_3$ is independently:
(a) —(C$_1$-C$_6$)alkyl, —(C$_1$-C$_6$)alkyl-OR$_{13}$, —C(O)R$_{13}$, —C(O)OR$_{13}$, —N(R$_{13}$)C(O)R$_{13}$, or —C(O)N(R$_{13}$)$_2$;
(b) two R$_3$ groups together form =O;
(c) two R$_3$ groups together form a (C$_2$-C$_6$) bridge, which is unsubstituted or substituted with 1, 2 or 3 independently selected R$_{13}$ groups, and which bridge optionally contains —HC=CH— within the (C$_2$-C$_6$) bridge; or
(d) two R$_3$ groups together form a —CH$_2$—N(R$_a$)—CH$_2$— bridge, a —CH$_2$—N(R$_b$)(C=O)—CH$_2$— bridge, or a —CH$_2$—N(R$_b$)(S(=O)$_2$)—CH$_2$— bridge;

R$_4$ is —H, -halo, —(C$_1$-C$_6$)alkyl, —CH$_2$OR$_7$, —CH$_2$(halo), —CH(halo)$_2$, —C(halo)$_3$, —OC(halo)$_3$, —OR$_7$, —SR$_7$, —C(O)OR$_7$, —C(O)R$_7$, —OC(O)R$_7$, —OC(O)N(R$_8$)$_2$, —NR$_7$C(O)R$_{13}$, —C(O)N(R$_8$)$_2$, —S(O)$_2$R$_7$, or —NO$_2$;

$R_5$ is —H, —($C_1$-$C_6$)alkyl, —($C_3$-$C_8$)cycloalkyl, —($C_1$-$C_6$)alkyl-OC(O)$R_7$, —C(O)$R_7$, or —C(O)N($R_8$)$_2$;

Ak is ($C_1$-$C_6$)alkylene, ($C_2$-$C_6$)alkenylene, or ($C_2$-$C_6$)alkynylene;

$R_d$ and $R_e$ are each independently —H or —($C_1$-$C_6$)alkyl;

each $R_6$ is independently —($C_1$-$C_6$)alkyl or two $R_6$ groups together form =O;

each $R_7$ is independently —H or —($C_1$-$C_6$)alkyl;

each $R_8$ is independently —H, —($C_1$-$C_6$)alkyl, —($C_2$-$C_6$)alkenyl, —($C_2$-$C_6$)alkynyl, —($C_3$-$C_8$)cycloalkyl, or phenyl;

each $R_9$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 7-membered)heterocycle, —($C_1$-$C_6$)haloalkyl, —($C_2$-$C_6$)haloalkenyl, —($C_2$-$C_6$)haloalkynyl, —($C_1$-$C_6$)hydroxyalkyl, —($C_2$-$C_6$)hydroxyalkenyl, —($C_2$-$C_6$)hydroxyalkynyl, —($C_1$-$C_6$)alkoxy($C_1$-$C_6$)alkyl, —($C_1$-$C_6$)alkoxy($C_2$-$C_6$)alkenyl, —($C_1$-$C_6$)alkoxy($C_2$-$C_6$)alkynyl, —CN, -halo, —$N_3$, —$NO_2$, —CH=$NR_{13}$, —N($R_{13}$)$_2$, —$NR_{13}OR_{13}$, —$OR_{13}$, —$SR_{13}$, —O(CH$_2$)$_b$OR$_{13}$, —O(CH$_2$)$_b$SR$_{13}$, —O(CH$_2$)$_b$N(R$_{13}$)$_2$, —N(R$_{13}$)(CH$_2$)$_b$OR$_{13}$, —N(R$_{13}$)(CH$_2$)$_b$SR$_{13}$, —N(R$_{13}$)(CH$_2$)$_b$N(R$_{13}$)$_2$, —N(R$_{13}$)C(O)R$_{13}$, —C(O)R$_{13}$, —C(O)OR$_{13}$, —OC(O)R$_{13}$, —OC(O)OR_, —S(O)R$_{13}$, —S(O)$_2$R$_{13}$, —S(O)$_2$N(R$_{13}$)$_2$, —S(O)$_2$-(3- to 7-membered)heterocycle, —C(O)N(R$_{13}$)$_2$, —($C_1$-$C_6$)alkyl-C=N—OR$_{13}$, —($C_1$-$C_6$)alkyl-C(O)N(R$_{13}$)$_2$, —($C_1$-$C_6$)alkyl-NHS(O)$_2$N(R$_{13}$)$_2$, or —($C_1$-$C_6$)alkyl-C(=NH)—N(R$_{13}$)$_2$, each of which -phenyl, -(3- to 7-membered)heterocycle, or —($C_3$-$C_8$)cycloalkyl is unsubstituted or substituted with 1, 2 or 3 independently selected $R_{13}$ groups;

each $R_{10}$ is independently:
(a) —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, or -phenyl, each of which is unsubstituted or substituted with 1 or 2 —OH groups;
(b) —CH$_2$CH$_2$(halo), —CH$_2$CH(halo)$_2$, —CH$_2$C(halo)$_3$, —C(halo)$_3$, —CH(halo)$_2$, —CH$_2$(halo), —CN, -halo, —$N_3$, —$NO_2$, —CH=NR$_{13}$, —N(R$_{13}$)$_2$, —NR$_{13}$OR$_{13}$, —OR$_{13}$, —C(O)R$_{13}$, —C(O)OR$_{13}$, —OC(O)R$_{13}$, —OC(O)OR$_{13}$, —SR$_{13}$, —S(O)R$_{13}$, or —S(O)$_2$R$_{13}$; or
(c) two $R_{10}$ groups on adjacent carbon atoms together form a ($C_1$-$C_2$)alkylenedioxy bridge, which is unsubstituted or substituted 1, 2 or 3 independently selected $R_{13}$ groups;

each $R_{12}$ is independently —H, —($C_1$-$C_6$)alkyl, —($C_3$-$C_8$)cycloalkyl, —C(O)R$_{13}$, —C(O)OR$_{13}$, or —C(O)N(R$_{13}$)$_2$;

each $R_{13}$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -benzyl, —($C_1$-$C_6$)haloalkyl, —($C_1$-$C_6$)hydroxyalkyl, —($C_1$-$C_6$)alkoxy($C_1$-$C_6$)alkyl, —($C_1$-$C_6$)alkyl-N(R$_8$)$_2$, or —C(O)N(R$_8$)$_2$;

$Y_1$, $Y_2$, $Y_3$ are each independently C, N, or O;

wherein no more than one of $Y_1$, $Y_2$, or $Y_3$ can be O, no more than two of $Y_1$, $Y_2$, or $Y_3$ can be N and for each $Y_1$, $Y_2$, and $Y_3$ that is N, the N is bonded to one $R_{14}$ group, and for each $Y_1$, $Y_2$, and $Y_3$ that is C, the C is bonded to two $R_5$ groups, provided that there are no more than a total of two ($C_1$-$C_6$) alkyl groups substituted on all of $Y_1$, $Y_2$, and $Y_3$;

$Y_a$ and $Y_b$ are each independently —H, -halo, or —($C_1$-$C_6$) alkyl, or $Y_a$ and $Y_b$, together with the carbon to which they are attached, form a 3-8 member carbocyclic ring;

=E is =O, =S, =C(R$_7$)$_2$, =CH(C$_2$-C$_6$)alkenyl, =N(R$_7$)$_2$, or =N—OR$_5$;

$R_a$ is —H, —($C_1$-$C_6$)alkyl, —($C_3$-$C_8$)cycloalkyl, —CH$_2$—C(O)R$_c$, —(CH$_2$)—C(O)OR$_c$, —(CH$_2$)—C(O)N(R$_c$)$_2$, —(CH$_2$)$_2$—OR$_c$, —(CH$_2$)$_2$—S(O)$_2$N(R$_c$)$_2$, or —(CH$_2$)$_2$—N(R$_c$)S(O)$_2$R$_c$;

$R_b$ is:
(a) —H, —($C_1$-$C_6$)alkyl, —($C_3$-$C_8$)cycloalkyl, -(3- to 7-membered)heterocycle, —N(R$_c$)$_2$, —N(R$_c$)—($C_3$-$C_8$)cycloalkyl, or —N(R$_c$)-(3- to 7-membered)heterocycle, each of which -(3- to 7-membered)heterocycle or —($C_3$-$C_8$)cycloalkyl is unsubstituted or substituted with 1, 2 or 3 independently selected $R_{13}$ groups; or
(b) -phenyl, -(5- or 6-membered)heteroaryl, —N(R$_c$)-phenyl, or —N(R$_c$)-(5- to 10-membered)heteroaryl, each of which is unsubstituted or substituted with 1, 2 or 3 independently selected $R_{13}$ groups;

each $R_c$ is independently —H or —($C_1$-$C_4$)alkyl;

each $R_{14}$ is independently —H, —($C_1$-$C_6$)alkyl, —C(O)R$_{13}$, —S(O)R$_{13}$, —S(O)$_2$R$_{13}$, each halo is independently —F, —Cl, —Br, or —I;

h is the integer 0 or 1;

k is the integer 0 or 1;

n is the integer 0, 1, or 2;

m is the integer 0, 1, or 2;

p is the integer 0 or 1;

q is the integer 0, 1, 2, 3, or 4;

s is the integer 0, 1, 2, 3, 4, or 5;

t is the integer 0, 1, 2, or 3;

u is the integer 0, 1, 2 or 3;

v is the integer 0, 1, 2 or 3;

b is the integer 1 or 2; and c is the integer 0, 1, or 2;

provided that when $Ar_1$ is and Y is then $Ar_2$ is not

2) The compound according to the above 1) or a pharmaceutically acceptable derivative thereof, wherein Ar₁ is

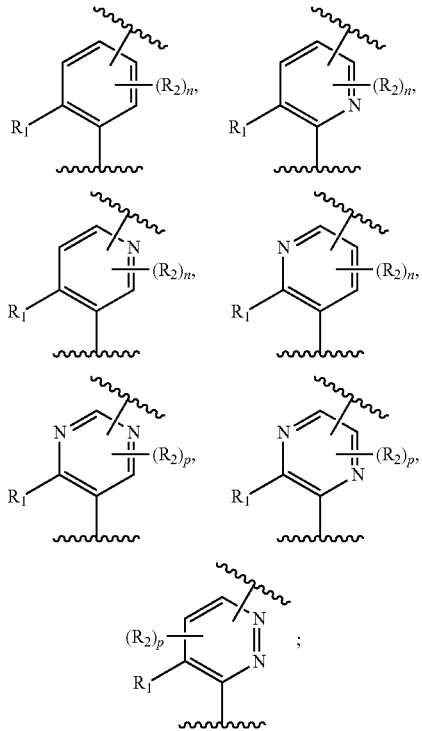

Y is

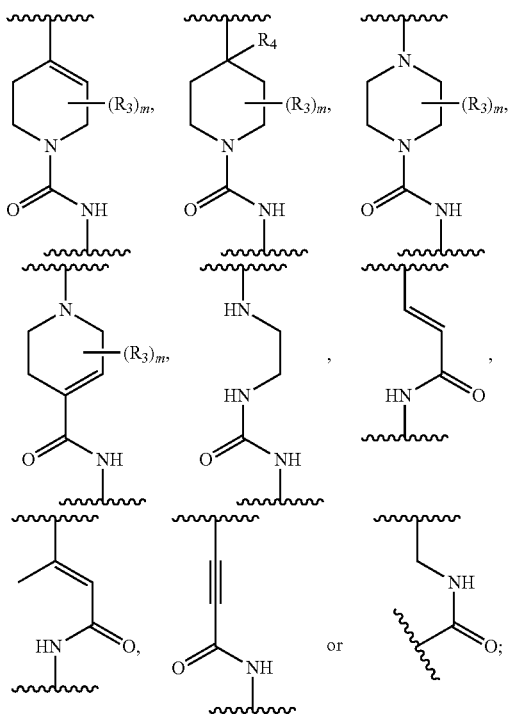

Ar₂ is

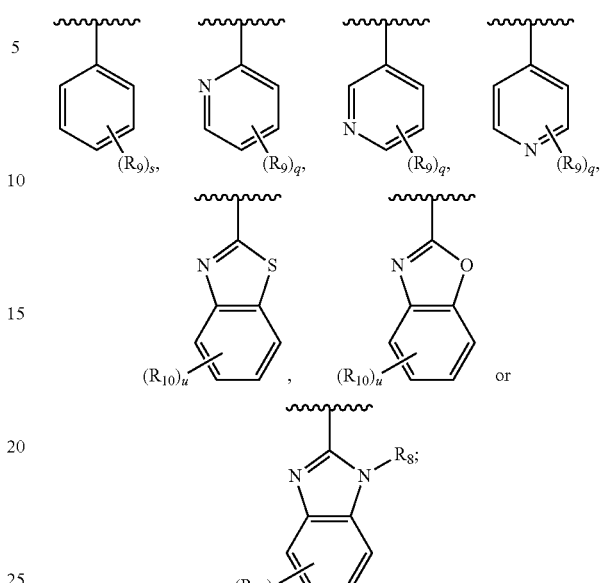

and

L₁ and L₂ are each independently a bond, —CH₂— or —CH=CH—.

3) The compound according to the above 1 or 2 or a pharmaceutically acceptable derivative thereof, wherein Z is (a) —($C_1$-$C_3$)alkyl substituted with 1 or 2 —OH groups, or (c) —OH; and v is 1, 2 or 3.

4) The compound according to the above 1) or a pharmaceutically acceptable derivative thereof, wherein Ar₁ is

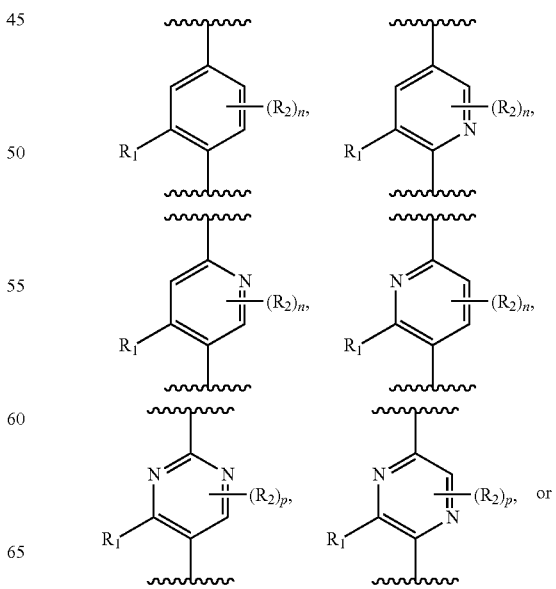

-continued

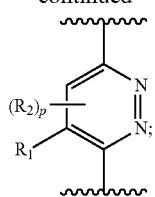

Y is

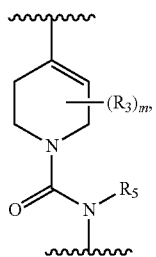 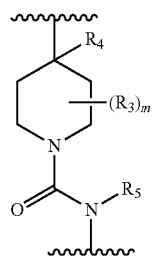 or 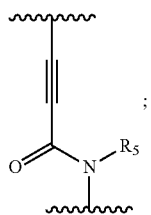 ;

$L_1$ and $L_2$ are each independently a bond.

5) The compound according to the above 1) or a pharmaceutically acceptable derivative thereof, wherein $Ar_1$ is

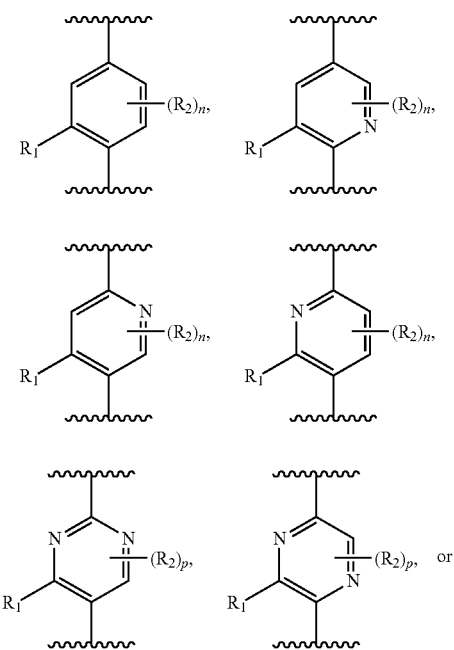

Y is

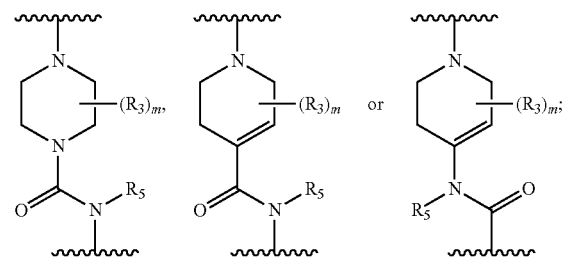

$Ar_3$ is -(5- or 6-membered) aromatic heterocycle which is unsubstituted or substituted with 1 or 2 independently selected $R_6$ groups;

Z is
(a) —$(C_1-C_2)$alkyl substituted with 1 or 2 —OH groups, or
(c) —OH;

$L_1$ and $L_2$ are each independently a bond.

6) The compound according to the above 1) or a pharmaceutically acceptable derivative thereof, wherein $Ar_1$ is

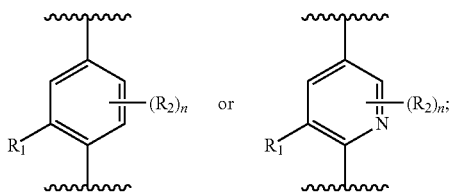

Y is

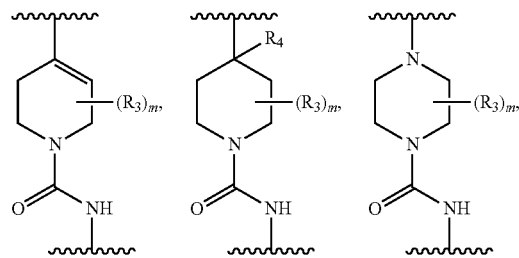

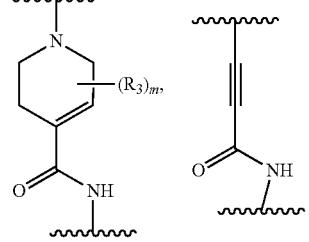

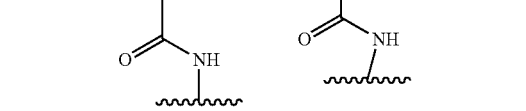

$Ar_2$ is

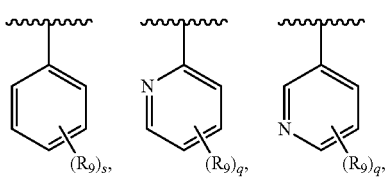

-continued

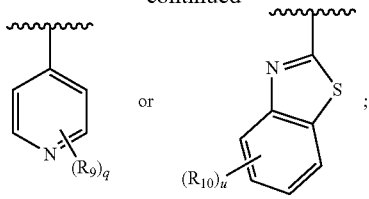

Ar₃ is -(5- or 6-membered) aromatic heterocycle which is unsubstituted or substituted with 1 or 2 independently selected R₆ groups;

Z is (a) —($C_1$-$C_6$)alkyl substituted with 1 or 2 —OH groups, or (c) —OH; and $L_1$ is a bond or —CH₂—;

$L_2$ is a bond; and

X is O.

7) The compound according to the above 6) or a pharmaceutically acceptable derivative thereof, wherein $L_1$ and $L_2$ are each independently a bond.

8) The compound according to any one of the above 1), 2) and 4) or a pharmaceutically acceptable derivative thereof, wherein Z is —OH, —($C_1$-$C_3$)alkyl substituted with 1 or 2 —OH groups, or —($C_2$-$C_4$)alkenyl substituted with 1 or 2 —OH groups; and v is 1 or 2.

9) The compound according to any one of the above 1) to 4) or a pharmaceutically acceptable derivative thereof, wherein Z is —OH or —($C_1$-$C_3$)alkyl substituted with 1 or 2 —OH groups; and v is 1 or 2.

10) The compound according to any one of the above 1) to 4) or a pharmaceutically acceptable derivative thereof, wherein Z is —($C_2$-$C_3$)alkyl substituted with 2 —OH groups; and v is 1 or 2.

11) The compound according to any one of the above 1) to 9) or a pharmaceutically acceptable derivative thereof, wherein Z is —OH, —CH₂OH, —CH₂CH₂OH, or —CH(OH)CH(OH); and v is 1 or 2.

12) The compound according to any one of the above 1), 2), 3), 4), 8), 9), 10) and 11) or a pharmaceutically acceptable derivative thereof, wherein Ar₃ is -(5- or 6-membered) aromatic heterocycle which is unsubstituted or substituted with 1 or 2 independently selected R₆ groups.

13) The compound according to any one of the above 1) to 12) or a pharmaceutically acceptable derivative thereof, wherein Ar₃ is oxadiazole, isoxazole, oxazole, furan or pyrazole, each of which is unsubstituted or substituted with 1 or 2 independently selected R₆ groups.

14) The compound according to any one of the above 1) to 13) or a pharmaceutically acceptable derivative thereof, wherein Ar₃ is -(5- or 6-membered) aromatic heterocycle, Z is —OH or —($C_1$-$C_3$)alkyl substituted with 1 or 2 —OH groups; and v is 1 or 2.

15) The compound according to any one of the above 1) to 9), and 11) to 13) or a pharmaceutically acceptable derivative thereof, wherein

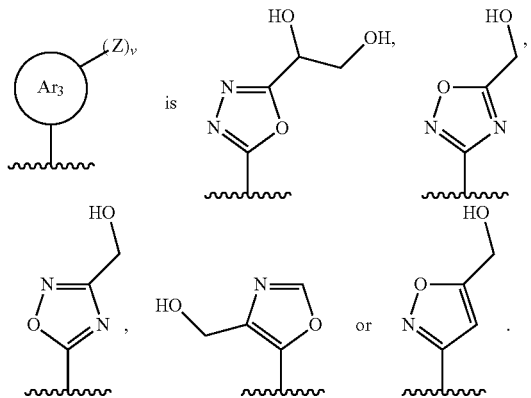

16) The compound according to the above 1) to 15) or a pharmaceutically acceptable derivative thereof, wherein $R_1$ is -methyl, -halo or —C(halo)₃.

17) The compound according to any one of the above 1) to 16) or a pharmaceutically acceptable derivative thereof, wherein $R_4$ is —H or -halo.

18) The compound according to any one of the above 1) to 17) or a pharmaceutically acceptable derivative thereof, wherein each $R_9$ is independently selected from -halo, —C(halo)₃, —($C_1$-$C_6$)alkyl, —($C_1$-$C_6$)alkoxy, —OC(halo)₃, and —S(O)₂C(halo)₃.

19) The compound according to any one of the above 1) to 18) or a pharmaceutically acceptable derivative thereof, wherein Ar₂ is

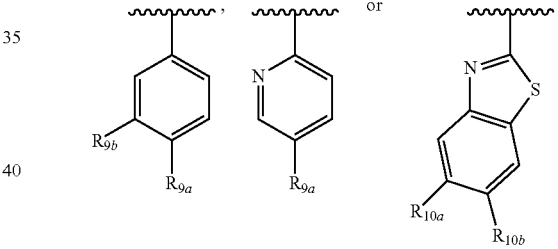

$R_{9a}$ is —C(halo)₃ or —OC(halo)₃;

$R_{9b}$ is —H, -halo, -methyl, or —OCH₃; and $R_{10a}$ and $R_{10b}$ are independently selected from —H, -halo, and -methyl.

20) The compound according to any one of the above 1) to 19) or a pharmaceutically acceptable derivative thereof, wherein n or p=0.

21) The compound according to any one of the above 1) to 20) or a pharmaceutically acceptable derivative thereof, wherein m=0.

22) The compound according to any one of the above 1) to 21) or a pharmaceutically acceptable derivative thereof wherein the pharmaceutically acceptable derivative is a pharmaceutically acceptable salt.

23) A composition comprising a compound of any one of the above 1) to 22) or a pharmaceutically acceptable derivative thereof and a pharmaceutically acceptable carrier or excipient.

24) A composition for treating or preventing pain, UI, an ulcer, IBD, or IBS in an animal comprising a compound of any one of the above 1) to 22) or a pharmaceutically acceptable derivative thereof and a pharmaceutically acceptable carrier or excipient.

25) A composition for inhibiting TRPV1 function comprising a compound of any one of the above 1) to 22) or a pharmaceutically acceptable derivative thereof and a pharmaceutically acceptable carrier or excipient.

26) A method for treating or preventing pain, UI, an ulcer, IBD, or IBS in an animal, comprising administering to an animal in need thereof, an effective amount of a compound of any one of the above 1) to 22) or a pharmaceutically acceptable derivative thereof.

27) A method of inhibiting TRPV1 function in a cell comprising contacting a cell capable of expressing TRPV1 with an effective amount of a compound of any one of the above 1) to 22) or a pharmaceutically acceptable derivative thereof.

28) A compound according to any one of the above 1) to 22) or a pharmaceutically acceptable derivative thereof for use in treatment or prevention of pain, UI, an ulcer, IBD, or IBS in an animal.

29) A compound according to any one of the above 1) to 22) or a pharmaceutically acceptable derivative thereof for the use in inhibiting TRPV1 function.

The invention further relates to use of a compound of Formula I or a pharmaceutically acceptable derivative thereof in the manufacture of a medicament for treating and/or preventing a Condition.

The invention still further relates to a method for preparing a composition comprising the step of admixing a compound of Formula I or a pharmaceutically acceptable derivative thereof, and a pharmaceutically acceptable carrier or excipient.

The invention still further relates to a kit comprising a container containing an effective amount of a compound of Formula I or a pharmaceutically acceptable derivative thereof.

Compounds of Formula I or a pharmaceutically acceptable derivative thereof are highly soluble in aqueous solutions at either pH 6.8 or pH 1.2, are exceptionally potent at TRPV1 receptors, have excellent bioavailability, have a high therapeutic index, and are believed to be highly efficacious in animals for the treatment of pain.

The invention can be understood more fully by reference to the following detailed description and illustrative examples, which are intended to exemplify non-limiting embodiments of the invention.

BRIEF DESCRIPTION OF THE FIGURES

FIG. 1. 96-well plate with different agonist solutions (Agonist Plate). Seven different sulfuric acid solutions, or agonist solutions, with different sulfuric acid ($H_2SO_4$) concentrations (of from 15.0 mM to 18 mM as indicated) were used for the pH assay as indicated. For the wells in row A, measuring buffer alone was used. The final concentration of sulfuric acid in the wells for each row, after a 1:4 dilution of the agonist solution, is also indicated in each row in parenthesis.

FIG. 3. (A) A 96-well plate with two different sulfuric acid concentrations. Wells in columns 1 to 6 had one final sulfuric acid concentration; wells in columns 7 to 12 had a different final sulfuric acid concentration. The final sulfuric acid concentration was reached by 1:4 dilution of two different agonist solutions with sulfuric acid concentrations of X mM and (X+0.5) mM, respectively. In the experiment described in Section 2 of Protocol 2, X was determined to be 16 mM. (B) A 96-well plate with different test compound, or antagonist, concentrations indicated in nM. Only one kind of test compound was applied per 96-well plate. Since two different sulfuric acid concentrations were used (columns 1-6 vs. columns 7-12), seven wells were tested for each combination of test compound concentration and agonist solution (e.g., wells A1, B1, C1, E1, F1, G1, and H1 were tested for test compound concentration 0.977 nM and agonist solution with sulfuric acid solution X mM). The wells in row D did not include an antagonist in order to measure the maximal $Ca^{2+}$ response.

DETAILED DESCRIPTION OF THE INVENTION

Compounds of Formula I

Figure 2:
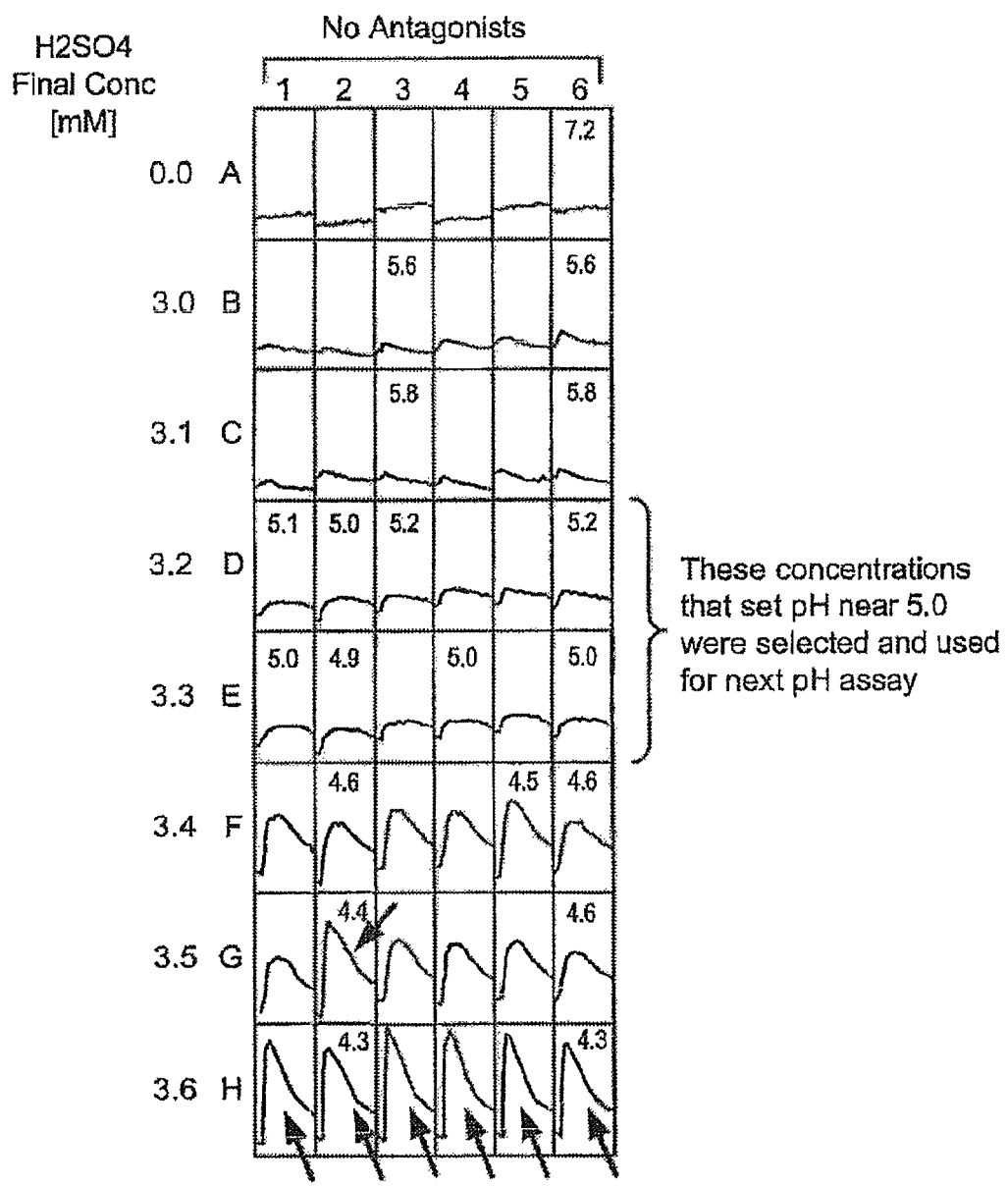
FIG. 2. pH dependent $Ca^{2+}$ responses in TRPV1/CHO cells. $Ca^{2+}$ influx into TRPV1/CHO cells as measured by Fura-2 AM fluorescence is indicated by the graph within each rectangular field. The graph presents the fluorescence intensity over time starting from the addition of agonist solution. Each rectangular field presents one experiment performed in one well of a 96-well plate. Each row presents six experiments performed at the same final sulfuric acid concentration; the final sulfuric acid concentration is indicated at the left. Actual pH values were measured after the experiment and are indicated above the graph. No antagonists were added to the cell culture. Final sulfuric acid concentrations of 3.2 and 3.3 mM produced an appropriate $Ca^{2+}$ response and were selected for subsequent assays. These final sulfuric acid concentrations can be obtained by 1:4 dilutions of agonist solution with sulfuric acid concentrations of 16.0 mM or 16.5 mM, respectively (see FIG. 1).

The invention encompasses compounds of Formula I:

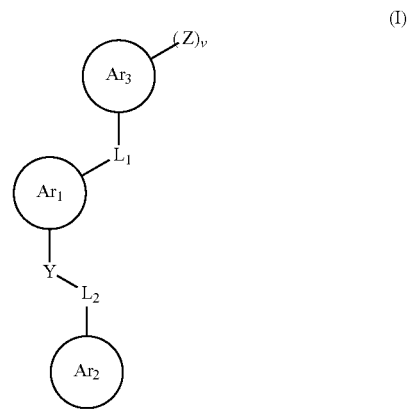

(I)

or a pharmaceutically acceptable derivative thereof, wherein $Ar_1$, $Ar_2$, $Ar_3$, $L_1$, $L_2$, Y, Z and v are defined above for compounds of Formula I.

Certain embodiments of Formula I are presented below.

In one embodiment, a compound of Formula I is a pharmaceutically acceptable derivative of a compound of Formula I.

In another embodiment, a compound of Formula I is a pharmaceutically acceptable salt of a compound of Formula I.

In another embodiment, $Ar_1$ is a pyridyl group.
In another embodiment, $Ar_1$ is a pyrimidinyl group.
In another embodiment, $Ar_1$ is a pyrazinyl group.
In another embodiment, $Ar_1$ is a pyridazinyl group.
In another embodiment, $Ar_1$ is a phenyl group.
In another embodiment, $R_1$ is —H.
In another embodiment, $R_1$ is -halo.
In another embodiment, $R_1$ is —Cl.
In another embodiment, $R_1$ is —F.
In another embodiment, $R_1$ is -methyl.
In another embodiment, $R_1$ is —$NO_2$.
In another embodiment, $R_1$ is —CN.

In another embodiment, $R_1$ is —OH.
In another embodiment, $R_1$ is —OCH$_3$.
In another embodiment, $R_1$ is —NH$_2$).
In another embodiment, $R_1$ is —C(halo)$_3$.
In another embodiment, $R_1$ is —CF$_3$.
In another embodiment, $R_1$ is —CH(halo)$_2$.
In another embodiment, $R_1$ is —CH$_2$(halo).
In another embodiment, n is 2.
In another embodiment, n or p is 1.
In another embodiment, n or p is 0.
In another embodiment, Ar$_1$ is a pyridyl group, $R_1$ is -halo or —(C$_1$-C$_4$)alkyl, and n is 0.
In another embodiment, Ar$_1$ is a pyrazinyl group, $R_1$ is -halo or —(C$_1$-C$_4$)alkyl, and n is 0.
In another embodiment, Ar$_1$ is a pyrimidinyl group, $R_1$ is -halo or —(C$_1$-C$_4$)alkyl, and n is 0.
In another embodiment, Ar$_1$ is a pyridazinyl group, $R_1$ is -halo or —(C$_1$-C$_4$)alkyl, and n is 0.
In another embodiment, Ar$_1$ is a phenyl group, $R_1$ is -halo or —(C$_1$-C$_4$)alkyl, and n is 0.
In another embodiment, Y is

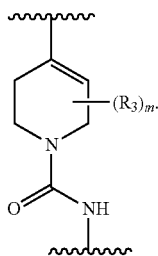

In another embodiment, Y is

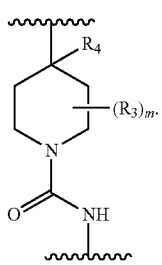

In another embodiment, $R_4$ is —OH.
In another embodiment, $R_4$ is —OCF$_3$
In another embodiment, $R_4$ is -halo.
In another embodiment, $R_4$ is —F.
In another embodiment, $R_4$ is —Cl.
In another embodiment, $R_4$ is —(C$_1$-C$_6$)alkyl.
In another embodiment, $R_4$ is -methyl.
In another embodiment, $R_4$ is —CH$_2$OH.
In another embodiment, $R_4$ is —CH$_2$Cl.
In another embodiment, $R_4$ is —CH$_2$Br.
In another embodiment, $R_4$ is —CH$_2$I.
In another embodiment, $R_4$ is —CH$_2$F.
In another embodiment, $R_4$ is —CH(halo)$_2$.
In another embodiment, $R_4$ is —CF$_3$.
In another embodiment, $R_4$ is —NO$_2$.
In another embodiment, $R_4$ is —OR$_7$.
In another embodiment, $R_4$ is —SR$_7$.
In another embodiment, $R_4$ is —C(O)R$_7$.
In another embodiment, $R_4$ is —C(O)OR$_7$.
In another embodiment, $R_4$ is —C(O)OH.
In another embodiment, $R_4$ is —C(O)H.
In another embodiment, $R_4$ is —OC(O)R$_7$.
In another embodiment, $R_4$ is —S(O)$_2$R$_7$.
In another embodiment, $R_4$ is —OC(O)NHR$_7$.
In another embodiment, $R_4$ is —NHC(O)R$_8$.
In another embodiment, $R_4$ is —C(O)N(R$_8$)$_2$.
In another embodiment, Y is

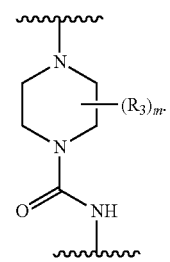

In another embodiment, Y is

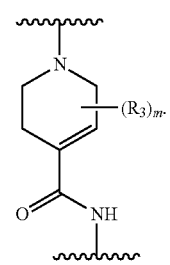

In another embodiment, m is 2.
In another embodiment, m is 1.
In another embodiment, m is 0.
In another embodiment, m is 1 and $R_3$ is —(C$_1$-C$_6$)alkyl.
In another embodiment, m is 1 and $R_3$ is -methyl.
In another embodiment, m is 2 and two $R_3$ groups together form =O.
In another embodiment, two $R_3$ groups together form a (C$_2$-C$_6$)bridge, which is unsubstituted or substituted with 1, 2 or 3 independently selected $R_{10}$ groups, and which bridge optionally contains —HC=CH— within the (C$_2$-C$_6$)bridge.
In another embodiment, two $R_3$ groups together form a (C$_2$-C$_6$)bridge, which is unsubstituted or substituted with an $R_{10}$ group, and which bridge optionally contains —HC=CH— within the (C$_2$-C$_6$) bridge.
In another embodiment, two $R_3$ groups together form a (C$_2$-C$_3$) bridge, which is unsubstituted or substituted with an $R_{10}$ group, and which bridge optionally contains —HC=CH— within the (C$_2$-C$_3$) bridge.
In another embodiment, two $R_3$ groups together form a (C$_2$-C$_3$) bridge, which is unsubstituted and which bridge optionally contains —HC=CH— within the (C$_2$-C$_3$) bridge.
In another embodiment, two $R_3$ groups together form a (C$_{2-}$) bridge, a —HC=CH-bridge, or a (C$_{3-}$) bridge each of which is unsubstituted.
In another embodiment, two $R_3$ groups together form a (C$_2$-C$_6$) bridge, which is unsubstituted or substituted with 1, 2 or 3 independently selected $R_{10}$ groups, which bridge optionally contains —HC=CH— within the (C$_2$-C$_6$) bridge, and which bridge joins positions 2 and 6 of the piperidine, 1,2,3,6-tetrahydropyridine or piperazine ring.

In another embodiment, two $R_3$ groups together form a $(C_2-C_6)$ bridge, which is unsubstituted or substituted with an $R_{10}$ group, which bridge optionally contains —HC=CH— within the $(C_2-C_6)$ bridge, and which bridge joins positions 2 and 6 of the piperidine, 1,2,3,6-tetrahydropyridine or piperazine ring.

In another embodiment, two $R_3$ groups together form a $(C_2-C_3)$ bridge, which is unsubstituted or substituted with an $R_{10}$ group, which bridge optionally contains —HC=CH— within the $(C_2-C_3)$ bridge, and which bridge joins positions 2 and 6 of the piperidine, 1,2,3,6-tetrahydropyridine or piperazine ring.

In another embodiment, two $R_3$ groups together form a $(C_2-C_3)$ bridge, which is unsubstituted, which bridge optionally contains —HC=CH— within the $(C_2-C_3)$ bridge, and which bridge joins positions 2 and 6 of the piperidine, 1,2,3,6-tetrahydropyridine or piperazine ring.

In another embodiment, two $R_3$ groups together form a —CH$_2$CH$_2$— bridge, a —HC=CH— bridge, or a —CH$_2$CH$_2$CH$_2$-bridge, and which bridge joins positions 2 and 6 of the piperidine, 1,2,3,6-tetrahydropyridine or piperazine ring.

In another embodiment, two $R_3$ groups together form

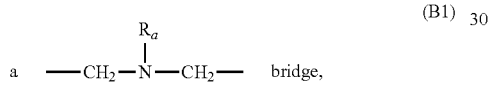

(B1)

a —CH$_2$—N—CH$_2$— bridge,

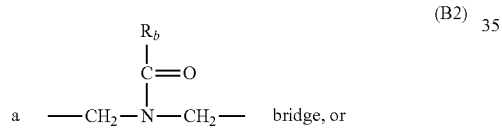

(B2)

a —CH$_2$—N—CH$_2$— bridge, or

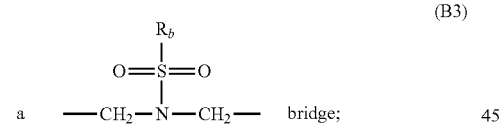

(B3)

a —CH$_2$—N—CH$_2$— bridge;

wherein $R_a$ is —H, —$(C_1-C_6)$alkyl, —$(C_3-C_8)$cycloalkyl, —CH$_2$—C(O)—$R_c$, —(CH$_2$)—C(O)—OR$_c$, —(CH$_2$)—C(O)—N(R$_c$)$_2$, —(CH$_2$)$_2$—O—R$_c$, —(CH$_2$)$_2$—S(O)$_2$—N(R$_c$)$_2$, or —(CH$_2$)$_2$—N(R$_c$)S(O)$_2$—R$_c$;

$R_b$ is (a) —H, —$(C_1-C_6)$alkyl, —$(C_3-C_8)$cycloalkyl, -(3- to 7-membered)heterocycle, —N(R$_c$)$_2$, —N(R$_c$)—$(C_3-C_8)$cycloalkyl, or —N(R$_c$)-(3- to 7-membered)heterocycle; or (b) -phenyl, -(5- or 6-membered)heteroaryl, —N(R$^c$)-phenyl, or —N(R$^c$)-(5- to 10-membered)heteroaryl, each of which is unsubstituted or substituted with 1, 2 or 3 independently selected $R_{13}$ groups; and each $R_1$ is independently —H or —$(C_1-C_4)$alkyl.

In another embodiment, the B1, B2, or B3 bridge joins positions 2 and 6 of the piperidine, 1,2,3,6-tetrahydropyridine or piperazine ring.

In another embodiment, Y is

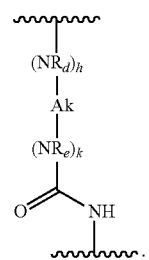

In another embodiment, Ak is $(C_1-C_3)$alkylene.
In another embodiment, Ak is $(C_2-C_3)$alkenylene.
In another embodiment, Ak is $(C_2-C_3)$alkynylene.
In another embodiment, h is 1 and $R_d$ is —H.
In another embodiment, h is 0.
In another embodiment, k is 1 and $R_e$ is —H.
In another embodiment, k is 0.
In another embodiment, X is O.
In another embodiment, X is S.
In another embodiment, X is N—CN.
In another embodiment, X is N—OR$_7$.
In another embodiment, X is N—OH.
In another embodiment, $R_5$ is —H.
In another embodiment, $R_5$ is —$(C_1-C_6)$alkyl.
In another embodiment, Ar$_2$ is

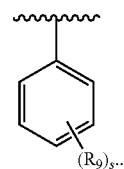

In another embodiment, Ar$_2$ is

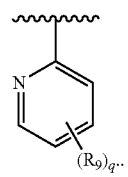

In another embodiment, Ar$_2$ is

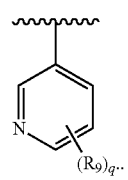

In another embodiment, Ar$_2$ is

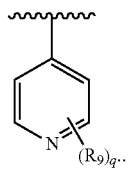

In another embodiment, Ar$_2$ is

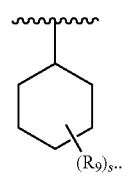

In another embodiment, s or q is 0.
In another embodiment, s or q is 1.
In another embodiment, s or q is 2.
In another embodiment, Ar$_2$ is

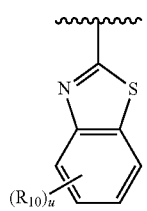

In another embodiment, Ar$_2$ is

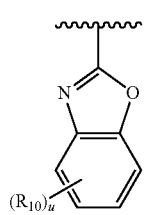

In another embodiment, Ar$_2$ is

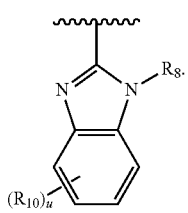

In another embodiment, Ar$_2$ is

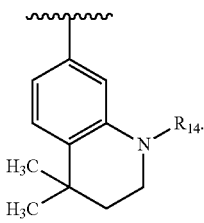

In another embodiment, Ar$_2$ is

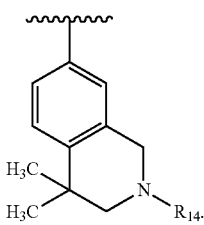

In another embodiment, Ar$_2$ is

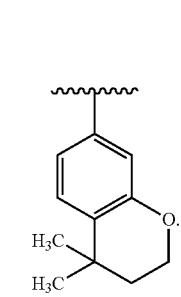

In another embodiment, Ar$_2$ is

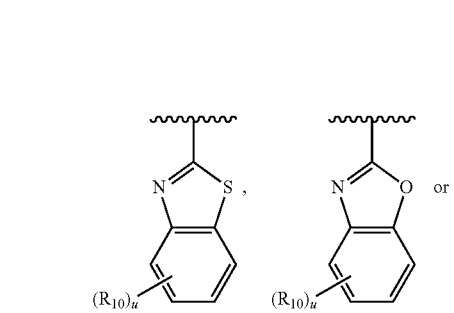

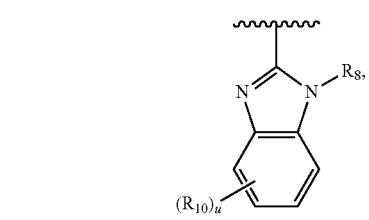

u is 1 and R$_{10}$ is -halo.

In another embodiment, Ar$_2$ is

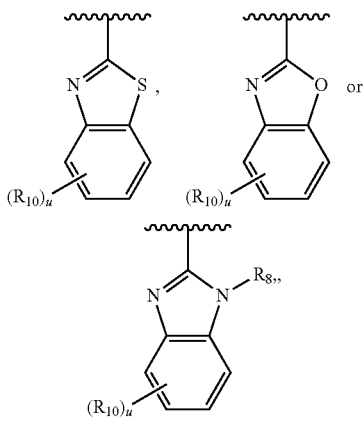

u is 1 and R$_{10}$ is —(C$_1$-C$_4$)alkyl.

In another embodiment, Ar$_2$ is

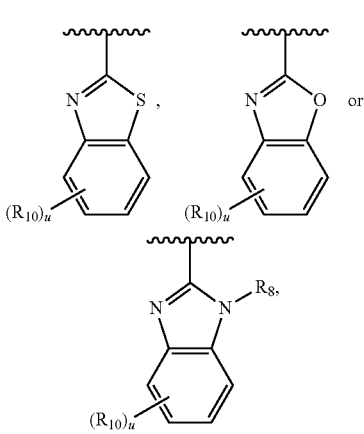

u is 2 and R$_{10}$ are each independently —(C$_1$-C$_4$)alkyl.

In another embodiment, Ar$_2$ is

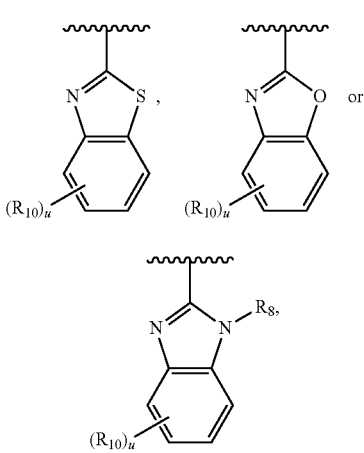

and u is 0.

In another embodiment, Ar$_2$ is

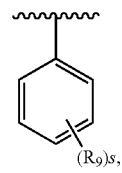

s is 1 and R$_9$ is —(C$_1$-C$_6$)alkyl, -halo, —C(halo)$_3$, —OR$_{13}$, —N(R$_{13}$)$_2$, or —S(O)$_2$R$_{13}$.

In another embodiment, Ar$_2$ is

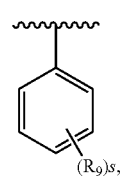

s is 1 and R$_9$ is —(C$_1$-C$_6$)alkyl, -halo, —C(halo)$_3$, —OC(halo)$_3$, or —(C$_1$-C$_6$)alkoxy.

In another embodiment, Ar$_2$ is

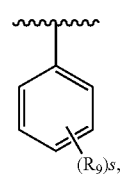

s is 1 and R$_9$ is —(C$_1$-C$_6$)alkyl, -halo, —CF$_3$, or —OCF$_3$.

In another embodiment, Ar$_2$ is

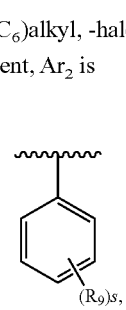

s is 1 and R$_9$ is —CF$_3$.

In another embodiment, Ar$_2$ is

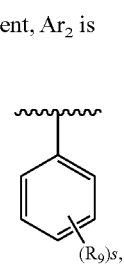

s is 2, and each R$_9$ group independently is —(C$_1$-C$_6$)alkyl, -halo, —C(halo)$_3$, —OR$_{13}$, —N(R$_{13}$)$_2$, or —S(O)$_2$R$_{13}$.

In another embodiment, Ar$_2$ is

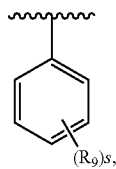

s is 2, and each R$_9$ group independently is —(C$_1$-C$_6$)alkyl, -halo, —CF$_3$, —OCF$_3$ or —(C$_1$-C$_6$)alkoxy.

In another embodiment, Ar$_2$ is

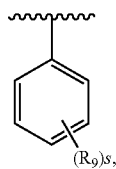

s is 2, and each R$_9$ group independently is -methyl, —Cl, —F, —CF$_3$, —OCF$_3$, or —OCH$_3$.

In another embodiment, Ar$_2$ is

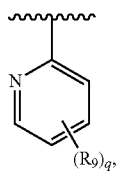

q is 1 and R$_9$ is —(C$_1$-C$_6$)alkyl, -halo, —C(halo)$_3$, —OR$_{13}$, —N(R$_{13}$)$_2$, or —S(O)$_2$R$_{13}$.

In another embodiment, Ar$_2$ is

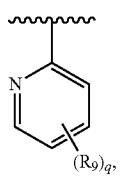

q is 1 and R$_9$ is —(C$_1$-C$_6$)alkyl, -halo, —C(halo)$_3$, —OC(halo)$_3$, or —(C$_1$-C$_6$)alkoxy.

In another embodiment, Ar$_2$ is

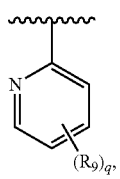

q is 1 and R$_9$ is —(C$_1$-C$_6$)alkyl, -halo, —CF$_3$, or —OCF$_3$.

In another embodiment, Ar$_2$ is

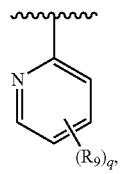

q is 1 and R$_9$ is —CF$_3$.

In another embodiment, Ar$_3$ is -(3- to 7-membered)heterocycle which is unsubstituted or substituted with 1 or 2 independently selected R$_6$ groups.

In another embodiment, Ar$_3$ is (5- or 6-membered) aromatic heterocycle which is unsubstituted or substituted with 1 or 2 independently selected R$_6$ groups.

In another embodiment, R$_6$ is —(C$_1$-C$_6$)alkyl.

In another embodiment, two R$_6$ groups together form =O.

In another embodiment, Ar$_3$ is (5- or 6-membered) aromatic heterocycle.

In another embodiment, Ar$_3$ is oxadiazole, isoxazole, oxazole, furan or pyrazole.

In another embodiment, Ar$_3$ is oxadiazole, isoxazole or oxazole.

In another embodiment, Z is —OR$_{12}$.

In another embodiment, Z is —(C$_1$-C$_6$)alkyl substituted with 1 or 2 —OR$^{12}$ groups.

In another embodiment, Z is —(C$_2$-C$_6$)alkenyl substituted with 1 or 2 —OR$^{12}$ groups.

In another embodiment, each R$_{12}$ is —H.

In another embodiment, each R$_{12}$ is —(C$_1$-C$_6$)alkyl.

In another embodiment, each R$_{12}$ is -acetyl.

In another embodiment, each R$_{12}$ is —C(O)OH.

In another embodiment, each R$_{17}$ is —C(O)NH$_2$.

In another embodiment, Z is —OH.

In another embodiment, Z is —(C$_1$-C$_6$)alkyl substituted with 1 or 2 —OH groups.

In another embodiment, Z is —(C$_2$-C$_6$)alkenyl substituted with 1 or 2 —OH groups.

In another embodiment, Z is —(C$_1$-C$_3$)alkyl substituted with 1 or 2 —OH groups.

In another embodiment, Z is —(C$_1$-C$_3$)alkyl substituted with 2 —OH groups.

In another embodiment, Z is —(C$_2$-C$_4$)alkenyl substituted with 1 or 2 —OH groups.

In another embodiment, Z is —(C$_2$-C$_4$)alkenyl substituted with 2 —OH groups.

In another embodiment, v is 1 and Z is —(C$_1$-C$_6$)alkyl substituted with 1 or 2 —OH groups.

In another embodiment, v is 1 and Z is —(C$_1$-C$_3$)alkyl substituted with 1 or 2 —OH groups.

In another embodiment, v is 1 and Z is —CH$_2$OH or —CH$_2$CH$_2$OH.

In another embodiment, v is 1 or 2 and Z is unsubstituted —(C$_1$-C$_6$)alkyl.

In another embodiment, v is 1 or 2 and Z is unsubstituted —(C$_1$-C$_3$)alkyl.

In another embodiment, v is 1 and Z is unsubstituted —(C$_1$-C$_3$)alkyl.

In another embodiment, v is 1 and Z is —(C$_2$-C$_6$)alkenyl which is substituted with 1 or 2 —OH groups.

In another embodiment, v is 1 and Z is —(C$_2$-C$_4$)alkenyl which is substituted with 1 or 2 —OH groups.

In another embodiment, v is 1 or 2 and Z is unsubstituted —(C$_2$-C$_6$)alkenyl.

In another embodiment, v is 1 or 2 and Z is unsubstituted —(C$_2$-C$_4$)alkenyl.

In another embodiment, v is 1 and Z is unsubstituted —(C$_2$-C$_4$)alkenyl.

In another embodiment, v is 1 or 2 and Z is —OH.

In another embodiment, v is 2 and Z is —OH.

In another embodiment, v is 1 and Z is —C(O)OH.

In another embodiment, v is 1 and Z is —C(O)O—(C$_1$-C$_6$)alkyl.

In another embodiment, Z is

[structure: HOCH$_2$-CH(OH)- with wavy bond]

wherein the compound of Formula I is racemic.

In another embodiment, Z is

[two enantiomer structures with OH and wavy bonds] and wherein the % ee of the R enantiomer is greater than 60%, 70%, 80% 90% or 99%.

In another embodiment, Z is

[two enantiomer structures with OH and wavy bonds] and wherein the % ee of the S enantiomer is greater than 60%, 70%, 80%, 90% or 99%.

In another embodiment,

[structure: Ar$_3$ with (Z)$_v$] is

[several heterocyclic structures with (Z)$_v$ substituents: oxadiazoles, oxazoles shown]

In another embodiment,

[structure: Ar$_3$ with (Z)$_v$] is

[several heterocyclic structures shown]

In another embodiment, L$_1$ is a bond.

In another embodiment, L$_1$ is (C$_1$-C$_3$)alkylene.

In another embodiment, L$_1$ is (C$_2$-C$_3$)alkenylene.

In another embodiment, L$_1$ is (C$_2$-C$_3$)alkynylene.

In another embodiment, L$_2$ is a bond.

In another embodiment, L$_2$ is (C$_1$-C$_3$)alkylene.

In another embodiment, L$_2$ is (C$_2$-C$_3$)alkenylene.

In another embodiment, L$_2$ is (C$_2$-C$_3$)alkynylene.

In another embodiment, L$_1$ is a bond and L$_2$ is a bond.

le;3qCompounds of Formula I of interest are compounds of Formula II, III, IV, V, VI, VII, VIII, IX, X, XI, XII, XIII, XIV, XV, XVII, XVII, XVIII or XIX:
(II)
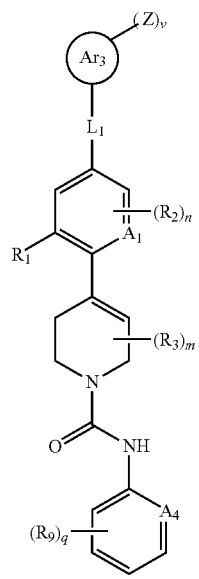
(III)
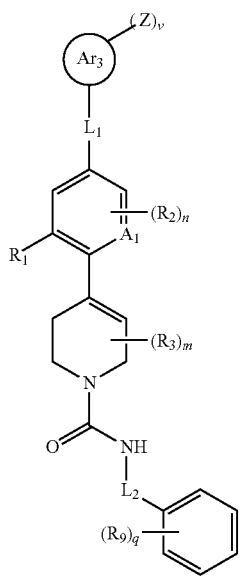
(IV)
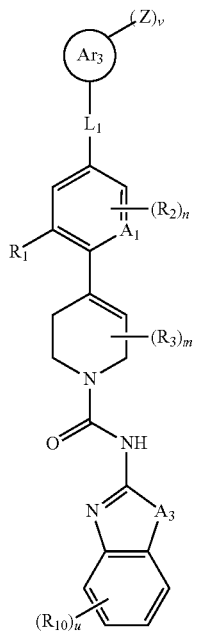
(V)
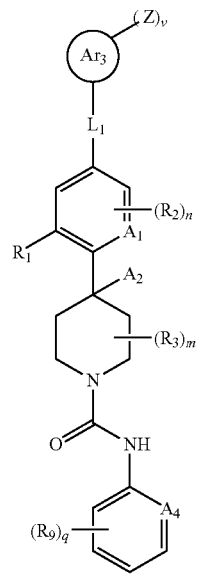

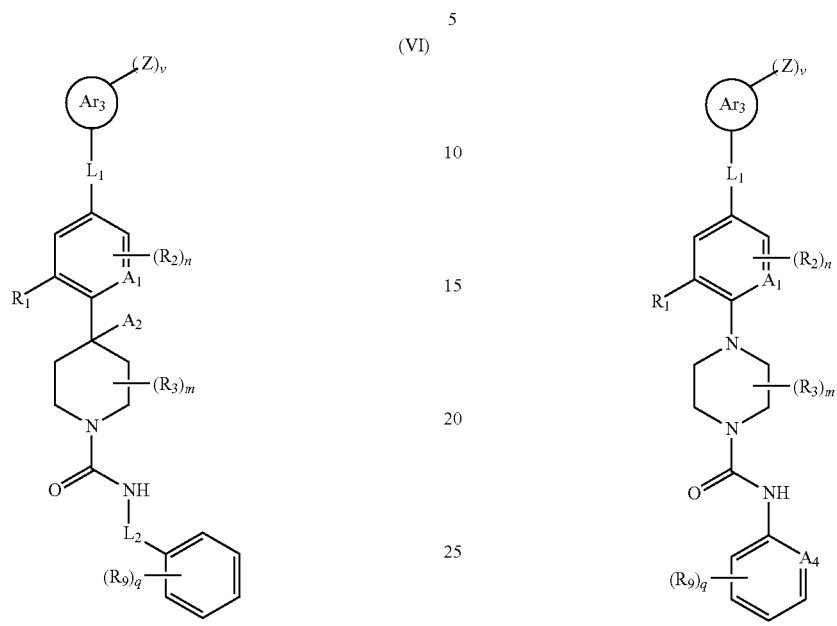
(VI)
(VIII)
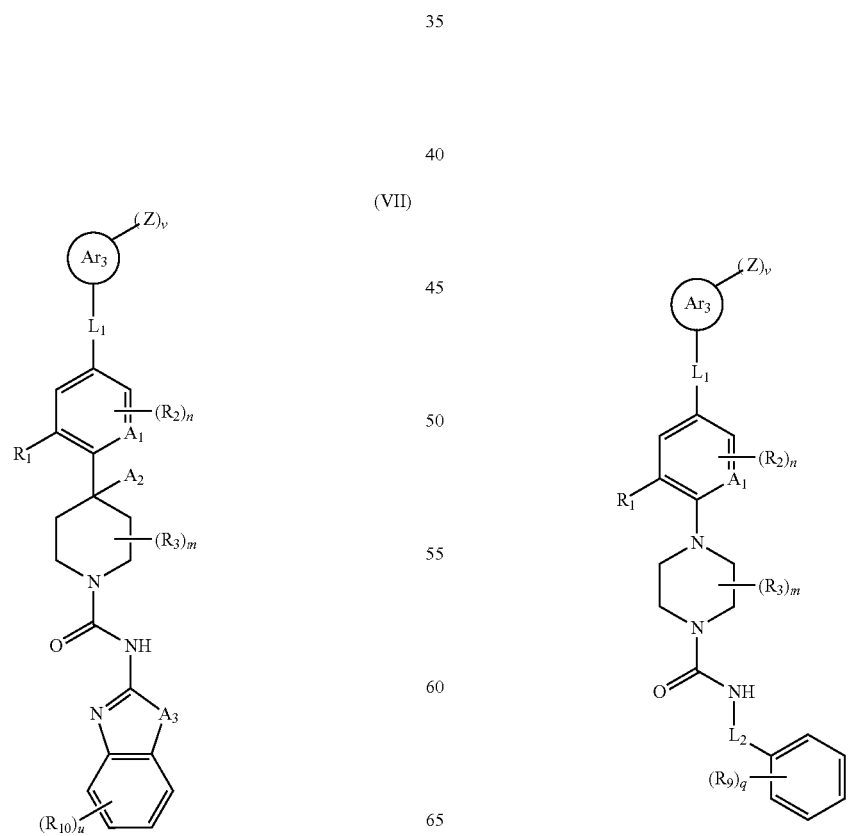
(VII)
(IX)

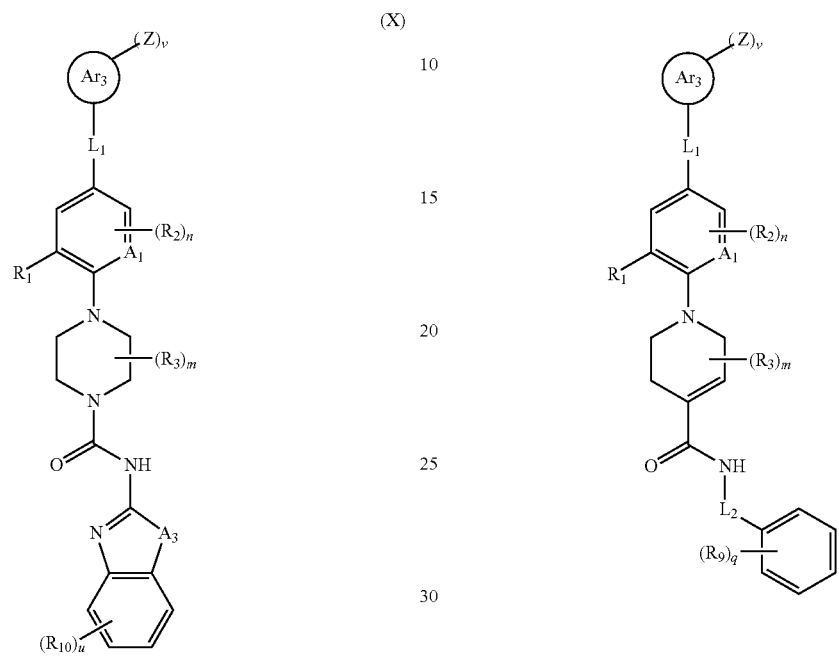
(X)
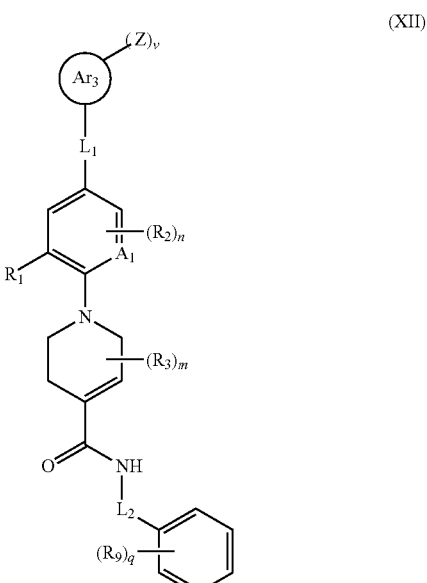
(XII)
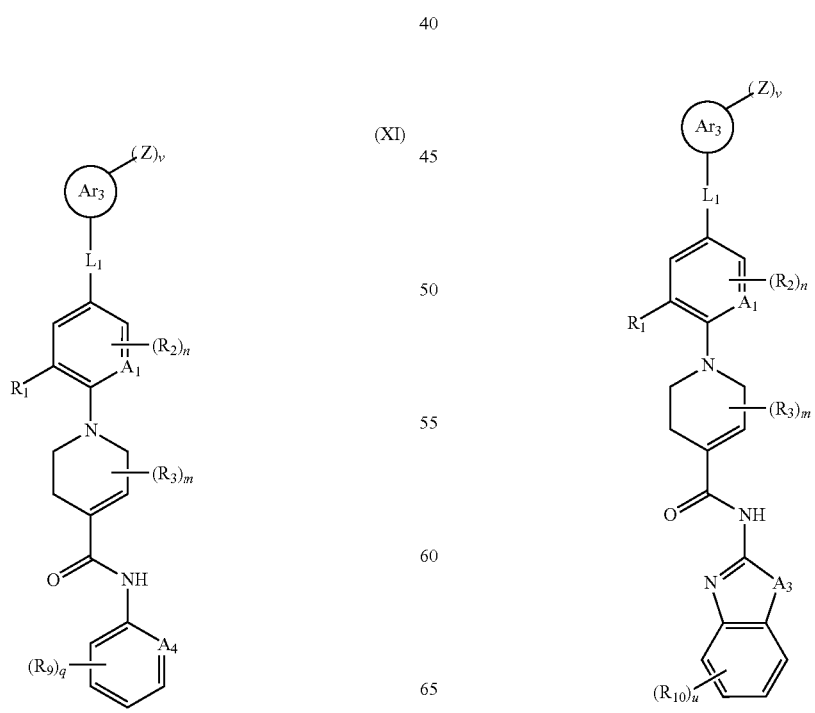
(XI)
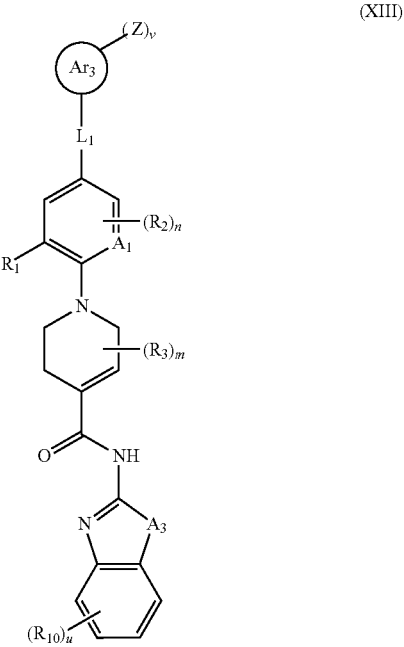
(XIII)

(XIV)
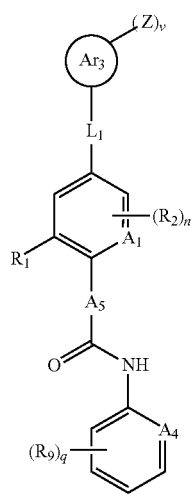
(XV)
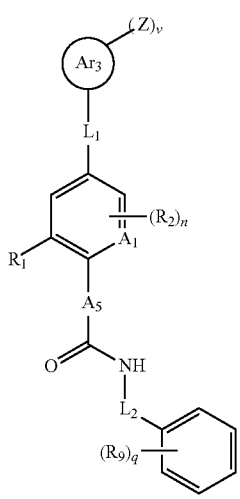
(XVI)
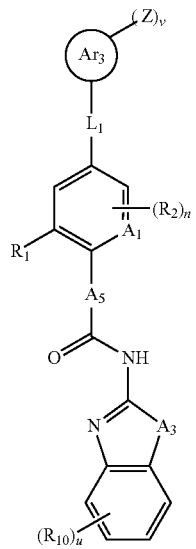
(XVII)
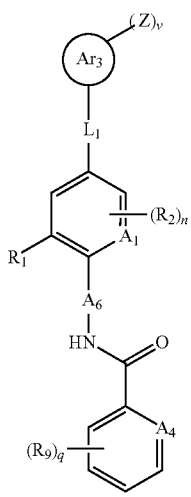
(XVIII)
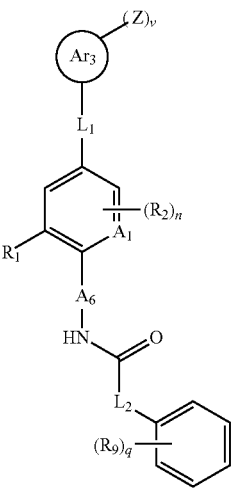
(XIX)
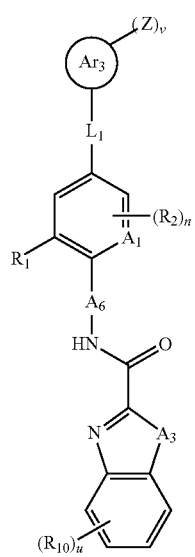
or a pharmaceutically acceptable derivative thereof, wherein $A_1$ is CH or N, $A_2$ is —H or -halo, $A_3$ is S or NH, $A_4$ is CH or N, $L_2$ is $CH_2$ or CH=CH, $A_5$ is $CH_2$, CH=CH, C(Me)=CH, ethynylene or NHCH$_2$CH$_2$NH, A$_6$ is CH$_2$, CH=CH, C(Me)=CH or ethynylene, and Z, L$_1$, Ar$_3$, R$_1$, R$_2$, R$_3$, R$_9$, R$_{10}$, n, m, v, q and u are as defined above for compounds of Formula I.

In one embodiment, compounds of Formula II, III, IV, V, VI, VII, VIII, IX, X, XI, XII, XIII, XIV, XV, XVII, XVII, XVIII or XIX of interest are compounds wherein
A$_1$ is CH or N, A$_2$ is H or halo, A$_3$ is S or NH, A$_4$ is CH or N, L$_2$ is CH$_2$ or CH=CH, A$_5$ is CH$_2$, CH=CH, C(Me)=CH, ethynylene or NHCH$_2$CH$_2$NH, A$_6$ is CH$_2$, CH=CH, C(Me)=CH or ethynylene,
Z is —OH, -methyl, —CH$_2$OH, —CH$_2$CH$_2$OH, —CH(OH)CH$_2$(OH) or —C(O)OMe,
L$_1$ is a bond, —CH$_2$— or —CH(OH)—,
Ar$_3$ is oxazole, isoxazole, oxadiazole, furan, pyrazole, pyrrolidine or dihydrooxazole, each of which is unsubstituted or substituted with oxo,
R$_1$ is -halo or -methyl,
R$_9$ is -halo, -methyl, -tert-butyl, —CF$_3$, —OCF$_3$,
R$_{10}$ is -halo,
n is 0, m is 0, v is 0, 1 or 2, q is 0, 1 or 2, and u is 0, 1 or 2.

In one embodiment, compounds of Formula II, III, IV, V, VI, VII, VIII, IX, X, XI, XII, XIII, XIV, XV, XVII, XVII, XVIII or XIX of interest are compounds wherein
A$_1$ is CH or N, A$_2$ is —H or -halo, A$_3$ is S or NH, A$_4$ is CH or N, L$_2$ is CH$_2$ or CH=CH, A$_5$ is CH$_2$, CH=CH, C(Me)=CH, ethynylene or NHCH$_2$CH$_2$NH, A$_6$ is CH$_2$, CH=CH, C(Me)=CH or ethynylene,

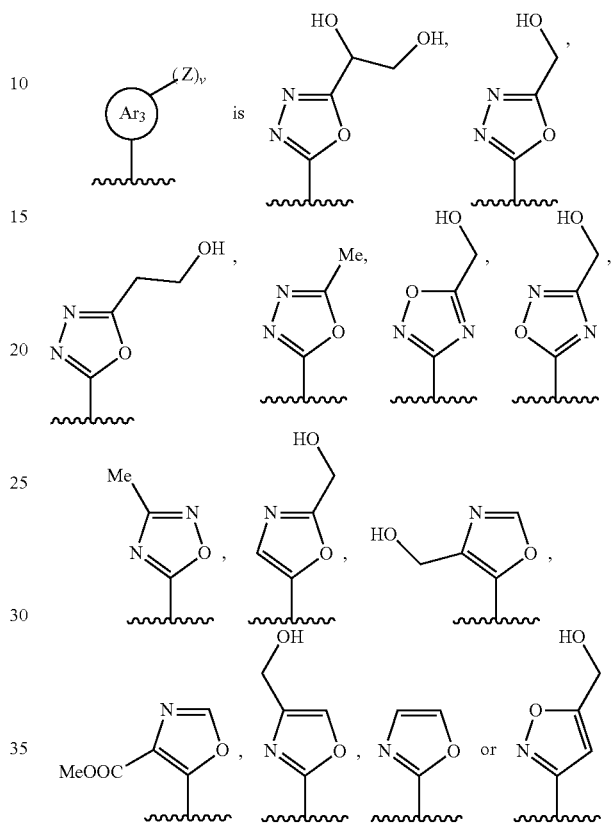

Z is —OH, -methyl, —CH$_2$OH, —CH$_2$CH$_2$OH, —CH(OH)CH$_2$(OH) or —C(O)OMe,
L$_1$ is a bond, —CH$_2$— or —CH(OH)—,
R$_1$ is -halo or -methyl,
R$_9$ is -halo, -methyl, -tert-butyl, —CF$_3$, —OCF$_3$,
R$_{10}$ is -halo,
n is 0, m is 0, v is 0, 1 or 2, q is 0, 1 or 2, and u is 0, 1 or 2.

In one embodiment, compounds of Formula II, III, IV, V, VI, VII, VIII, IX, X, XI, XII, XIII, XIV, XV, XVII, XVII, XVIII or XIX of interest are compounds wherein
A$_1$ is CH or N, A$_2$ is —H or -halo, A$_3$ is S or NH, A$_4$ is CH or N, L$_2$ is CH$_2$ or CH=CH, A$_5$ is CH$_2$, CH=CH, C(Me)=CH, ethynylene or NHCH$_2$CH$_2$NH, A$_6$ is CH$_2$, CH=CH, C(Me)=CH or ethynylene,
L$_1$ is a bond, —CH$_2$— or —CH(OH)—, R$_1$ is -halo or -methyl,
R$_9$ is -halo, -methyl, -tert-butyl, —CF$_3$ or —OCF$_3$,
R$_{10}$ is -halo,
n is 0, m is 0, q is 0, 1 or 2, and u is 0, 1 or 2.

In one embodiment, compounds of Formula II, IV, V, VIII, XI or XIV of interest are compounds wherein A$_1$ is CH or N, A$_2$ is -halo, A$_3$ is S, A$_4$ is CH or N, A$_5$ is ethynylene,

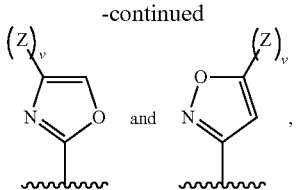

Z is —CH$_2$OH or —CH$_2$CH$_2$OH, L$_1$ is a bond or —CH$_2$—, R$_1$ is -halo or -methyl, R$_9$ is -halo, -methyl, -tert-butyl, —CF$_3$ or —OCF$_3$, R$_{10}$ is -halo, n is 0, m is 0, v is 1, q is 1 or 2, and u is 1 or 2.

In one embodiment, compounds of Formula II, IV, V, VIII, XI or XIV of interest are compounds wherein A$_1$ is CH or N, A$_2$ is halo, A$_3$ is S, A$_4$ is CH or N, A$_5$ is ethynylene, Z is —CH$_2$OH or —CH$_2$CH$_2$OH, L$_1$ is a bond or —CH$_2$—, Ar$_3$ is oxazole, isoxazole or oxadiazole, R$_1$ is -halo or -methyl, R$_9$ is -halo, -methyl, -tert-butyl, —CF$_3$ or —OCF$_3$, R$_{10}$ is -halo, n is 0, m is 0, v is 1, q is 1 or 2, and u is 1 or 2.

In one embodiment, compounds of Formula II, IV, V, VIII, XI or XIV of interest are compounds wherein A$_1$ is CH or N, A$_2$ is -halo, A$_3$ is S, A$_4$ is CH or N, A$_5$ is ethynylene,

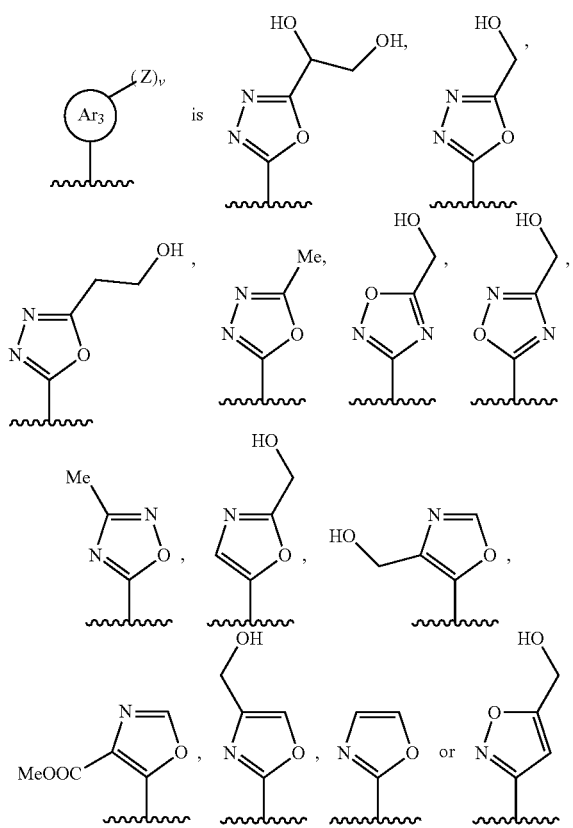

L$_1$ is a bond or —CH$_2$—, R$_1$ is -halo or -methyl, R$_9$ is -halo, -methyl, -tert-butyl, —CF$_3$ or —OCF$_3$, R$_{10}$ is -halo, n is 0, m is 0, q is 1 or 2, and u is 1 or 2.

In one embodiment, compounds of Formula II, V or XIV of interest are compounds wherein A$_1$ is CH or N, A$_2$ is -halo, A$_4$ is CH or N, A$_5$ is ethynylene, Z is —CH$_2$OH, L$_1$ is a bond, Ar$_3$ is oxadiazole, R$_1$ is -halo, R$_9$ is -halo, -methyl or —CF$_3$, n is 0, m is 0, v is 1 and q is 1 or 2.

In one embodiment, compounds of Formula II, V or XIV of interest are compounds wherein A$_1$ is CH or N, A$_2$ is -halo, A$_4$ is CH or N, A$_5$ is ethynylene,

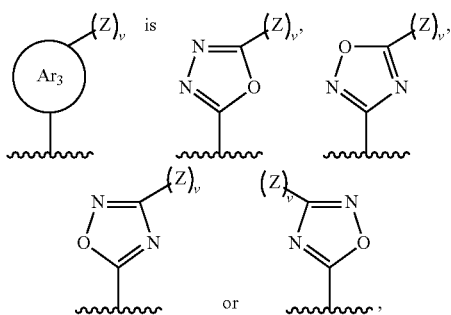

Z is —CH$_2$OH, L$_1$ is a bond, R$_1$ is -halo, R$_9$ is -halo, -methyl or —CF$_3$, n is 0, m is 0, v is 1 and q is 1 or 2.

In one embodiment, compounds of Formula II, V or XIV of interest are compounds wherein A$_1$ is CH or N, A$_2$ is -halo, A$_4$ is CH or N, A$_5$ is ethynylene,

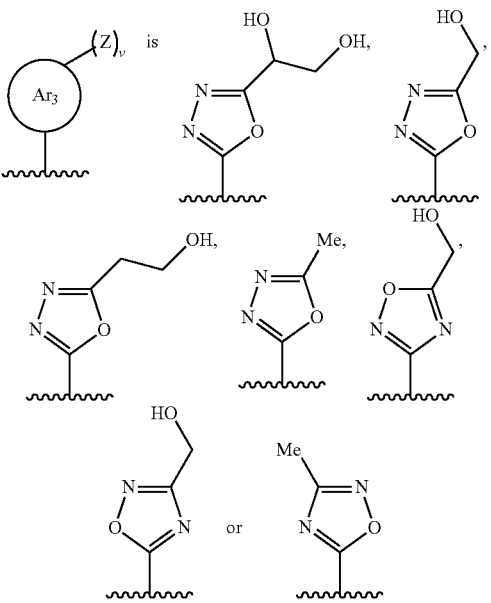

L$_1$ is a bond, R$_1$ is -halo, R$_9$ is -halo, -methyl or —CF$_3$, n is 0, m is 0, and q is 1 or 2.

In one embodiment, a compound of Formula I is a pharmaceutically acceptable derivative of a compound of Formula I.

In another embodiment, a compound of Formula I is a compound of Formula I wherein the derivative is a pharmaceutically acceptable salt.

Aqueous solubility of compounds is often a desirable feature. For example, aqueous solubility of a compound permits that compound to be more easily formulated into a variety of dosage forms that may be administered to an animal. When a compound is not fully soluble in the blood, it may precipitate in the blood, and the animal's exposure to the drug will accordingly not correspond to the administered dose. Aqueous solubility increases the likelihood that a compound will not precipitate in an animal's blood, and increases the ability to predict exposure at the target sight of the compound.

Compounds of Formula I are highly soluble in aqueous solution. For example, the aqueous solubility at pH 6.8, in µM, compounds of Formula I are >3.0, >10.0, >20.0, 30.0 or >50.0. The aqueous solubility at pH 1.2, in µM, of compounds of Formula I are >3.0, >10.0, >20.0, 30.0 or >50.0. Additionally, the aqueous solubility at either pH 6.8 or pH 1.2 of each of compounds of Formula I is >50 μM.

In addition to being highly soluble in aqueous solution, compounds of Formula I are desirable because side effects are less severe (e.g., attenuation or removal of central nervous system side effects) in animals administered a compound of Formula I. For example, muscle relaxation is attenuated or absent in animals administered a compound of Formula I. Sedation is attenuated or absent in animals administered a compound of Formula I. Ataxia is attenuated or absent in animals administered a compound of Formula I. Flat body posture is attenuated or absent in animals administered a compound of Formula I. Tremor is attenuated or absent in animals administered a compound of Formula I. When a compound induces less severe side effects, the therapeutic index, which is the difference between an effective dose and a dose that causes adverse effects, is increased. Therapeutic index is a measure of the safety of a compound when administered to an animal. The greater the therapeutic index, the safer the compound.

Compounds of Formula I also have excellent pharmacokinetic properties. Specifically, the plasma level of a compound of Formula I in an animal is dose proportionate. Therefore, the amount of compound in the plasma of an animal can be more readily controlled according to the dose of the compound administered to the animal.

In addition to being highly soluble in aqueous solution at both pH 6.8 and pH 1.2, having a very high therapeutic index, and having excellent pharmacokinetic parameters as described for Formula I, compounds of Formula I are of interest because they are also very bioavailable, and are believed to be highly efficacious in animals for the treatment of pain. Bioavailability is a measure of how much of the dose administered reaches systemic circulation after oral administration.

Moreover, compounds of Formula I may have one or more of the following characteristics:
high selectivity to TRPV1 receptor,
high stability
high oral absorbability,
high bioavailability,
low clearance,
easily transfers to brain
long half-life,
long efficacy of a medicine
less side effect and/or
high protein-unbound fraction.

Therefore se compounds of Formula I are considered useful as inhibitors of TRPV1 receptor.

Definitions

As used herein, the terms used above having following meaning:

"—$(C_1-C_{10})$alkyl" means a straight chain or branched non-cyclic hydrocarbon having from 1 to 10 carbon atoms. Representative straight chain —$(C_1-C_{10})$alkyls include -methyl, -ethyl, -n-propyl, -n-butyl, -n-pentyl, -n-hexyl, -n-heptyl, -n-octyl, -n-nonyl, and -n-decyl. Representative branched —$(C_1-C_{10})$alkyls include -iso-propyl, -sec-butyl, -iso-butyl, -tert-butyl, -iso-pentyl, -neo-pentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

"—$(C_1-C_6)$alkyl" means a straight chain or branched non-cyclic hydrocarbon having from 1 to 6 carbon atoms. Representative straight chain —$(C_1-C_6)$alkyls include -methyl, -ethyl, -n-propyl, -n-butyl, -n-pentyl, and -n-hexyl. Representative branched —$(C_1-C_6)$alkyls include -iso-propyl, -sec-butyl, -iso-butyl, -tert-butyl, -iso-pentyl, -neo-pentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, and 3,3-dimethylbutyl.

Each of $(C_1-C_6)$alkyl part for "—$(C_1-C_6)$alkyl-$OR_{13}$", "—$(C_1-C_6)$alkyl-OC(O)$R_7$", "—$(C_1-C_6)$alkyl-C=N—$OR_{13}$", "—$(C_1-C_6)$alkyl-C(O)N$(R_{13})_2$", "—$(C_1-C_6)$alkyl-NHS(O)$_2$N$(R_{13})_2$", "—$(C_1-C_6)$alkyl-C(=NH)—N$(R_{13})_2$" and "—$(C_1-C_6)$alkyl-N$(R_8)_2$" is the same as the above "—$(C_1-C_6)$alkyl".

"—$(C_1-C_6)$haloalkyl" means a straight chain or branched non-cyclic hydrocarbon having from 1 to 6 carbon atoms as defined above for —$(C_1-C_6)$alkyl that is substituted with 1, 2 or 3 independently selected halo groups.

"—$(C_1-C_6)$hydroxyalkyl" means a straight chain or branched non-cyclic hydrocarbon having from 1 to 6 carbon atoms as defined above for —$(C_1-C_6)$alkyl that is substituted with 1, 2 or 3 hydroxyl groups.

"—$(C_1-C_4)$alkyl" means a straight chain or branched non-cyclic hydrocarbon having from 1 to 4 carbon atoms. Representative straight chain —$(C_1-C_4)$alkyls include -methyl, -ethyl, -n-propyl, and -n-butyl. Representative branched —$(C_1-C_4)$alkyls include -iso-propyl, -sec-butyl, -iso-butyl, and -tert-butyl.

"—$(C_1-C_3)$alkyl" means a straight chain or branched non-cyclic hydrocarbon having from 1 to 3 carbon atoms. Representative —$(C_1-C_3)$alkyls include -methyl, -ethyl, -n-propyl and -iso-propyl.

"—$(C_2-C_3)$alkyl" include -ethyl, -n-propyl and -iso-propyl.

"—$(C_1-C_2)$alkyl" include -methyl and -ethyl.

"—$(C_2-C_{10})$alkenyl" means a straight chain or branched non-cyclic hydrocarbon having from 2 to 10 carbon atoms and including at least one carbon-carbon double bond. Representative straight chain and branched $(C_2-C_{10})$alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like.

"—$(C_2-C_6)$alkenyl" means a straight chain or branched non-cyclic hydrocarbon having from 2 to 6 carbon atoms and including at least one carbon-carbon double bond. Representative straight chain and branched $(C_2-C_6)$alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, 2-hexenyl, 3-hexenyl and the like.

"—$(C_2-C_4)$alkenyl" means a straight chain or branched non-cyclic hydrocarbon having from 2 to 4 carbon atoms and including at least one carbon-carbon double bond. Representative straight chain and branched $(C_2-C_4)$alkenyls include -vinyl, -allyl, -1-butenyl, -2-butenyl, -iso-butylenyl and the like.

The $(C_2-C_6)$alkenyl part of "=CH$(C_2-C_6)$alkenyl" is defined in the same way as the above "—$(C_2-C_6)$alkenyl".

"—($C_2$-$C_6$)haloalkenyl" means a straight chain or branched non-cyclic hydrocarbon having from 2 to 6 carbon atoms and including at least one carbon-carbon double bond as defined above for —($C_2$-$C_6$)alkenyl that is substituted with 1, 2 or 3 independently selected halo groups.

"—($C_2$-$C_6$)hydroxyalkenyl" means a straight chain or branched non-cyclic hydrocarbon having from 2 to 6 carbon atoms and including at least one carbon-carbon double bond as defined above for —($C_2$-$C_6$)alkenyl that is substituted with 1, 2 or 3 hydroxyl groups.

"—($C_2$-$C_{10}$)alkynyl" means a straight chain or branched non-cyclic hydrocarbon having from 2 to 10 carbon atoms and including at least one carbon-carbon triple bond. Representative straight chain and branched —($C_2$-$C_{10}$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl and the like.

"—($C_2$-$C_6$)alkynyl" means a straight chain or branched non-cyclic hydrocarbon having from 2 to 6 carbon atoms and including at least one carbon-carbon triple bond. Representative straight chain and branched ($C_2$-$C_6$)alkynyls include -ethynyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl and the like.

"—($C_2$-$C_6$)haloalkynyl" means a straight chain or branched non-cyclic hydrocarbon having from 2 to 6 carbon atoms and including at least one carbon-carbon triple bond that is substituted with 1, 2 or 3 independently selected halo groups.

"—($C_2$-$C_6$)hydroxyalkynyl" means a straight chain or branched non-cyclic hydrocarbon having from 2 to 6 carbon atoms and including at least one carbon-carbon triple bond that is substituted with 1, 2 or 3 hydroxyl groups.

"—($C_1$-$C_6$)alkoxy" means a straight chain or branched non-cyclic hydrocarbon having one or more ether groups and from 1 to 6 carbon atoms. Representative straight chain and branched —($C_1$-$C_6$)alkoxys include methoxy, ethoxy, propoxy, butoxy, pentoxy, hexoxy and the like.

"—($C_1$-$C_6$)alkoxy($C_1$-$C_6$)alkyl" means a straight chain or branched non cyclic hydrocarbon having one or more ether groups and from 1 to 6 carbon atoms as defined above for —($C_1$-$C_6$)alkyl group that is substituted with a —($C_2$-$C_6$)alkoxy group.

"—($C_1$-$C_6$)alkoxy($C_2$-$C_6$)alkenyl" means a straight chain or branched non cyclic hydrocarbon from 2 to 6 carbon atoms and including at least one carbon-carbon double bond as defined above for —($C_2$-$C_6$)alkenyl group that is substituted with a —($C_1$-$C_6$)alkoxy group.

"—($C_1$-$C_6$)alkoxy($C_2$-$C_6$)alkynyl" means a straight chain or branched non cyclic hydrocarbon having from 2 to 10 carbon atoms and including at least one carbon-carbon triple bond as defined above for ($C_2$-$C_6$)alkynyl that is substituted with a —($C_1$-$C_6$)alkoxy group.

"($C_1$-$C_6$)alkylene" includes a straight or branched divalent carbon chain of a carbon number of 1 to 6, preferably a carbon number of 1 to 3. Examples include methylene, dimethylene, trimethylene, tetramethylene, and methyltrimethylene.

"($C_2$-$C_6$)alkenylene" includes a straight or branched divalent carbon chain of a carbon number of 2 to 6, preferably a carbon number of 2 to 4, having a double bond at an optional position. Examples include vinylene, propenylene, butenylene, butadienylene, methylpropenylene, pentenylene and hexenylene.

"($C_2$-$C_6$)alkynylene" includes a straight or branched divalent carbon chain of a carbon number of 2 to 6, more preferably a carbon number of 2 to 4, having a triple bond at an optional position and, further, optionally having a double bond. Examples include ethynylene, propynylene, butynylene, pentynylene and hexynylene.

"—($C_3$-$C_8$)cycloalkyl" means a saturated cyclic hydrocarbon having from 3 to 8 carbon atoms. Representative ($C_3$-$C_8$)cycloalkyls include -cyclopropyl, -cyclobutyl, -cyclopentyl, -cyclohexyl, -cycloheptyl, and -cyclooctyl.

The cycloalkyl part of "—N($R_c$)—($C_3$-$C_8$)cycloalkyl" is defined in the same way as the above "—($C_3$-$C_8$)cycloalkyl".

"—($C_5$-$C_8$)cycloalkenyl" means a cyclic non-aromatic hydrocarbon having at least one carbon-carbon double bond in the cyclic system and from 5 to 8 carbon atoms. Representative —($C_5$-$C_8$)cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, - cyclooctatrienyl, -cyclooctatetraenyl and the like.

"—(3- to 7-membered)heterocycle" means a 3- to 7-membered monocyclic heterocyclic ring which is either saturated, unsaturated non-aromatic, or aromatic. A 3-membered heterocycle can contain up to 1 heteroatom, a 4-membered heterocycle can contain up to 2 heteroatoms, a 5-membered heterocycle can contain up to 4 heteroatoms, a 6-membered heterocycle can contain up to 4 heteroatoms, and a 7-membered heterocycle can contain up to 5 heteroatoms. Each heteroatom is independently selected from nitrogen, which can be quaternized; oxygen; and sulfur, including sulfoxide and sulfone. The -(3- to 7-membered)heterocycle can be attached via a nitrogen or carbon atom. Representative -(3- to 7-membered)heterocycles include pyridine, furan, thiophene, pyrrole, oxazole, imidazole, triazole, 1,2,3-thiadiazole, 1,3,4-thiadiazole, 1,2,5-thiadiazole, thiazole, isoxazole, 1,2,3-oxadiazole, 1,3,4-oxadiazole, 1,2,5-oxadiazole, pyrazole, tetrazole, isothiazole, pyridazine, pyrimidine, pyrazine, 1,3,5-triazine, morpholine, thiomorpholine, pyrrolidine, pyrroline, piperidine, piperazine, thiazolidine, 2,3-dihydrofuran, dihydrooxazole, dihydropyrane, oxirane, oxetane, tetrahydrofuran, tetrahydropyrane, dihydropyridine, tetrahydropyridine, tetrahydropyrimidine, tetrahydrothiophene, tetrahydrothiopyrane, dioxane, thiirane, oxirane, oxathiorane, azetidine, thiane, imidazolidine, imidazoline, pyrazolidine, pyrazoline, dihydropyridine, dihydrothiazole, tetrahydrothiazole, tetrahydroisothiazole, dihydrooxazine, hexahydroazepine, tetrahydrodiazepine, tetrahydropyridazine and the like.

Each of heterocycle part for "—N($R_c$)-(3- to 7-membered)heterocycle" and "—S(O)$_2$-(3- to 7-membered)heterocycle" is the same as the above "-(3- to 7-membered)heterocycle."

"—(5- to 10-membered)heteroaryl" means an aromatic heterocycle ring of 5 to 10 members, including both mono- and bicyclic ring systems, where at least one carbon atom of one or both of the rings is replaced with a heteroatom independently selected from nitrogen, oxygen, and sulfur, or at least two carbon atoms of one or both of the rings are replaced with a heteroatom independently selected from nitrogen, oxygen, and sulfur. In one embodiment, one of the -(5- to 10-membered)heteroaryl's rings contain at least one carbon atom. In another embodiment, both of the -(5- to 10-membered)heteroaryl's rings contain at least one carbon atom. Representative -(5- to 10-membered)heteroaryls include pyridyl, furyl, benzofuryl, thienyl, benzothienyl, quinolinyl, isoquinolinyl, pyrrolyl, indolyl, oxazolyl, benzoxazolyl, imidazolyl, benzimidazolyl, triazolyl, thiadiazolyl, thiazolyl, benzothiazolyl, isoxazolyl, oxadiazolyl, pyrazolyl, tetrazolyl, isothiazolyl, pyridazinyl, pyrimidyl, pyrazinyl, triazinyl, cinnolinyl, phthalazinyl, and quinazolinyl.

Heteroaryl part for "—N(R$_c$)-(5- to 10-membered)heteroaryl" is the same as the above "-(5- to 10-membered) heteroaryl", "—(5- or 6-membered)aromatic heterocycle" and "-(5- or 6-membered)heteroaryl" includes a monocyclic aromatic heterocycle ring of 5 or 6 members where at least one carbon atom is replaced with a heteroatom independently selected from nitrogen, oxygen, and sulfur. In one embodiment, -(5- or 6-membered)aromatic heterocycle's ring and one of the -(5- or 6-membered)heteroaryl's ring contains at least one carbon atom. Representative -(5- or 6-membered) aromatic heterocycles include pyridine, furan, thiophene, pyrrole, oxazole, imidazole, triazole, 1,2,3-thiadiazole, 1,3,4-thiadiazole, 1,2,5-thiadiazole, thiazole, isoxazole, 1,2,3-oxadiazole, 1,3,4-oxadiazole, 1,2,5-oxadiazole, pyrazole, tetrazole, isothiazole, pyridazine, pyrimidine, pyrazine and 1,3,5-triazine.

Representative -(5- or 6-membered)heteroaryls include pyridyl, furyl, thienyl, pyrrolyl, oxazolyl, imidazolyl, triazolyl, 1,2,3-thiadiazolyl, 1,3,4-thiadiazolyl, 1,2,5-thiadiazolyl, thiazolyl, isoxazolyl, 1,2,3-oxadiazolyl, 1,3,4-oxadiazolyl, 1,2,5-oxadiazolyl, pyrazolyl, tetrazolyl, isothiazolyl, pyridazinyl, pyrimidyl, pyrazinyl, and 1,3,5-triazinyl.

"—CH$_2$(halo)" means a methyl group where one of the hydrogens of the methyl group has been replaced with a halogen. Representative —CH$_2$(halo) groups include —CH$_2$F, —CH$_2$Cl, —CH$_2$Br, and —CH$_2$I.

"—CH$_2$CH$_2$(halo)" means a ethyl group where one of the hydrogens of the ethyl group has been replaced with a halogen. Representative —CH$_2$CH$_2$(halo) groups include —CH$_2$CH$_2$F, —CH$_2$CH$_2$Cl, —CH$_2$CH$_2$Br, and —CH$_2$CH$_2$I.

"—CH(halo)$_2$" means a methyl group where two of the hydrogens of the methyl group have been replaced with a halogen. Representative —CH(halo)$_2$ groups include —CHF$_2$, —CHCl$_2$, —CHBr$_2$, —CHBrCl, —CHClI, and —CHI$_2$.

"—CH$_2$CH(halo)$_2$" means a ethyl group where two of the hydrogens of the ethyl group have been replaced with a halogen. Representative —CH$_2$CH(halo)$_2$ groups include —CH$_2$CHF$_2$, —CH$_2$CHCl$_2$, —CH$_2$CHBr$_2$, —CH$_2$CHBrCl, —CH$_2$CHClI, and —CHI$_2$.

"—C(halo)$_3$" means a methyl group where each of the hydrogens of the methyl group has been replaced with a halogen. Representative —C(halo)$_3$ groups include —CF$_3$, —CCl$_3$, —CBr$_3$, and —Cl$_3$.

"—CH$_2$C(halo)$_3$" means a ethyl group where three of the hydrogens of the ethyl group have been replaced with a halogen. Representative —CH$_2$C(halo)$_3$ groups include —CH$_2$CF$_3$, —CH$_2$CCl$_3$, —CH$_2$CBr$_3$, and —CH$_2$Cl$_3$.

C(halo)$_3$ part for "—S(O)$_2$C(halo)$_3$" is the same as the above "—C(halo)$_3$".

"—OCH$_2$(halo)" means a methoxy group where one of the hydrogens of the methoxy group has been replaced with a halogen. Representative —OCH$_2$(halo) groups include —OCH$_2$F, —OCH$_2$Cl, —OCH$_2$Br, and —OCH$_2$I.

"—OCH(halo)$_2$" means a methoxy group where two of the hydrogens of the methoxy group have been replaced with a halogen. Representative —OCH(halo)$_2$ groups include —OCHF$_2$, —OCHCl$_2$, —OCHBr$_2$, —OCHBrCl, —OCHClI, and —OCHI$_2$.

"—OC(halo)$_3$" means a methoxy group where each of the hydrogens of the methoxy group has been replaced with a halogen. Representative —OC(halo)$_3$ groups include —OCF$_3$, —OCCl$_3$, —OCBr$_3$, and —OCl$_3$.

"halogen" or "-halo" means —F, —Cl, —Br, or —I.

"(C$_2$-C$_6$) bridge" as used herein means a hydrocarbon chain containing 2 to 6 carbon atoms joining two atoms of the 1,2,3,6-tetrahydropyridine, piperidine or piperazine ring of the compounds of formulas (a), (b) and/or (c) to form a fused bicyclic ring system. The positions of the piperidine, 1,2,3,6-tetrahydropyridine or piperazine ring are denoted as follows:

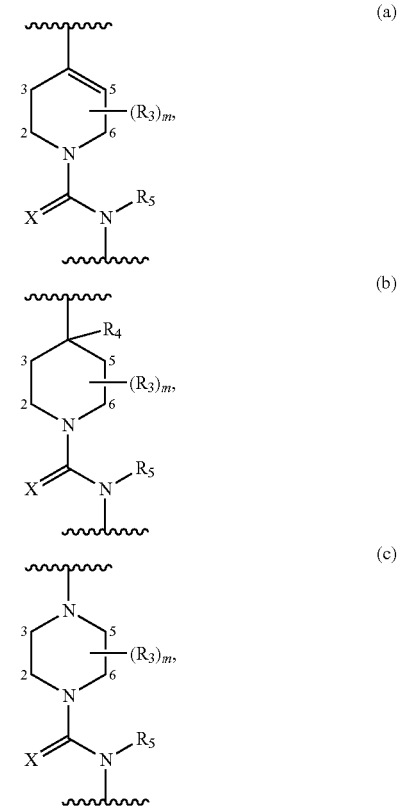

For example, compounds of the invention can comprise a (C$_2$-C$_6$) bridge joining positions 2 and 6 of the piperidine, 1,2,3,6-tetrahydropyridine or piperazine ring (two R$_3$ groups can together form a (C$_2$-C$_6$) bridge). Examples of compounds where two R$_3$ groups can together form a (C$_2$-C$_6$) bridge include compounds comprising the following ring systems: 8-aza-bicyclo[3.2.1]octane; 8-azabicyclo[3.2.1]oct-3-ene; 3,8-diazabicyclo[3.2.1]octane; 8-azabicyclo[3.2.1]oct-6-ene; 8-azabicyclo[3.2.1]octa-3,6-diene; 3,8-diazabicyclo[3.2.1]oct-6-ene; 9-aza-bicyclo[3.3.1]nonane; 9-azabicyclo[3.3.1]non-3-ene; 9-azabicyclo[3.3.1]non-6-ene; 9-azabicyclo[3.3.1]nona-3,6-diene; 9-azabicyclo[3.3.1]nona-3,7-diene; 3,9-diazabicyclo[3.3.1]nonane; 3,9-diazabicyclo[3.3.1]non-6-ene; 3,9-diazabicyclo[3.3.1]non-7-ene; 10-azabicyclo[4.3.1]decane; 10-azabicyclo[4.3.1]dec-8-ene; 8,10-diazabicyclo[4.3.1]decane; 8,10-diazabicyclo[4.3.1]dec-3-ene; 8,10-diazabicyclo[4.3.1]dec-4-ene; 8-azabicyclo[4.3.1]dec-4-ene; 8-azabicyclo[4.3.1]dec-3-ene; 8-azabicyclo[4.3.1]deca-2,6(10)-diene; 8-azabicyclo[4.3.1]deca-3,6 (10)-diene; 8-azabicyclo[4.3.1]deca-4,6(10)-diene; 11-azabicyclo[5.3.1]undecane; 11-azabicyclo[5.3.1]undec-8-ene; 9,11-diazabicyclo[5.3.1]undecane; 12-aza-bicyclo[6.3.1] dodecane; 12-azabicyclo[6.3.1]dodec-9-ene; and 10,12-diazabicyclo[6.3.1]dodecane.

"(C$_1$-C$_2$)alkylenedioxy bridge" as used herein means —OCH$_2$O— bridge and —OCH$_2$CH$_2$O— bridge.

"A 3-8 member carbocyclic ring" as used herein means a $(C_3-C_8)$cycloalkane ring and a $(C_5-C_8)$cycloalkene ring, and includes cyclopropane, cyclobutane, cyclopentane, cyclohexane, cycloheptane, cyclooctane, cyclopentene, cyclopentadiene, cyclohexene, cyclohexadiene, cycloheptene, cyclooctene and the like.

Examples of compounds where $Y_a$ and $Y_b$, together with the carbon to which they are attached, form a 3-8 member carbocyclic ring include compounds comprising the following:

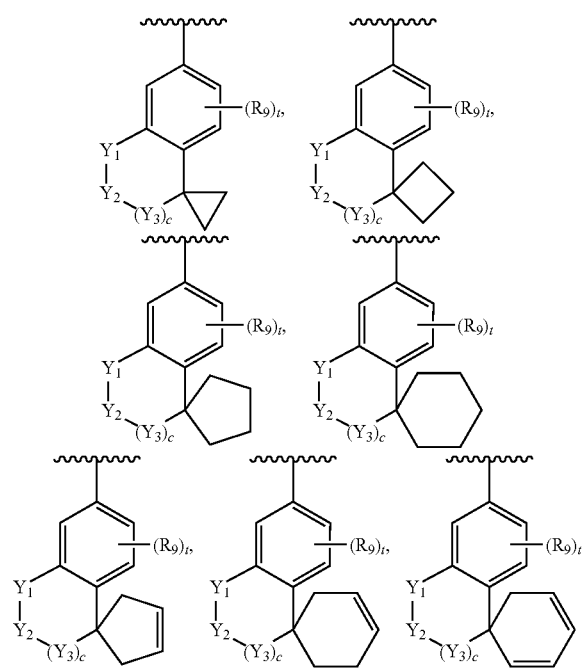

and the like.

In connection with the $Ar_2$ group

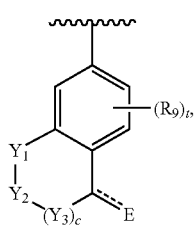

when $=\!=\!E$ is $—N(R_7)_2$ it is to be understood that the dashed line in the above $Ar_2$ group is absent, i.e., the $Ar_2$ group is

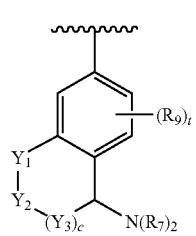

where $Y_1$, $Y_2$, $Y_3$, $R_9$, c and t are as defined above for compounds of Formula I. When $=\!=\!E$ is $=\!O$, $=\!S$, $=\!C(R_7)_2$, $=\!CH(C_2-C_6)$alkenyl, or $=\!N—OR_5$, it is to be understood that the dashed line in the above $Ar_2$ group is present, i.e., the $Ar_2$ group is

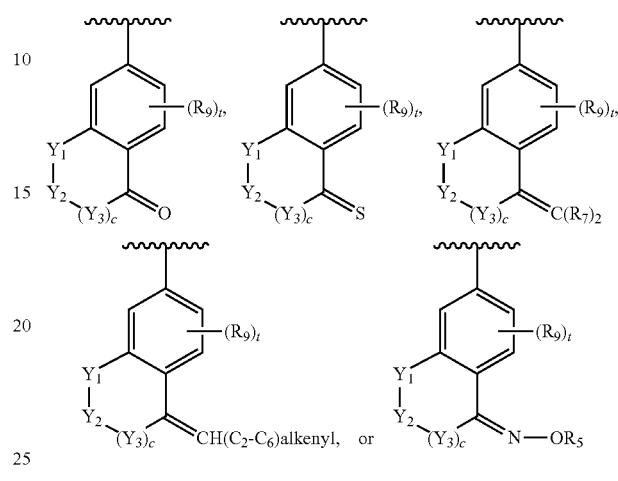

respectively, where $Y_1$, $Y_2$, $Y_3$, $R_9$, c and t are as defined above for compounds of Formula I.

The phrase "$Ar_1$ is

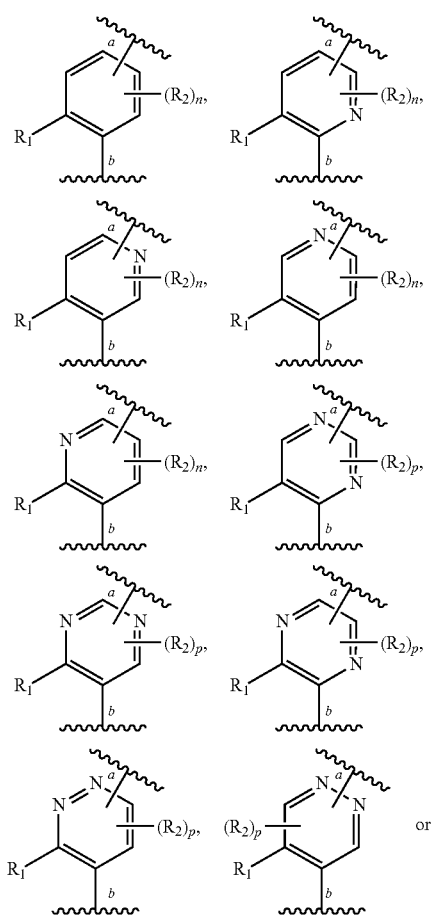

or

-continued

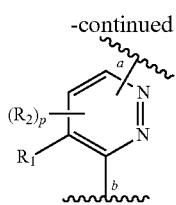

means the "bond a" bonds to $L_1$ and the "bond b" bonds to Y.

The phrase "$Ar_1$ is a phenyl group" means

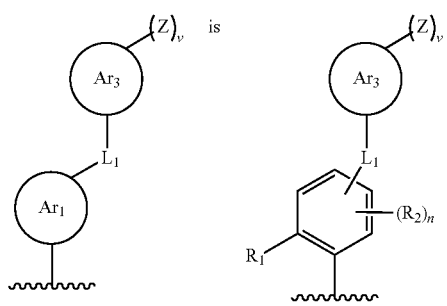

where $Ar_3$, $L_1$, Z, $R_1$, $R_2$, n and v are as defined above for compounds of Formula I.

The phrase "$Ar_1$ is a pyridyl group" means

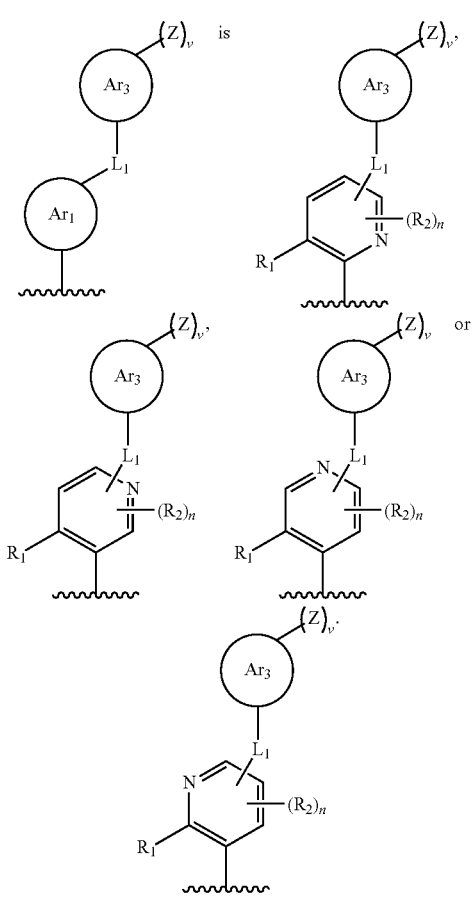

where $Ar_3$, $L_1$, Z, $R_1$, $R_2$, n and v are as defined above for compounds of Formula I.

The phrase "$Ar_1$ is a pyrazinyl group" means

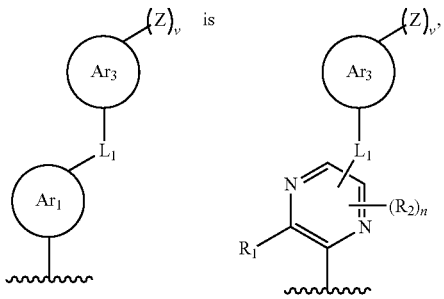

where $Ar_3$, $L_1$, Z, $R_1$, $R_2$, n and v are as defined above for compounds of Formula I.

The phrase "$Ar_1$ is a pyrimidinyl group" means

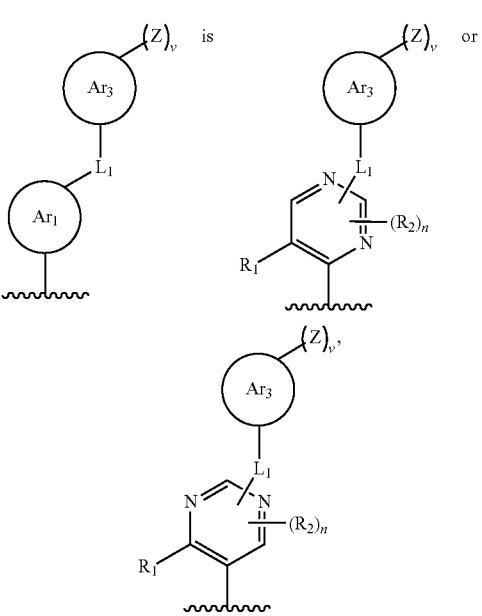

where $Ar_3$, $L_1$, Z, $R_1$, $R_2$, n and v are as defined above for compounds of Formula I.

The phrase "$Ar_1$ is a pyridazinyl group" means

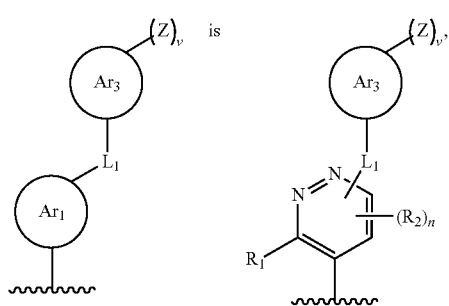

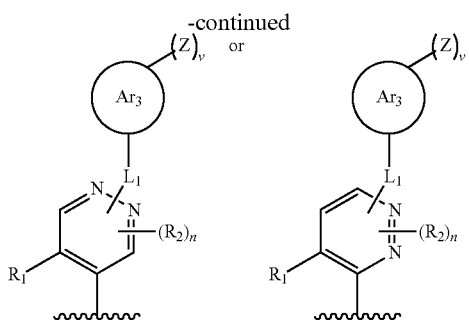

where $Ar_3$, $L_1$, Z, $R_1$, $R_2$, n and v are as defined above for compounds of Formula I.

The phrase "no more than one of $Y_1$, $Y_2$, or $Y_3$ can be 0" means only one of $Y_1$, $Y_2$, and $Y_3$ can be O.

The phrase "no more than two of $Y_1$, $Y_2$, or $Y_3$ can be N" means that zero, one or two of $Y_1$, $Y_2$ and $Y_3$ can be N.

The term "animal," includes, but is not limited to, a cow, monkey, baboon, chimpanzee, horse, sheep, pig, chicken, turkey, quail, cat, dog, mouse, rat, rabbit, guinea pig, and human.

The phrase "pharmaceutically acceptable derivative," as used herein, includes any pharmaceutically acceptable salt, solvate, prodrug, radiolabeled form, stereoisomer, enantiomer, diastereomer, other stereoisomeric form, racemic mixture, geometric isomer, and/or tautomer, e.g., of a compound of Formula I of the invention.

In one embodiment, the pharmaceutically acceptable derivative is a pharmaceutically acceptable salt, solvate, radiolabeled form, stereoisomer, enantiomer, diastereomer, other stereoisomeric form, racemic mixture, geometric isomer, and/or tautomer, e.g., of a compound of Formula I of the invention. In another embodiment, the pharmaceutically acceptable derivative is a pharmaceutically acceptable salt, radiolabeled form, stereoisomer, enantiomer, diastereomer, other stereoisomeric form, racemic mixture, geometric isomer, and/or tautomer, e.g., of a compound of Formula I of the invention. In another embodiment, the pharmaceutically acceptable derivative is a pharmaceutically acceptable salt, radiolabeled form, stereoisomer, enantiomer, diastereomer, racemic mixture, geometric isomer, and/or tautomer, e.g., of a compound of Formula I of the invention. In another embodiment, the pharmaceutically acceptable derivative is a pharmaceutically acceptable salt, e.g., of a compound of Formula I of the invention.

The phrase "pharmaceutically acceptable salt," as used herein, is any pharmaceutically acceptable salt that can be prepared from a compound of Formula I including a salt formed from an acid and a basic functional group, such as a nitrogen group, of a compound of Formula I. Illustrative salts include, but are not limited to, sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, malate, maleate, gentisinate, fumarate, gluconate, glucoronate, saccharate, formate, benzoate, phthalate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also includes a salt prepared from a compound of Formula I having an acidic functional group, such as a carboxylic acid functional group, and a pharmaceutically acceptable inorganic or organic base. Suitable bases include, but are not limited to, hydroxides of alkali metals such as sodium, potassium, cesium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; picoline; N-methyl, N-ethylamine; diethylamine; triethylamine; mono-, bis-, or tris-(2-hydroxy-($C_1$-$C_3$)alkyl amines), such as mono-, bis-, or tris-(2-hydroxyethyl)amine, 2-hydroxy-tert-butylamine, or tris-(hydroxymethyl)methylamine, N,N-di-[($C_1$-$C_3$)alkyl]-Nydroxy-($C_1$-$C_3$)alkyl)-amines, such as N,N-dimethyl-N-(2-hydroxyethyl)amine, or tri-(2-hydroxyethyl)amine; N-methyl-D-glucamine; and amino acids such as arginine, lysine, and the like. One skilled in the art will recognize that, e.g., acid addition salts of a compound of Formula I can be prepared by reaction of the compounds with the appropriate acid via a variety of known methods.

Compounds of Formula I encompass all solvates of compounds of Formula I. "Solvates" are known in the art and are considered to be a combination, physical association and/or solvation of a compound of Formula I with a solvent molecule, e.g., a disolvate, monosolvate or hemisolvate when the ratio of the solvent molecule to the molecule of the compound of Formula I is 2:1, 1:1 or 1:2, respectively. This physical association involves varying degrees of ionic and covalent bonding, including hydrogen bonding. In certain instances, the solvate can be isolated, for example when one or more solvent molecules are incorporated into the crystal lattice of a crystalline solid. Thus, "solvate," as used herein, encompasses both solution-phase and isolatable solvates. A compound of Formula I of the invention may be present as a solvated form with a pharmaceutically acceptable solvent, such as water, methanol, ethanol, and the like, and it is intended that the invention include both solvated and unsolvated compound of Formula I forms. As "hydrate" relates to a particular subgroup of solvates, i.e., where the solvent molecule is water, hydrates are included within the solvates of the invention. Preparation of solvates is known in the art. For example, M. Caira et al., *J. Pharmaceut. Sci.*, 93(3):601-611 (2004), describes the preparation of solvates of fluconazole with ethyl acetate and with water. Similar preparations of solvates, hemisolvate, hydrates, and the like are described by E. C. van Tonder et al., *AAPS Pharm. Sci. Tech.*, 5(1), article 12 (2004), and A. L. Bingham et al., *Chem. Commun.*, pp. 603-604 (2001). A typical, non-limiting, process involves dissolving the compound of Formula I in a desired amount of the desired solvent (organic, water or mixtures thereof) at temperatures above from about 20° C. to about 25° C., cooling the solution at a rate sufficient to form crystals, and isolating the crystals by known methods, e.g., filtration. Analytical techniques, for example, infrared spectroscopy, can be used to show the presence of the solvent in a crystal of the solvate.

The invention disclosed herein is also meant to encompass all prodrugs of the compounds of the invention. "Prodrugs" are known in the art and, while not necessarily possessing any pharmaceutical activity as such, are considered to be any covalently bonded carrier(s) that releases the active parent drug in vivo. In general, such prodrugs will be a functional derivative of a compound of Formula I which is readily convertible in vivo, e.g., by being metabolized, into the required compound of Formula I. Conventional procedures for the selection and preparation of suitable prodrug derivatives are described in, for example, *Design of Prodrugs*, H. Bundgaard ed., Elsevier (1985); "Drug and Enzyme Targeting, Part A," K. Widder et al. eds., Vol. 112 in *Methods in Enzymology*, Academic Press (1985); Bundgaard, "Design and Application of Prodrugs," Chapter 5 (pp. 113-191) in *A Textbook of Drug Design and Development*, P. Krogsgaard-Larsen and H. Bundgaard eds., Harwood Academic Publishers (1991); Bundgaard et al., *Adv. Drug Delivery Revs.* 8:1-38 (1992); Bundgaard et al., *J. Pharmaceut. Sci.* 77:285 (1988); and Kakeya et al., *Chem. Pharm. Bull.* 32:692-698 (1984).

In addition, one or more hydrogen, carbon or other atoms of a compound of Formula I can be replaced by an isotope of the hydrogen, carbon or other atoms. Compounds of Formula I include all radiolabeled forms of compounds of Formula I "radiolabeled," "radiolabeled form", and the like of a compound of Formula I, each of which is encompassed by the invention, is useful as a research and/or diagnostic tool in metabolism pharmacokinetic studies and in binding assays. Examples of isotopes that can be incorporated into a compound of Formula I of the invention include isotopes of hydrogen, carbon, nitrogen, oxygen, phosphorous, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Radiolabeled compounds of the invention can be prepared by methods known in the art. For example, tritiated compounds of Formula I can be prepared by introducing tritium into the particular compound of Formula I, for example, by catalytic dehalogenation with tritium. This method may include reacting a suitably halogen-substituted precursor of a compound of Formula I with tritium gas in the presence of a suitable catalyst, for example, Pd/C, in the presence or absence of a base. Other suitable methods for preparing tritiated compounds can be found in Filer, "The Preparation and Characterization of Tritiated Neurochemicals," Chapter 6, pp. 155-192 in *Isotopes in the Physical and Biomedical Sciences, Vol. 1, Labeled Compounds (Part A)* (1987). $^{14}$C-labeled compounds can be prepared by employing starting materials having a $^{14}$C carbon.

A compound of Formula I can contain one or more asymmetric centers and may thus give rise to enantiomers, diastereomers, and other stereoisomeric forms. Compounds of Formula I encompass all such possible forms as well as their racemic and resolved forms or any mixture thereof. When a compound of Formula I contains an olefinic double bond or other center of geometric asymmetry, and unless specified otherwise, it is intended to include all "geometric isomers," e.g., both E and Z geometric isomers. All "tautomers," e.g., ketone-enol, amide-imidic acid, lactam-lactim, enamine-imine, amine-imine, and enamine-enimine tautomers, are intended to be encompassed by the invention as well.

As used herein, the terms "stereoisomer," "stereoisomeric form", and the like are general terms for all isomers of individual molecules that differ only in the orientation of their atoms in space. It includes enantiomers and isomers of compounds with more than one chiral center that are not mirror images of one another ("diastereomers").

The term "chiral center" refers to a carbon atom to which four different groups are attached.

The term "enantiomer" or "enantiomeric" refers to a molecule that is nonsuperimposeable on its mirror image and hence optically active where the enantiomer rotates the plane of polarized light in one direction and its mirror image rotates the plane of polarized light in the opposite direction.

The term "racemic" refers to a mixture of equal parts of enantiomers which is optically inactive.

The term "resolution" refers to the separation or concentration or depletion of one of the two enantiomeric forms of a molecule.

Optical isomers of a compound of Formula I can be obtained by known techniques such as chiral chromatography or formation of diastereomeric salts from an optically active acid or base.

Optical purity can be stated in terms of enantiomeric excess (% ee), which is determined by the formula:

$$\% \ ee = \left[ \frac{\text{major enantiomer(mol)} - \text{minor enantiomer(mol)}}{\text{major enantiomer(mol)} + \text{minor enantiomer(mol)}} \right] \times 100\%.$$

The phrase "effective amount," when used in connection with a compound of Formula I means an amount effective for: (a) treating or preventing a Condition; or (b) inhibiting TRPV1 function in a cell.

The phrase "effective amount," when used in connection with the another therapeutic agent means an amount for providing the therapeutic effect of the therapeutic agent.

The phrase "therapeutic index," describes the gap between the dose that is effective, and the dose that induces adverse effects.

When a first group is "substituted with 1 or 2" second groups or "substituted with 1, 2 or 3" second groups, "1 or 2" or "1, 2 or 3" hydrogen atoms of the first group is replaced with a corresponding number of second groups. When the number of second groups is two or greater, each second group can be the same or different. In one embodiment, the number of second groups is one or two. In another embodiment, the number of second groups is two. In another embodiment, the number of second groups is one.

The term "Py" means pyridine.
The term "Ph" means phenyl.
The term "Me" means methyl.
The term "Bn" means benzyl.
The term "Ms" means methanesulfonyl.
The term "i-Pr" means iso-propyl.
The term "Et" means ethyl.
The term "Boc" means tert-butyloxycarbonyl.
The term "TBS" means tert-butyldimethylsilyl.
The term "AcOH" means acetic acid.
The term "AIBN" means azobisisobutyronitrile.
The term "t-BME" means tert-butyl methyl ether, i.e., 2-methoxy-2-methylpropane.
The term "CME" means cyclopentyl methyl ether, i.e., methoxycyclopentane.
The term "CPME" means cyclopentyl methyl ether.
The term "DBU" means 1,8-Diazabicyclo[5.4.0]undec-7-ene.
The term "DEE" means diethyl ether, i.e., ethoxyethane.
The term "DIBAL-H" means diisobutylaluminium hydride.
The term "DIEA" means N,N-diisopropylethylamine or N-ethyldiisopropylamine, i.e., N-ethyl-N-isopropylpropan-2-amine.
The term "DIPEA" means N,N-diisopropylethylamine.
The term "DME" means 1,2-dimethoxyethane, i.e., ethylene glycol dimethyl ether.
The term "DMF" means N,N-dimethylformamide.
The term "DMSO" means dimethylsulfoxide, i.e., methylsulfinylmethane.
The term "EtOH" means ethanol, i.e., ethyl alcohol.
The term "EtOAc" means ethyl acetate.
The term "HATU" means O-(7-azabenzotriazole-1-yl)-N,N,N,N-tetramethyluronium hexafluorophosphate.
The term "MeOH" means methanol, i.e., methyl alcohol.
The term "NaHMDS" means sodium hexamethyldisilazide.
The term "NMP" means N-methylpyrrolidone.
The term "TBAF" means tetra-n-butylammonium fluoride.

The term "t-BuOH" means tert-butyl alcohol, i.e., 2-methylpropan-2-ol.

The term "TBTU" means 2-(1H-Benzotriazole-1-yl)-1,1,3,3-tetramethyluronium tetrafluoroborate.

The term "THF" means tetrahydrofuran.

The term "UI" means urinary incontinence.

The term "IBD" means inflammatory-bowel disease.

The term "IBS" means irritable-bowel syndrome.

The term "ALS" means amyotrophic lateral sclerosis.

The phrases "treatment of," "treating" and the like include the amelioration or cessation of a Condition or a symptom thereof.

In one embodiment, treating includes inhibiting, for example, decreasing the overall frequency of episodes of a Condition or a symptom thereof.

The phrases "prevention of," "preventing" and the like include the avoidance of the onset of a Condition or a symptom thereof.

Methods for Making Compounds of Formula I

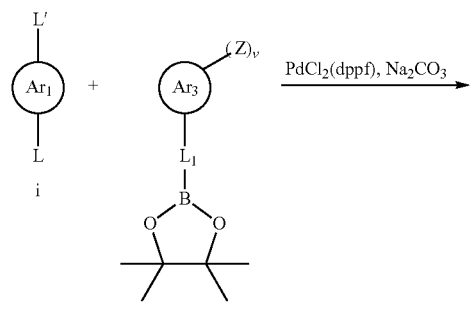

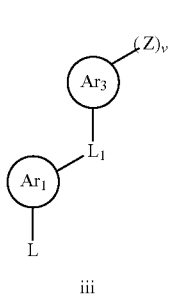

wherein L and L' are each a leaving group such as bromo, chloro or the like and L' is more reactive than L, and $Ar_1$, $Ar_3$, $L_1$, Z and v are as defined above for compounds of Formula I.

To a solution of a compound of formula i in THF, toluene, ethanol, DME, 1,4-dioxane, a mixed solvent thereof or the like are added 1 to 1.2 equivalents of a compound of formula ii, 0.01 to 0.1 equivalents of $PdCl_2(dppf)$ and 2 to 5 equivalents of a sodium carbonate (2M in $H_2O$) at room temperature under nitrogen. Then the reaction mixture is heated up at 70 to 90° C. After being stirred for 1 to 6 hrs at 70 to 90° C., the reaction mixture is quenched with $NH_4Cl$ and diluted with ethyl acetate. The resulting organic layer is separated and the aqueous layer is extracted with ethyl acetate, DEE or the like, the combined organic layers are washed with brine, dried over $Na_2SO_4$, $MgSO_4$ or the like and concentrated in vacuo. The resulting product is chromatographed on silica gel or recrystallization to provide a compound of formula iii.

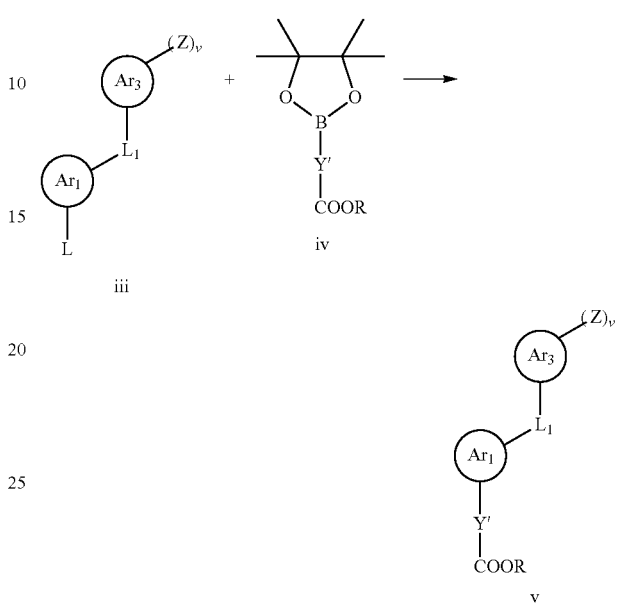

wherein L is a leaving group such as halogen,

Y' is

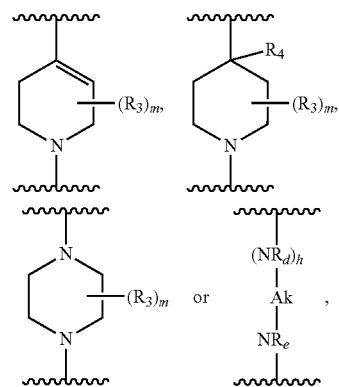

R is $(C_1-C_6)$alkyl, and $Ar_1$, $Ar_3$, $R_1$, $L_1$, Y, Z and v are as defined above for compounds of Formula I.

To a solution of a compound of formula iii in THF or dioxane and EtOH are added 1 to 3 equivalents of a compound of formula iv, 0.01 to 0.1 equivalents of $PdCl_2(PPh_3)_4$ and 2 to 5 equivalents of a potassium carbonate. Then the reaction mixture is stirred at 25° C. to 85° C. After being stirred for 3 to 24 hrs at 25° C. to 85° C., the reaction mixture is quenched with aqueous solution and extracted with ethyl acetate, DEE or the like. The resulting organic layer is washed with brine, dried over $Na_2SO_4$, $MgSO_4$ or the like and concentrated in vacuo. The resulting product is chromatographed on silica gel or recrystallization to provide a compound of formula v.

Scheme 1.3

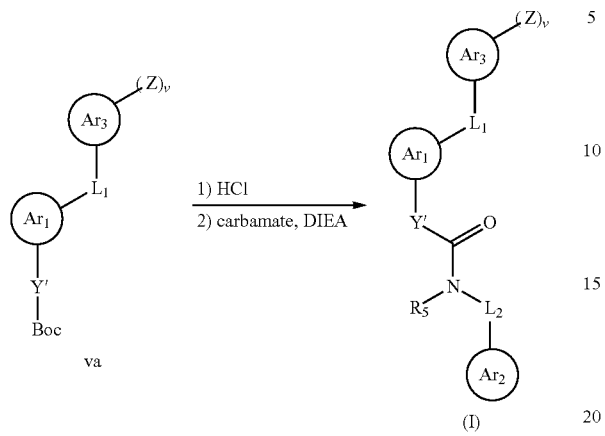

wherein y' is

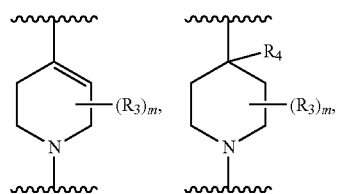

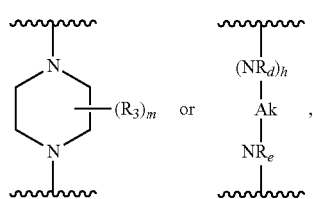

and $Ar_1$, $Ar_2$, $Ar_3$, $L_1$, $L_2$, Z and v are as defined above for compounds of Formula I.

To a solution of a compound of formula va in $CH_2Cl_2$ is added excess amount of 4N HCl in dioxane at room temperature. After being stirred for 1 to 2 hrs, the reaction mixture is concentrated in vacuo. The residue is used for the next reaction without further purification.

To a suspension of crude product in $CH_2Cl_2$ is added 1 to 5 equivalents of DIVA and 1 to 3 equivalents of carbamate at room temperature under nitrogen. After being stirred overnight at room temperature, the reaction mixture is quenched with $H_2O$ and diluted with ethyl acetate. The resulting organic layer is separated and the aqueous layer is extracted with ethyl acetate, DEE or the like, the combined organic layers are washed with brine, dried over $Na_2SO_4$, $MgSO_4$ or the like and concentrated in vacuo. The resulting product is chromatographed on silica gel or recrystallization to provide a compound of Formula I.

Scheme 2

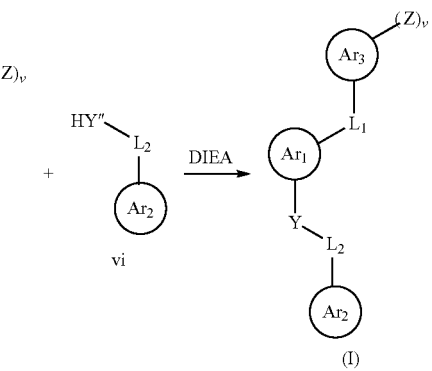

wherein L is a leaving group such as halogen,

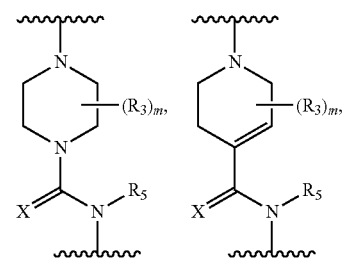

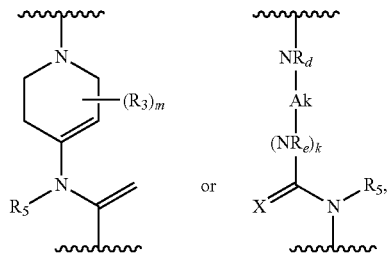

and $Ar_1$, $Ar_2$, $Ar_3$, Y, $L_1$, $L_2$, Z and v are as defined above for compounds of Formula I. To a solution of a compound of formula iii in NMP are added 1.5 to 5 equivalents of a compound of formula vi and 2 to 5 equivalents of DIEA at room temperature under nitrogen. Then the reaction mixture is heated to 100° C. to 120° C. by microwave. After being stirred for 1 to 5 hrs at 100° C. to 120° C., the reaction mixture is quenched with $H_2O$ and extracted with ethyl acetate, DEE or the like. The resulting organic layer is washed with $H_2O$ and brine, dried over $Na_2SO_4$, $MgSO_4$ or the like and concentrated in vacuo. The resulting product is chromatographed on silica gel or recrystallization to provide a compound of Formula I.

Scheme 3

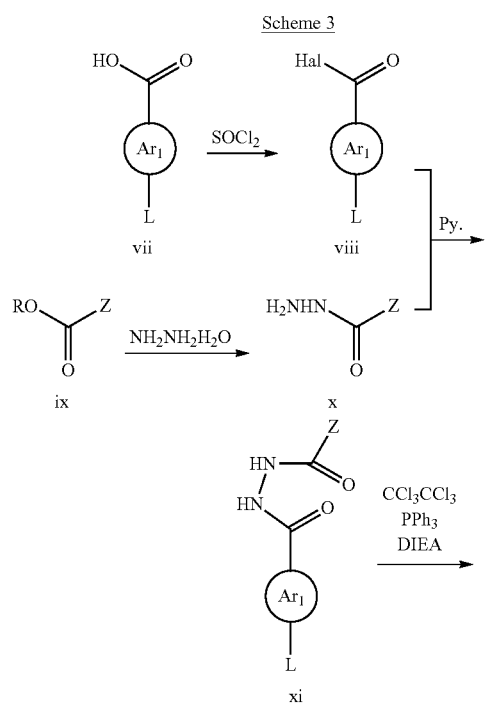

Scheme 4

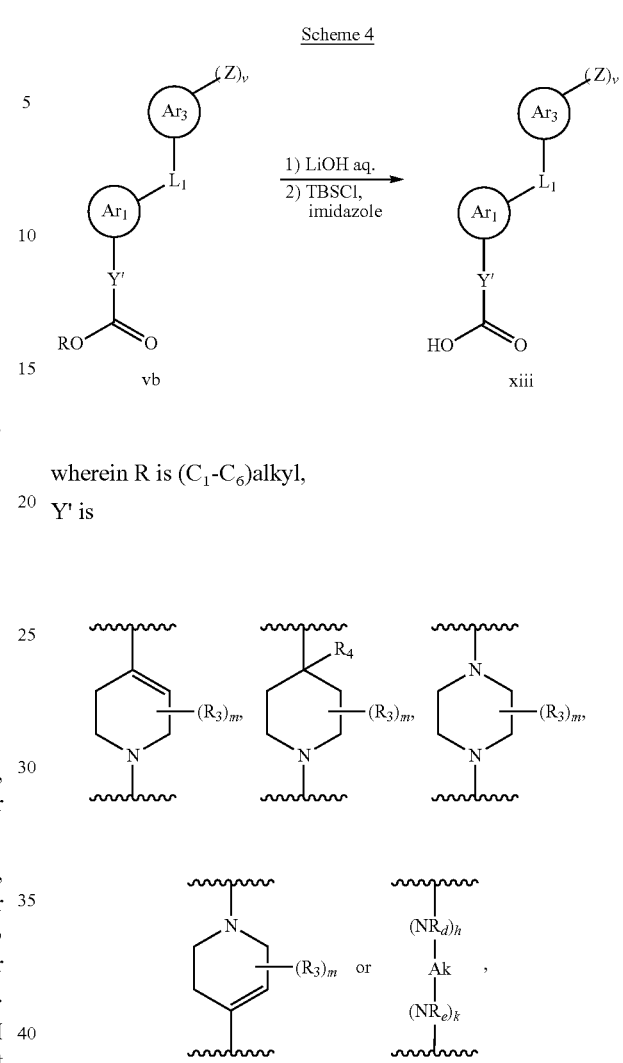

wherein R is $(C_1-C_6)$alkyl,

Y' is and $Ar_1$, $Ar_3$, Y, $L_1$, Z and v are as defined above for compounds of Formula I.

wherein L is a leaving group such as halogen, Hal is halogen, R is $(C_1-C_6)$alkyl, and $Ar^1$, $R_1$ and Z are as defined above for compounds of Formula I.

To a solution of a compound of formula vii in toluene, ethanol, DME, 1,4-dioxane, THF, a mixed solvent thereof or the like are added 1 to 3 equivalents of $SOCl_2$, 0.01 to 0.03 equivalents of DMF at 25° C. to reflux temperature, for 1 hour to 8 hrs. Then the reaction mixture is concentrated in vacuo.

To a solution of a compound of formula ix in EtOH, MeOH or the like are added 5 to 15 equivalents of $NH_2NH_2H_2O$ at 25° C. to 90° C., for 1 hour to 8 hrs. Then the reaction mixture is quenched with $H_2O$ and extracted with ethyl acetate, DEE or the like. The resulting organic layer is washed with brine, dried over $Na_2SO_4$, $MgSO_4$ or the like and concentrated in vacuo.

To a solution of a compound of formula viii in toluene, $CH_2Cl_2$ or the like are added 3 to 8 equivalents of pyridine, $NEt_3$ or the like and then dropwise added 1 to 1.2 equivalents of a compound of formula x in THF, DEE, t-BME, CME or the like via a droping funnel 0° C. under nitrogen. After being stirred for 1 to 3 hrs, the reaction mixture is quenched with sat. $NaHCO_3$ and extracted with ethyl acetate, DEE or the like. The resulting organic layer is washed with brine, dried over $Na_2SO_4$, $MgSO_4$ or the like and concentrated in vacuo.

To a crude product in $CH_3CN$ are added 3 to 8 equivalents of DIEA, 1 to 2 equivalents of $PPh_3$ and 1 to 1.5 equivalents of perchloroethane 0° C. under nitrogen. After being stirred for 3 to 6 hrs, the reaction mixture is quenched with $H_2O$ and extracted with ethyl acetate, DEE or the like. The resulting organic layer is washed with brine, dried over $Na_2SO_4$, $MgSO_4$ or the like and concentrated in vacuo. The resulting product is chromatographed on silica gel to provide a compound of formula xii.

To a solution of a compound of formula vb in THF and EtOH or DMSO are added 1.5 to 2 equivalents of LiOH aq. at room temperature under nitrogen. After being stirred overnight at room temperature, the reaction mixture is quenched with 1M HCl aq. and extracted with ethyl acetate, DEE or the like. The resulting organic layer is washed with brine, dried over $Na_2SO_4$, $MgSO_4$ or the like and concentrated in vacuo. The residue is used for the next reaction without further purification.

To a solution of resulting crude compound in THF are added 3 equivalents of imidazole and 2 to 3 equivalents of TBSCl at room temperature under nitrogen. After being stirred for 0.5 to 3 hrs at room temperature, the reaction mixture is quenched with sat. $NaHCO_3$ aq. and extracted with ethyl acetate, DEE or the like. The resulting organic layer is washed with brine, dried over $Na_2SO_4$, $MgSO_4$ or the like and concentrated in vacuo. The resulting product xiii can be used for the next reaction, e.g. the reaction in Scheme 6, without further purification.

Scheme 5.1

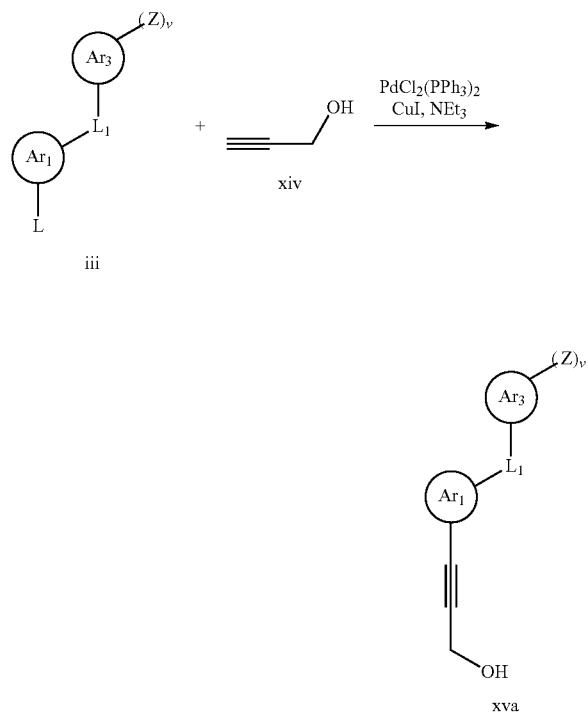

wherein L is a leaving group such as halogen, Ar$_1$, Ar$_3$, Y, L$_1$, L$_2$, Z and v are as defined above for compounds of Formula I.

To a solution of a compound of formula iii in DMF are added 1 to 2 equivalents of a compound of formula xiv 0.01 to 0.08 equivalents of PdCl$_2$(PPh$_3$)$_2$, 0.05 to 0.3 equivalents of CuI and 1 to 3 equivalents of NEt$_3$ at room temperature under nitrogen. Then the reaction mixture is heated to 85° C. After being stirred for 2 hrs at 85° C., the reaction mixture is quenched with H$_2$O and extracted with ethyl acetate, DEE or the like. The resulting organic layer is washed with H$_2$O and brine, dried over Na$_2$SO$_4$, MgSO$_4$ or the like and concentrated in vacuo. The resulting product is chromatographed on silica gel to provide a compound of formula xva.

Scheme 5.2

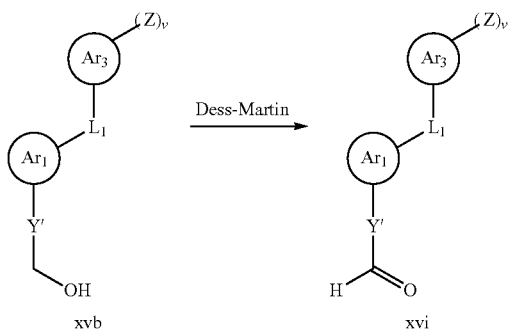

wherein
Y is

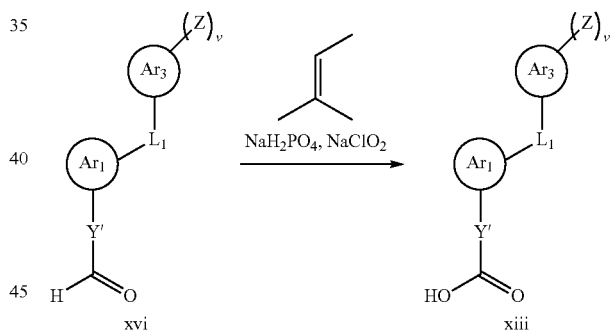

and Ar$_1$, Ar$_3$, L$_1$, Z and v are as defined above for compounds of Formula I.

To a solution of a compound of formula xvb in CH$_2$Cl$_2$ are added 1 to 2 equivalents of Dess-Martin at 0° C. under nitrogen. After being stirred for 15 min to 1 hr at 0° C. to 15° C., the reaction mixture is quenched with sat. NaHCO$_3$ and diluted with ethyl acetate. The resulting organic layer is separated and the aqueous layer is extracted with ethyl acetate, DEE or the like, the combined organic layers are washed with Na$_2$S$_2$O$_3$, H$_2$O and brine, dried over Na$_2$SO$_4$, MgSO$_4$ or the like and concentrated in vacuo. The resulting product is chromatographed on silica gel to provide a compound of formula xvi.

Scheme 5.3 wherein
Y' is and $Ar_1$, $Ar_3$, $L_1$, Z and v are as defined above for compounds of Formula I.

To a solution of a compound of formula xvi in t-BuOH and $H_2O$ are added extra 2-methylbut-2-ene, 1 to 2 equivalents of $NaH_2PO_4.2H_2O$ and 1 to 5 equivalents of $NaClO_4$ at 0° C. After being stirred overnight at room temperature, the reaction mixture is quenched with 1M HCl aq. and diluted with ethyl acetate. The resulting organic layer is separated and the aqueous layer is extracted with ethyl acetate, DEE or the like, the combined organic layers are washed with $Na_2S_2O_3$ and brine, dried over $Na_2SO_4$, $MgSO_4$ or the like and concentrated in vacuo. The resulting product xiii can be used for the next reaction without further purification.

Scheme 6

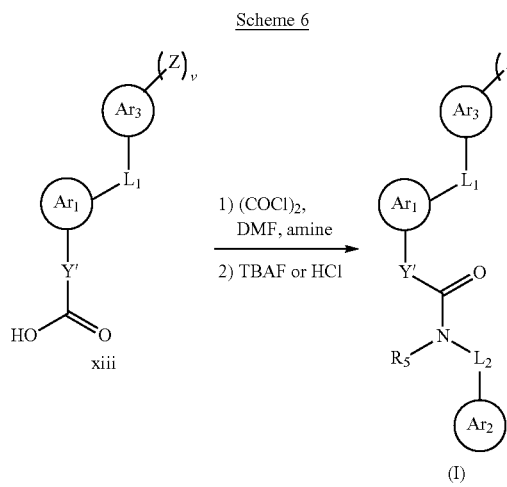

wherein Y' is

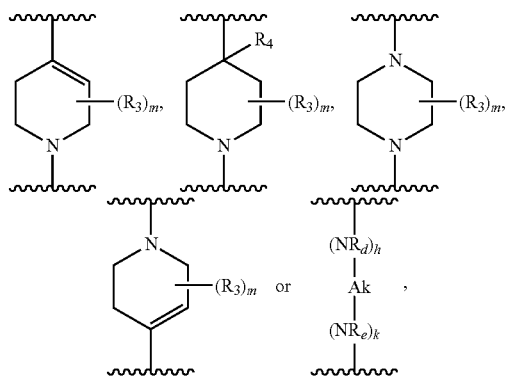

and $Ar_1$, $Ar_2$, $Ar_3$, $L_1$, $L_2$, Z, $R_5$ and v are as defined above for compounds of Formula I.

To a solution of a compound of formula xiii in $CH_2Cl_2$ is added 1 to 3 equivalents of $(COCl)_2$ and catalitic of DMF at 0° C. under nitrogen. After being stirred for 1 to 2 hrs, 1 to 5 equivalents of DIEA and an amine corresponding to the target compound is added to the reaction mixture at 0° C. and stirred at 0° C. to room temperature for 30 min to 2 hrs. The reaction mixture is quenched with $H_2O$ and diluted with ethyl acetate. The resulting organic layer is separated and the aqueous layer is extracted with ethyl acetate, DEE or the like, the combined organic layers are washed with brine, dried over $Na_2SO_4$, $MgSO_4$ or the like and concentrated in vacuo. The residue is used for the next reaction without further purification.

To a crude product in THF is added 1.5 to 2 equivalents of TBAF or extra molar of HCl-dioxane at 0° C. under nitrogen. After being stirred for 30 min to 1 hr, the reaction mixture is quenched with sat. $NaHCO_3$ and diluted with ethyl acetate. The resulting organic layer is separated and the aqueous layer is extracted with ethyl acetate, DEE or the like, the combined organic layers are washed with brine, dried over $Na_2Sa_4$, $MgSO_4$ or the like and concentrated in vacuo. The resulting product is chromatographed on silica gel or recrystallization to provide a compound of Formula I.

Scheme 7

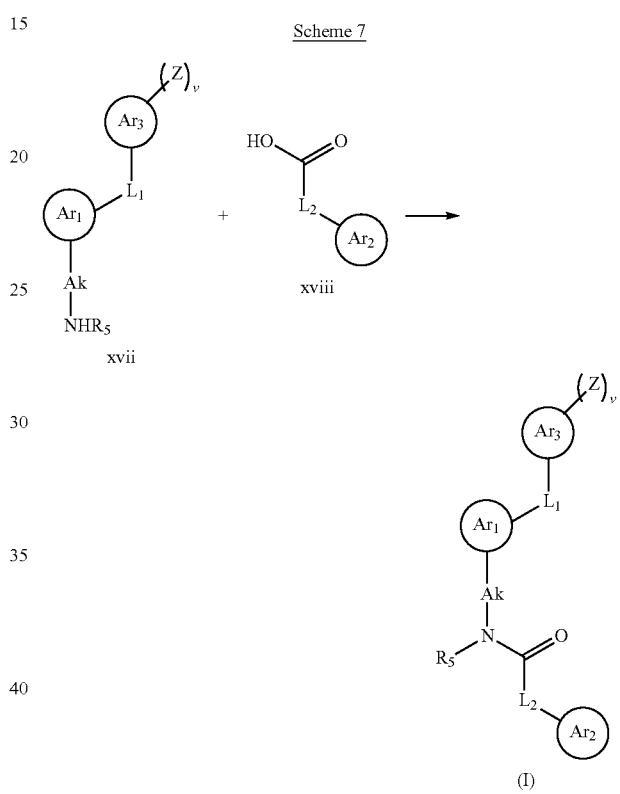

wherein $Ar_1$, $Ar_2$, $Ar_3$, $L_1$, $L_2$, Z, Ak, $R_5$ and v are as defined above for compounds of Formula I.

To a solution of a compound of formula xvii and 1 to 2 equivalent of a compound of formula xviii in DMF or tetrahydrofuran is added 1 to 2 equivalents of HATU, WSCD, HOBt, PyBoP or the like condensation agent and 1 to 3 equivalent of DIEA or $NEt_3$ at room temperature under nitrogen. After being stirred overnight, the reaction mixture is quenched with $H_2O$ and diluted with ethyl acetate. The resulting organic layer is separated and the aqueous layer is extracted with ethyl acetate, DEE or the like, the combined organic layers are washed with brine, dried over $Na_2SO_4$, $MgSO_4$ or the like and concentrated in vacuo. The resulting product is chromatographed on silica gel or recrystallization to provide a compound of Formula I.

Therapeutic Uses of Compounds of Formula I

In accordance with the invention, the compounds of Formula I are administered to an animal in need of treatment or prevention of a Condition.

In one embodiment, an effective amount of a compound of Formula I can be used to treat or prevent any condition treatable or preventable by inhibiting TRPV1. Examples of Conditions that are treatable or preventable by inhibiting TRPV1 include, but are not limited to, pain, UI, an ulcer, IBD, and IBS.

The compounds of Formula I, or a pharmaceutically acceptable derivative thereof, can be used to treat or prevent acute or chronic pain. Examples of pain treatable or preventable using the compounds of Formula I include, but are not limited to, cancer pain, labor pain, myocardial infarction pain, pancreatic pain, colic pain, post-operative pain, headache pain, muscle pain, arthritic pain, and pain associated with a periodontal disease, including gingivitis and periodontitis.

The compounds of Formula I, or a pharmaceutically acceptable derivative thereof, can also be used for treating or preventing pain associated with inflammation or with an inflammatory disease in an animal. Such pain can arise where there is an inflammation of the body tissue which can be a local inflammatory response and/or a systemic inflammation. For example, the compounds of Formula I can be used to treat or prevent pain associated with inflammatory diseases including, but not limited to: organ transplant rejection; reoxygenation injury resulting from organ transplantation (see Grupp et al., *J. Mol. Cell. Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory diseases of the gum, including gingivitis and periodontitis; tuberculosis; leprosy; inflammatory diseases of the kidney, including uremic complications, glomerulonephritis and nephrosis; inflammatory diseases of the skin, including sclerodermatitis, psoriasis and eczema; inflammatory diseases of the central nervous system, including chronic demyelinating diseases of the nervous system, multiple sclerosis, AIDS-related neurodegeneration and Alzheimer s disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microaluminuria and progressive diabetic nephropathy), polyneuropathy, mononeuropathies, autonomic neuropathy, gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum); immune-complex vasculitis, and systemic lupus erythematosus (SLE); inflammatory diseases of the heart, such as cardiomyopathy, ischemic heart disease hypercholesterolemia, and atherosclerosis; as well as various other diseases that can have significant inflammatory components, including preeclampsia, chronic liver failure, brain and spinal cord trauma, and cancer. The compounds of Formula I can also be used for inhibiting, treating, or preventing pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is adminstered as a treatment for cancer.

The compounds of Formula I, or a pharmaceutically acceptable derivative thereof, can be used to treat or prevent UI. Examples of UI treatable or preventable using the compounds of Formula I include, but are not limited to, urge incontinence, stress incontinence, overflow incontinence, neurogenic incontinence, and total incontinence.

The compounds of Formula I, or a pharmaceutically acceptable derivative thereof, can be used to treat or prevent an ulcer. Examples of ulcers treatable or preventable using the compounds of Formula I include, but are not limited to, a duodenal ulcer, a gastric ulcer, a marginal ulcer, an esophageal ulcer, or a stress ulcer.

The compounds of Formula I, or a pharmaceutically acceptable derivative thereof, can be used to treat or prevent IBD, including Crohn's disease and ulcerative colitis.

The compounds of Formula I, or a pharmaceutically acceptable derivative thereof, can be used to treat or prevent IBS. Examples of IBS treatable or preventable using the compounds of Formula I include, but are not limited to, spastic-colon-type IBS and constipation-predominant IBS.

Applicants believe that the compounds of Formula I, or a pharmaceutically acceptable derivative thereof, are antagonists for TRPV1. The invention also relates to methods for inhibiting TRPV1 function in a cell comprising contacting a cell capable of expressing TRPV1 with an effective amount of a compound of Formula I, or a pharmaceutically acceptable derivative thereof. This method can be used in vitro, for example, as an assay to select cells that express TRPV1 and, accordingly, are useful as part of an assay to select compounds useful for treating or preventing pain, UI, an ulcer, IBD, or IBS. The method is also useful for inhibiting TRPV1 function in a cell in vivo, in an animal, a human in one embodiment, by contacting a cell, in an animal, with an effective amount of a compound of Formula I, or a pharmaceutically acceptable derivative thereof. In one embodiment, the method is useful for treating or preventing pain in an animal. In another embodiment, the method is useful for treating or preventing UI in an animal. In another embodiment, the method is useful for treating or preventing an ulcer in an animal. In another embodiment, the method is useful for treating or preventing IBD in an animal. In another embodiment, the method is useful for treating or preventing IBS in an animal.

Examples of tissue comprising cells capable of expressing TRPV1 include, but are not limited to, neuronal, brain, kidney, urothelium, and bladder tissue. Methods for assaying cells that express TRPV1 are known in the art.

Therapeutic/Prophylactic Administration and Compositions of the Invention

Due to their activity, compounds of Formula I, or a pharmaceutically acceptable derivative thereof, are advantageously useful in veterinary and human medicine. As described above, compounds of Formula I, or a pharmaceutically acceptable derivative thereof, are useful for treating or preventing a Condition.

When administered to an animal, compounds of Formula I, or a pharmaceutically acceptable derivative thereof, are typically administered as a component of a composition that comprises a pharmaceutically acceptable carrier or excipient. The invention compositions, which comprise a compound of Formula I, or a pharmaceutically acceptable derivative thereof, can be administered orally. Compounds of Formula I, or a pharmaceutically acceptable derivative thereof, can also be administered by any other convenient route, for example, by infusion or bolus injection, by absorption through epithelial or mucocutaneous linings (e.g., oral, rectal, and intestinal mucosa, etc.) and can be administered together with another therapeutically active agent. Administration can be systemic or local. Various delivery systems are known, e.g., encapsulation in liposomes, microparticles, microcapsules, capsules, etc., and can be used to administer the compound of Formula I, or a pharmaceutically acceptable derivative thereof.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner. In most instances, administration will result in the release of compounds of Formula I, or a pharmaceutically acceptable derivative thereof, into the bloodstream.

In specific embodiments, it can be desirable to administer the compounds of Formula I, or a pharmaceutically acceptable derivative thereof, locally. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the compounds of Formula I, or a pharmaceutically acceptable derivative thereof, into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of Formula I can be formulated as a suppository, with traditional binders and excipients such as triglycerides.

In another embodiment, the compounds of Formula I, or a pharmaceutically acceptable derivative thereof, can be delivered in a vesicle, in particular a liposome (see Langer, *Science* 249:1527-1533 (1990) and Treat et al., "Liposome Encapsulated Doxorubicin Preliminary Results of Phase I and Phase II Trials," pp. 317-327 and 353-365 in *Liposomes in the Therapy of Infectious Disease and Cancer* (1989)).

In yet another embodiment, the compounds of Formula I, or a pharmaceutically acceptable derivative thereof, can be delivered in a controlled-release system or sustained-release system (see, e.g., Goodson, "Dental Applications," pp. 115-138 in *Medical Applications of Controlled Release, Vol. 2, Applications and Evaluation*, Langer and Wise, Eds., CRC Press (1984)). Other controlled- or sustained-release systems discussed in the review by Langer, *Science* 249:1527-1533 (1990) can be used. In one embodiment, a pump can be used (Langer, *Science* 249:1527-1533 (1990); Sefton, "Implantable Pumps," in *CRC Crit. Rev. Biomed. Eng.* 14:201-240 (1987); Buchwald et al., Surgery 88:507-516 (1980); and Saudek et al., *N. Engl. J. Med.* 321:574-579 (1989)). In another embodiment, polymeric materials can be used (see Langer et al., "Classes of Systems," *Medical Applications of Controlled Release* Vol. I, CRC Press, Boca Raton, Fla. (1984); Smolen et al., "Drug Product Design and Performance," *Controlled Drug Bioavailability* Vol. 1, John Wiley & Sons, New York (1984); Langer and Peppas, *J. Macromol. Sci. Rev. Macromol. Chem.* C23(1):61-126 (1983); Levy et al., Science 228:190-192 (1985); During et al., *Ann. Neurol.* 25:351-356 (1989); and Howard et al., *J. Neurosurg.* 71:105 (1989)). In yet another embodiment, a controlled- or sustained-release system can be placed in proximity of a target of the compounds of Formula I, e.g., the spinal column, brain, or gastrointestinal tract, thus requiring only a fraction of the systemic dose.

The invention compositions can optionally comprise a suitable amount of a pharmaceutically acceptable excipient so as to provide the form for proper administration to the animal.

Such pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to an animal. Water is a particularly useful excipient when the compound of Formula I is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The invention compositions, if desired, can also contain minor amounts of wetting or emulsifying agents, or can contain pH buffering agents.

The invention compositions can take the form of solutions, suspensions, emulsion, tablets, pills, pellets, multiparticulates, capsules, capsules containing liquids, powders, multiparticulates, sustained-release formulations, suppositories, emulsions, aerosols, sprays, suspensions, or any other form suitable for use. In one embodiment, the composition is in the form of a capsule (see e.g., U.S. Pat. No. 5,698,155). Other examples of suitable pharmaceutical excipients are described in Radebough et al., "Preformulation," pp. 1447-1676 in *Remington's Pharmaceutical Sciences* (Alfonso R. Gennaro ed., 19th ed. 1995), incorporated herein by reference.

In one embodiment, the compounds of Formula I, or a pharmaceutically acceptable derivative thereof, are formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs, for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

The compounds of Formula I, or a pharmaceutically acceptable derivative thereof, can be administered by controlled-release or sustained-release means or by delivery devices that are known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, ethylcellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained release counterparts. In one embodiment, a controlled- or sustained-release composition comprises a minimal amount of a compound of Formula I to cure or control the condition in a minimum amount of time. Advantages of controlled- or sustained-release compositions include extended activity of the drug, reduced dosage frequency, and increased patient compliance. In addition, controlled- or sustained-release compositions can favorably affect the time of onset of action or other characteristics, such as blood levels of the compound of Formula I, and can thus reduce the occurrence of adverse side effects.

Controlled- or sustained-release compositions can be designed to immediately release an amount of a compound of Formula I, or a pharmaceutically acceptable derivative thereof, that promptly produces the desired therapeutic or prophylactic effect, and gradually and continually release other amounts of the compound of Formula I to maintain this level of therapeutic or prophylactic effect over an extended period of time. To maintain a constant level of the compound of Formula I in the body, the compound of Formula I can be released from the dosage form at a rate that will replace the amount of compound of Formula I being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

In another embodiment, the compounds of Formula I, or a pharmaceutically acceptable derivative thereof, can be formulated for intravenous administration. Typically, compositions for intravenous administration comprise sterile isotonic aqueous buffer. Where necessary, the compositions can also include a solubilizing agent. Compositions for intravenous administration can optionally include a local anaesthetic such as lignocaine to lessen pain at the site of the injection. Generally, the ingredients are supplied either separately or a mixed together in unit dosage form, for example, as a dry lyophilized powder or water free concentrate in a hermetically sealed container such as an ampoule or sachette indicating the quantity of active agent. Where the compounds of Formula I are to be administered by infusion, they can be dispensed, for example, with an infusion bottle containing sterile pharmaceutical grade water or saline. Where the compounds of Formula I, or a pharmaceutically acceptable derivative thereof, are administered by injection, an ampoule of sterile water for injection or saline can be provided so that the ingredients can be mixed prior to administration.

The amount of the compound of Formula I, or a pharmaceutically acceptable derivative thereof, that is effective in the treatment or prevention of a Condition can be determined by standard clinical techniques. In addition, in vitro or in vivo assays can optionally be employed to help identify optimal dosage ranges. The precise dose to be employed will also depend on the route of administration, and the seriousness of the Condition and can be decided according to the judgment of a practitioner and/or each animal's circumstances. Suitable effective dosage amounts, however, will typically range from about 0.01 mg/kg of body weight to about 2500 mg/kg of body weight, although they are typically about 100 mg/kg of body weight or less. In one embodiment, the effective dosage amount ranges from about 0.01 mg/kg of body weight to about 100 mg/kg of body weight of a compound of Formula I; in another embodiment, about 0.02 mg/kg of body weight to about 50 mg/kg of body weight; and in another embodiment, about 0.025 mg/kg of body weight to about 20 mg/kg of body weight.

In one embodiment, an effective dosage amount is administered about every 24 h until the Condition is abated. In another embodiment, an effective dosage amount is administered about every 12 h until the Condition is abated. In another embodiment, an effective dosage amount is administered about every 8 h until the Condition is abated. In another embodiment, an effective dosage amount is administered about every 6 h until the Condition is abated. In another embodiment, an effective dosage amount is administered about every 4 h until the Condition is abated.

The effective dosage amounts described herein refer to total amounts administered; that is, if more than one compound of Formula I, or a pharmaceutically acceptable derivative thereof, is administered, the effective dosage amounts correspond to the total amount administered.

Where a cell capable of expressing TRPV1 is contacted with a compound of Formula I in vitro, the amount effective for inhibiting the TRPV1 receptor function in a cell will typically range from about 0.01 µg/L to about 5 mg/L; in one embodiment, from about 0.01 µg/L to about 2.5 mg/L; in another embodiment, from about 0.01 µg/L to about 0.5 mg/L; and in another embodiment, from about 0.01 µg/L to about 0.25 mg/L, of a solution or suspension of a pharmaceutically acceptable carrier or excipient. In one embodiment, the volume of solution or suspension comprising the compound of Formula I, or a pharmaceutically acceptable derivative thereof, is from about 0.01 µL to about 1 mL. In another embodiment, the volume of solution or suspension is about 200 µL.

The compounds of Formula I, or a pharmaceutically acceptable derivative thereof, can be assayed in vitro or in vivo for the desired therapeutic or prophylactic activity prior to use in humans. Animal model systems can be used to demonstrate safety and efficacy.

The invention methods for treating or preventing a Condition in an animal in need thereof can further comprise administering to the animal being administered a compound of Formula I, or a pharmaceutically acceptable derivative thereof, another therapeutic agent. In one embodiment, the other therapeutic agent is administered in an effective amount.

The invention methods for inhibiting TRPV1 function in a cell capable of expressing TRPV1 can further comprise contacting the cell with an effective amount of another therapeutic agent.

Effective amounts of the other therapeutic agents are known in the art. However, it is within the skilled artisan's purview to determine the other therapeutic agent's optimal effective-amount range. In one embodiment of the invention, where another therapeutic agent is administered to an animal, the effective amount of the compound of Formula I is less than its effective amount would be where the other therapeutic agent is not administered. In this case, without being bound by theory, it is believed that the compounds of Formula I and the other therapeutic agent act synergistically to treat or prevent a Condition.

The other therapeutic agent can be, but is not limited to, an opioid agonist, a non-opioid analgesic, a non-steroid anti-inflammatory agent, an antimigraine agent, a Cox-II inhibitor, an antiemetic, a β-adrenergic blocker, an anticonvulsant, an antidepressant, a $Ca^{2+}$-channel blocker, an anticancer agent, an agent for treating or preventing UI, an agent for treating or preventing an ulcer, an agent for treating or preventing IBD, an agent for treating or preventing IBS, an agent for treating addictive disorder, an agent for treating Parkinson's disease and parkinsonism, an agent for treating anxiety, an agent for treating epilepsy, an agent for treating a stroke, an agent for treating a seizure, an agent for treating a pruritic condition, an agent for treating psychosis, an agent for treating Huntington's chorea, an agent for treating ALS, an agent for treating a cognitive disorder, an agent for treating a migraine, an agent for treating vomiting, an agent for treating dyskinesia, or an agent for treating depression, and mixtures thereof. In one embodiment, the other therapeutic agent is an opioid agonist, e.g., an opioid analgesic. In another embodiment, the other therapeutic agent is a non-opioid analgesic. In another embodiment, the other therapeutic agent is an antiemetic agent. In another embodiment, the other therapeutic agent is an anticonvulsant. In another embodiment, the other therapeutic agent is an antidepressant. In another embodiment, the other therapeutic agent is duloxetine, hydrocodone, hydromorphone, morphine, oxycodone, pregabaline, pharmaceutically acceptable derivatives thereof, and mixtures thereof. In another embodiment, the other therapeutic agent is a 4-Tetrazolyl-4-phenylpiperidine Compound or pharmaceutically acceptable derivatives thereof, such as is disclosed in U.S. Pat. No. 7,202,259 at column 2, line 5 to column 6, line 2 and exemplified therein, which patent is hereby incorporated by reference in its entirety. In another embodiment, the 4-Tetrazolyl-4-phenylpiperidine Compound other therapeutic agent is administered intrathecally, e.g., as described at column 74, lines 14-17 of U.S. Pat. No. 7,202,259.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable derivatives thereof, and mixtures thereof. In other embodiments, the opioid agonist is selected from hydrocodone, hydromorphone, morphine, oxycodone, pharmaceutically acceptable derivatives thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable derivatives thereof, and mixtures thereof. Other suitable non-opioid analgesics include the following, non-limiting, chemical classes of analgesic, antipyretic, nonsteroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see *Paul A. Insel, Analgesic-Antipyretic and Anti-inflammatory Agents and Drugs Employed in the Treatment of Gout, in Goodman & Gilman's The Pharmacological Basis of Therapeutics* pp. 617-657 (Goodman et al. eds., 9$^{th}$ ed., McGraw-Hill, New York, 1996) and Glen R. Hanson, *Analgesic, Antipyretic and Anti-Inflammatory Drugs in Remington: The Science and Practice of Pharmacy Vol II* pp. 1196-1221 (A. R. Gennaro ed., 19th ed. 1995) which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, rofecoxib and celecoxib.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

The other therapeutic agent can also be an agent useful for reducing any potential side effects of a compound of Formula I. For example, the other therapeutic agent can be an antiemetic agent. Examples of useful antiemetic agents include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, e.g., Lyrica, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, e.g., Cymbalta, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, and perhexyline.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, fluorocitabine, fosquidone, fostriecin sodium, gemcitabine, gemcitabine hydrochloride, hydroxyurea, idarubicin hydrochloride, ifosfamide, ilmofosine, interleukin II (including recombinant interleukin II or rIL2), interferon alpha-2a, interferon alpha-2b, interferon alpha-nl, interferon alpha-n3, interferon beta-Ia, interferon gamma-Ib, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

Examples of other anti-cancer drugs include, but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dihydrotaxol; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sd±1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Examples of useful therapeutic agents for treating or preventing UI include, but are not limited to, propantheline, imipramine, hyoscyamine, oxybutynin, and dicyclomine.

Examples of useful therapeutic agents for treating or preventing an ulcer include, antacids such as aluminum hydroxide, magnesium hydroxide, sodium bicarbonate, and calcium bicarbonate; sucraflate; bismuth compounds such as bismuth subsalicylate and bismuth subcitrate; $H_2$ antagonists such as cimetidine, ranitidine, famotidine, and nizatidine; $H^+$, $K^+$-ATPase inhibitors such as omeprazole, iansoprazole, and lansoprazole; carbenoxolone; misprostol; and antibiotics such as tetracycline, metronidazole, timidazole, clarithromycin, and amoxicillin.

Examples of useful therapeutic agents for treating or preventing IBD include, but are not limited to, anticholinergic drugs; diphenoxylate; loperamide; deodorized opium tincture; codeine; broad-spectrum antibiotics such as metronidazole; sulfasalazine; olsalazie; mesalamine; prednisone; azathioprine; mercaptopurine; and methotrexate.

Examples of useful therapeutic agents for treating or preventing IBS include, but are not limited to, propantheline; muscarine receptor antagonists such as pirenzapine, methoctramine, ipratropium, tiotropium, scopolamine, methscopolamine, homatropine, homatropine methylbromide, and methantheline; and antidiarrheal drugs such as diphenoxylate and loperamide.

Examples of useful therapeutic agents for treating or preventing an addictive disorder include, but are not limited to, methadone, desipramine, amantadine, fluoxetine, buprenorphine, an opiate agonist, 3-phenoxypyridine, levomethadyl acetate hydrochloride, and serotonin antagonists.

Examples of useful therapeutic agents for treating or preventing Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsaprione, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating or preventing epilepsy include, but are not limited to, carbamazepine, ethosuximide, gabapentin, lamotrignine, phenobarbital, phenyloin, primidone, valproic acid, trimethadione, bemzodiaepines, gabapentin, lamotrigine, γ-vinyl GABA, acetazolamide, and felbamate.

Examples of useful therapeutic agents for treating or preventing stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating or preventing a seizure include, but are not limited to, carbamazepine, ethosuximide, gabapentin, lamotrignine, phenobarbital, phenyloin, primidone, valproic acid, trimethadione, bemzodiaepines, gabapentin, lamotrigine, γ-vinyl GABA, acetazolamide, and felbamate.

Examples of useful therapeutic agents for treating or preventing a pruritic condition include, but are not limited to, naltrexone; nalmefene; danazol; tricyclics such as amitriptyline, imipramine, and doxepin; antidepressants such as those given below, menthol; camphor; phenol; pramoxine; capsaicin; tar; steroids; and antihistamines.

Examples of useful therapeutic agents for treating or preventing psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating or preventing Huntington's chorea include, but are not limited to, haloperidol and pimozide.

Examples of useful therapeutic agents for treating or preventing ALS include, but are not limited to, baclofen, neurotrophic factors, riluzole, tizanidine, benzodiazepines such as clonazepan and dantrolene.

Examples of useful therapeutic agents for treating or preventing cognitive disorders include, but are not limited to, agents for treating or preventing dementia such as tacrine; donepezil; ibuprofen; antipsychotic drugs such as thioridazine and haloperidol; and antidepressant drugs such as those given below.

Examples of useful therapeutic agents for treating or preventing a migraine include, but are not limited to, sumatriptan; methysergide; ergotamine; caffeine; and beta-blockers such as propranolol, verapamil, and divalproex.

Examples of useful therapeutic agents for treating or preventing vomiting include, but are not limited to, 5-$HT_3$ receptor antagonists such as ondansetron, dolasetron, granisetron, and tropisetron; dopamine receptor antagonists such as prochlorperazine, thiethylperazine, chlorpromazin, metoclopramide, and domperidone; glucocorticoids such as dexamethasone; and benzodiazepines such as lorazepam and alprazolam.

Examples of useful therapeutic agents for treating or preventing dyskinesia include, but are not limited to, reserpine and tetrabenazine.

Examples of useful therapeutic agents for treating or preventing depression include, but are not limited to, tricyclic antidepressants such as amitryptyline, amoxapine, bupropion, clomipramine, desipramine, doxepin, imipramine, nefazadone, nortriptyline, protriptyline, trazodone, trimipramine, and venlaflaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A compound of Formula I, or a pharmaceutically acceptable derivative thereof, and the other therapeutic agent can act additively or, in one embodiment, synergistically. In one embodiment, a compound of Formula I is administered concurrently with another therapeutic agent; for example, a composition comprising an effective amount of a compound of Formula I and an effective amount of another therapeutic agent can be administered. Alternatively, a composition comprising an effective amount of a compound of Formula I and a different composition comprising an effective amount of another therapeutic agent can be concurrently administered. In another embodiment, an effective amount of a compound of Formula I is administered prior or subsequent to administration of an effective amount of another therapeutic agent. In this embodiment, the compound of Formula I is administered while the other therapeutic agent exerts its therapeutic effect, or the other therapeutic agent is administered while the compound of Formula I exerts its therapeutic effect for treating or preventing a Condition.

A composition of the invention is prepared by a method comprising admixing a compound of Formula I or a pharmaceutically acceptable derivative and a pharmaceutically acceptable carrier or excipient. Admixing can be accomplished using methods known for admixing a compound (or salt) and a pharmaceutically acceptable carrier or excipient.

In one embodiment, the compound of Formula I is present in the composition in an effective amount.

Kits

The invention further encompasses kits that can simplify the administration of a compound of Formula I, or a pharmaceutically acceptable derivative thereof, to an animal.

A typical kit of the invention comprises a unit dosage form of a compound of Formula I. In one embodiment, the unit dosage form is a container, which can be sterile, containing an effective amount of a compound of Formula I and a pharmaceutically acceptable carrier or excipient. The kit can further comprise a label or printed instructions instructing the use of the compound of Formula I to treat a Condition. The kit can also further comprise a unit dosage form of another therapeutic agent, for example, a second container containing an effective amount of the other therapeutic agent and a pharmaceutically acceptable carrier or excipient. In another embodiment, the kit comprises a container containing an effective amount of a compound of Formula I, an effective amount of another therapeutic agent and a pharmaceutically acceptable carrier or excipient. Examples of other therapeutic agents include, but are not limited to, those listed above.

Kits of the invention can further comprise a device that is useful for administering the unit dosage forms. Examples of such a device include, but are not limited to, a syringe, a drip bag, a patch, an inhaler, and an enema bag.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

Example 1

Step 1

N'-(2-(tert-butyldimethylsilyloxy)acetyl)-5,6-dichloronicotinohydrazide (3)

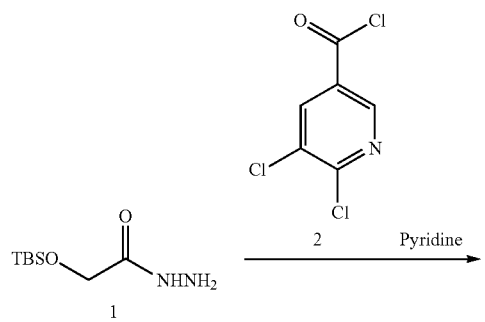

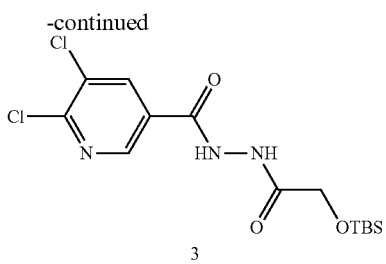

To a solution of (1) (341 mg, 1.668 mmol) in Toluene (5 ml) were added Pyridine (0.162 ml, 2.001 mmol) and (2) (351 mg, 1.668 mmol) in Toluene (1.0 ml) at 0° C. under nitrogen. The mixture was stirred at 0° C. for 1 hr.

After quenching with $H_2O$ (5 ml) and sat. aq.$NaHCO_3$ (5 ml), the aqueous layer was extracted with AcOEt (X3), washed with brine, dried over $MgSO_4$ and concentrated.

The crude product was used for the next reaction without further purification.

3: $^1H$ NMR: δ(300 MHz, DMSO): 10.75 (1H, s), 9.83 (1H, s), 8.81 (1H, s), 8.49 (1H, s), 4.19 (2H, s), 0.90 (9H, s), 0.11 (6H, s).

Step 2

2-((tert-butyldimethylsilyloxy)methyl)-5-(5,6-dichloropyridin-3-yl)-1,3,4-oxadiazole (5)

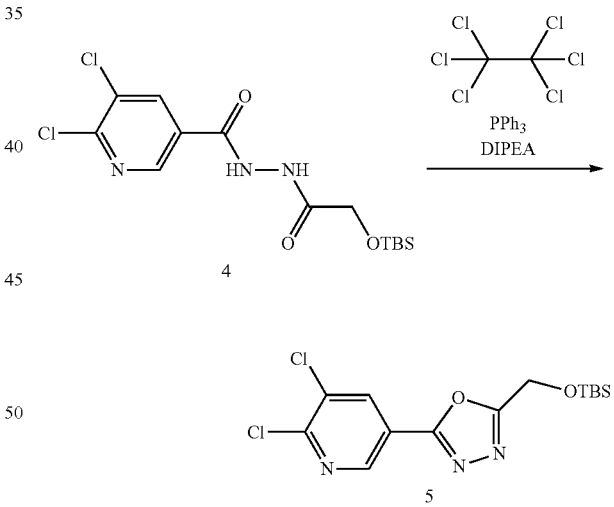

To a solution of (4) (691 mg, 1.826 mmol) in Acetonitrile (7 ml) were added DIPEA (1.850 ml, 10.59 mmol), $PPh_3$ (814 mg, 3.10 mmol) and hexachloroethane (562 mg, 2.374 mmol) at 0° C. under nitrogen. The mixture was stirred at room temperature for 2 hrs.

After quenching with $H_2O$ (5 ml), the mixture was extracted with AcOEt (X3), washed with brine, dried over $MgSO_4$ and concentrated. The crude product was chromatographed on silica gel eluting with Hex/EtOAc 4:1. Collected fractions were evaporated to afford (5) (646 mg, 1.793 mmol, 98%) as a white solid.

5: ¹H NMR: δ (300 MHz, CDCl3): 8.96 (1H, s), 8.46 (1H, s), 4.96 (2H, s), 0.94 (9H, s), 0.17 (6H, s).

Step 3 tert-butyl-4-(5-(5-(((tert-butyldimethylsilyloxy)methyl)-1,3,4-oxadiazol-2-yl)-3-chloropyridin-2-yl)-5,6-dihydropyridine-1(2H)-carboxylate (7)

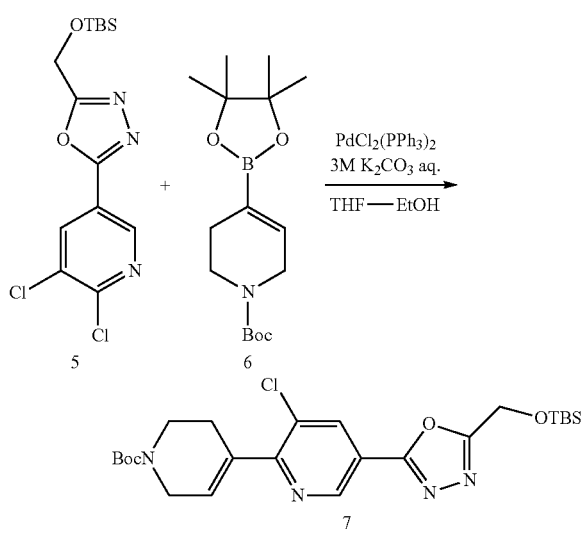

To a solution of (5) (743 mg, 2.062 mmol) in THF (3.0 ml)-EtOH (1.51 ml)-3M K₂CO₃ aq. (1.512 ml, 4.54 mmol) were added tert-butyl4-(4,4,5,5-tetramethyl-1,3,2-dioxaborolan-2-yl)-5,6-dihydropyridine-1(2H)-carboxylate (6) (765 mg, 2.475 mmol) and PdCl₂(PPh₃)₂ (72.4 mg, 0.103 mmol) at room temperature under nitrogen. The mixture was stirred at 85° C. for 2 hrs.

After quenching with H₂O (5 ml), the mixture was extracted with AcOEt (X3), washed with brine, dried over MgSO₄ and concentrated.

The crude product was chromatographed on silica gel eluting with Hex/EtOAc (2:1) Collected fractions were evaporated to afford (7) (1040 mg, 2.051 mmol 99%) as a yellow oil.

7: ¹H NMR: δ (300 MHz, CDCl3): 9.10 (1H, s), 8.37 (1H, s), 6.30 (1H, m), 4.96 (2H, s), 4.13 (2H, m), 3.67 (2H, m), 2.64 (2H, m), 1.51 (9H, s), 0.94 (9H, s), 0.17 (6H, s).

Step 4

2-((tert-butyldimethylsilyloxy)methyl)-5-(5-chloro-6-(1,2,3,6-tetrahydropyridin-4-yl)pyridin-3-yl)-1,3,4-oxadiazole (8)

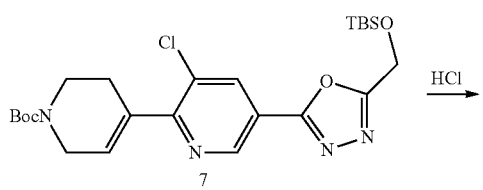

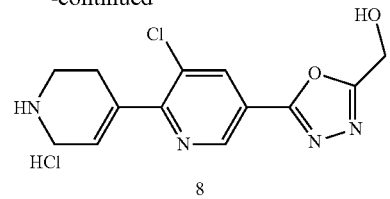

To a solution of (7 (1.055 g, 2.080 mmol) in CH₂Cl₂ (10 ml) was added 4M HCl in dioxane (2.080 ml, 8.32 mmol) at 0° C. The mixture was stirred at room temperature for 3 hrs.

The white solid was precipitated. The solid was filtered and rinsed with AcOEt and collected to afford (8) (680 mg, 2.066 mmol, 99%) as a white solid.

Step 5

4-(3-chloro-5-(5-(hydroxymethyl)-1,3,4-oxadiazol-2-yl)pyridin-2-yl)-N-(5-(trifluoromethyl)pyridin-2-yl)-5,6-dihydropyridine-1(2H)-carboxamide (I-9)

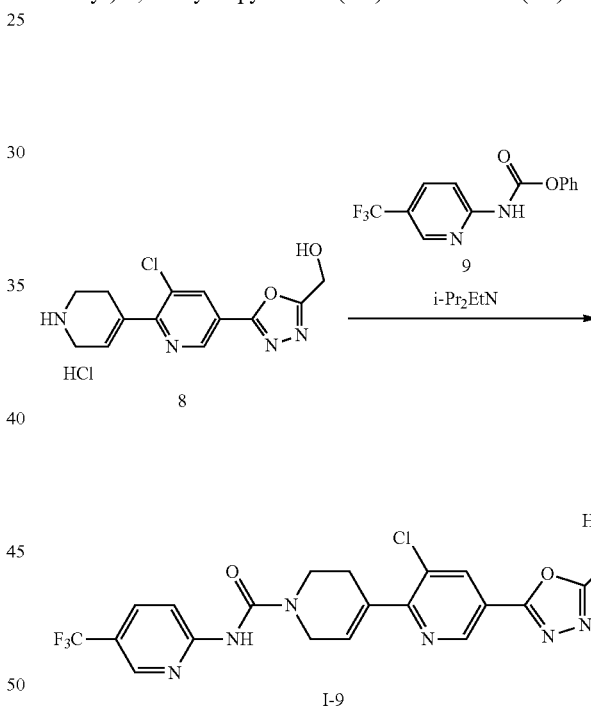

To a solution of (8) (158.4 mg, 0.481 mmol) in CH₂Cl₂ (3 ml) was added i-Pr₂EtN (0.378 ml, 2.165 mmol) at room temperature under nitrogen. The mixture was stirred at room temperature for 30 min and (9) was added at 0° C. The resulting mixture was stirred at room temperature for 18 hrs. After quenching with H₂O (5 ml), the mixture was extracted with CHCl₃ (X3), washed with brine, dried over MgSO₄ and concentrated.

The resulting solid was rinsed with AcOEt and collected to afford I-9 (113 mg 0.235 mmol, 49%) as a white solid.

I-9: ¹H NMR: δ (300 MHz, DMSO): 9.85 (1H, s), 9.07 (1H, s), 8.61 (1H, m), 8.44 (1H, s), 8.76 (1H, d, J=9.0 Hz). 7.98 (1H, d, J=9.0 Hz), 6.40 (1H, s), 6.02 (1H, t, J=6.0 Hz), 4.75 (2H, d, J=6.0 Hz), 4.26 (2H, m), 3.72 (2H, m), 2.63 (2H, m).

Example 2

The following compound was obtained in the same manner to Example 1. 4-(3-chloro-5-(5-(hydroxymethyl)-1,3,4-oxadiazol-2-yl)pyridin-2-yl)-N-(4-(trifluoromethyl)phenyl)-5,6-dihydropyridine-1(2H)-carboxamide (I-10)

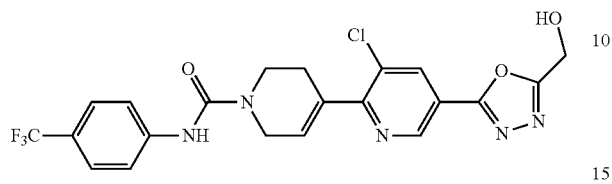

I-10: $^1$H NMR: δ(300 MHz, DMSO): 9.08, (1H, s), 8.98 (1H, s), 8.44 (1H, s), 7.72 (2H, d, J=9.0 Hz), 7.59 (2H, d, J=9.0 Hz), 6.42 (1H, s), 6.20 (1H, t, J=6.0 Hz), 4.74 (2H, d, J=6.0 Hz), 4.24 (2H, m), 3.71 (2H, m), 2.64 (2H, m).

Example 3

The following compound was obtained in the same manner to Example 1. N-(3-chloro-4-(trifluoromethyl)phenyl)-4-(3-chloro-5-(5-(hydroxymethyl)-1,3,4-oxadiazol-2-yl)pyridin-2-yl)-5,6-dihydropyridine-1(2H)-carboxamide (I-11)

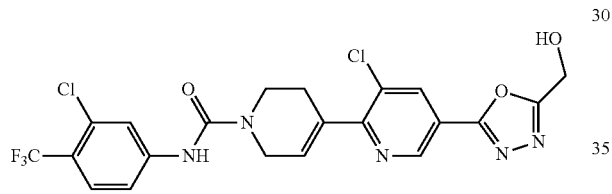

I-11: $^1$H NMR: δ(300 MHz, DMSO): 9.15, (1H, s), 9.07 (1H, s), 8.44 (1H, s), 7.92 (1H, s), 7.73 (1H, d, J=9.0 Hz), 7.64 (1H, d, J=9.0 Hz), 6.42 (1H, m), 6.03 (1H, t, J=6.0 Hz), 4.74 (2H, d, J=6.0 Hz), 4.24 (2H, m), 3.71 (2H, m), 2.64 (2H, m).

Reference Example 1

The other compounds were obtained in the same manner as Example 1, Steps 1 and 2.

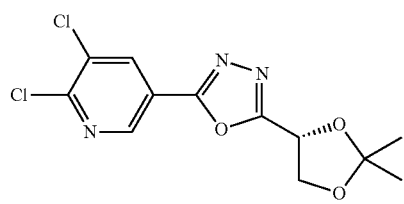

10a

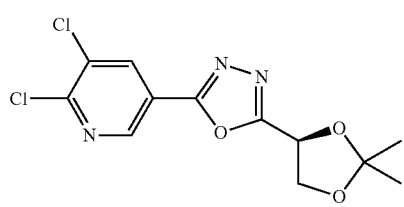

10b

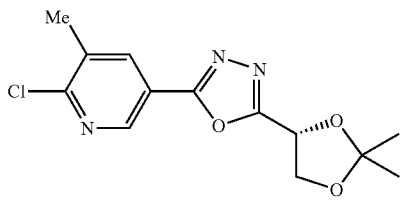

10c

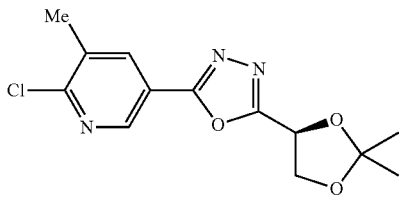

10d

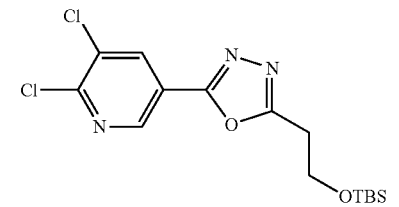

10e

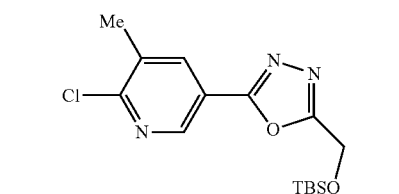

10f

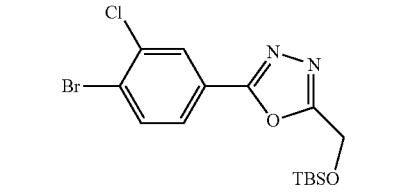

10g

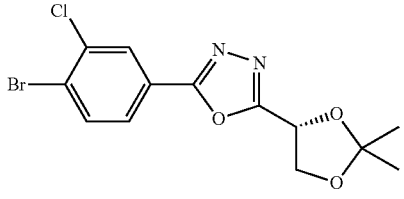

10h

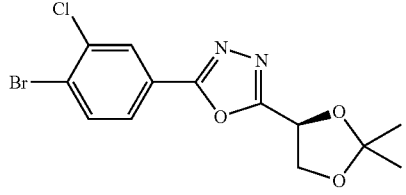

10i

10a: 83% as a yellow solid (R)-2-(5,6-dichloropyridin-3-yl)-5-(2,2-dimethyl-1,3-dioxolan-4-yl)-1,3,4-oxadiazole $^1$H-NMR (DMSO-d6) δ: 8.98 (1H, d, J=1.98 Hz), 8.66 (1H, d, J=1.98 Hz), 5.48 (1H, t, J=6.06 Hz), 4.41 (2H, d, J=6.06 Hz), 1.46 (3H, s), 1.41 (3H, s). LC/MS (M+1): 316.

10b: 77% as a yellow solid (S)-2-(5,6-dichloropyridin-3-yl)-5-(2,2-dimethyl-1,3-dioxolan-4-yl)-1,3,4-oxadiazole ¹H-NMR (DMSO-d6) δ: 8.98 (1H, d, J=1.98 Hz), 8.66 (1H, d, J=1.98 Hz), 5.48 (1H, t, J=6.06 Hz), 4.41 (2H, d, J=6.06 Hz), 1.46 (3H, s), 1.41 (3H, s). LC/MS (M+1): 316.

10c: 70% as a yellow solid (R)-2-(6-chloro-5-methylpyridin-3-yl)-5-(2,2-dimethyl-1,3-dioxolan-4-yl)-1,3,4-oxadiazole ¹H-NMR (DMSO-d6) δ: 8.83 (1H, s), 8.40 (1H, s), 5.47 (1H, t, J=6.06 Hz), 4.41 (2H, d, J=6.06 Hz), 2.45 (3H, s), 1.45 (3H, s), 1.41 (3H, s). LC/MS (M+1): 296.

10d: 63% as a yellow solid (S)-2-(6-chloro-5-methylpyridin-3-yl)-5-(2,2-dimethyl-1,3-dioxolan-4-yl)-1,3,4-oxadiazole ¹H-NMR (DMSO-d6) δ: 8.84 (1H, s), 8.41 (1H, s), 5.47 (1H, t, J=5.31 Hz), 4.41 (2H, d, J=5.31 Hz), 2.46 (3H, s), 1.45 (3H, s), 1.41 (3H, s). LC/MS (M+1): 296.

10e: 89% as a white solid 2-(2-(tert-butyldimethylsilyloxy)ethyl)-5-(5,6-dichloropyridin-3-yl)-1,3,4-oxadiazole ¹H-NMR (DMSO-d6) δ: 8.96 (1H, s), 8.64 (1H, s), 4.05 (2H, t, J=6.06 Hz), 3.17 (2H, t, J=6.06 Hz), 0.79 (9H, s), 0.00 (6H, s). LC/MS (M+1): 374.

10f: 80% as a white solid 2-((tert-butyldimethylsilyloxy)methyl)-5-(6-chloro-5-methylpyridin-3-yl)-1,3,4-oxadiazole ¹H-NMR (DMSO-d6) δ: 8.88 (1H, s), 8.46 (1H, s), 5.04 (2H, s), 2.56 (3H, s), 0.95 (9H, s), 0.20 (6H, s).

10g: 90% as a white solid 2-(4-bromo-3-chlorophenyl)-5-((tert-butyldimethylsilyloxy)methyl)-1,3,4-oxadiazole ¹H-NMR (DMSO-d6) δ: 7.99 (1H, s), 7.90 (1H, d, J=8.08 Hz), 7.71 (1H, d, J=8.08 Hz), 4.84 (2H, s), 0.76 (9H, s), 0.00 (6H, s). LC/MS (M+1): 405.

10h: 80% as a yellow oil (R)-2-(4-bromo-3-chlorophenyl)-5-(2,2-dimethyl-1,3-dioxolan-4-yl)-1,3,4-oxadiazole ¹H-NMR (DMSO-d6) δ: 8.13 (1H, s), 8.01 (1H, d, J=8.08 Hz), 7.85 (1H, d, J=8.08 Hz), 5.45 (1H, t, J=5.05 Hz), 4.39 (2H, d, J=5.05 Hz), 1.45 (3H, s), 1.40 (3H, s).
LC/MS (M+1): 359.

10j: 84% as a orange oil (S)-2-(4-bromo-3-chlorophenyl)-5-(2,2-dimethyl-1,3-dioxolan-4-yl)-1,3,4-oxadiazole ¹H-NMR (DMSO-d6) δ: 8.16 (1H, s), 8.04 (1H, d, J=8.08 Hz), 7.87 (1H, d, J=8.08 Hz), 5.46 (1H, t, J=5.05 Hz), 4.39 (2H, d, J=5.05 Hz), 1.45 (3H, s), 1.41 (3H, s).
LC/MS (M+1): 359.

Reference Example 2

Step 1

5,6-dichloro-N'-hydroxynicotinimidamide

To a solution of amide (11) (942 mg, 4.93 mmol) in CHCl₃ (6 ml) was added POCl₃ (2 ml, 21.5 mmol) at 0° C. under nitrogen. After being stirred for 2 hrs at 85° C., the reaction mixture was concentrated in vacuo. The residue was quenched with sat.NaHCO₃ and diluted with CH₂Cl₂. The resulting organic layer was separated and the aqueous layer was extracted with ethyl acetate, the combined organic layers were washed with H₂O and brine, dried over Na₂SO₄ and concentrated in vacuo. The residue was used for the next reaction without further purification.

To a solution of NH₂OH HCl (514 mg, 7.40 mmol) in EtOH (10 ml) was added NEt₃ (2.1 ml, 14.8 mmol) at room temperature under nitrogen. After being stirred for 10 min at room temperature, the reaction mixture was added above crude product and heated to reflux temperature. After being stirred for 1 hr at the same temperature, the reaction mixture was quenched with H₂O and diluted with ethyl acetate. The resulting organic layer was separated and the aqueous layer was extracted with ethyl acetate, the combined organic layers were washed with brine, dried over Na₂SO₄ and concentrated in vacuo. The residue was triturated with CHCl₃. The resulting solid was filtered through a glass funnel, rinsed with hexane, and collected to afford 894 mg of the desired product (12) in 88% yield as a white solid. ¹H-NMR (DMSO-d6) δ: 10.11 (1H, s), 8.67 (1H, s), 8.31 (1H, s), 6.13 (2H, s). LC/MS (M+1): 206.

Step 2

(3-(5,6-dichloropyridin-3-yl)-1,2,4-oxadiazol-5-yl)methyl acetate

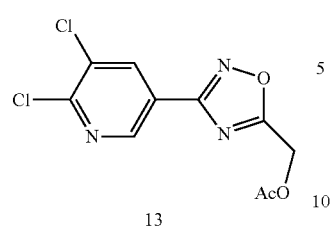

To a solution of amidoxime (12) (350 mg, 1.70 mmol) in DMF (3 ml) were added 2-acetoxyacetic acid (201 mg, 1.70 mmol), TBTU (545 mg, 1.70 mmol), HOBt (46 mg, 0.349 mmol) and DMA (1.5 ml, 8.49 mmol) at 0° C. under nitrogen. After being stirred for 1 hr at room temperature, the reaction mixture was quenched with sat.NaHCO$_3$ and diluted with ethyl acetate. The resulting organic layer was separated and the aqueous layer was extracted with ethyl acetate, the combined organic layers were washed with H$_2$O and brine, dried over Na$_2$SO$_4$ and concentrated in vacuo. The residue was used for the next reaction without further purification.

To a solution of crude product in toluene (8 ml) was heated to reflux temperature under nitrogen. After being stirred for 5 hrs at the same temperature, the reaction mixture was concentrated in vacuo. The crude product was chromatographed on silica gel eluting with a gradient of hexane/ethyl acetate (10-30%) to afford 368 mg of the desired product (13) in 75% yield as a white solid. $^1$H-NMR (DMSO-d6) δ: 8.96 (1H, s), 8.60 (1H, s), 5.51 (2H, s), 2.18 (3H, s). LC/MS (M+1): 289.

Reference Example 3

Step 1 ethyl 5-(5,6-dichloropyridin-3-yl)-1,2,4-oxadiazole-3-carboxylate

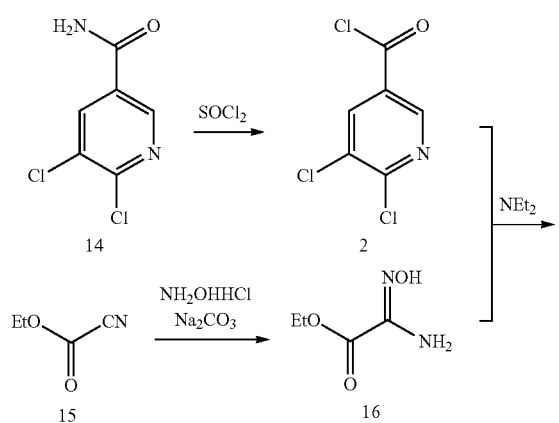

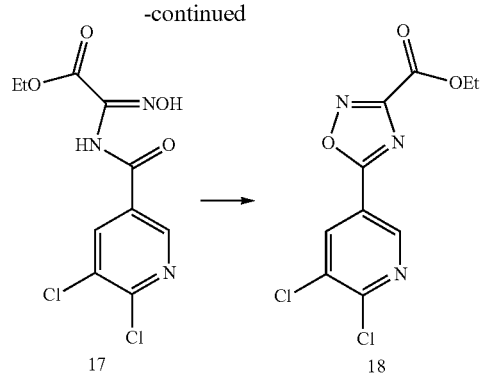

To a solution of 5,6-dichloronicotinic acid (14) (2.0 g, 1.83 mmol) in toluene (10 ml) were added SOCl$_2$ (1.14 ml, 15.6 mmol) and 0.01 equivalent of DMF (16 µl, 0.208 mmol) at 25° C. risen up to reflux temperature for 3 hrs. Then the reaction mixture was concentrated in vacuo.

To a solution of ethyl carbonocyanidate (15) in EtOH (13 ml) and H$_2$O (7.5 ml) were added NH$_2$OHHCl (1.44 g, 20.7 mmol) and Na$_2$CO$_3$ (1.17 g, 11.1 mmol) at 25° C. After being stirred for 2 hrs, the reaction mixture was concentrated in vacuo. The residue was diluted with CH$_2$Cl$_2$, quenched with brine and extracted with CH$_2$Cl$_2$. The resulting organic layer was washed with brine, dried over Na$_2$SO$_4$ and concentrated in vacuo.

To a solution of (16) (1.27 g, 9.60 mmol) in CH$_2$Cl$_2$ was added NEt$_3$ (6.65 ml, 48.0 mmol) and then dropwise added resulting 5,6-dichloronicotinoyl chloride (2) in toluene (3 ml) via a droping funnel 0° C. under nitrogen. After being stirred for 2 hrs, the reaction mixture was added to CHCl$_3$/hexane. The resulting solid was filtered through a glass funnel, rinsed with hexane, and collected.

To a solution of crude product in DMF (30 ml) was heated to reflux temperature under nitrogen. After being stirred for 2.5 hrs at the same temperature, the reaction mixture quenched with H$_2$O and diluted with ethyl acetate. The resulting organic layer was separated and the aqueous layer was extracted with ethyl acetate, the combined organic layers were washed with brine, dried over Na$_2$SO$_4$ and concentrated in vacuo. The residue was triturated with CHCl$_3$/hexane. The resulting solid was filtered through a glass funnel, rinsed with hexane, and collected to afford 1.04 g of the desired product (18) in 40% yield as a white solid. $^1$H-NMR (DMSO-d6) δ: 9.13 (1H, s), 8.86 (1H, s), 4.47 (2H, q, J=6.91 Hz), 1.37 (3H, t, J=6.91 Hz). LC/MS (M+1): 288.

Step 2

(5-(5,6-dichloropyridin-3-yl)-1,2,4-oxadiazol-3-yl)methanol

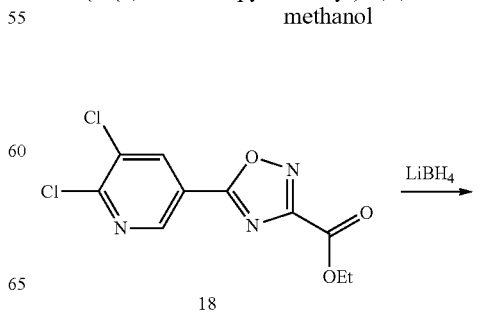

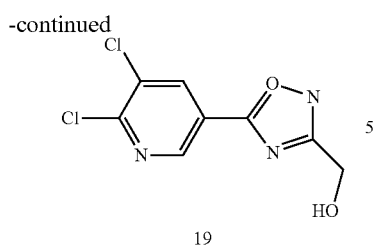

19

To a solution of ester (18) (300 mg, 1.04 mmol) in THF (8 ml) and EtOH (8 ml) was added LiBH$_4$ (34 mg, 1.56 mmol) at 0° C. under nitrogen. After being stirred overnight at room temperature, the reaction mixture was added LiBH$_4$ (13.6 mg, 0.625 mmol) at 0° C. After being stirred overnight at room temperature, the reaction mixture was quenched with 10% citric acid and diluted with ethyl acetate. The resulting organic layer was separated and the aqueous layer was extracted with ethyl acetate, the combined organic layers were washed with H$_2$O and brine, dried over Na$_2$SO$_4$ and concentrated in vacuo. The crude product was chromatographed on silica gel eluting with a gradient of hexane/ethyl acetate (30-50%) to afford 85.4 mg of the desired product (19) in 33% yield as a white solid. LC/MS (M+1): 246.

Reference Example 4

Step 1 methyl 2-(5,6-dichloronicotinamido)-3-hydroxypropanoate

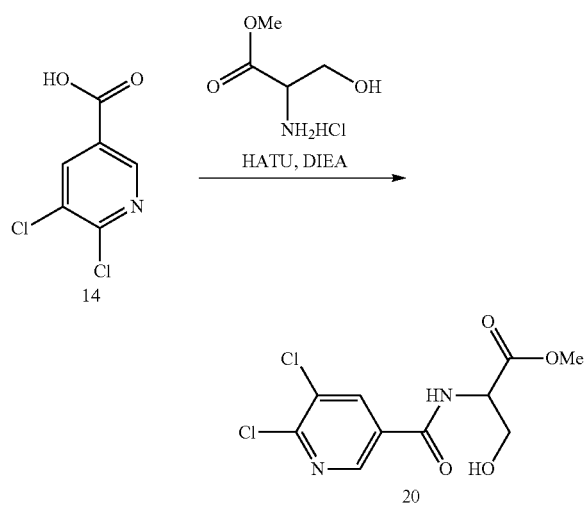

To a solution of 5,6-dichloronicotinic acid (14) (1 g, 5.21 mmol) in DMF (10 ml) were added methyl 2-amino-3-hydroxypropanoate hydrochloride (972 mg, 6.25 mmol), HATU (2.2 g, 5.73 mmol) and DIEA (2.73 ml, 15.6 mmol) at 0° C. under nitrogen. After being stirred overnight at room temperature, the reaction mixture was quenched with H$_2$O and diluted with ethyl acetate. The resulting organic layer was separated and the aqueous layer was extracted with ethyl acetate, the combined organic layers were washed with brine, dried over Na$_2$SO$_4$ and concentrated in vacuo. The crude product was chromatographed on silica gel eluting with a gradient of hexane/ethyl acetate (30-50%) to afford 460 mg of the desired product (20) in 43% yield as a yellow oil. $^1$H-NMR (DMSO-d6) δ: 9.09 (1H, d, J=6.57 Hz), 8.83 (1H, s), 8.57 (1H, s), 5.13 (1H, br), 4.57 (1H, m), 3.80 (2H, m), 3.67 (3H, s). LC/MS (M+1): 294.

Step 2 methyl 2-(5,6-dichloropyridin-3-yl)oxazole-4-carboxylate

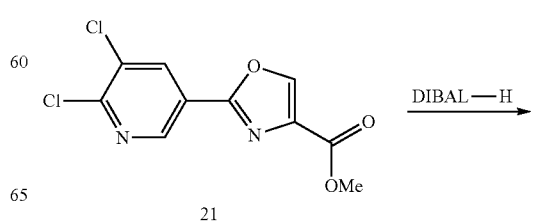

To a solution of (20) (443 mg, 1.51 mmol) in CH$_2$Cl$_2$ (2.0 ml) was dropwise added Deoxo-Fluor (Bis(2-methoxyethyl) aminosulfur trifluoride, 334 μl, 1.80 mmol) via a droping funnel at −20° C. under nitrogen. After being stirred for 30 min at −20° C., the reaction mixture was dropwise added bromotrichloromethane (596 μl, 6.05 mmol), DBU (911 μl, 6.05 mmol) and then risen up to 2-3° C. After being stirred for additional 6 hrs, the reaction mixture was quenched with sat. NaHCO$_3$ and diluted with ethyl acetate. The resulting organic layer was separated and the aqueous layer was extracted with ethyl acetate, the combined organic layers were washed with H$_2$O and brine, dried over Na$_2$SO$_4$ and concentrated in vacuo. The crude product was chromatographed on silica gel eluting with a gradient of ethyl acetate (10-30%)/hexanes to afford 263 mg of the desired product (21) in 64% yield as a white solid. $^1$H-NMR (DMSO-d6) δ: 9.13 (1H, s), 8.98 (1H, s), 8.64 (1H, s), 3.87 (3H, s). LC/MS (M+1): 273.

Step 3

(2-(5,6-dichloropyridin-3-yl)oxazol-4-yl)methanol

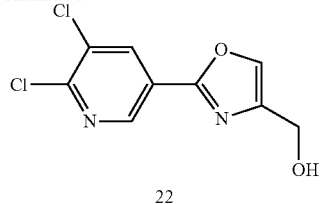

To a solution of ester (21) (253 mg, 0.925 mmol) in CH$_2$Cl$_2$ (15 ml) was dropwise added DIBAL-H (1M in toluene) (2.29 ml, 2.31 mmol) via a droping funnel at −78° C. under nitrogen. After being stirred for 30 min at −78° C., the reaction mixture was allowed to warm to −30° C. over 1.5 hrs. The reaction mixture was quenched with 10% citric acid and diluted with ethyl acetate. The resulting organic layer was separated and the aqueous layer was extracted with ethyl acetate, the combined organic layers were washed with H$_2$O and brine, dried over Na$_2$SO$_4$ and concentrated in vacuo. The crude product was chromatographed on silica gel eluting with a gradient of ethyl acetate (10-40%)/hexanes to afford 105 mg of the desired product (22) in 46% yield as a white solid.

$^1$H-NMR (DMSO-d6) δ: 8.92 (1H, s), 8.55 (1H, s), 8.18 (1.H, s), 5.34 (1H, br), 4.47 (2H, d, J=6.06 Hz). LC/MS (M+1): 245.

Reference Example 5

Step 1 methyl 2-(5,6-dichloronicotinamido)-3-hydroxypropanoate

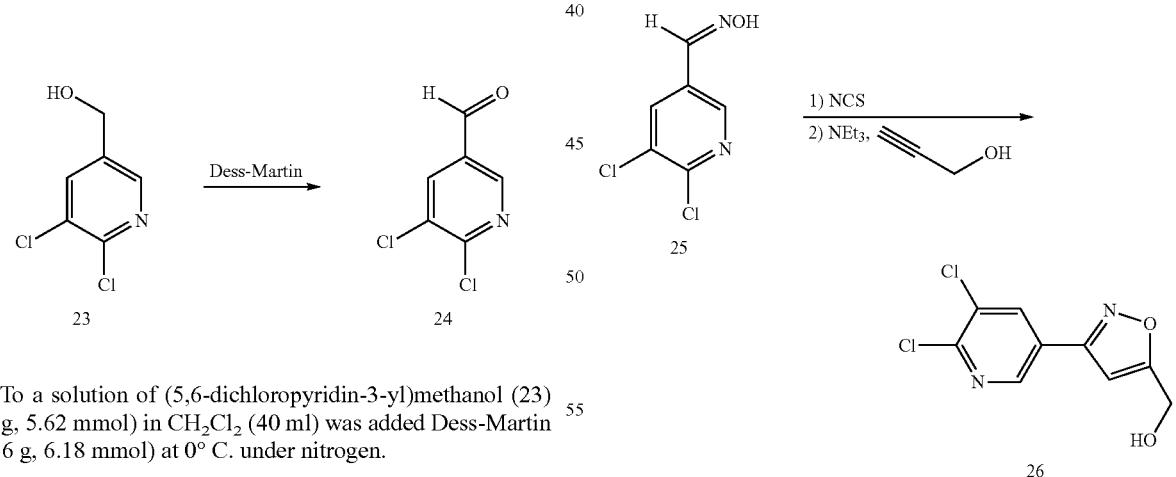

To a solution of (5,6-dichloropyridin-3-yl)methanol (23) (1 g, 5.62 mmol) in CH$_2$Cl$_2$ (40 ml) was added Dess-Martin (2.6 g, 6.18 mmol) at 0° C. under nitrogen.

After being stirred for 30 min at 0° C., the reaction mixture was quenched with sat. NaHCO$_3$ and diluted with CH$_2$Cl$_2$. The resulting organic layer was separated and the aqueous layer was extracted with CH$_2$Cl$_2$, the combined organic layers were washed with Na$_2$S$_2$O$_3$, H$_2$O and brine, dried over Na$_2$SO$_4$ and concentrated in vacuo. The residue was triturated with CHCl$_3$. The resulting solid was filtered through a glass funnel, rinsed with CHCl$_3$. The liquid residue was chromatographed on silica gel eluting with a gradient of hexane/ethyl acetate (10-20%) to afford 867 mg of the desired product (24) in 88% yield as a white solid. $^1$H-NMR (DMSO-d6) δ: 10.09 (1H, s), 8.90 (1H, s), 8.55 (1H, s). LC/MS (M+1): 176.

Step 2

5,6-dichloronicotinaldehyde oxime

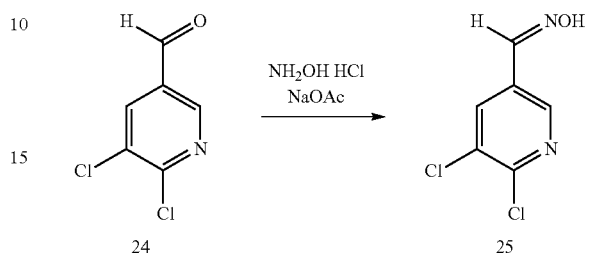

To a solution of (24) (866 mg, 4.92 mmol) in EtOH (16 ml) were added NH$_2$OH HCl (581 mg, 8.36 mmol) and NaOAc (848 mg, 10.3 mmol) at room temperature under nitrogen. After being stirred for 3 hrs at reflux temperature, the reaction mixture was poured into H$_2$O and filtered through glass fiber paper. The resulting solid was re-dissolved in CH$_2$Cl$_2$ and the solution was dried over Na$_2$SO$_4$ and concentrated in vacuo. The residue was triturated with hexane. The resulting solid was filtered through a glass funnel, rinsed with hexane, and collected to afford 681 mg of the desired product (25) in 72% yield as a white solid. $^1$H-NMR (DMSO-d6) δ: 11.85 (1H, s), 8.59 (1H, s), 8.26 (1H, s), 8.21 (1H, s). LC/MS (M+1): 191.

Step 3

(3-(5,6-dichloropyridin-3-yl)isoxazol-5-yl)methanol

To a solution of (25) (758 mg, 3.96 mmol) in DMF (10 ml) was added NCS (582 mg, 4.36 mmol) at 0° C. under nitrogen. After being stirred for 2 hrs at room temperature, the reaction mixture was poured into H$_2$O and filtered through glass fiber paper. The resulting solid was re-dissolved in ethyl acetate and the solution was dried over Na$_2$SO$_4$ and concentrated in vacuo. The residue was used for the next reaction without further purification.

To a solution of crude product and prop-2-yn-1-ol (555 mg, 9.90 mmol) in toluene (20 ml) was dropwise added NEt₃ (1.0 ml, 7.92 mmol) in toluene (10 ml) via a droping funnel at 0° C. under nitrogen. After being stirred for 7 hrs at the same temperature, the reaction mixture was quenched with brine and diluted with ethyl acetate. The resulting organic layer was separated and the aqueous layer was extracted with ethyl acetate, the combined organic layers were washed brine, dried over Na₂SO₄ and concentrated in vacuo. The residue was triturated with CHCl₃/hexane. The resulting solid was filtered through a glass funnel, rinsed with hexane, and collected to afford 654 mg of the desired product (26) in 67% yield as a white solid. ¹H-NMR (DMSO-d6) δ: 8.91 (1H, s), 8.62 (1H, s), 7.14 (1H, s), 5.81 (1H, t, J=4.55 Hz), 4.65 (2H, d, J=4.55 Hz). LC/MS (M+1): 245.

Reference Example 6

Step 1 methyl 5-(5,6-dichloropyridin-3-yl)oxazole-4-carboxylate

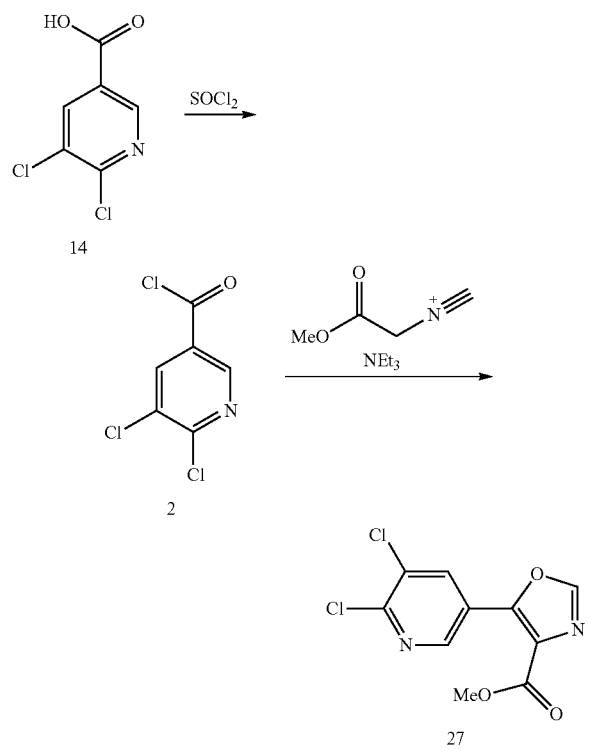

To a solution of 5,6-dichloronicotinic acid (14) (500 mg, 2.60 mmol) in toluene (2 ml) were added SOCl₂ (285 µl, 3.91 mmol) and 0.01 equivalent of DMF (4.05 µl, 0.052 mmol) at 25° C. risen up to reflux temperature for 6 hrs. Then the reaction mixture was concentrated in vacuo.

To a solution of resulting product (2) (547 mg) and 2-methoxy-N-methylidyne-2-oxoethanaminium (260 mg, 2.59 mmol) in CH₂Cl₂ (5 ml) was dropwise added NEt₃ (1.44 ml, 10.4 mmol) in CH₂Cl₂ (2.5 ml) at 0° C. under nitrogen. After being stirred for 4 hrs at the same temperature, the reaction mixture was quenched with H₂O and extracted with ethyl acetate. The resulting organic layer was washed with brine, dried over Na₂SO₄ and concentrated in vacuo. The liquid residue was chromatographed on silica gel eluting with a gradient of hexane/ethyl acetate (20-45%) to afford 558 mg of the desired product (27) in 79% yield as a yellow solid. LC/MS (M+1): 273.

Step 2

(5-(5,6-dichloropyridin-3-yl)oxazol-4-yl)methanol

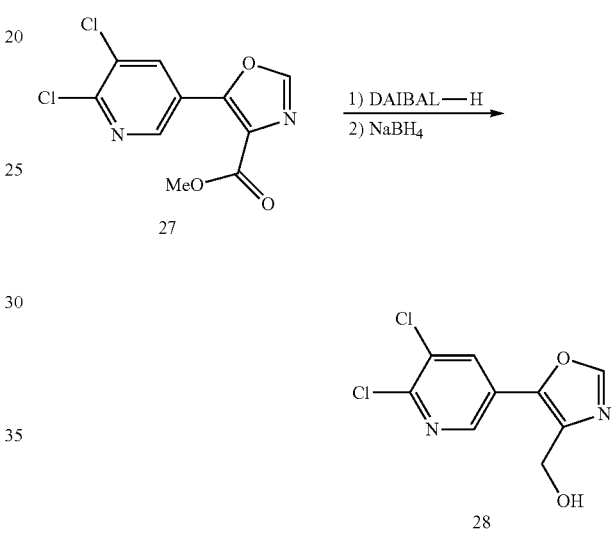

To a solution of (27) (500 mg, 1.83 mmol) in CH₂Cl₂ (20 ml) was dropwise added DIBAL-H (1.0M in THF) (4.58 ml, 4.58 mmol) at −78° C. After being stirred for 40 min at the same temperature, the reaction mixture was diluted with ethyl acetate, quenched with 10% aqueous potassium sodium tartrate at −78° C. and risen up to room temperature. After being stirred for 1 hr at the same temperature, the reaction mixture was extracted with ethyl acetate. The resulting organic layer was washed with brine, dried over Na₂SO₄ and concentrated in vacuo.

To a solution of crude product (445 mg) in THF (6 ml)-EtOH (6 ml) was added NaBH₄ (80 mg, 2.11 mmol) at 0° C. under nitrogen. After being stirred for 30 min at the same temperature, the reaction mixture was quenched with 10% citric acid and extracted with ethyl acetate. The resulting organic layer was washed with brine, dried over Na₂SO₄ and concentrated in vacuo. The liquid residue was chromatographed on silica gel eluting with a gradient of hexane/ethyl acetate (20-40%) to afford 292 mg of the desired product (28) in 65% yield as a brown solid. ¹H-NMR (DMSO-d6) δ: 8.73 (1H, s), 8.54 (1H, s), 8.42 (1H, s), 5.54 (1H, t, J=4.55 Hz), 4.58 (2H, d, J=4.55 Hz).

LC/MS (M+1): 245.

Reference Example 7

Step 1

1-(5,6-dichloropyridin-3-yl)ethanone

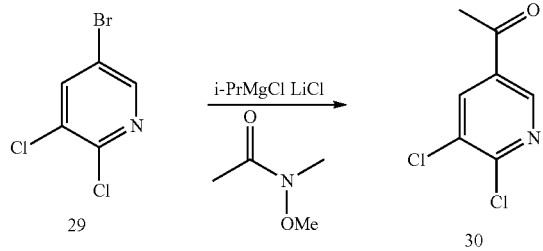

To a solution of 5-bromo-2,3-dichloropyridine (29) (702 mg, 3.09 mmol) in THF (7 ml) was dropwise added isopropylmagnesium chloride lithium chloride complex (3.09 ml, 4.02 mmol) at 0° C. for 10 min. Then N-methoxy-N-methylacetamide (658 μl, 6.19 mmol) in THF (2 ml) was dropwise added to the reaction mixture at the same temperature and stirred at for 2 hrs. Then the reaction mixture was quenched with aqueous solution and extracted with ethyl acetate. The resulting organic layer was washed with brine, dried over $Na_2SO_4$ and concentrated in vacuo. The resulting product was chromatographed on silica gel eluting with a gradient of hexane/ethyl acetate (5-15%) to afford 232 mg of the desired product (30) in 40% yield as a white solid. $^1$H-NMR (DMSO-d6) δ: 8.91 (1H, s), 8.55 (1H, s), 2.65 (3H, s).

Step 2

2-azido-1-(5,6-dichloropyridin-3-yl)ethanone

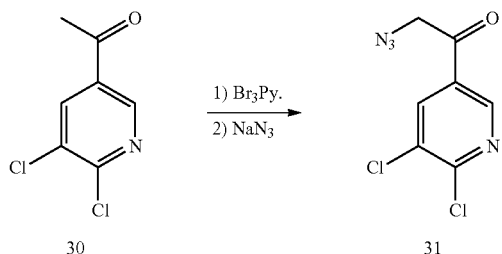

To a solution of (30) (983 mg, 5.17 mmol) in toluene (30 ml) was added pyridinium tribromide (1.95 g, 5.68 mmol) at 0° C. After being stirred overnight at room temperature, the reaction mixture was quenched with $H_2O$, diluted with ethyl acetate and extracted with ethyl acetate. The resulting organic layer was washed with brine, dried over $Na_2SO_4$ and concentrated in vacuo.

To a solution of crude product (1.4 g) in DMSO (13 ml) was added $NaN_3$ (403 mg, 6.20 mmol) at 0° C. under nitrogen. After being stirred for 3 hrs at the same temperature, the reaction mixture was quenched with $H_2O$ and extracted with ethyl acetate. The resulting organic layer was washed with brine, dried over $Na_2SO_4$ and concentrated in vacuo. The resulting product was chromatographed on silica gel eluting with a gradient of hexane/ethyl acetate (5-15%) to afford 464 mg of the desired product (31) in 39% yield as a orange solid. $^1$H-NMR (DMSO-d6) δ: 8.87 (1H, s), 8.54 (1H, s), 4.91 (2H, s). LC/MS (M+1): 231.

Step 3

(E)-2-azido-1-(5,6-dichloropyridin-3-yl)vinyl 2-acetoxyacetate

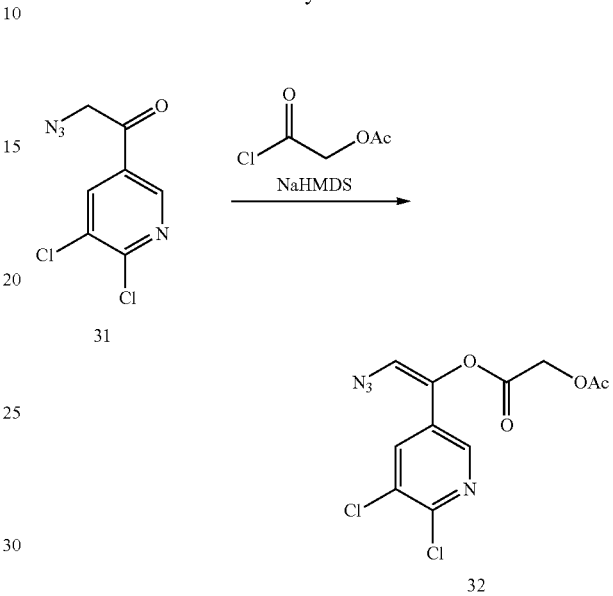

To a solution of (31) (464 mg, 2.00 mmol) in THF (9 ml) was dropwise added NaHMDS (2.21 ml, 2.21 mmol) at −78° C. After being stirred for 30 min at the same temperature, the reaction mixture was dropwise added to 2-chloro-2-oxoethyl acetate (548 mg, 4.01 mmol) at −78° C. After being stirred for 1 hr at the same temperature, the reaction mixture was allowed to warm to room temperature for 30 min, quenched with $H_2O$, diluted with ethyl acetate and extracted with ethyl acetate. The resulting organic layer was washed with brine, dried over $Na_2SO_4$ and concentrated in vacuo. The resulting product was purified by silica gel chromatography column eluting with a gradient of hexane/ethyl acetate (10-25%) to afford 347 mg of the desired product (32) in 52% yield as a yellow solid. $^1$H-NMR (DMSO-d6) δ: 8.48 (1H, s), 8.17 (1H, s), 7.84 (1H, s), 5.03 (2H, s), 2.14 (3H, s).

Step 4

(5-(5,6-dichloropyridin-3-yl)oxazol-2-yl)methyl acetate

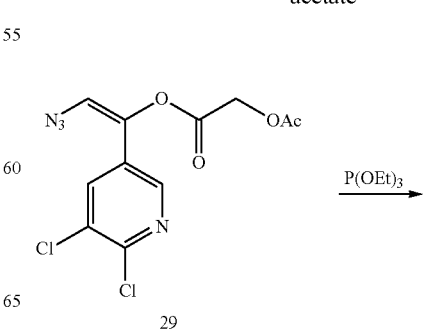

-continued

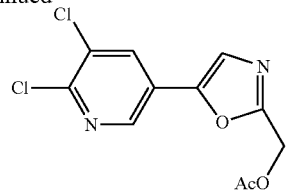

33

To a solution of (29) (347 mg, 1.05 mmol) in dioxane (25 ml) was added P(OEt)$_3$ (1.83 ml, 10.5 mmol) at room temperature. After being stirred for 1 hr at the same temperature, the reaction mixture was risen up to 90° C. After being stirred for 2.5 hrs, the reaction mixture was quenched with H$_2$O, diluted with ethyl acetate and extracted with ethyl acetate. The resulting organic layer was washed with brine, dried over Na$_2$SO$_4$ and concentrated in vacuo. The resulting product was chromatographed on silica gel eluting with a gradient of hexane/ethyl acetate (15-35%) to afford 484 mg of the desired product (33) in quant as a yellow oil. LC/MS (M+1): 287.

Reference Example 8

(5-(6-chloro-5-fluoropyridin-3-yl)-1,2,4-oxadiazol-3-yl)methanol

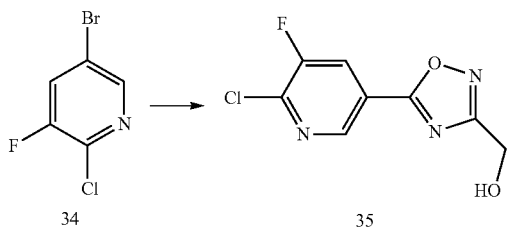 [SMILES: Fc1cc(Br)cnc1Cl ; OCc1noc(-c2cnc(Cl)c(F)c2)n1]

Compound (35) was obtained in the same manner to Example 1, steps 1 and 2. LC/MS (M+1): 230

Reference Example 9

The following compounds were obtained in similar manner to Reference Example 16 Step 1.

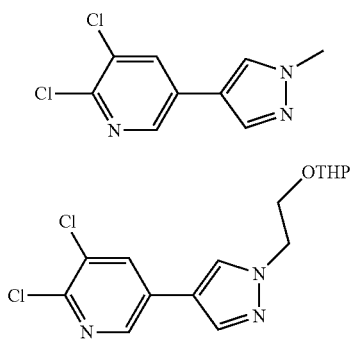

36a: 99% yield as a yellow solid.

2,3-dichloro-5-(1-methyl-1H-pyrazol-4-yl)pyridine $^1$H-NMR (400 MHz, DMSO-d6) δ: 8.66 (1H, s), 8.37 (2H, s), 8.07 (1H, s), 3.89 (3H, s).

LC/MS (M+1): 229.

36b: 97% yield as a yellow amorphous.

2,3-dichloro-5-(1-(2-(tetrahydro-2H-pyran-2-yloxy)ethyl)-1H-pyrazol-4-yl)pyridine

LC/MS (M+1): 342.

Reference Example 10

Step 1

(4R,5R)—N-(5,6-dichloropyridin-3-yl)-5-(hydroxymethyl)-2,2-dimethyl-1,3-dioxolane-4-carboxamide

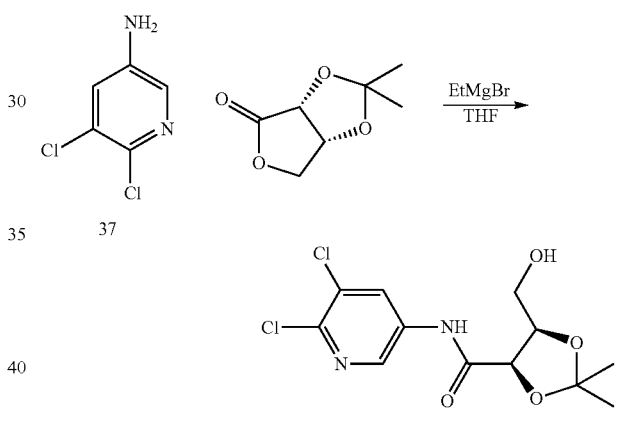

To a solution of 5,6-dichloropyridin-3-amine (37) (1.8 g, 11.0 mmol) in THF (6.0 ml) was dropwise added EtMgBr (1.0 M in THF) (14.3 ml, 14.3 mmol) via a droping funnel −78° C. under nitrogen to produce a tan solution. After being stirred for 20 min, the temperature of the reaction mixture was risen up to 0° C. The reaction mixture was stirred for additional 10 min and dropwise added (3aR,6aR)-2,2-dimethyldihydrofuro[3,4-d][1,3]dioxol-4 (3aH)-one (1.663 ml, 19.22 mmol) in THF (6 ml) at −78° C. Then after being stirred for 1 hr, the reaction mixture was quenched with 10% citric acid and diluted with ethyl acetate. The resulting organic layer was separated and the aqueous layer was extracted with ethyl acetate, the combined organic layers were washed with brine, dried over Na$_2$SO$_4$ and concentrated in vacuo. The crude product was chromatographed on silica gel eluting with a gradient of ethyl acetate (30-50%)/hexanes to afford 1.45 g of the desired product (38) in 41% yield as a brown oil.

$^1$H-NMR (DMSO-d6) δ: 10.09 (1H, s), 8.61 (1H, s), 8.43 (1H, s), 4.77 (1H, br), 4.70 (1H, d, J=7.58 Hz), 4.43 (1H, m), 3.58 (1H, m), 3.45 (1H, m), 1.55 (3H, s), 1.36 (3H, s).

LC/MS (M+1): 321.

Step 2

(3aR,6aR)-5-(5,6-dichloropyridin-3-yl)-2,2-dimethyldihydro-3aH-[1,3]dioxolo[4,5-c]pyrrol-4(5H)-one

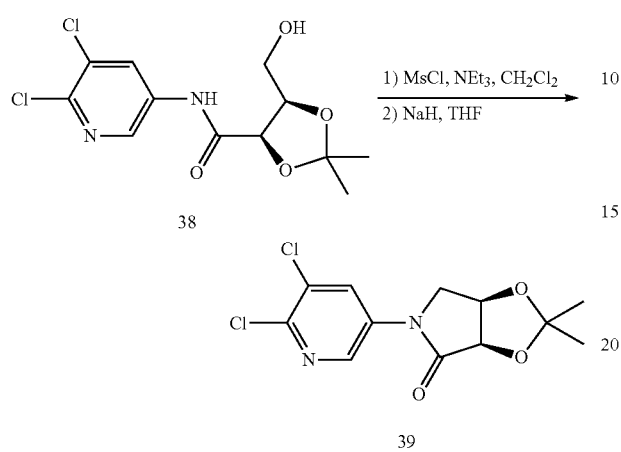

To a solution of alcohol (38) (190 mg, 0.592 mmol) in CH$_2$Cl$_2$ (2 ml) were added NEt$_3$ (205 μl, 1.48 mmol) and MsCl (60 μl, 0.77 mmol) at 0° C. under nitrogen. After being stirred for 30 min at room temperature, the reaction mixture was quenched with sat.NaHCO$_3$ and diluted with CH$_2$Cl$_2$. The resulting organic layer was separated and the aqueous layer was extracted with CH$_2$Cl$_2$, the combined organic layers were washed with H$_2$O and brine, dried over Na$_2$SO$_4$ and concentrated in vacuo. The residue was used for the next reaction without further purification.

To a solution of crude product in THF (3 ml) was added NaH (in 60 w % of oil) (70.9 mg, 1.77 mmol) at room temperature under nitrogen. After being stirred overnight at room temperature, the reaction mixture was quenched with 10% citric acid and diluted with ethyl acetate. The resulting organic layer was separated and the aqueous layer was extracted with ethyl acetate, the combined organic layers were washed with sat. NaHCO$_3$ and brine, dried over Na$_2$SO$_4$ and concentrated in vacuo. The crude product was chromatographed on silica gel eluting with a gradient of ethyl acetate (20-50%)/hexanes to afford 153 mg of the desired product (39) in 85% yield as a white solid. $^1$H-NMR (DMSO-d6) δ: 8.76 (1H, s), 8.55 (1H, s), 4.92-4.85 (2H, m), 4.10 (1H, dd, J=11.6, 4.29 Hz), 3.98 (1H, d, J=11.6 Hz), 1.35 (6H, s). LC/MS (M+1): 303.

Reference Example 11

The following compounds were obtained in the same manner to Example 1, Step 3.

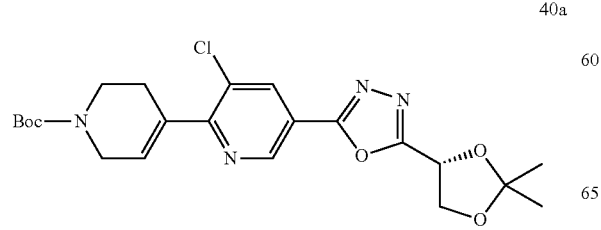

40a

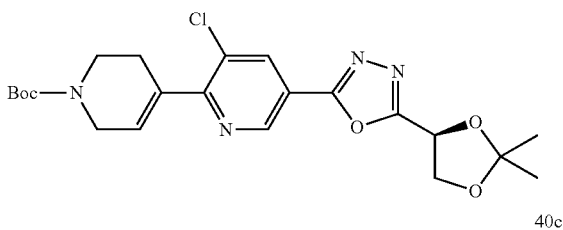

40b

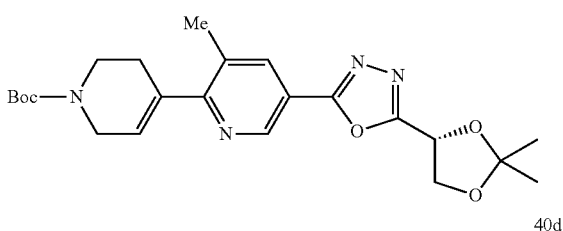

40c

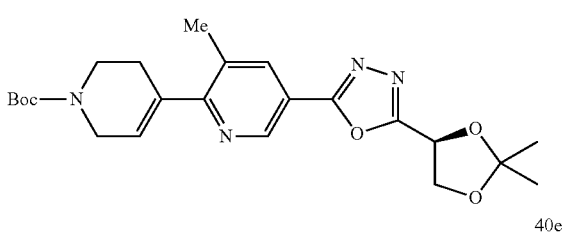

40d

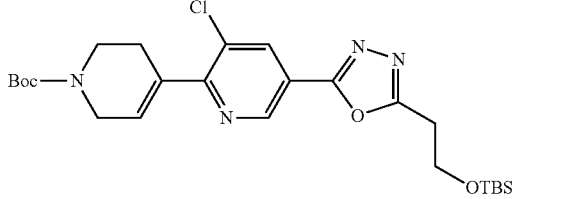

40e

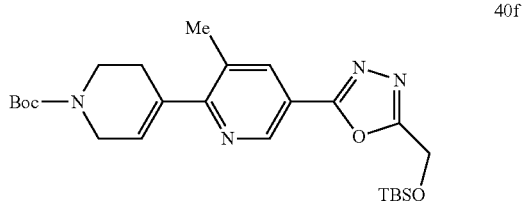

40f

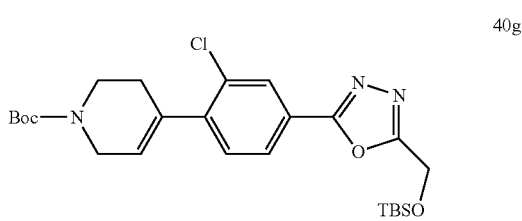

40g

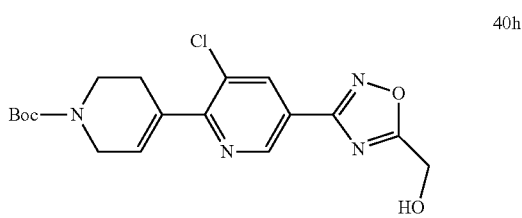

40h

-continued

40i 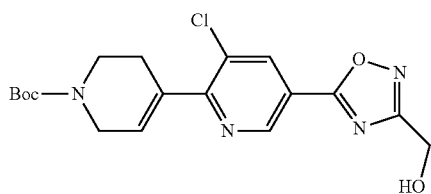

40j 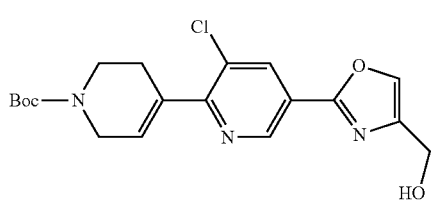

40k 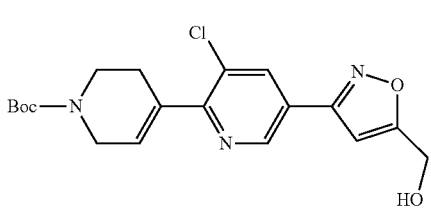

40l 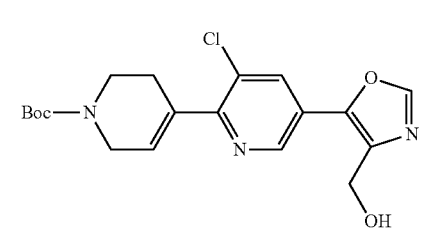

40m 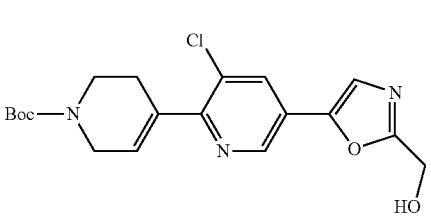

40n 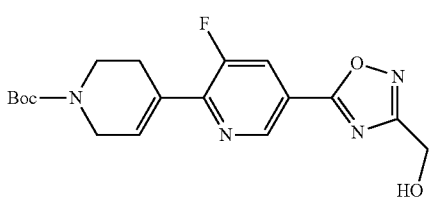

40o 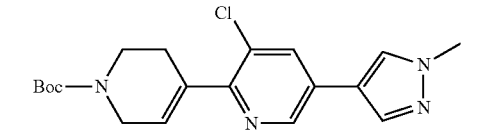

40p 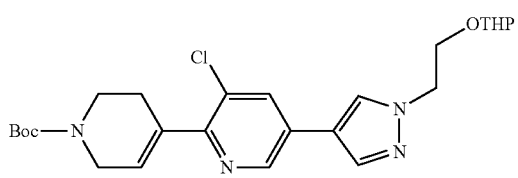

-continued

40q 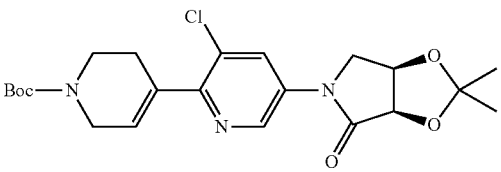

40a: quant as a orange oil (R)-tert-butyl4-(3-chloro-5-(5-(2,2-dimethyl-1,3-dioxolan-4-yl)-1,3,4-oxadiazol-2-yl)pyridin-2-yl)-5,6-dihydropyridine-1(2H)-carboxylate ¹H-NMR (DMSO-d6) δ: 9.08 (1H, d, J=1.98 Hz), 8.45 (1H, d, J=1.98 Hz), 6.37 (1H, br), 5.47 (1H, d, J=6.06 Hz), 4.41 (2H, br), 4.08 (2H, t, J=6.06 Hz), 3.56 (2H, br), 1.45 (12H, s) 1.42 (3H, s). LC/MS (M+1): 463.

40b: 96% as a orange amorphous (S)-tert-butyl4-(3-chloro-5-(5-(2,2-dimethyl-1,3-dioxolan-4-yl)-1,3,4-oxadiazol-2-yl)pyridin-2-yl)-5,6-dihydropyridine-1(2H)-carboxylate ¹H-NMR (DMSO-d6) δ: 9.08 (1H, d, J=1.98 Hz), 8.45 (1H, d, J=1.98 Hz), 6.37 (1H, br), 5.47 (1H, d, J=6.06 Hz), 4.41 (2H, br), 4.08 (2H, t, J=6.06 Hz), 3.56 (2H, br), 1.45 (12H, s) 1.42 (3H, s). LC/MS (M+1): 463.

40c: quant as a yellow amorphous (R)-tert-butyl4-(5-(5-(2,2-dimethyl-1,3-dioxolan-4-yl)-1,3,4-oxadiazol-2-yl)-3-methylpyridin-2-yl)-5,6-dihydropyridine-1(2H)-carboxylate

LC/MS (M+1): 443.

40d: quant as a yellow solid (S)-tert-butyl4-(5-(5-(2,2-dimethyl-1,3-dioxolan-4-yl)-1,3,4-oxadiazol-2-yl)-3-methylpyridin-2-yl)-5,6-dihydropyridine-1(2H)-carboxylate

LC/MS (M+1): 443.

40e: 98% as a yellow solid tert-butyl 4-(5-(5-(2-(tert-butyldimethylsilyloxy)ethyl)-1,3,4-oxadiazol-2-yl)-3-chloropyridin-2-yl)-5,6-dihydropyridine-1(2H)-carboxylate ¹H-NMR (DMSO-d6) δ: 9.06 (1H, s), 8.42 (1H, s), 6.36 (1H, br), 4.08-4.03 (4H, m), 3.56 (2H, br), 3.17 (2H, t, J=5.81 Hz), 2.54 (2H, br), 1.45 (9H, s), 0.79 (9H, s), 0.00 (6H, s). LC/MS (M+1): 521.

40f: quant as a yellow amorphous tert-butyl 4-(5-(5-((tert-butyldimethylsilyloxy)methyl)-1,3,4-oxadiazol-2-yl)-3-methylpyridin-2-yl)-5,6-dihydropyridine-1(2H)-carboxylate

LC/MS (M+1): 487.

40g: 90% as a yellow oil tert-butyl 4-(4-(5-((tert-butyldimethylsilyloxy)methyl)-1,3,4-oxadiazol-2-yl)-2-chlorophenyl)-5,6-dihydropyridine-1(2H)-carboxylate ¹H-NMR (DMSO-d6) δ: 7.98 (1H, s), 7.92 (1H, d, J=8.08 Hz), 7.53 (1H, d, J=8.08 Hz), 5.84 (1H, br), 4.97 (2H, s), 4.00

(2H, br), 3.55 (2H, br), 2.40 (2H, br), 1.44 (9H, s), 0.89 (9H, s), 0.13 (6H, s). LC/MS (M+1): 506.

40h: 92% as a yellow oil tert-butyl4-(3-chloro-5-(5-(hydroxymethyl)-1,2,4-oxadiazol-3-yl)pyridin-2-yl)-5,6-dihydropyridine-1(2H)-carboxylate ¹H-NMR (DMSO-d6) δ: 9.07 (1H, s), 8.40 (1H, s), 6.33 (1H, br), 6.14 (1H, t, J=6.06 Hz), 4.84 (2H, d, J=6.06 Hz), 4.07 (2H, br), 3.56 (2H, br), 2.53 (2H, br), 1.45 (9H, s). LC/MS (M+1): 393.

40i: 72% as a yellow oil tert-butyl4-(3-chloro-5-(3-(hydroxymethyl)-1,2,4-oxadiazol-5-yl)pyridin-2-yl)-5,6-dihydropyridine-1(2H)-carboxylate ¹H-NMR (DMSO-d6) δ: 9.17 (1H, s), 8.57 (1H, s), 6.39 (1H, br), 5.84 (1H, t, J=4.08 Hz), 4.66 (2H, d, J=4.04 Hz), 4.08 (2H, br), 3.57 (2H, t, J=5.56 Hz), 2.55 (2H, br), 1.45 (9H, s). LC/MS (M+1): 393.

40j: 65% as a yellow oil tert-butyl4-(3-chloro-5-(4-(hydroxymethyl)oxazol-2-yl)pyridin-2-yl)-5,6-dihydropyridine-1(2H)-carboxylate ¹H-NMR (DMSO-d6) δ: 9.04 (1H, s), 8.35 (1H, s), 8.15 (1H, s), 6.32 (1H, br), 5.32 (1H, br), 4.47 (2H, d, J=6.06 Hz), 4.06 (2H, br), 3.56 (2H, br), 2.51 (2H, br), 1.45 (9H, s). LC/MS (M+1): 392.

40k: quant as a yellow oil tert-butyl4-(3-chloro-5-(5-(hydroxymethyl)isoxazol-3-yl)pyridin-2-yl)-5,6-dihydropyridine-1(2H)-carboxylate

LC/MS (M+1): 392.

40l: quant as a brown oil.

tert-butyl4-(3-chloro-5-(4-(hydroxymethyl)oxazol-5-yl)pyridin-2-yl)-5,6-dihydropyridine-1(2H)-carboxylate

LC/MS (M+1): 392.

40m: 92% as a yellow oil tert-butyl4-(3-chloro-5-(2-(hydroxymethyl)oxazol-5-yl)pyridin-2-yl)-5,6-dihydropyridine-1(2H)-carboxylate ¹H-NMR (DMSO-d6) δ: 8.85 (1H, s), 8.25 (1H, s), 7.86 (1H, s), 6.26 (1H, br), 5.79 (1H, t, J=5.05 Hz), 4.59 (0.2H, d, J=5.05 Hz), 4.05 (2H, br), 3.55 (2H, br), 2.51 (2H, br), 1.45 (9H, s). LC/MS (M+1): 392.

40n: 41% yield as a yellow solid tert-butyl4-(3-fluoro-5-(3-(hydroxymethyl)-1,2,4-oxadiazol-5-yl)pyridin-2-yl)-5,6-dihydropyridine-1(2H)-carboxylate ¹H-NMR (DMSO-d6) δ: 9.08 (1H, s), 8.37 (1H, d, J=12.13 Hz), 6.77 (1H, br), 5.83 (1H, t, J=5.56 Hz), 4.66 (2H, d, J=5.56 Hz), 4.12 (2H, br), 3.55 (2H, br), 2.63 (2H, br), 1.44 (9H, s). LC/MS (M+1): 376.

40o: 23% yield as a orange solid tert-butyl-4-(3-chloro-5-(1-methyl-1H-pyrazol-4-yl)pyridin-2-yl)-5,6-dihydropyridine-1(2H)-carboxylate ¹H-NMR (DMSO-d6) δ: 8.76 (1H, s), 8.34 (1H, s), 8.13 (1H, s), 8.04 (1H, s), 6.18 (1H, br), 4.03 (2H, t, J=5.41 Hz), 3.88 (3H, s), 3.54 (2H, br), 2.58 (2H, br), 1.44 (9H, s).

LC/MS (M+1): 375.

40p: 68% yield as a orange oil.

tert-butyl-4-(3-chloro-5-(1-(2-(tetrahydro-2H-pyran-2-yloxy)ethyl)-1H-pyrazol-4-yl)pyridin-2-yl)-5,6-dihydropyridine-1(2H)-carboxylate ¹H-NMR (DMSO-d6) δ: 8.78 (1H, d, J=1.83 Hz), 8.39 (1H, s), 8.15 (1H, d, J=1.83 Hz), 8.08 (1H, s), 6.19 (1H, br), 4.55 (1H, br), 4.31 (2H, br), 4.03-3.94 (4H, br), 3.76 (1H, m), 3.54 (3H, br), 1.67-1.30 (6H, m). LC/MS (M+1): 489.

40q: 97% yield as a orange amorphous.

tert-butyl4-(3-chloro-5-((3aR,6aR)-2,2-dimethyl-4-oxo-3aH-[1,3]dioxolo[4,5-c]pyrrol-5(4H,6H,6aH)-yl)pyridin-2-yl)-5,6-dihydropyridine-1(2H)-carboxylate ¹H-NMR (DMSO-d6) δ: 8.84 (1H, s), 8.36 (1H, s), 6.18 (1H, br), 4.88 (2H, m), 4.12-3.96 (4H, m), 3.54 (2H, br), 2.51 (2H, br), 1.44 (9H, s), 1.34 (6H, s). LC/MS (M+1): 450.

Reference Example 12

Step 1

2,5-dibromo-3-chloropyridine

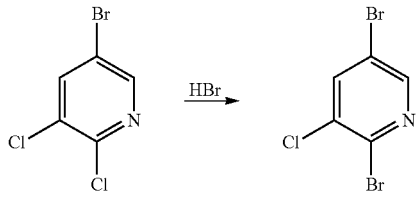

29  41

To 5-bromo-2,3-dichloropyridine (29) (11.7 g, 51.6 mmol) was added HBr (5M in AcOH) (51.6 ml, 258 mmol) at room temperature. Then the reaction mixture was heated to 70° C. After being stirred for 7 hrs at 70° C., the reaction mixture was diluted with ethyl acetate, quenched with H₂O and extracted with ethyl acetate. The resulting organic layer was washed with 1M NaOH, dried over over Na₂SO₄ and concentrated in vacuo. The residue was recrystallized from hexane-ethyl acetate to afford 11.2 g of the desired product (41) in 80% yield as a white solid. ¹H-NMR (DMSO-d6) δ: 8.55 (1H, s), 8.49 (1H, s).

Step 2 tert-butyl4-(5-bromo-3-chloropyridin-2-yl)-4-hydroxypiperidine-1-carboxylate

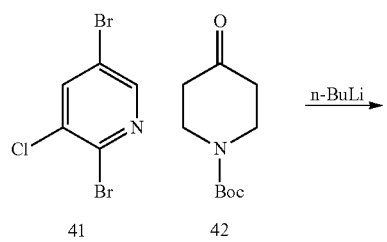

To a solution of (41) (11.2 g, 41.2 mmol) in toluene (150 ml) was dropwise added n-butyl lithium (2.73 M in hexane) (16.6 ml, 45.3 mmol) at −60° C. and stirred at the same temperature for 10 min. The solution of tert-butyl4-oxopiperidine-1-carboxylate (42) (8.62 g, 43.3 mmol) in toluene (14 ml) was dropwise added to the reaction mixture at −60° C. After being stirred for 1 hr at −60° C., the reaction mixture was quenched with 10% citric acid and extracted with ethyl acetate. The resulting organic layer was washed with brine, dried over $Na_2SO_4$ and concentrated in vacuo. The crude product was chromatographed on silica gel eluting with a gradient of hexane/ethyl acetate (15-20%) to afford 9.1 g of the desired product (43) in 56% yield as a colorless amorphous. $^1$H-NMR (DMSO-d6) δ: 8.62 (1H, s), 8.24 (1H, s), 5.40 (1H, s), 3.77 (2H, d, J=10.61 Hz), 3.20 (2H, br), 2.02 (2H, m), 1.87 (2H, d, J=12.63 Hz), 1.40 (9H, s).

Step 3 tert-butyl4-(5-bromo-3-chloropyridin-2-yl)-4-fluoropiperidine-1-carboxylate

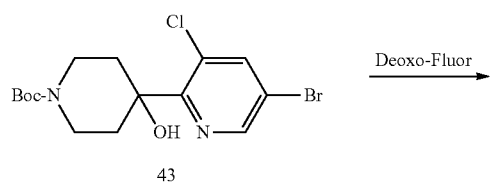

To a solution of alcohol (43) (9.1 g, 23.2 mmol) in toluene (100 ml) was added Deoxo-Fluor (Bis(2-methoxyethyl)aminosulfur trifluoride, 4.71 ml, 25.5 mmol) at −40° C. Then the reaction mixture was risen up to 0° C. over 1 hr and stirred at the same temperature for 2 hrs. Then the reaction mixture was quenched with $H_2O$ and extracted with ethyl acetate. The resulting organic layer was washed with sat. $NaHCO_3$ and brine, dried over $Na_2SO_4$ and concentrated in vacuo. The crude product was chromatographed on silica gel eluting with a gradient of hexane/ethyl acetate (15-20%) to afford 6.0 g of the desired product (44) in 65% yield as a white solid. $^1$H-NMR (DMSO-d6) δ: 8.69 (1H, s), 8.39 (1H, s), 3.92 (2H, m), 3.14 (2H, br), 2.19-2.04 (4H, m), 1.41 (9H, s).

Step 4 tert-butyl-4-(3-chloro-5-cyanopyridin-2-yl)-4-fluoropiperidine-1-carboxylate

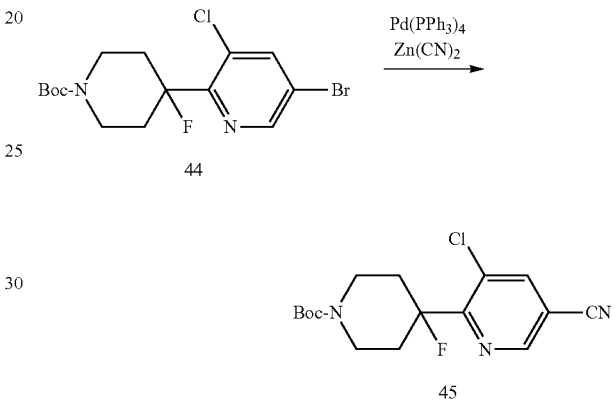

To a solution of (44) (902 mg, 2.29 mmol) in DMF (9 ml) was added $Zn(CN)_2$ together with $Pd(PPh_3)_4$ at room temperature. The reaction mixture was heated to 120° C. for 1 hr by microwave. Then the reaction mixture was quenched with $H_2O$ and extracted with ethyl acetate. The resulting organic layer was washed with brine, dried over $Na_2SO_4$ and concentrated in vacuo. The crude product was chromatographed on silica gel eluting with a gradient of hexane/ethyl acetate (5-15%) to afford 494 mg of the desired product (45) in 63% yield as a white solid. $^1$H-NMR (DMSO-d6) δ: 9.02 (1H, s), 8.67 (1H, s), 3.94 (2H, m), 3.14 (2H, br), 2.20-2.09 (4H, m), 1.41 (9H, s).

Step 5 tert-butyl-4-(3-chloro-5-(5-(hydroxymethyl)-1,2,4-oxadiazol-3-yl)pyridin-2-yl)-4-fluoropiperidine-1-carboxylate

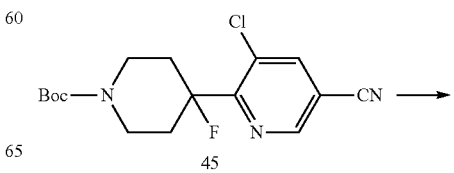

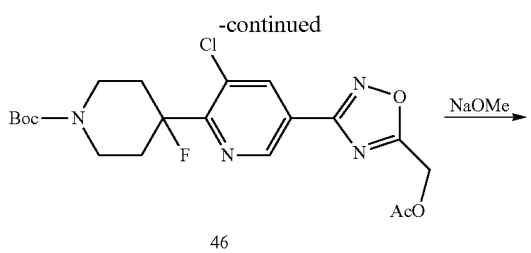

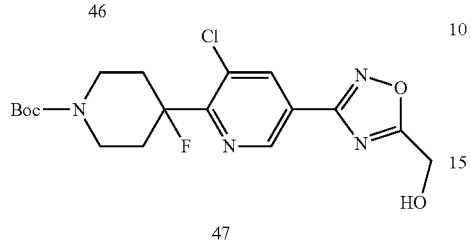

The compound (46) was obtained using the procedures shown Reference Example 2, Steps 1 and 2. The residue was used for the next reaction without further purification.

To a solution of (46) (359 mg, 0.788 mmol) in THF (2 ml) and MeOH (2 ml) was added NaOMe (42.6 mg, 0.788 mmol) at 0° C. After being stirred for 30 min at the same temperature, the reaction mixture was quenched with $H_2O$ and extracted with ethyl acetate. The resulting organic layer was washed with brine, dried over $Na_2SO_4$ and concentrated in vacuo. The crude product was chromatographed on silica gel eluting with a gradient of hexane/ethyl acetate (20-40%) to afford 310 mg of the desired product (47) in 95% yield as a white amorphous. $^1$H-NMR (DMSO-d6) δ: 9.09 (1H, s), 8.44 (1H, s), 6.15 (1H, t, J=5.05 Hz), 4.85 (2H, d, J=5.05 Hz), 3.96 (2H, m), 3.17 (2H, br), 2.25-2.13 (4H, m), 1.42 (9H, s). LC/MS (M+1): 413.

Reference Example 13

Step 1 tert-butyl-4-(3-chloro-5-formylpyridine-2-yl)-4-fluoropiperidine-1-carboxylate

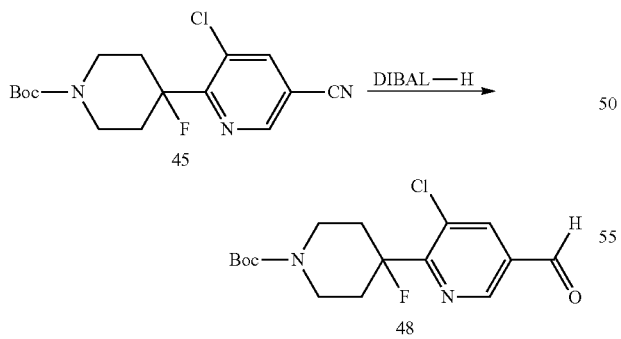

To a solution of (45) (100 mg, 0.294 mmol) in toluene (2 ml) was added DIBAL-H (0.95M in toluene) (1.95 ml, 1.85 mmol) at −78° C. After being stirred for 5 hrs at the same temperature, the reaction mixture was quenched with $H_2O$ and extracted with ethyl acetate. The resulting organic layer was washed with brine, dried over $Na_2SO_4$ and concentrated in vacuo. The crude product was chromatographed on silica gel eluting with a gradient of hexane/ethyl acetate (15-20%) to afford 43 mg of the desired product (48) in 42% yield as a colorless oil. $^1$H-NMR (DMSO-d6) δ: 10.11 (1H, s), 9.00 (1H, s), 8.39 (1H, s), 3.96 (2H, m), 3.15 (2H, br), 2.23-2.12 (4H, m), 1.42 (9H, s).

Step 2 tert-butyl-4-(3-chloro-5-(5-(hydroxymethyl)isoxazol-3-yl)pyridin-2-yl)-4-fluoropiperidine-1-carboxylate

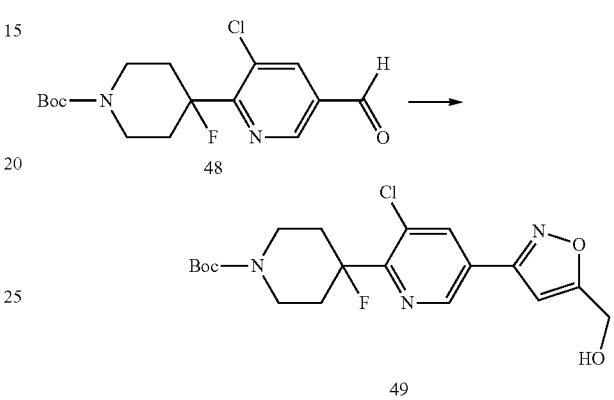

The compound (49) was obtained using the procedure shown Reference Example 5, Steps 2 and 3 and chromatographed on silica gel eluting with a gradient of hexane/ethyl acetate (20-40%) to afford 463 mg of the desired product (49) in 72% yield as a white amorphous. $^1$H-NMR (DMSO-d6) δ: 9.02 (1H, s), 8.43 (1H, s), 7.14 (1H, s), 5.80 (1H, t, J=5.81 Hz), 4.65 (2H, d, J=5.81 Hz), 3.95 (2H, m), 3.17 (2H, br), 2.25-2.13 (4H, m), 1.42 (9H, s). LC/MS (M+1): 412.

Reference Example 14

Step 1

6-(1-(tert-butoxycarbonyl)-4-fluoropiperidin-4-yl)-5-chloronicotinic acid

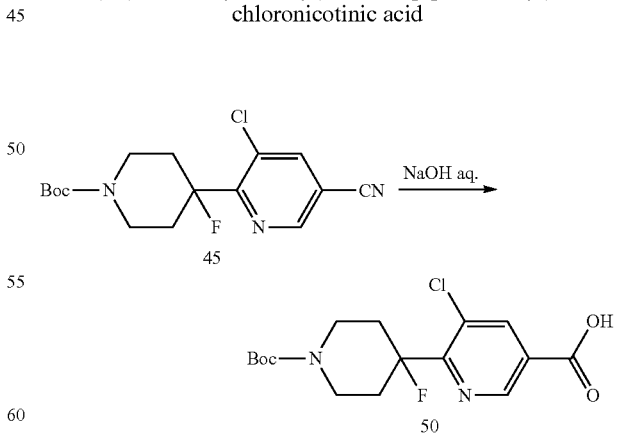

To a solution of (45) (1.26 g, 3.71 mmol) in THF (10 ml) and EtOH (20 ml) was added NaOH aq. (2M in $H_2O$) (18.5 ml, 37.1 mmol) at 0° C. After being stirred for 2 hrs at reflux temperature, the reaction mixture was quenched with 1M HCl aq and extracted with ethyl acetate. The resulting organic layer was dried over Na₂SO₄ and concentrated in vacuo. The residue was used for the next reaction without further purification. ¹H-NMR (DMSO-d6) δ: 8.96 (1H, s), 8.31 (1H, s), 3.95 (2H, m), 3.16 (2H, br), 2.23-2.12 (4H, m), 1.42 (9H, s). LC/MS (M+1): 359.

Step 2 tert-butyl-4-(3-chloro-5-(4-(hydroxymethyl)oxazol-5-yl)pyridin-2-yl)-4-fluoropiperidine-1-carboxylate

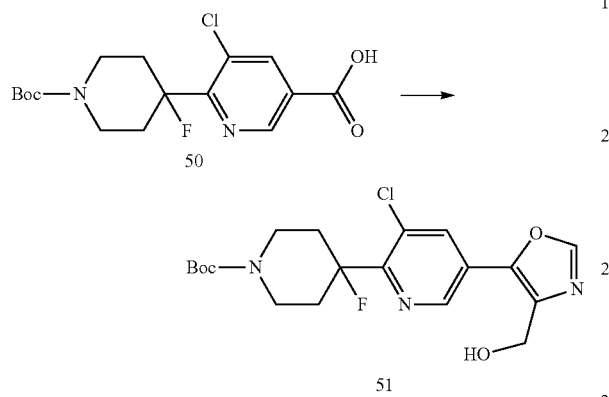

The compound (51) was obtained using the procedure shown Reference Example 6, Steps 1 and 2 and chromatographed on silica gel eluting with a gradient of hexane/ethyl acetate (30-60%) to afford 204 mg of the desired product (51) in 42% yield as a brown amorphous. ¹H-NMR (DMSO-d6) δ: 8.88 (1H, s), 8.53 (1H, s), 8.27 (1H, s), 5.51 (1H, br), 4.59 (2H, br), 3.95 (2H, m), 3.16 (2H, br), 2.25-2.12 (4H, m), 1.42 (9H, s).

Reference Example 15 tert-butyl-4-(3-chloro-5-(3-(hydroxymethyl)-1,2,4-oxadiazol-5-yl)pyridin-2-yl)-4-fluoropiperidine-1-carboxylate

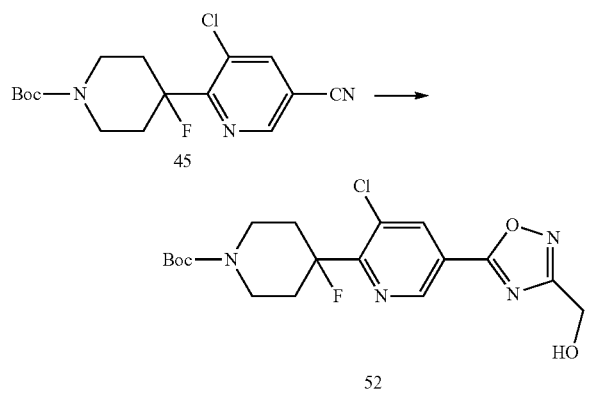

The compound (52) was obtained using the procedure shown Reference Example 3, Steps 1 and 2 and chromatographed on silica gel eluting with a gradient of hexane/ethyl acetate (30-60%) to afford 368 mg of the desired product (52) in 90% yield as a brown amorphous. LC/MS (M+1): 413.

Reference Example 16

Step 1 tert-butyl-4-fluoro-4-(5-(5-formylfuran-2-yl)-3-methylpyridin-2-yl)piperidine-1-carboxylate

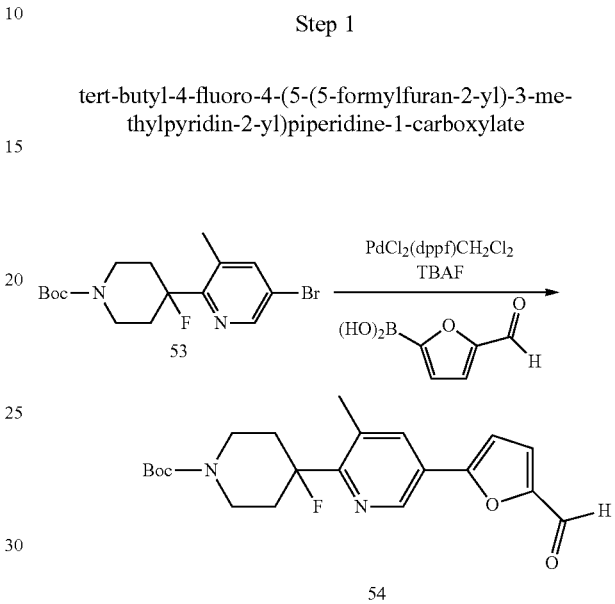

To a solution of (53) (1 g, 2.68 mmol) in THF (10 ml) was added 5-formylfuran-2-yl boronic acid (431 mg, 3.08 mmol) together with PdCl₂(dppf)CH₂Cl₂ (131 mg, 0.161 mmol) at room temperature. The reaction mixture was heated to 85° C. for 1 hr. Then the reaction mixture was quenched with H₂O and extracted with ethyl acetate. The resulting organic layer was washed with brine, dried over Na₂SO₄ and concentrated in vacuo. The crude product waschromatographed on silica gel eluting with a gradient of hexane/ethyl acetate (10-35%) to afford 905 mg of the desired product (54) in 87% yield as an orange amorphous. ¹H-NMR (DMSO-d6) δ: 9.65 (1H, s), 8.88 (1H, s), 8.09 (1H, s), 7.69 (1H, d, J=3.54 Hz), 7.43 (1H, d, J=3.54 Hz), 3.96 (2H, brm), 3.13 (2H, br), 2.54 (3H, s), 2.25-2.01 (4H, m), 1.43 (9H, s).

Step 2 tert-butyl-4-fluoro-4-(5-(5-(hydroxymethyl)furan-2-yl)-3-methylpyridin-2-yl)piperidine-1-carboxylate

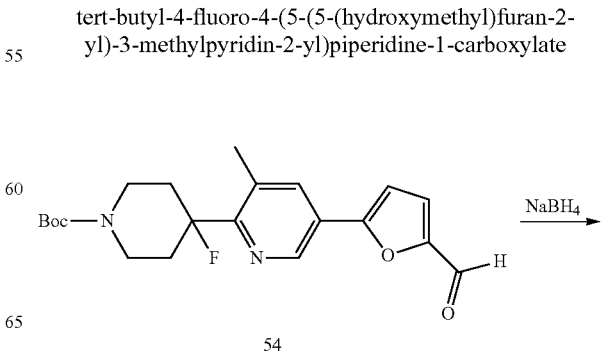

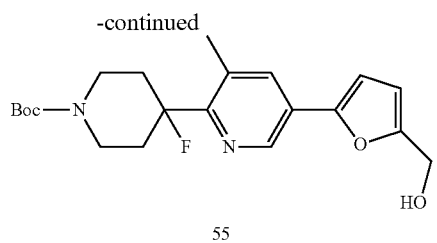

To a solution of (54) (1.05 g, 2.70 mmol) in THF (10 ml) and EtOH (10 ml) was added NaBH$_4$ (107 mg, 2.84 mmol) at 0° C. under nitrogen. After being stirred for 30 min at the same temperature, the reaction mixture was quenched with 10% citric acid and extracted with ethyl acetate. The resulting organic layer was washed with brine, dried over Na$_2$SO$_4$ and concentrated in vacuo. The liquid residue was chromatographed on silica gel eluting with a gradient of hexane/ethyl acetate (20-40%) to afford 940 mg of the desired product (55) in 89% yield as a brown solid. $^1$H-NMR (DMSO-d6) δ: 8.69 (1H, s), 7.88 (1H, s), 7.03 (1H, s), 6.45 (1H, s), 5.34 (1H, br), 4.47 (2H, br), 3.95 (2H, m), 3.14 (2H, br), 2.20-2.01 (4H, m), 1.43 (9H, s).

Reference Example 17 tert-butyl-2-(5-(5-((tert-butyldimethylsilyloxy)methyl)-1,3,4-oxadiazol-2-yl)-3-chloropyridin-2-ylamino)ethylcarbamate

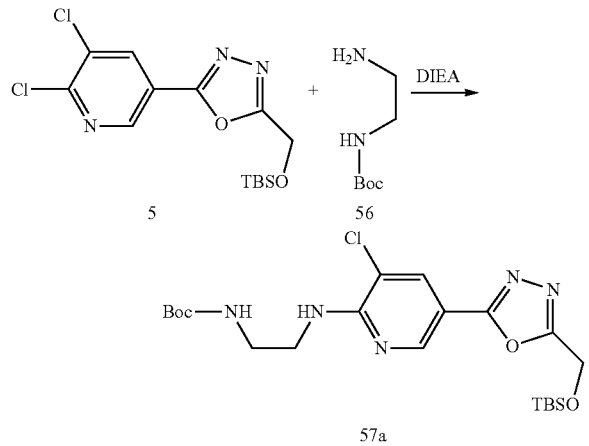

To a solution of (5) (400 mg, 1.11 mmol) in NMP (1.0 ml) were added tert-butyl 2-aminoethylcarbamate (445 mg, 2.78 mmol) and DIEA (0.388 ml, 2.22 mmol) at room temperature under nitrogen. Then the reaction mixture was heated to 120° C. by microwave. After being stirred for 1 hr at the same temperature, the reaction mixture was quenched with H$_2$O and extracted with ethyl acetate. The resulting organic layer was washed with H$_2$O and brine, dried over Na$_2$SO$_4$ and concentrated in vacuo. The liquid residue was chromatographed on silica gel eluting with a gradient of hexane/ethyl acetate (20-40%) to afford 412 mg of the desired product (57a) in 77% as a colorless amorphous.
$^1$H-NMR (DMSO-d6) δ: 8.55 (1H, s), 8.04 (1H, s), 7.35 (1H, br), 6.95 (1H, br), 4.93 (2H, s), 3.50 (2H, m), 3.18 (2H, m), 1.38 (9H, s), 0.89 (9H, s), 0.13 (6H, s). LC/MS (M+1): 484.

Reference Example 18

The following compounds were synthesized in similar manner to Reference Example 17.

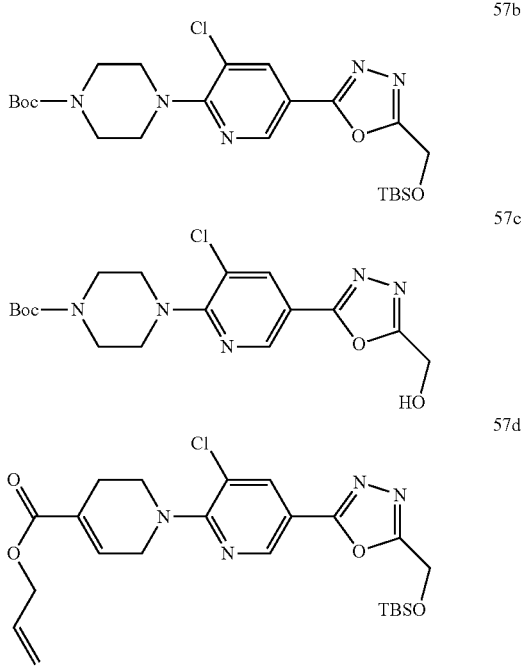

57b: 98% as a yellow oil tert-butyl-4-(5-(5-((tert-butyldimethylsilyloxy)methyl)-1,3,4-oxadiazol-2-yl)-3-chloropyridin-2-yl)piperazine-1-carboxylate $^1$H-NMR (DMSO-d6) δ: 8.73 (1H, s), 8.22 (1H, s), 4.95 (2H, s), 3.47 (8H, brm), 1.43 (9H, s), 0.89 (9H, s), 0.13 (6H, s). LC/MS (M+1): 510.

57c: 88% as a yellow solid tert-butyl-4-(3-chloro-5-(3-(hydroxymethyl)-1,2,4-oxadiazol-5-yl)pyridin-2-yl)piperazine-1-carboxylate $^1$H-NMR (DMSO-d6) δ: 8.86 (1H, s), 8.34 (1H, s), 5.77 (1H, t, J=5.05 Hz), 4.61 (2H, d, J=5.05 Hz), 3.50 (8H, br), 1.43 (9H, s). LC/MS (M+1): 396.

57d: 56% as a yellow oil allyl-1-(5-(5-((tert-butyldimethylsilyloxy)methyl)-1,3,4-oxadiazol-2-yl)-3-chloropyridin-2-yl)-1,2,3,6-tetrahydropyridine-4-carboxylate $^1$H-NMR (DMSO-d6) δ: 8.73 (1H, s), 8.25 (1H, s), 6.93 (1H, d, J=7.58 Hz), 5.93 (1H, br), 5.32 (1H, d, J=17.18 Hz), 5.23 (1H, d, J=10.61 Hz), 4.94 (3H, brm), 4.60 (2H, d, J=3.54 Hz), 3.74 (2H, brm), 3.65 (1H, brm), 2.05 (2H, brm), 0.88 (9H, s), 0.12 (6H, s).
LC/MS (M+1): 491.

Reference Example 19

(E)-ethyl-3-(5-(5-(((tert-butyldimethylsilyloxy)methyl)-1,3,4-oxadiazol-2-yl)-3-chloropyridin-2-yl)acrylate

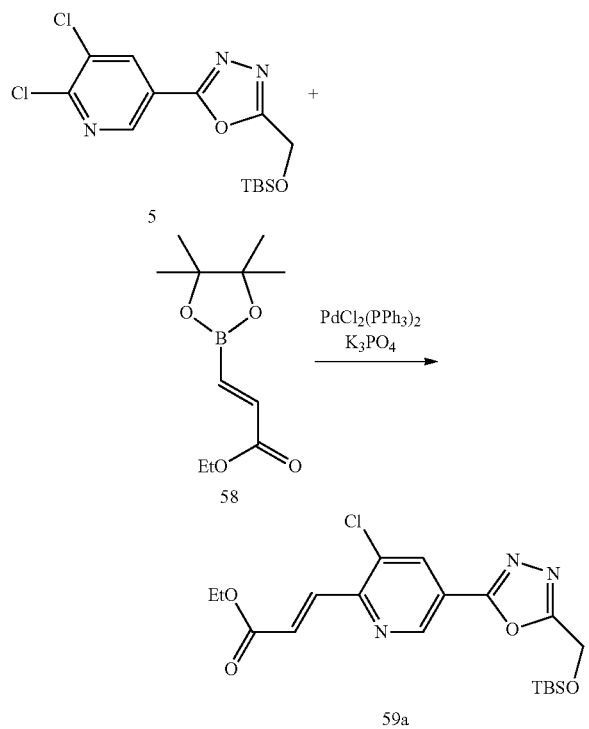

To a solution of (5) (109 mg, 0.302 mmol) in dioxane (1.0 ml) and EtOH (1.0 ml) were added (E)-ethyl 3-(4,4,5,5-tetramethyl-1,3,2-dioxaborolan-2-yl)acrylate (82 mg, 0.363 mmol), PdCl$_2$(PPh$_3$)$_4$ (12.7 mg, 0.018 mmol) and K$_3$PO$_4$ (64.2 mg, 0.302 mmol) at room temperature under nitrogen. Then the reaction mixture was heated to 90° C. After being stirred for 6 hrs at 90° C., the reaction mixture was quenched with H$_2$O and extracted with ethyl acetate. The resulting organic layer was washed with H$_2$O and brine, dried over Na$_2$SO$_4$ and concentrated in vacuo. The liquid residue was chromatographed on silica gel eluting with a gradient of hexane/ethyl acetate (5-15%) to afford 81.9 mg of the desired product (59a) in 64% as a yellow solid.

$^1$H-NMR (DMSO-d6) δ: 9.14 (1H, s), 8.51 (1H, s), 7.98 (1H, d, J=16.17 Hz), 7.06 (1H, d, J=15.16 Hz), 4.99 (2H, s), 4.25 (2H, q, J=7.07 Hz), 1.28 (3H, t, J=7.07 Hz), 0.89 (9H, s), 0.14 (6H, s). LC/MS (M+1): 424.

Reference Example 20

The following compounds were synthesized in similar manner to Reference Example 19.

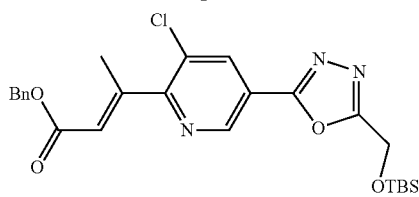

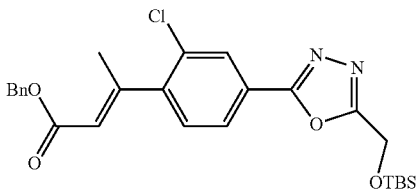

59b: 47% as a colorless oil (E)-benzyl-3-(5-(5-(((tert-butyldimethylsilyloxy)methyl)-1,3,4-oxadiazol-2-yl)-3-chloropyridin-2-yl)but-2-enoate $^1$H-NMR (DMSO-d6) δ: 9.08 (1H, s), 8.47 (1H, s), 7.40-7.30 (5H, m), 6.18 (1H, s), 5.21 (2H, s), 4.99 (2H, s), 2.47 (3H, s), 0.88 (9H, s), 0.13 (6H, s). LC/MS (M+1): 500.

59c: 32% as a yellow oil (E)-benzyl-3-(4-(5-(((tert-butyldimethylsilyloxy)methyl)-1,3,4-oxadiazol-2-yl)-2-chlorophenyl)but-2-enoate $^1$H-NMR (DMSO-d6) δ: 8.02 (1H, s), 7.95 (1H, d, J=7.58 Hz), 7.58 (1H, d, J=7.58 Hz), 7.40-7.34 (5H, m), 5.95 (1H, s), 5.20 (2H, s), 4.96 (2H, s), 2.44 (3H, s), 0.88 (9H, s), 0.12 (6H, s). LC/MS (M+1): 499.

Reference Example 21

(E)-3-(4-(5-(((tert-butyldimethylsilyloxy)methyl)-1,3,4-oxadiazol-2-yl)-2-chlorophenyl)but-2-enoic acid

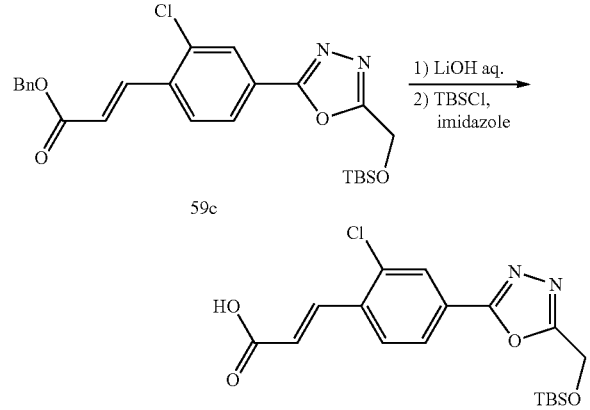

To a solution of 59c (613 mg, 0.60 mmol) in THF (3 ml) and EtOH (3 ml) was added LiOH aq. (38 mg, 0.90 mmol) in H$_2$O (1 ml) at room temperature. After being stirred for overnight at the same temperature, the reaction mixture was quenched with 1M HCl aq. and extracted with ethyl acetate. The resulting organic layer was washed with brine, dried over Na$_2$SO$_4$ and concentrated in vacuo. The residue was used for the next reaction without further purification. To a solution of resulting crude compound in THF (2 ml) were added imidazole (246 mg, 3.60 mmol) and TBSCl (362 mg, 2.40 mmol) at room temperature under nitrogen. After being stirred for 5 hrs at the same temperature, the reaction mixture was quenched with 1M HCl aq. and extracted with ethyl acetate. The resulting organic layer was washed with brine, dried over Na$_2$SO$_4$ and concentrated in vacuo. The resulting product was used for the next reaction without further purification.

LC/MS (M+1): 409.

Reference Example 22

The following compounds were synthesized in similar manner to Reference Example 21.

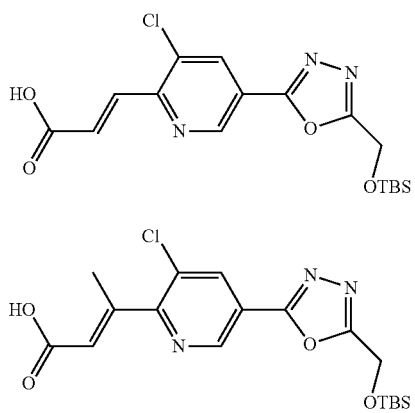

60a: (E)-3-(5-(5-((tert-butyldimethylsilyloxy)methyl)-1,3,4-oxadiazol-2-yl)-3-chloropyridin-2-yl)acrylic acid

LC/MS (M+1): 396.

60b: (E)-3-(5-(5-((tert-butyldimethylsilyloxy)methyl)-1,3,4-oxadiazol-2-yl)-3-chloropyridin-2-yl)but-2-enoic acid $^1$H-NMR (DMSO-d6) δ: 9.10 (1H, s), 8.50 (1H, s), 6.06 (1H, s), 5.00 (2H, s), 2.44 (3H, s), 0.89 (9H, s), 0.14 (6H, s).LC/MS (M+1): 410.

Reference Example 23

3-(4-(5-((tert-butyldimethylsilyloxy)methyl)-1,3,4-oxadiazol-2-yl)-2-chlorophenyl)prop-2-yn-1-ol

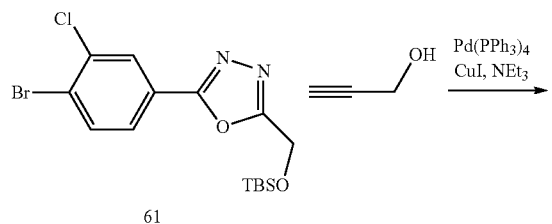

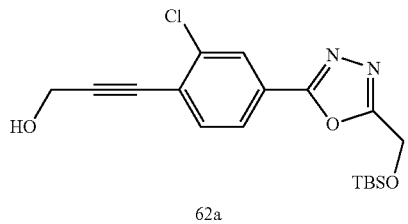

To a solution of (61) (300 mg, 0.743 mmol) in DMF (3 ml) were added prop-2-yn-1-ol (58.3 mg, 1.04 mmol), Pd(PPh$_3$)$_4$ (51.5 mg, 0.045 mmol), CuI (14.2 mg, 0.074 mmol) and NEt$_3$ (0.206 ml, 1.486 mmol) at room temperature under nitrogen. Then the reaction mixture was heated to 85° C. After being stirred for 2 hrs at 85° C., the reaction mixture was quenched with H$_2$O and extracted with ethyl acetate. The resulting organic layer was washed with H$_2$O and brine, dried over Na$_2$SO$_4$ and concentrated in vacuo. The liquid residue was chromatographed on silica gel eluting with a gradient of hexane/ethyl acetate (10-30%) to afford 281 mg of the desired product (62a) in quant as a yellow solid. $^1$H-NMR (DMSO-d6) δ: 8.07 (1H, s), 7.93 (1H, d, J=8.08 Hz), 7.78 (1H, d, J=8.08 Hz), 5.50 (1H, t, J=5.56 Hz), 4.97 (2H, s), 4.40 (2H, d, J=5.56 Hz), 0.89 (9H, s), 0.13 (6H, s). LC/MS (M+1): 379.

Reference Example 24

The following compounds were synthesized in similar manner to Reference Example 23.

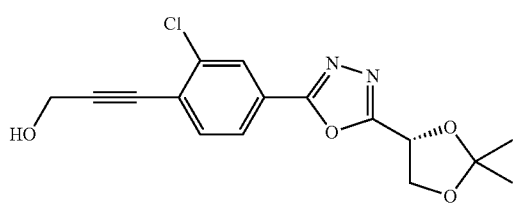

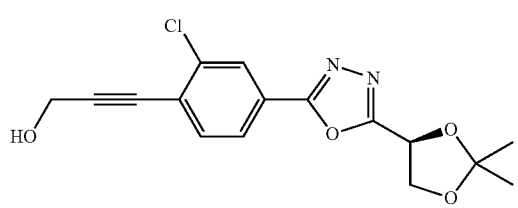

62b: 85% as a yellow solid (R)-3-(2-chloro-4-(5-(2,2-dimethyl-1,3-dioxolan-4-yl)-1,3,4-oxadiazol-2-yl)phenyl)prop-2-yn-1-ol $^1$H-NMR (DMSO-d6) δ: 8.09 (1H, s), 7.95 (1H, d, J=8.08 Hz), 7.78 (1H, d, J=8.08 Hz), 5.52 (1H, t, J=6.32 Hz), 5.46 (1H, t, J=5.56 Hz), 4.40 (4H, m), 1.45 (3H, s), 1.41 (3H, s). LC/MS (M+1): 335.

62c: 79% as an orange solid (S)-3-(2-chloro-4-(5-(2,2-dimethyl-1,3-dioxolan-4-yl)-1,3,4-oxadiazol-2-yl)phenyl)prop-2-yn-1-ol ¹H-NMR (DMSO-d6) δ: 8.09 (1H, s), 7.95 (1H, d, J=8.08 Hz), 7.78 (1H, d, J=8.08 Hz), 5.52 (1H, t, J=6.32 Hz), 5.46 (1H, t, J=5.56 Hz), 4.40 (4H, m), 1.45 (3H, s), 1.41 (3H, s). LC/MS (M+1): 335.

Reference Example 25

3-(4-(5-((tert-butyldimethylsilyloxy)methyl)-1,3,4-oxadiazol-2-yl)-2-chlorophenyl)propiolaldehyde

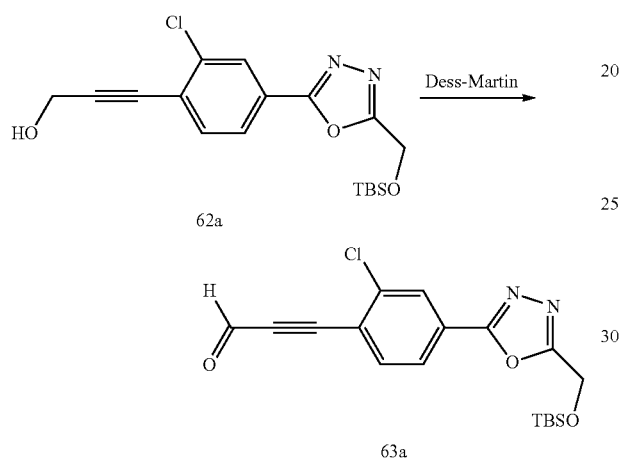

To a solution of (62a) (280 mg, 0.739 mmol) in CH₂Cl₂ (3 ml) was added Dess-Martin (376 mg, 0.887 mmol) at 0° C. under nitrogen. After being stirred for 30 min at 0° C., the reaction mixture was quenched with sat. NaHCO₃ and diluted with ethyl acetate. The resulting organic layer was separated and the aqueous layer was extracted with ethyl acetate, the combined organic layers were washed with Na₂S₂O₃, H₂O and brine, dried over Na₂SO₄ and concentrated in vacuo. The liquid residue was chromatographed on silica gel eluting with a gradient of hexane/ethyl acetate (15-20%) to afford 211 mg of the desired product (63a) in 76% as a white solid. ¹H-NMR (DMSO-d6) δ: 9.52 (1H, s), 8.18 (1H, s), 8.04 (2H, s), 4.99 (2H, s), 0.89 (9H, s), 0.14 (6H, s).

Reference Example 26

The following compounds were synthesized in similar manner to Reference Example 25.

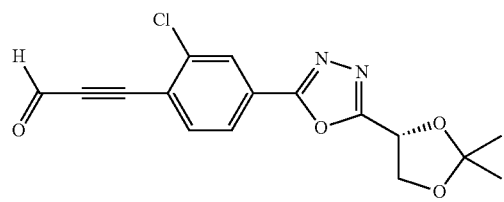

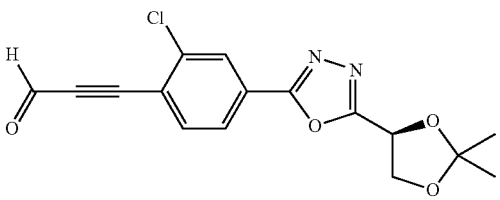

63b: quant as a white solid (R)-3-(2-chloro-4-(5-(2,2-dimethyl-1,3-dioxolan-4-yl)-1,3,4-oxadiazol-2-yl)phenyl)propiolaldehyde

LC/MS (M+1): 333.

63c: 93% as a white solid (S)-3-(2-chloro-4-(5-(2,2-dimethyl-1,3-dioxolan-4-yl)-1,3,4-oxadiazol-2-yl)phenyl)propiolaldehyde

LC/MS (M+1): 333.

Reference Example 27

3-(4-(5-((tert-butyldimethylsilyloxy)methyl)-1,3,4-oxadiazol-2-yl)-2-chlorophenyl)propiolic acid

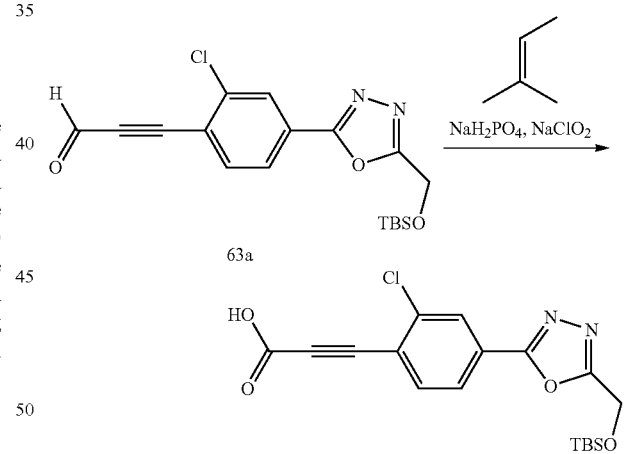

To a solution of (63a) (211 mg, 0.560 mmol) in t-BuOH (2 ml) and H₂O (1 ml) were added extra 2-methylbut-2-ene (1 ml), NaH₂PO₄.2H₂O (131 mg, 0.840 mmol) and NaClO₄ (152 mg, 1.68 mmol) at 0° C. After being stirred overnight at room temperature, the reaction mixture was quenched with 1M HCl aq. and diluted with ethyl acetate. The resulting organic layer was separated and the aqueous layer was extracted with ethyl acetate, the combined organic layers were washed with Na₂S₂O₃ and brine, dried over Na₂SO₄ and concentrated in vacuo. The resulting product was used for the next reaction without further purification. LC/MS (M+1): 393.

119

Reference Example 28

The following compounds were synthesized in similar manner to Reference Example 27.

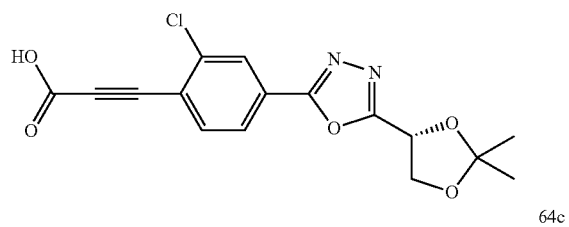

64b

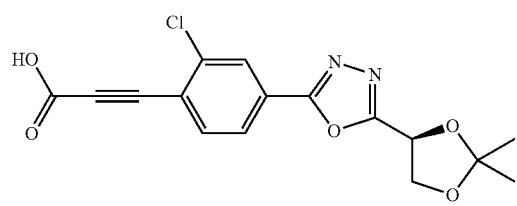

64c

64b: (R)-3-(2-chloro-4-(5-(2,2-dimethyl-1,3-dioxolan-4-yl)-1,3,4-oxadiazol-2-yl)phenyl)propiolic acid

LC/MS (M+1): 349.

64c: (S)-3-(2-chloro-4-(5-(2,2-dimethyl-1,3-dioxolan-4-yl)-1,3,4-oxadiazol-2-yl)phenyl)propiolic acid

LC/MS (M+1): 349.

Reference Example 29

1-(5-(5-(((tert-butyldimethylsilyloxy)methyl)-1,3,4-oxadiazol-2-yl)-3-chloropyridin-2-yl)-1,2,3,6-tetrahydropyridine-4-carboxylic acid

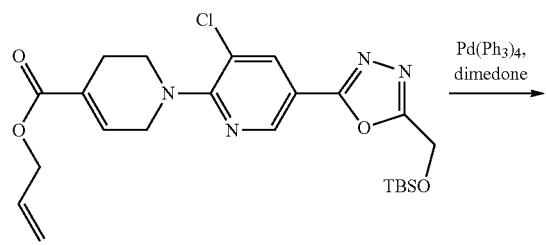

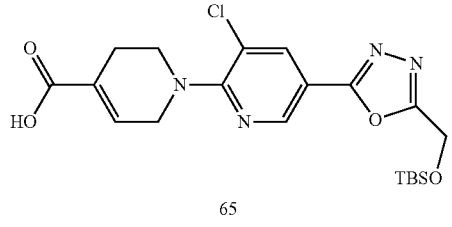

120

To a solution of (57d) (153 mg, 0.311 mmol) in THF (2 ml) were added 5,5-dimethylcyclohexane-1,3-dione (65 mg, 0.467 mmol) and Pd(Ph$_3$)$_4$ (36 mg, 0.031 mmol) at room temperature. After being stirred for 1 hr at the same temperature, the reaction mixture was quenched with H$_2$O and extracted with ethyl acetate. The resulting organic layer was separated and the aqueous layer was extracted with ethyl acetate. The combined organic layers were washed with brine and dried over Na$_2$SO$_4$ and concentrated in vacuo. The residue was used for the reaction in Example 2 without further purification. LC/MS (M+1): 451.

Example 4

The following compounds were obtained in similar manner to Example 1, Steps 4 and 5.

I-12

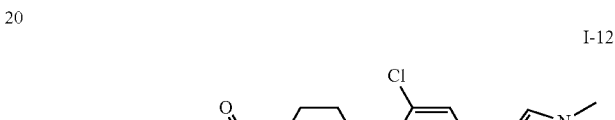

I-13

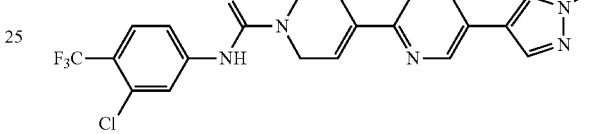

I-14

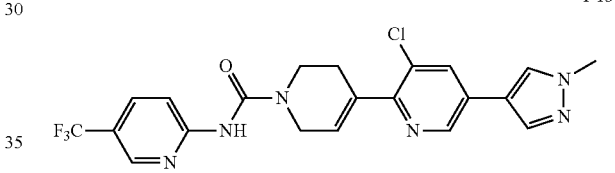

I-15

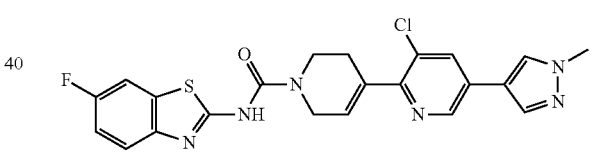

I-16

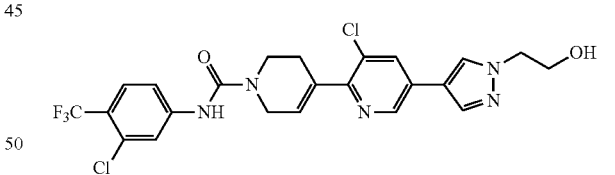

I-17

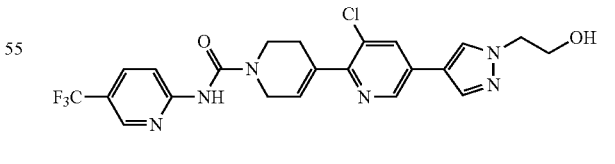

-continued

I-71
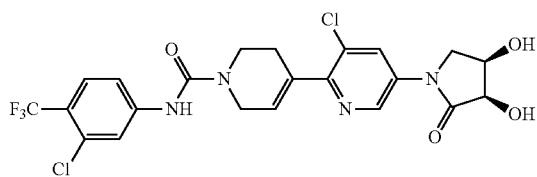

I-85
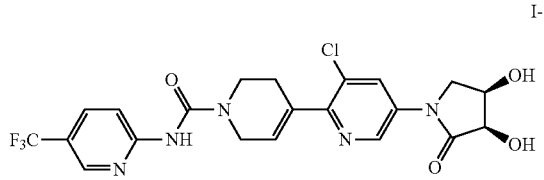

I-72
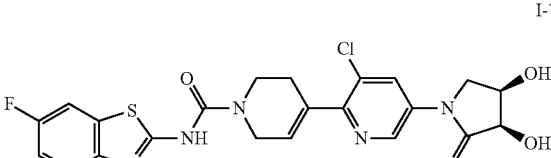

I-74
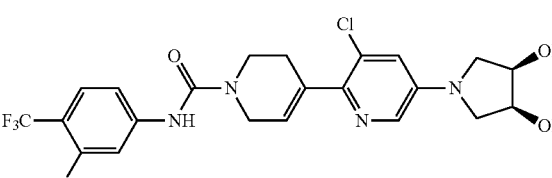

I-86
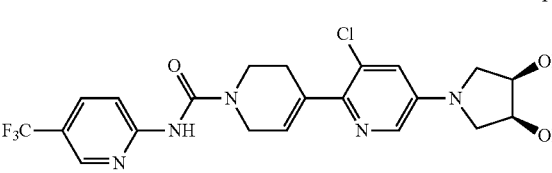

I-73
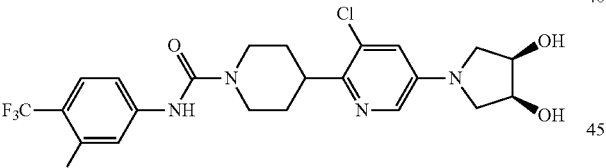

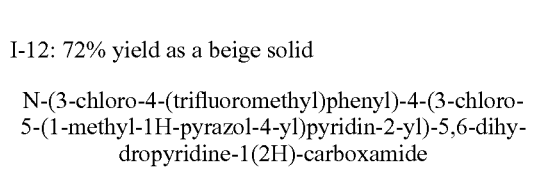

I-12: 72% yield as a beige solid

N-(3-chloro-4-(trifluoromethyl)phenyl)-4-(3-chloro-5-(1-methyl-1H-pyrazol-4-yl)pyridin-2-yl)-5,6-dihydropyridine-1(2H)-carboxamide $^1$H-NMR (DMSO-d6) δ: 9.13 (1H, s), 8.76 (1H, d, J=1.68 Hz), 8.33 (1H, s), 8.14 (1H, d, J=1.86 Hz), 8.04 (1H, s), 7.92 (1H, s), 7.71 (1H, d, J=8.85 Hz), 7.63 (1H, d, J=8.85 Hz), 6.25 (1H, br), 4.20 (2H, d, J=2.44 Hz), 3.87 (3H, s), 3.69 (2H, t, J=5.41 Hz), 2.59 (1H, br). LC/MS (M+1): 496.

I-13: 47% yield as a white solid 4-(3-chloro-5-(1-methyl-1H-pyrazol-4-yl)pyridin-2-yl)-N-(5-(trifluoromethyl)pyridin-2-yl)-5,6-dihydropyridine-1(2H)-carboxamide $^1$H-NMR (DMSO-d6) δ: 9.82 (1H, s), 8.76 (1H, d, J=1.83 Hz), 8.61 (1H, d, J=1.98 Hz), 8.33 (1H, s), 8.13 (1H, d, J=1.83 Hz), 8.05 (1H, dd, J=1.98, 8.85 Hz), 8.04 (1H, s), 7.98 (1H, d, J=8.85 Hz), 6.23 (1H, br), 4.21 (2H, br), 3.87 (3H, s), 3.71 (2H, t, J=5.41 Hz), 2.58 (2H, br). LC/MS (M+1): 463.

I-14: 62% as a white solid 4-(3-chloro-5-(1-methyl-1H-pyrazol-4-yl)pyridin-2-yl)-N-(6-fluorobenzo[d]thiazol-2-yl)-5,6-dihydropyridine-1(2H)-carboxamide $^1$H-NMR (DMSO-d6) δ: 8.76 (1H, d, J=1.68 Hz), 8.33 (1H, s), 8.13 (1H, d, J=1.68 Hz), 8.04 (1H, s), 7.77 (1H, dd, J=2.75, 7.17 Hz), 7.55 (1H, br), 7.20 (1H, td, J=9.07, 2.75 Hz), 6.25 (1H, br), 4.26 (2H, br), 3.87 (3H, s), 3.78 (2H, t, J=5.41 Hz), 2.57 (2H, br). LC/MS (M+1): 469.

I-15: 59% yield as a white solid.

N-(3-chloro-4-(trifluoromethyl)phenyl)-4-(3-chloro-5-(1-(2-hydroxyethyl)-1H-pyrazol-4-yl)pyridin-2-yl)-5,6-dihydropyridine-1(2H)-carboxamide $^1$H-NMR (DMSO-d6) δ: 9.13 (1H, s), 8.78 (1H, d, J=1.98 Hz), 8.36 (1H, s), 8.16 (1H, d, J=1.98 Hz), 8.06 (1H, s), 7.92 (1H, d, J=1.68 Hz), 7.71 (1H, d, J=8.85 Hz), 7.63 (1H, dd, J=8.85, 1.68 Hz), 6.25 (1H, br), 4.94 (1H, t, J=5.26 Hz), 4.20 (2H, d, J=2.75 Hz), 4.16 (2H, t, J=5.57 Hz), 3.76 (2H, dt, J=5.57, 5.26 Hz), 3.69 (2H, t, J=5.57 Hz), 2.59 (2H, s). LC/MS (M+1): 526.

I-16: 70% yield as a white solid 4-(3-chloro-5-(1-(2-hydroxyethyl)-1H-pyrazol-4-yl)pyridin-2-yl)-N-(5-(trifluoromethyl)pyridin-2-yl)-5,6-dihydropyridine-1(2H)-carboxamide $^1$H-NMR (DMSO-d6) δ: 9.81 (1H, s), 8.77 (1H, d, J=1.83 Hz), 8.61 (1H, m), 8.35 (1H, s), 8.15 (1H, d, J=1.83 Hz), 8.06 (1H, s), 8.05 (1H, dd, J=8.85, 2.44 Hz), 7.98 (1H, d, J=8.85 Hz), 6.23 (1H, br), 4.94 (1H, t, J=5.26 Hz), 4.22 (2H, d, J=2.75 Hz), 4.15 (2H, t, J=5.57 Hz), 3.78-3.69 (4H, m), 2.58 (2H, br). LC/MS (M+1): 493.

I-17: 59% yield as a white solid 4-(3-chloro-5-(1-(2-hydroxyethyl)-1H-pyrazol-4-yl)pyridin-2-yl)-N-(6-fluorobenzo[d]thiazol-2-yl)-5,6-dihydropyridine-1(2H)-carboxamide $^1$H-NMR (DMSO-d6) δ: 8.77 (1H, d, J=1.98 Hz), 8.35 (1H, s), 8.15 (1H, d, J=1.98 Hz), 8.06 (1H, s), 7.77 (1H, dd, J=8.69, 2.59 Hz), 7.56 (1H, m), 7.20 (1H, td, J=8.69, 2.59 Hz), 6.25 (1H, br), 4.94 (1H, t, J=5.34 Hz), 4.26 (2H, br), 4.16 (2H, t, J=5.57 Hz), 3.76 (4H, m), 2.58 (2H, br). LC/MS (M+1): 499.

I-71: 47% as an orange solid

N-(3-chloro-4-(trifluoromethyl)phenyl)-4-(3-chloro-5-((3R,4R)-3,4-dihydroxy-2-oxopyrrolidin-1-yl)pyridin-2-yl)-5,6-dihydropyridine-1(2H)-carboxamide $^1$H-NMR (DMSO-d6) δ: 9.12 (1H, s), 8.82 (1H, d, J=2.29 Hz), 8.32 (1H, d, J=2.29 Hz), 7.92 (1H, d, J=1.60 Hz), 7.71 (1H, d, J=8.62 Hz), 7.63 (1H, dd, J=8.62, 1.60 Hz), 6.24 (1H, br), 5.74 (1H, d, J=6.41 Hz), 5.24 (1H, d, J=2.75 Hz), 4.31 (2H, d, J=4.88 Hz), 4.19 (2H, d, J=2.90 Hz), 3.92 (1H, dd, J=10.29, 2.75 Hz), 3.67 (3H, m), 2.57 (2H, br). LC/MS (M+1): 531.

I-85: 31% yield as a beige solid 4-(3-chloro-5-((3R,4R)-3,4-dihydroxy-2-oxopyrrolidin-1-yl)pyridin-2-yl)-N-(5-(trifluoromethyl)pyridin-2-yl)-5,6-dihydropyridine-1(2H)-carboxamide ¹H-NMR (DMSO-d6) δ: 9.80 (1H, s), 8.81 (1H, d, J=2.29 Hz), 8.60 (1H, d, J=2.36 Hz), 8.32 (1H, d, J=2.29 Hz), 8.05 (1H, dd, J=9.00, 2.36 Hz), 7.97 (1H, d, J=9.00 Hz), 6.22 (1H, br), 5.73 (1H, d, J=6.71 Hz), 5.23 (1H, d, J=3.05 Hz), 4.31 (2H, d, J=5.34 Hz), 4.21 (2H, d, J=2.59 Hz), 3.92 (1H, dd, J=10.45, 3.05 Hz), 3.72-3.63 (3H, m), 2.57 (2H, br). LC/MS (M+1): 498.

I-72: 56% yield as a beige solid 4-(3-chloro-5-((3R,4R)-3,4-dihydroxy-2-oxopyrrolidin-1-yl)pyridin-2-yl)-N-(6-fluorobenzo[d]thiazol-2-yl)-5,6-dihydropyridine-1(2H)-carboxamide ¹H-NMR (DMSO-d6) δ: 8.81 (1H, d, J=2.29 Hz), 8.31 (1H, d, J=2.29 Hz), 7.77 (1H, dd, J=8.69, 2.44 Hz), 7.55 (1H, m), 7.20 (1H, td, J=8.69, 2.64 Hz), 6.24 (1H, br), 5.73 (1H, d, J=6.25 Hz), 5.23 (1H, br), 4.28 (4H, m), 3.92 (1H, dd, J=10.83, 2.67 Hz), 3.77 (2H, t, J=5.49 Hz), 3.65 (1H, d, J=10.83 Hz), 2.56 (2H, br). LC/MS (M+1): 504.

I-74: 62% as an orange solid

N-(3-chloro-4-(trifluoromethyl)phenyl)-4-(3-chloro-5-((3S,4R)-3,4-dihydroxypyrrolidin-1-yl)pyridin-2-yl)-5,6-dihydropyridine-1(2H)-carboxamide ¹H-NMR (DMSO-d6) δ: 9.08 (1H, s), 7.92 (1H, d, J=1.53 Hz), 7.83 (1H, d, J=2.59 Hz), 7.70 (1H, d, J=8.85 Hz), 7.63 (1H, dd, J=8.85, 1.53 Hz), 6.91 (1H, d, J=2.59 Hz), 6.08 (1H, br), 4.97 (2H, d, J=4.58 Hz), 4.15 (4H, br), 3.66 (2H, t, J=5.64 Hz), 3.45 (2H, dd, J=9.46, 5.49 Hz), 3.14 (2H, dd, J=9.91, 4.27 Hz), 2.53 (2H, br). LC/MS (M+1): 517.

I-86: 73% yield as a beige solid 4-(3-chloro-5-((3S,4R)-3,4-dihydroxypyrrolidin-1-yl)pyridin-2-yl)-N-(5-(trifluoromethyl)pyridin-2-yl)-5,6-dihydropyridine-1(2H)-carboxamide ¹H-NMR (DMSO-d6) δ: 9.75 (1H, s), 8.60 (1H, d, J=2.44 Hz), 8.04 (1H, dd, J=8.85, 2.44 Hz), 7.97 (1H, d, J=8.85 Hz), 7.82 (1H, d, J=2.44 Hz), 6.90 (1H, d, J=2.44 Hz), 6.06 (1H, br), 4.97 (2H, d, J=4.42 Hz), 4.17-4.13 (4H, m), 3.67 (2H, t, J=5.57 Hz), 3.44 (2H, dd, J=9.68, 4.42 Hz), 3.13 (2H, dd, J=9.91, 4.42 Hz), 2.53 (2H, br). LC/MS (M+1): 484.

I-73: 80% as a beige solid

N-(3-chloro-4-(trifluoromethyl)phenyl)-4-(3-chloro-5-((3S,4R)-3,4-dihydroxypyrrolidin-1-yl)pyridin-2-yl)-5,6-dihydropyridine-1(2H)-carboxamide ¹H-NMR (DMSO-d6) δ: 9.07 (1H, s), 7.90 (1H, d, J=1.22 Hz), 7.79 (1H, d, J=2.44 Hz), 7.69 (1H, d, J=8.85 Hz), 7.60 (1H, dd, J=8.85, 1.22 Hz), 6.88 (1H, d, J=2.44 Hz), 4.94 (2H, d, J=4.58 Hz), 4.23 (2H, d, J=13.12 Hz), 4.12 (2H, d, J=3.51 Hz), 3.41 (2H, dd, J=8.77, 4.96 Hz), 3.21 (1H, m), 3.10 (2H, dd, J=9.76, 4.27 Hz), 3.00-2.91 (2H, m), 1.69 (4H, br). LC/MS (M+1): 519.

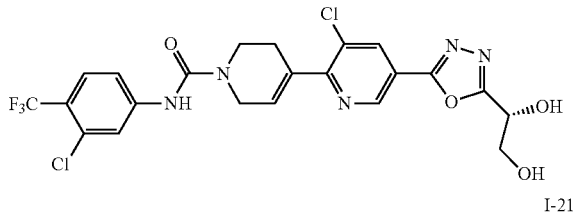

I-20

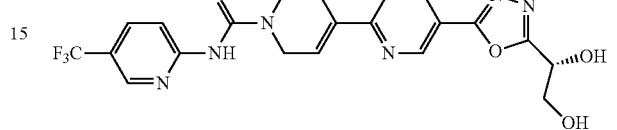

I-21

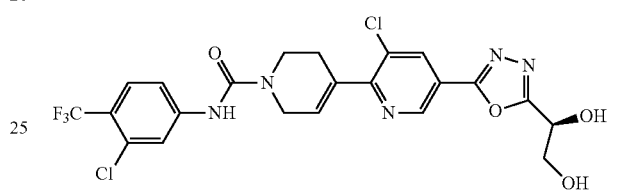

I-18

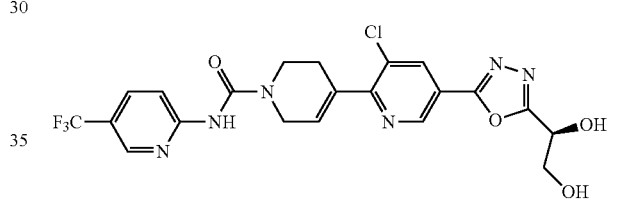

I-19

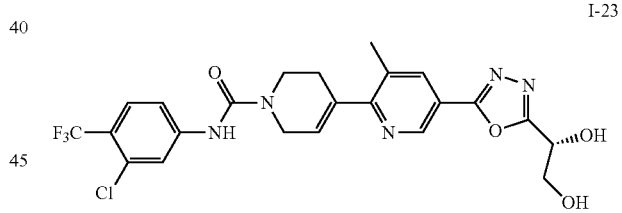

I-23

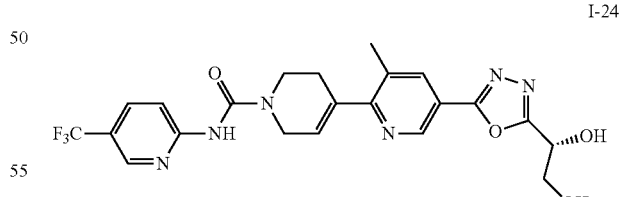

I-24

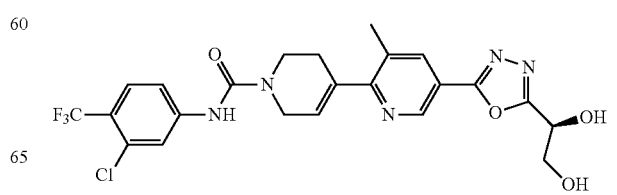

I-22

-continued

I-75

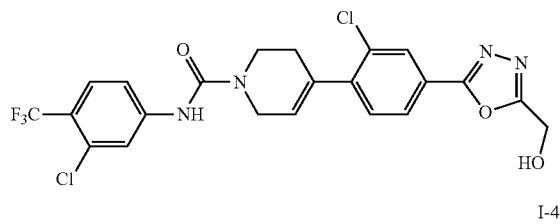

I-43

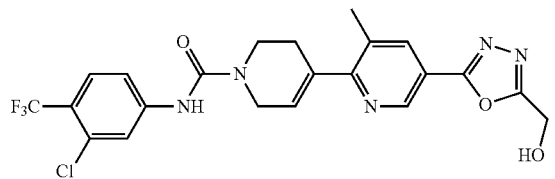

I-76

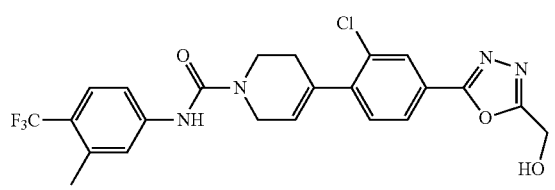

I-44

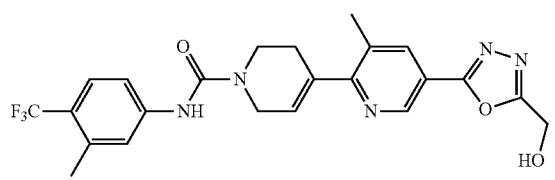

I-49

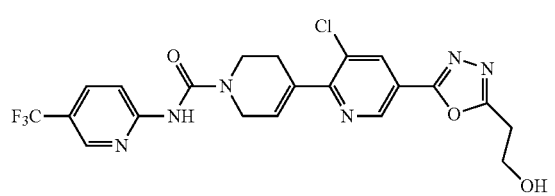

I-89

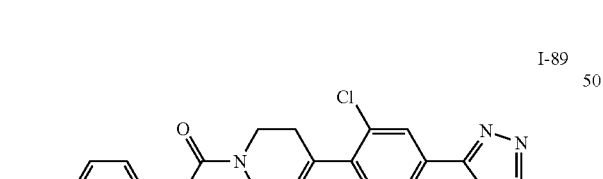

I-48

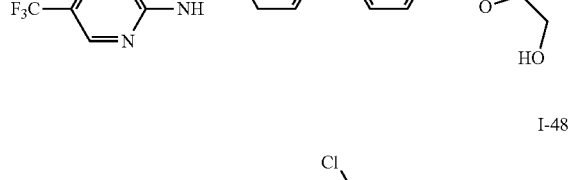

-continued

I-50

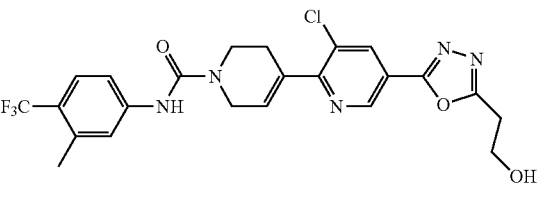

I-51

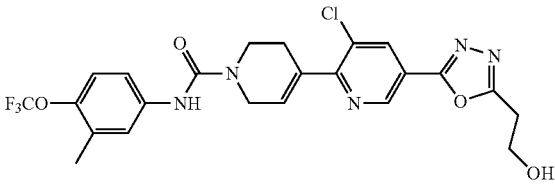

I-20: 47% yield as a yellow amorphous.

(R)—N-(3-chloro-4-(trifluoromethyl)phenyl)-4-(3-chloro-5-(5-(1,2-dihydroxyethyl)-1,3,4-oxadiazol-2-yl)pyridin-2-yl)-5,6-dihydropyridine-1(2H)-carboxamide $^1$H-NMR (DMSO-d6) δ: 9.14 (1H, s), 9.09 (1H, d, J=1.83 Hz), 8.45 (1H, d, J=1.83 Hz), 7.92 (1H, d, J=1.53 Hz), 7.72 (1H, d, J=8.85 Hz), 7.64 (1H, dd, J=8.85, 1.53 Hz), 6.43 (1H, br), 6.20 (1H, d, J=5.64 Hz), 5.05 (1H, t, J=5.64 Hz), 4.87 (1H, q, J=5.64 Hz), 4.24 (2H, d, J=2.75 Hz), 3.78 (2H, q, J=5.64 Hz), 3.72 (2H, t, J=5.41 Hz), 2.64 (2H, br). LC/MS (M+1): 544.

I-21: 38% yield as a beige solid (R)-4-(3-chloro-5-(5-(1,2-dihydroxyethyl)-1,3,4-oxadiazol-2-yl)pyridin-2-yl)-N-(5-(trifluoromethyl)pyridin-2-yl)-5,6-dihydropyridine-1(2H)-carboxamide $^1$H-NMR (DMSO-d6) δ: 9.83 (1H, s), 9.08 (1H, d, J=1.83 Hz), 8.61 (1H, d, J=2.36 Hz), 8.45 (1H, d, J=1.83 Hz), 8.06 (1H, dd, J=8.85, 2.36 Hz), 7.98 (1H, d, J=8.85 Hz), 6.41 (1H, br), 6.20 (1H, d, J=6.05 Hz), 5.05 (1H, t, J=6.02 Hz), 4.87 (1H, q, J=6.05 Hz), 4.26 (2H, d, J=2.59 Hz), 3.81-3.71 (4H, m), 2.64 (2H, br). LC/MS (M+1): 511.

I-18: 46% yield as a beige solid (S)—N-(3-chloro-4-(trifluoromethyl)phenyl)-4-(3-chloro-5-(5-(1,2-dihydroxyethyl)-1,3,4-oxadiazol-2-yl)pyridin-2-yl)-5,6-dihydropyridine-1(2H)-carboxamide $^1$H-NMR (DMSO-d6) δ: 9.15 (1H, s), 9.09 (1H, d, J=1.98 Hz), 8.45 (1H, d, J=1.98 Hz), 7.93 (1H, d, J=1.37 Hz), 7.72 (1H, d, J=8.85 Hz), 7.64 (1H, dd, J=8.85, 1.37 Hz), 6.43 (1H, br), 6.20 (1H, d, J=6.10 Hz), 5.06 (1H, t, J=6.02 Hz), 4.87 (1H, q, J=6.10 Hz), 4.24 (2H, d, J=2.44 Hz), 3.81-3.70 (4H, m), 2.64 (2H, br). LC/MS (M+1): 544.

I-19: 36% yield as a white solid (S)-4-(3-chloro-5-(5-(1,2-dihydroxyethyl)-1,3,4-oxadiazol-2-yl)pyridin-2-yl)-N-(5-(trifluoromethyl)pyridin-2-yl)-5,6-dihydropyridine-1(2H)-carboxamide $^1$H-NMR (DMSO-d6) δ: 9.83 (1H, s), 9.08 (1H, d, J=1.83 Hz), 8.61 (1H, d, J=2.36 Hz), 8.45 (1H, d, J=1.83 Hz), 8.06

(1H, dd, J=9.00, 2.36 Hz), 7.98 (1H, d, J=9.00 Hz), 6.41 (1H, br), 6.21 (1H, d, J=6.10 Hz), 5.07 (1H, t, J=5.95 Hz), 4.87 (1H, q, J=6.10 Hz), 4.26 (2H, d, J=2.44 Hz), 3.81-3.71 (4H, m), 2.63 (2H, br). LC/MS (M+1): 511.

I-23: 34% yield as a beige solid

(R)—N-(3-chloro-4-(trifluoromethyl)phenyl)-4-(5-(5-(1,2-dihydroxyethyl)-1,3,4-oxadiazol-2-yl)-3-methylpyridin-2-yl)-5,6-dihydropyridine-1(2H)-carboxamide $^1$H-NMR (DMSO-d6) δ: 9.15 (1H, s), 8.98 (1H, s), 8.24 (1H, d, J=0.82 Hz), 7.95 (1H, s), 7.73 (1H, d, J=8.79 Hz), 7.66 (1H, dd, J=8.79, 0.82 Hz), 6.18 (1H, d, J=6.04 Hz), 6.09 (1H, br), 5.06 (1H, t, J=6.04 Hz), 4.87 (1H, q, J=6.04 Hz), 4.22 (2H, d, J=1.92 Hz), 3.81-3.71 (4H, m), 2.60 (2H, br), 2.48 (3H, s). LC/MS (M+1): 524.

I-24: 32% yield as a beige solid

(R)-4-(5-(5-(1,2-dihydroxyethyl)-1,3,4-oxadiazol-2-yl)-3-methylpyridin-2-yl)-N-(5-(trifluoromethyl)pyridin-2-yl)-5,6-dihydropyridine-1(2H)-carboxamide $^1$H-NMR (DMSO-d6) δ: 9.82 (1H, s), 8.98 (1H, d, J=1.92 Hz), 8.62 (1H, d, J=2.06 Hz), 8.24 (1H, d, J=1.92 Hz), 8.07 (1H, dd, J=8.93, 2.06 Hz), 8.00 (1H, d, J=8.93 Hz), 6.18 (1H, d, J=6.04 Hz), 6.07 (1H, br), 5.06 (1H, t, J=6.04 Hz), 4.86 (1.0H, q, J=6.04 Hz), 4.24 (2H, d, J=1.92 Hz), 3.81-3.72 (4H, m), 2.59 (2H, br), 2.47 (3H, s).
LC/MS (M+1): 491.

I-22: 38% yield as a beige solid

(S)—N-(3-chloro-4-(trifluoromethyl)phenyl)-4-(5-(5-(1,2-dihydroxyethyl)-1,3,4-oxadiazol-2-yl)-3-methylpyridin-2-yl)-5,6-dihydropyridine-1(2H)-carboxamide $^1$H-NMR (DMSO-d6) δ: 9.14 (1H, s), 8.98 (1H, d, J=1.92 Hz), 8.24 (1H, d, J=1.92 Hz), 7.94 (1H, s), 7.73 (1H, d, J=8.79 Hz), 7.66 (1H, d, J=8.79 Hz), 6.18 (1H, d, J=6.04 Hz), 6.09 (1H, br), 5.06 (1H, t, J=6.04 Hz), 4.86 (1H, q, J=6.04 Hz), 4.22 (2H, d, J=2.20 Hz), 3.81-3.71 (4H, m), 2.60 (2H, br), 2.48 (3H, s). LC/MS (M+1): 524.

I-43: 40% yield as a white solid

N-(3-chloro-4-(trifluoromethyl)phenyl)-4-(5-(5-(hydroxymethyl)-1,3,4-oxadiazol-2-yl)-3-methylpyridin-2-yl)-5,6-dihydropyridine-1(2H)-carboxamide $^1$H-NMR (DMSO-d6) δ: 9.14 (1H, s), 8.97 (1H, d, J=1.83 Hz), 8.23 (1H, d, J=1.83 Hz), 7.95 (1H, s), 7.72 (1H, d, J=8.59 Hz), 7.66 (1H, d, J=8.59 Hz), 6.09 (1H, br), 6.01 (1H, br), 4.75 (2H, brs), 4.23 (2H, br), 3.73 (2H, br), 2.60 (2H, br), 2.47 (3H, s).
LC/MS (M+1): 494.

I-44: 50% yield as a white solid

4-(5-(5-(hydroxymethyl)-1,3,4-oxadiazol-2-yl)-3-methylpyridin-2-yl)-N-(3-methyl-4-(trifluoromethyl)phenyl)-5,6-dihydropyridine-1(2H)-carboxamide $^1$H-NMR (DMSO-d6) δ: 8.98 (1H, d, J=1.83 Hz), 8.90 (1H, s), 8.25 (1H, d, J=1.83 Hz), 7.57-7.54 (3H, m), 6.09 (1H, br), 6.00 (1H, t, J=5.56 Hz), 4.75 (2H, d, J=5.56 Hz), 4.22 (2H, br), 3.72 (2H, br), 2.59 (2H, br), 2.48 (3H, s), 2.39 (3H, s). LC/MS (M+1): 474.

I-75: 47% yield as a white solid

4-(2-chloro-4-(5-(hydroxymethyl)-1,3,4-oxadiazol-2-yl)phenyl)-N-(3-chloro-4-(trifluoromethyl)phenyl)-5,6-dihydropyridine-1(2H)-carboxamide $^1$H-NMR (DMSO-d6) δ: 9.14 (1H, s), 8.01 (1H, s), 7.94 (2H, s), 7.72 (1H, d, J=9.09 Hz), 7.65 (1H, d, J=9.09 Hz), 7.55 (1H, d, J=8.08 Hz), 5.99 (1H, t, J=5.81 Hz), 5.92 (1H, br), 4.73 (2H, d, J=5.81 Hz), 4.19 (2H, br), 3.72 (2H, br), 2.50 (2H, br). LC/MS (M+1): 513.

I-89: 45% yield as a white solid 4-(2-chloro-4-(5-(hydroxymethyl)-1,3,4-oxadiazol-2-yl)phenyl)-N-(5-(trifluoromethyl)pyridin-2-yl)-5,6-dihydropyridine-1(2H)-carboxamide $^1$H-NMR (DMSO-d6) δ: 9.82 (1H, s), 8.63 (1H, s), 8.07 (1H, d, J=7.58 Hz), 8.02 (1H, s), 8.00 (1H, d, J=7.58 Hz), 7.95 (1H, d, J=8.08 Hz), 7.56 (1H, d, J=8.08 Hz), 5.99 (1H, t, J=5.56 Hz), 5.90 (1H, br), 4.73 (2H, d, J=5.56 Hz), 4.21 (2H, br), 3.73 (2H, br), 2.50 (1H, br).LC/MS (M+1): 480.

I-76: 45% yield as a white solid

4-(2-chloro-4-(5-(hydroxymethyl)-1,3,4-oxadiazol-2-yl)phenyl)-N-(3-methyl-4-(trifluoromethyl)phenyl)-5,6-dihydropyridine-1(2H)-carboxamide $^1$H-NMR (DMSO-d6) δ: 8.89 (1H, s), 8.02 (1H, s), 7.96 (1H, d, J=8.59 Hz), 7.56-7.53 (4H, m), 5.99 (1H, t, J=6.06 Hz), 5.92 (1H, br), 4.73 (2H, d, J=6.06 Hz), 4.18 (2H, br), 3.71 (2H, br), 2.50 (2H, br), 2.39 (3H, s). LC/MS (M+1): 493.

I-50: 52% yield as a white solid

N-(3-chloro-4-(trifluoromethyl)phenyl)-4-(3-chloro-5-(5-(2-hydroxyethyl)-1,3,4-oxadiazol-2-yl)pyridin-2-yl)-5,6-dihydropyridine-1(2H)-carboxamide $^1$H-NMR (DMSO-d6) δ: 9.18 (1H, s), 9.08 (1H, s), 8.44 (1H, s), 7.94 (1H, s), 7.72 (1H, d, J=8.59 Hz), 7.65 (1H, d, J=8.59 Hz), 6.43 (1H, br), 5.00 (1H, t, J=5.05 Hz), 4.25 (2H, br), 3.86 (2H, dd, J=5.81, 5.05 Hz), 3.73 (2H, br), 3.10 (2H, t, J=5.81 Hz), 2.64 (2H, br). LC/MS (M+1): 528.

I-49: 23% yield as a white solid

4-(3-chloro-5-(5-(2-hydroxyethyl)-1,3,4-oxadiazol-2-yl)pyridin-2-yl)-N-(5-(trifluoromethyl)pyridin-2-yl)-5,6-dihydropyridine-1(2H)-carboxamide $^1$H-NMR (DMSO-d6) δ: 9.84 (1H, s), 9.08 (1H, s), 8.62 (1H, s), 8.44 (1H, s), 8.07 (1H, d, J=9.09 Hz), 8.00 (1H, d, J=9.09 Hz), 6.41 (1H, br), 4.99 (1H, t, J=5.56 Hz), 4.27 (2H, br), 3.86 (2H, dd, J=6.06, 5.56 Hz), 3.74 (2H, br), 3.10 (2H, t, J=6.06 Hz), 2.64 (2H, br). LC/MS (M+1): 495.

I-51: 48% yield as an orange solid

4-(3-chloro-5-(5-(2-hydroxyethyl)-1,3,4-oxadiazol-2-yl)pyridin-2-yl)-N-(3-methyl-4-(trifluoromethyl)phenyl)-5,6-dihydropyridine-1(2H)-carboxamide $^1$H-NMR (DMSO-d6) δ: 9.08 (1H, s), 8.92 (1H, s), 8.44 (1H, s), 7.56-7.53 (3H, m), 6.43 (1H, br), 5.00 (1H, t, J=5.05 Hz), 4.24 (2H, br), 3.86 (2H, dd, J=6.06, 5.05 Hz), 3.72 (2H, t, J=4.80 Hz), 3.10 (2H, t, J=6.06 Hz), 2.64 (2H, br), 2.38 (3H, s). LC/MS (M+1): 508.

I-48: 48% yield as a white solid 4-(3-chloro-5-(5-(2-hydroxyethyl)-1,3,4-oxadiazol-2-yl)pyridin-2-yl)-N-(3-methyl-4-(trifluoromethoxy)phenyl)-5,6-dihydropyridine-1(2H)-carboxamide $^1$H-NMR (DMSO-d6) δ: 9.07 (1H, s), 8.71 (1H, s), 8.43 (1H, s), 7.50 (1H, s), 7.42 (1H, d, J=8.08 Hz), 7.18 (1H, d, J=8.08 Hz), 6.42 (1H, br), 5.00 (1H, t, J=5.56 Hz), 4.22 (2H, br), 3.86 (2H, dd, J=6.06, 5.56 Hz), 3.70 (2H, t, J=5.05 Hz), 3.10 (2H, t, J=6.06 Hz), 2.62 (2H, br), 2.23 (3H, s). LC/MS (M+1): 524.
-continued
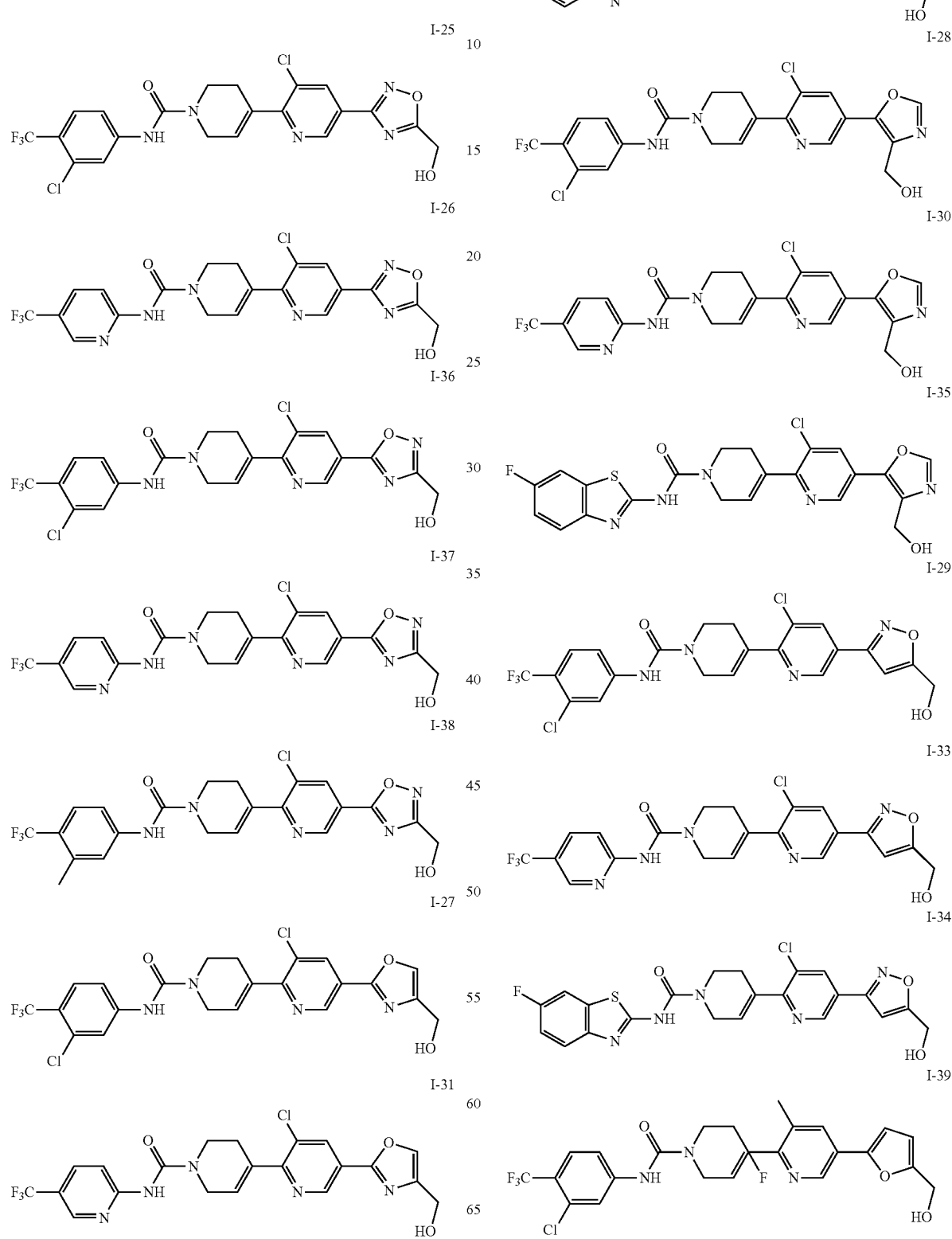

I-45

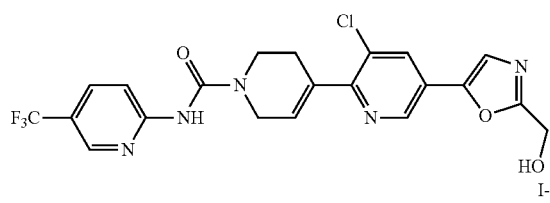

I-41

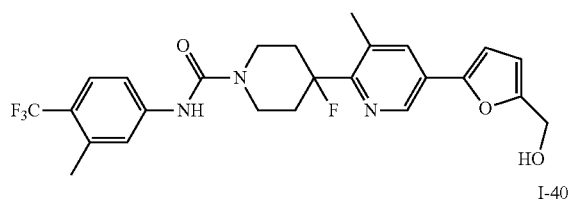

I-40

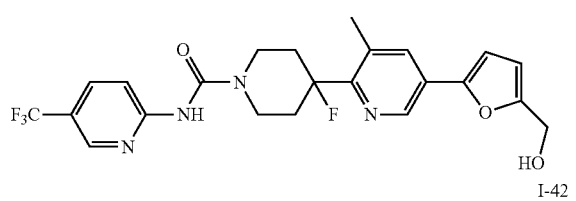

I-42

I-25: 51% yield as a yellow solid

N-(3-chloro-4-(trifluoromethyl)phenyl)-4-(3-chloro-5-(5-(hydroxymethyl)-1,2,4-oxadiazol-3-yl)pyridin-2-yl)-5,6-dihydropyridine-1(2H)-carboxamide $^1$H-NMR (DMSO-d6) δ: 9.14 (1H, s), 9.08 (1H, d, J=1.83 Hz), 8.41 (1H, d, J=1.83 Hz), 7.92 (1H, s), 7.71 (1H, d, J=8.69 Hz), 7.64 (1H, d, J=8.69 Hz), 6.40 (1H, br), 6.13 (1H, t, J=6.41 Hz), 4.83 (2H, d, J=6.41 Hz), 4.23 (2H, d, J=1.07 Hz), 3.71 (2H, t, J=5.19 Hz), 2.63 (2H, br). LC/MS (M+1): 514.

I-26: 45% yield as a yellow solid

4-(3-chloro-5-(5-(hydroxymethyl)-1,2,4-oxadiazol-3-yl)pyridin-2-yl)-N-(5-(trifluoromethyl)pyridin-2-yl)-5,6-dihydropyridine-1(2H)-carboxamide $^1$H-NMR (DMSO-d6) δ: 9.83 (1H, s), 9.07 (1H, d, J=1.83 Hz), 8.61 (1H, d, J=0.92 Hz), 8.40 (1H, d, J=1.83 Hz), 8.05 (1H, dd, J=8.85, 0.92 Hz), 7.98 (1H, d, J=8.85 Hz), 6.38 (1H, br), 6.13 (1H, t, J=6.41 Hz), 4.83 (2H, d, J=6.41 Hz), 4.25 (2H, d, J=1.53 Hz), 3.72 (2H, t, J=5.19 Hz), 2.63 (2H, br). LC/MS (M+1): 481.

I-36: 50% yield as a yellow solid

N-(3-chloro-4-(trifluoromethyl)phenyl)-4-(3-chloro-5-(3-(hydroxymethyl)-1,2,4-oxadiazol-5-yl)pyridin-2-yl)-5,6-dihydropyridine-1(2H)-carboxamide $^1$H-NMR (DMSO-d6) δ: 9.16 (2H, m), 8.56 (1H, d, J=1.83 Hz), 7.92 (1H, s), 7.72 (1H, d, J=8.69 Hz), 7.64 (1H, d, J=8.69 Hz), 6.45 (1H, br), 5.83 (1H, t, J=5.87 Hz), 4.65 (2H, d, J=5.87 Hz), 4.25 (2H, br), 3.71 (2H, t, J=5.49 Hz), 2.64 (2H, br). LC/MS (M+1): 514.

I-37: 80% yield as a white solid

4-(3-chloro-5-(3-(hydroxymethyl)-1,2,4-oxadiazol-5-yl)pyridin-2-yl)-N-(5-(trifluoromethyl)pyridin-2-yl)-5,6-dihydropyridine-1(2H)-carboxamide $^1$H-NMR (DMSO-d6) δ: 9.17 (1H, d, J=1.83 Hz), 8.62 (1H, s), 8.56 (1H, d, J=1.83 Hz), 8.07 (1H, d, J=8.59 Hz), 8.00 (1H, d, J=8.59 Hz), 6.45 (1H, br), 5.84 (1H, t, J=6.06 Hz), 4.67 (2H, d, J=6.06 Hz), 4.28 (2H, br), 3.74 (2H, br), 2.65 (2H, br). LC/MS (M+1): 481.

I-38: 35% yield as a beige solid

4-(3-chloro-5-(3-(hydroxymethyl)-1,2,4-oxadiazol-5-yl)pyridin-2-yl)-N-(3-methyl-4-(trifluoromethyl)phenyl)-5,6-dihydropyridine-1(2H)-carboxamide $^1$H-NMR (DMSO-d6) δ: 9.16 (1H, s), 8.90 (1H, d, J=1.83 Hz), 8.54 (1H, d, J=1.83 Hz), 7.55-7.52 (3H, m), 6.46 (1H, br), 5.84 (1H, t, J=5.56 Hz), 4.67 (2H, d, J=5.56 Hz), 4.25 (2H, br), 3.72 (2H, br), 2.64 (2H, br), 2.38 (3H, s). LC/MS (M+1): 494.

I-27: 53% yield as a beige solid

N-(3-chloro-4-(trifluoromethyl)phenyl)-4-(3-chloro-5-(4-(hydroxymethyl)oxazol-2-yl)pyridin-2-yl)-5,6-dihydropyridine-1(2H)-carboxamide $^1$H-NMR (DMSO-d6) δ: 8.95 (1H, s), 8.85 (1H, d, J=1.92 Hz), 8.16 (1H, d, J=1.92 Hz), 7.95 (1H, s), 7.74 (1H, s), 7.53 (1H, d, J=9.06 Hz), 7.45 (1H, d, J=9.06 Hz), 6.19 (1H, br), 4.26 (2H, s), 4.04 (2H, d, J=1.92 Hz), 3.51 (2H, t, J=5.49 Hz), 2.43 (2H, br).
LC/MS (M+1): 513.

I-31: 52% yield as a yellow solid

4-(3-chloro-5-(4-(hydroxymethyl)oxazol-2-yl)pyridin-2-yl)-N-(5-(trifluoromethyl)pyridin-2-yl)-5,6-dihydropyridine-1(2H)-carboxamide $^1$H-NMR (DMSO-d6) δ: 9.83 (1H, s), 9.03 (1H, d, J=1.53 Hz), 8.61 (1H, d, J=1.07 Hz), 8.33 (1H, d, J=1.53 Hz), 8.13 (1H, s), 8.05 (1H, dd, J=9.00, 1.07 Hz), 7.98 (1H, d, J=9.00 Hz), 6.36 (1H, br), 5.32 (1H, t, J=5.64 Hz), 4.45 (2H, d, J=5.64 Hz), 4.24 (2H, d, J=1.83 Hz), 3.72 (2H, t, J=5.49 Hz), 2.62 (2H, br). LC/MS (M+1): 480.

I-32: 54% yield as a brown solid 4-(3-chloro-5-(4-(hydroxymethyl)oxazol-2-yl)pyridin-2-yl)-N-(6-fluorobenzo[d]thiazol-2-yl)-5,6-dihydropyridine-1(2H)-carboxamide $^1$H-NMR (DMSO-d6) δ: 9.03 (1H, d, J=1.83 Hz), 8.34 (1H, d, J=1.83 Hz), 8.13 (1H, s), 7.77 (1H, dd, J=8.62, 1.75 Hz), 7.54 (1H, m), 7.20 (1H, m), 6.38 (1H, br), 5.32 (1H, br), 4.45 (2H, d, J=2.59 Hz), 4.29 (2H, br), 3.79 (2H, t, J=4.96 Hz), 2.61 (2H, br).
LC/MS (M+1): 486.

I-28: 51% yield as a yellow solid

N-(3-chloro-4-(trifluoromethyl)phenyl)-4-(3-chloro-5-(4-(hydroxymethyl)oxazol-5-yl)pyridin-2-yl)-5,6-dihydropyridine-1(2H)-carboxamide $^1$H-NMR (DMSO-d6) δ: 9.14 (1H, s), 8.85 (1H, d, J=1.83 Hz), 8.50 (1H, s), 8.23 (1H, d, J=1.83 Hz), 7.92 (1H, s), 7.71 (1H, d, J=8.54 Hz), 7.63 (1H, d, J=8.54 Hz), 6.35 (1H, br), 5.49 (1H, t, J=5.41 Hz), 4.57 (2H, d, J=5.41 Hz), 4.22 (2H, d, J=1.68 Hz), 3.71 (2H, t, J=5.11 Hz), 2.62 (2H, br). LC/MS (M+1): 513.

I-30: 33% yield as a yellow solid 4-(3-chloro-5-(4-(hydroxymethyl)oxazol-5-yl)pyridin-2-yl)-N-(5-(trifluoromethyl)pyridin-2-yl)-5,6-dihydropyridine-1(2H)-carboxamide ¹H-NMR (DMSO-d6) δ: 9.83 (1H, s), 8.85 (1H, d, J=1.83 Hz), 8.61 (1H, d, J=1.53 Hz), 8.50 (1H, s), 8.22 (1H, d, J=1.83 Hz), 8.05 (1H, dd, J=8.85, 1.53 Hz), 7.98 (1H, d, J=8.85 Hz), 6.33 (1H, br), 5.49 (1H, t, J=5.11 Hz), 4.56 (2H, d, J=5.11 Hz), 4.24 (2H, d, J=1.83 Hz), 3.72 (2H, t, J=5.26 Hz), 2.61 (2H, br). LC/MS (M+1): 480

I-35: 40% yield as a white solid 4-(3-chloro-5-(4-(hydroxymethyl)oxazol-5-yl)pyridin-2-yl)-N-(6-fluorobenzo[d]thiazol-2-yl)-5,6-dihydropyridine-1(2H)-carboxamide ¹H-NMR (DMSO-d6) δ: 8.66 (1H, d, J=1.92 Hz), 8.31 (1H, s), 8.04 (1H, d, J=1.92 Hz), 7.58 (1H, m), 7.36 (1H, br), 7.01 (1H, td, J=9.06, 2.47 Hz), 6.16 (1H, br), 5.29 (1H, t, J=5.36 Hz), 4.37 (2H, d, J=5.36 Hz), 4.09 (2H, br), 3.60 (2H, br), 2.41 (2H, br).
LC/MS (M+1): 486.

I-29: 44% yield as a beige solid

N-(3-chloro-4-(trifluoromethyl)phenyl)-4-(3-chloro-5-(5-(hydroxymethyl)isoxazol-3-yl)pyridin-2-yl)-5,6-dihydropyridine-1(2H)-carboxamide ¹H-NMR (DMSO-d6) δ: 9.14 (1H, s), 9.01 (1H, d, J=1.83 Hz), 8.41 (1H, d, J=1.83 Hz), 7.92 (1H, s), 7.71 (1H, d, J=8.69 Hz), 7.63 (1H, d, J=8.69 Hz), 7.12 (1H, s), 6.35 (1H, br), 5.78 (1H, t, J=5.64 Hz), 4.63 (2H, d, J=5.64 Hz), 4.22 (2H, d, J=1.98 Hz), 3.71 (2H, t, J=5.41 Hz), 2.62 (2H, br). LC/MS (M+1): 513.

I-33: 43% yield as a beige solid 4-(3-chloro-5-(5-(hydroxymethyl)isoxazol-3-yl)pyridin-2-yl)-N-(5-(trifluoromethyl)pyridin-2-yl)-5,6-dihydropyridine-1(2H)-carboxamide ¹H-NMR (DMSO-d6) δ: 9.83 (1H, s), 9.00 (1H, d, J=1.83 Hz), 8.61 (1H, d, J=2.21 Hz), 8.40 (H, d, J=1.83 Hz), 8.05 (1H, dd, J=9.00, 2.21 Hz), 7.98 (1H, d, J=9.00 Hz), 7.11 (1H, s), 6.33 (1H, br), 5.78 (1H, br), 4.63 (2H, br), 4.24 (2H, d, J=2.29 Hz), 3.72 (2H, t, J=5.34 Hz), 2.61 (2H, br). LC/MS (M+1): 480

I-34: 52% yield as a beige solid 4-(3-chloro-5-(5-(hydroxymethyl)isoxazol-3-yl)pyridin-2-yl)-N-(6-fluorobenzo[d]thiazol-2-yl)-5,6-dihydropyridine-1(2H)-carboxamide ¹H-NMR (DMSO-d6) δ: 9.01 (1H, s), 8.40 (1H, s), 7.78 (1H, br), 7.60 (1H, br), 7.20 (1H, t, J=8.62 Hz), 7.11 (1H, s), 6.35 (1H, br), 5.79 (1H, br), 4.63 (2H, s), 4.28 (2H, br), 3.79 (2H, br), 2.61 (2H, br). LC/MS (M+1): 486.

I-45: 44% yield as a white solid 4-(3-chloro-5-(2-(hydroxymethyl)oxazol-5-yl)pyridin-2-yl)-N-(5-(trifluoromethyl)pyridin-2-yl)-5,6-dihydropyridine-1(2H)-carboxamide ¹H-NMR (DMSO-d6) δ: 9.83 (1H, s), 8.86 (1H, d, J=1.83 Hz), 8.63 (1H, s), 8.24 (1H, d, J=1.83 Hz), 8.07 (1H, d, J=8.59 Hz), 8.00 (1H, d, J=8.59 Hz), 7.86 (1H, s), 6.32 (1H, br), 5.79 (1H, t, J=5.56 Hz), 4.59 (2H, d, J=5.56 Hz), 4.25 (2H, br), 3.73 (2H, br), 2.61 (2H, br). LC/MS (M+1): 480

I-39: 51% yield as a colorless amorphous

N-(3-chloro-4-(trifluoromethyl)phenyl)-4-fluoro-4-(5-(5-(hydroxymethyl)furan-2-yl)-3-methylpyridin-2-yl)piperidine-1-carboxamide ¹H-NMR (DMSO-d6) δ: 9.19 (1H, s), 8.70 (1H, s), 7.92 (1H, s), 7.90 (1H, s), 7.72 (1H, d, J=8.59 Hz), 7.63 (1H, d, J=8.59 Hz), 7.04 (1H, d, J=2.53 Hz), 6.45 (1H, d, J=2.53 Hz), 5.33 (1H, t, J=5.31 Hz), 4.47 (2H, d, J=5.31 Hz), 4.15 (2H, d, J=12.63 Hz), 3.26 (2H, t, J=12.63 Hz), 2.52 (3H, s), 2.35-2.19 (2H, m), 2.12 (2H, t, J=12.63 Hz).

LC/MS (M+1): 512.

I-40: 30% yield as a colorless amorphous 4-fluoro-4-(5-(5-(hydroxymethyl)furan-2-yl)-3-methylpyridin-2-yl)-N-(5-(trifluoromethyl)pyridin-2-yl)piperidine-1-carboxamide ¹H-NMR (DMSO-d6) δ: 9.89 (1H, s), 8.70 (1H, s), 8.62 (1H, s), 8.06 (1H, d, J=8.59 Hz), 7.99 (1H, d, J=8.59 Hz), 7.90 (1H, s), 7.04 (1H, d, J=2.53 Hz), 6.46 (1H, d, J=2.53 Hz), 5.33 (1H, t, J=3.54 Hz), 4.47 (2H, d, J=3.54 Hz), 4.18 (2H, d, J=11.62 Hz), 3.25 (2H, t, J=11.62 Hz), 2.36-2.20 (2H, m), 2.10 (2H, t, J=11.62 Hz). LC/MS (M+1): 479.

I-41: 40% yield as a colorless amorphous 4-fluoro-4-(5-(5-(hydroxymethyl)furan-2-yl)-3-methylpyridin-2-yl)-N-(3-methyl-4-(trifluoromethyl)phenyl)piperidine-1-carboxamide ¹H-NMR (DMSO-d6) δ: 8.95 (1H, s), 8.70 (1H, s), 7.90 (1H, s), 7.55-7.52 (3H, m), 7.04 (1H, s), 6.46 (1H, s), 5.33 (1H, t, J=4.55 Hz), 4.47 (2H, d, J=4.55 Hz), 4.15 (22H, d, J=12.38 Hz), 3.24 (2H, t, J=12.38 Hz), 2.39 (3H, s), 2.33-2.17 (2H, m), 2.11 (2H, t, J=12.38 Hz). LC/MS (M+1): 492.

I-42: 33% yield as a colorless amorphous 4-fluoro-4-(5-(5-(hydroxymethyl)furan-2-yl)-3-methylpyridin-2-yl)-N-(3-methyl-4-(trifluoromethoxy)phenyl)piperidine-1-carboxamide ¹H-NMR (DMSO-d6) δ: 8.76 (1H, s), 8.70 (1H, s), 7.90 (1H, s), 7.49 (1H, s), 7.41 (1H, d, J=8.59 Hz), 7.18 (1H, d, J=8.59 Hz), 7.04 (1H, s), 6.46 (1H, s), 5.33 (1H, t, J=5.05 Hz), 4.47 (2H, d, J=5.05 Hz), 4.13 (2H, d, J=12.13 Hz), 3.23 (2H, t, J=12.13 Hz), 2.33-2.10 (5H, m), 2.09 (2H, t, J=12.13 Hz). LC/MS (M+1): 508.

I-46

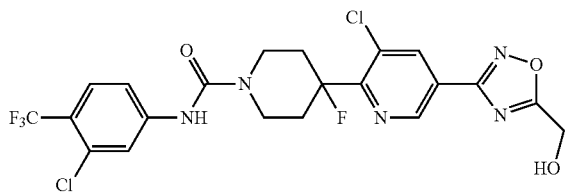

-continued
I-47
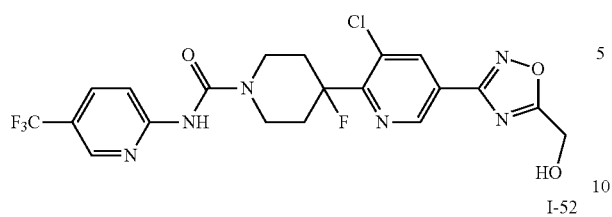
I-52
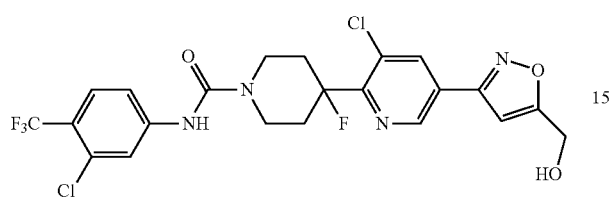
I-53
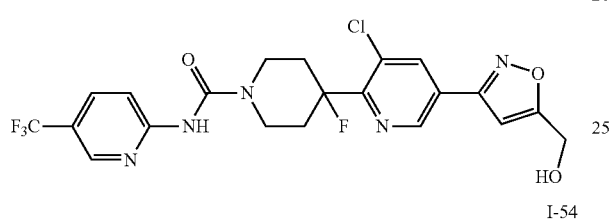
I-54
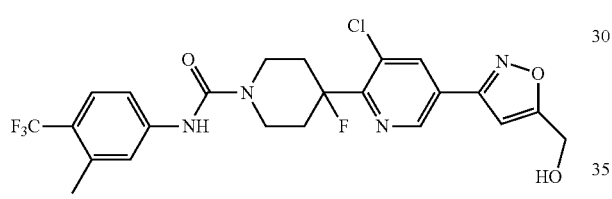
I-55
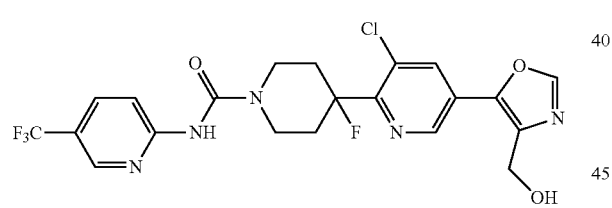
I-56
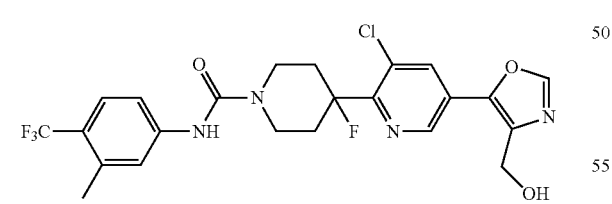
I-59
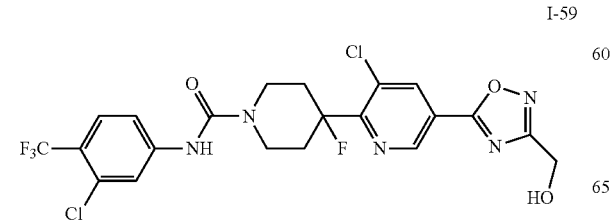
-continued
I-57
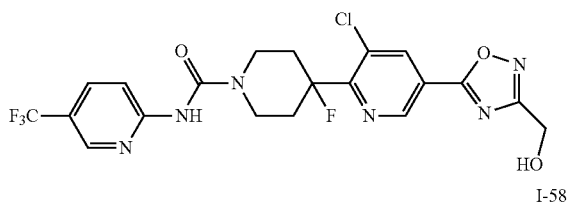
I-58
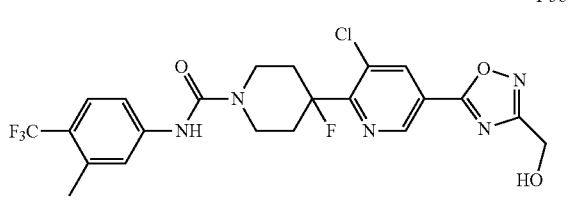
I-63
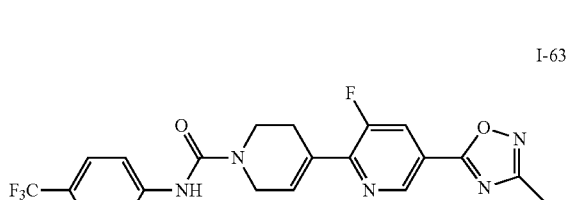
I-64
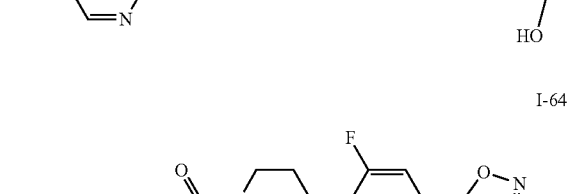
I-60
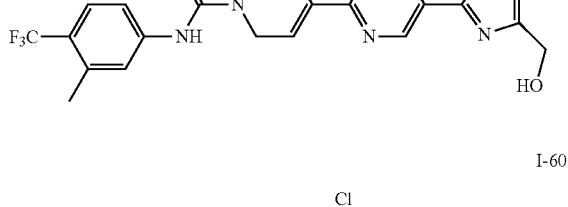
I-62
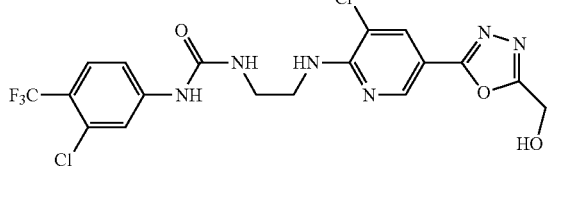
I-92
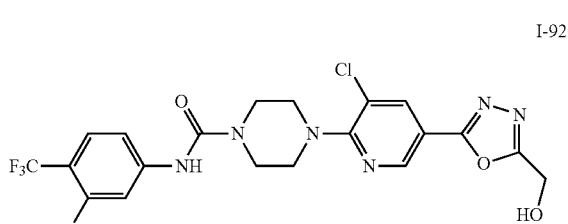

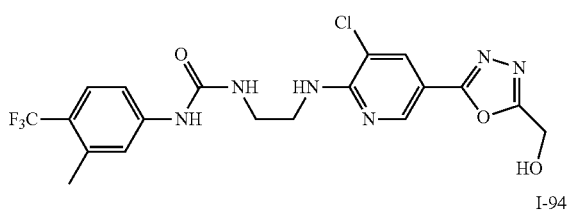

I-94

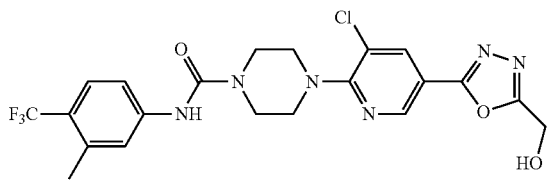

I-93

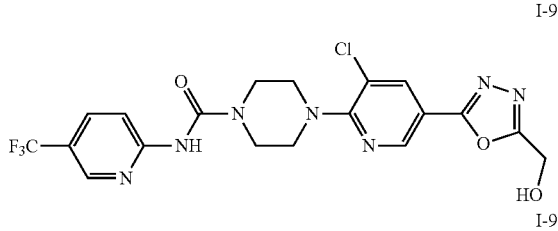

I-96

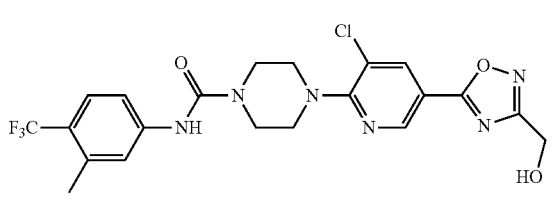

I-95

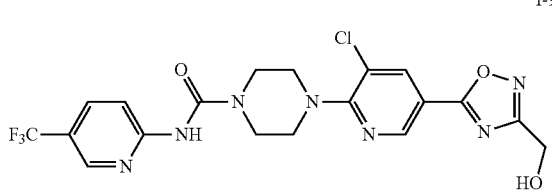

I-46: 92% yield as a colorless amorphous

N-(3-chloro-4-(trifluoromethyl)phenyl)-4-(3-chloro-5-(5-(hydroxymethyl)-1,2,4-oxadiazol-3-yl)pyridin-2-yl)-4-fluoropiperidine-1-carboxamide $^1$H-NMR (DMSO-d6) δ: 9.21 (1H, s), 9.10 (1H, s), 8.45 (1H, s), 7.91 (1H, s), 7.71 (1H, d, J=9.09 Hz), 7.62 (1H, d, J=9.09 Hz), 6.15 (1H, t, J=6.06 Hz), 4.85 (2H, d, J=6.06 Hz), 4.15 (2H, d, J=13.14 Hz), 3.31 (2H, t, J=13.14 Hz), 2.34-2.29 (4H, brm). LC/MS (M+1): 534.

I-47: 82% yield as a white solid 4-(3-chloro-5-(5-(hydroxymethyl)-1,2,4-oxadiazol-3-yl)pyridin-2-yl)-4-fluoro-N-(5-(trifluoromethyl)pyridin-2-yl)piperidine-1-carboxamide $^1$H-NMR (DMSO-d6) δ: 9.91 (1H, s), 9.09 (1H, s), 8.61 (1H, s), 8.44 (1H, s), 8.05 (1H, d, J=8.59 Hz), 7.98 (1H, d, J=8.59 Hz), 6.15 (1H, t, J=6.57 Hz), 4.85 (2H, d, J=6.57 Hz), 4.19 (2H, d, J=13.14 Hz), 3.28 (2H, t, J=13.14 Hz), 2.36-2.28 (4H, brm). LC/MS (M+1): 501.

I-52: 75% yield as a white solid

N-(3-chloro-4-(trifluoromethyl)phenyl)-4-(3-chloro-5-(5-(hydroxymethyl)isoxazol-3-yl)pyridin-2-yl)-4-fluoropiperidine-1-carboxamide $^1$H-NMR (DMSO-d6) δ: 9.21 (1H, s), 9.04 (1H, s), 8.46 (1H, s), 7.91 (1H, s), 7.72 (1H, d, J=8.59 Hz), 7.62 (1H, d, J=8.59 Hz), 7.15 (1H, s), 5.81 (1H, t, J=5.56 Hz), 4.65 (2H, d, J=5.56 Hz), 4.15 (2H, d, J=13.14 Hz), 3.30 (2H, t, J=13.14 Hz), 2.33-2.25 (4H, brm). LC/MS (M+1): 533.

I-53: 57% yield as a white solid 4-(3-chloro-5-(5-(hydroxymethyl)isoxazol-3-yl)pyridin-2-yl)-4-fluoro-N-(5-(trifluoromethyl)pyridin-2-yl)piperidine-1-carboxamide $^1$H-NMR (DMSO-d6) δ: 9.90 (1H, s), 9.04 (1H, s), 8.61 (1H, s), 8.45 (1H, s), 8.05 (1H, d, J=8.59 Hz), 7.97 (1H, d, J=8.59 Hz), 7.15 (1H, s), 5.80 (1H, t, J=5.56 Hz), 4.65 (2H, d, J=5.56 Hz), 4.18 (2H, d, J=13.64 Hz), 3.30 (2H, t, J=13.64 Hz), 2.32-2.28 (4H, brm). LC/MS (M+1): 500.

I-54: 78% yield as a white solid 4-(3-chloro-5-(5-(hydroxymethyl)isoxazol-3-yl)pyridin-2-yl)-4-fluoro-N-(3-methyl-4-(trifluoromethyl)phenyl)piperidine-1-carboxamide $^1$H-NMR (DMSO-d6) δ: 9.04 (1H, s), 8.96 (1H, s), 8.45 (1H, s), 7.54-7.51 (3H, m), 7.15 (1H, s), 5.80 (1H, t, J=5.56 Hz), 4.65 (2H, d, J=5.56 Hz), 4.14 (2H, d, J=13.14 Hz), 3.27 (2H, t, J=13.14 Hz), 2.38 (3H, s), 2.38-2.28 (4H, brm). LC/MS (M+1): 513.

I-55: 53% yield as a white solid 4-(3-chloro-5-(4-(hydroxymethyl)oxazol-5-yl)pyridin-2-yl)-4-fluoro-N-(5-(trifluoromethyl)pyridin-2-yl)piperidine-1-carboxamide $^1$H-NMR (DMSO-d6) δ: 9.90 (1H, s), 8.88 (1H, s), 8.61 (1H, s), 8.53 (1H, s), 8.28 (1H, s), 8.05 (1H, d, J=8.59 Hz), 7.97 (1H, d, J=8.59 Hz), 5.52 (1H, t, J=4.55 Hz), 4.59 (2H, d, J=4.55 Hz), 4.17 (2H, d, J=13.64 Hz), 3.30 (2H, t, J=13.64 Hz), 2.32-2.27 (4H, brm). LC/MS (M+1): 500.

I-56: 48% yield as a yellow amorphous 4-(3-chloro-5-(4-(hydroxymethyl)oxazol-5-yl)pyridin-2-yl)-4-fluoro-N-(3-methyl-4-(trifluoromethyl)phenyl)piperidine-1-carboxamide $^1$H-NMR (DMSO-d6) δ: 8.96 (1H, s), 8.88 (1H, s), 8.53 (1H, s), 8.28 (1H, s), 7.54-7.52 (3H, m), 5.52 (1H, t, J=5.05 Hz), 4.59 (2H, d, J=5.05 Hz), 4.14 (2H, d, J=13.14 Hz), 3.29 (2H, t, J=13.14 Hz), 2.38-2.28 (7H, m). LC/MS (M+1): 513.

I-59: 55% yield as a white solid

N-(3-chloro-4-(trifluoromethyl)phenyl)-4-(3-chloro-5-(3-(hydroxymethyl)-1,2,4-oxadiazol-5-yl)pyridin-2-yl)-4-fluoropiperidine-1-carboxamide $^1$H-NMR (DMSO-d6) δ: 9.21 (1H, s), 9.19 (1H, s), 8.59 (1H, s), 7.90 (1H, s), 7.71 (1H, d, J=8.59 Hz), 7.61 (1H, d, J=8.59 Hz), 5.84 (1H, t, J=4.04 Hz), 4.67 (2H, d, J=4.04 Hz), 4.16 (2H, d, J=12.63 Hz), 3.30 (2H, t, J=12.63 Hz), 2.33-2.29 (4H, m). LC/MS (M+1): 534.

I-57: 66% yield as a white solid

4-(3-chloro-5-(3-(hydroxymethyl)-1,2,4-oxadiazol-5-yl)pyridin-2-yl)-4-fluoro-N-(5-(trifluoromethyl)pyridin-2-yl)piperidine-1-carboxamide $^1$H-NMR (DMSO-d6) δ: 9.91 (1H, s), 9.20 (1H, s), 8.60 (1H, s), 8.06 (1H, d, J=8.08 Hz), 7.97 (1H, d, J=8.08 Hz), 5.84 (1H, t, J=6.06 Hz), 4.67 (2H, d, J=6.06 Hz), 4.19 (2H, d, J=14.15 Hz), 3.30 (2H, t, J=14.15 Hz), 2.32-2.28 (4H, m). LC/MS (M+1): 501.

I-58: 78% yield as a white solid

4-(3-chloro-5-(3-(hydroxymethyl)-1,2,4-oxadiazol-5-yl)pyridin-2-yl)-4-fluoro-N-(3-methyl-4-(trifluoromethyl)phenyl)piperidine-1-carboxamide $^1$H-NMR (DMSO-d6) δ: 9.20 (1H, s), 8.97 (1H, s), 8.60 (1H, s), 7.53-7.51 (3H, m), 5.84 (1H, t, J=5.56 Hz), 4.67 (2H, d, J=5.56 Hz), 4.16 (2H, d, J=13.14 Hz), 3.29 (2H, t, J=13.14 Hz), 2.38 (3H, s), 2.32-2.28 (4H, m). LC/MS (M+1): 514.

I-63: 62% yield as a white solid

4-(3-fluoro-5-(3-(hydroxymethyl)-1,2,4-oxadiazol-5-yl)pyridin-2-yl)-N-(5-(trifluoromethyl)pyridin-2-yl)-5,6-dihydropyridine-1(2H)-carboxamide $^1$H-NMR (DMSO-d6) δ: 9.84 (1H, s), 9.10 (1H, s), 8.63 (1H, s), 8.39 (1H, d, J=12.13 Hz), 8.07 (1H, d, J=9.09 Hz), 7.99 (1H, d, J=9.09 Hz), 6.82 (1H, br), 5.83 (1H, br), 4.66 (2H, d, J=3.54 Hz), 4.32 (2H, br), 3.74 (2H, t, J=5.05 Hz), 2.73 (2H, br). LC/MS (M+1): 465.

I-64: 60% yield as a white solid

4-(3-fluoro-5-(3-(hydroxymethyl)-1,2,4-oxadiazol-5-yl)pyridin-2-yl)-N-(3-methyl-4-(trifluoromethyl)phenyl)-5,6-dihydropyridine-1(2H)-carboxamide $^1$H-NMR (DMSO-d6) δ: 9.11 (1H, s), 8.91 (1H, s), 8.40 (1H, d, J=12.13 Hz), 7.55-7.53 (3H, m), 6.83 (1H, br), 5.84 (1H, t, J=6.06 Hz), 4.66 (2H, d, J=6.06 Hz), 4.29 (2H, br), 3.71 (2H, t, J=5.81 Hz), 2.73 (2H, br), 2.38 (3H, s). LC/MS (M+1): 478.

I-60: 35% yield as a white solid

1-(3-chloro-4-(trifluoromethyl)phenyl)-3-(2-(3-chloro-5-(5-(hydroxymethyl)-1,3,4-oxadiazol-2-yl)pyridin-2-ylamino)ethyl) urea $^1$H-NMR (DMSO-d6) δ: 9.22 (1H, s), 8.58 (1H, s), 8.06 (1H, s), 7.88 (1H, s), 7.67 (1H, d, J=8.59 Hz), 7.44-7.39 (2H, m), 6.60 (1H, br), 5.93 (1H, t, J=5.31 Hz), 4.68 (2H, d, J=5.31 Hz), 3.57 (2H, d, J=4.55 Hz), 3.37 (2H, brm). LC/MS (M+1): 491.

I-62: 22% yield as a white solid

1-(2-(3-chloro-5-(5-(hydroxymethyl)-1,3,4-oxadiazol-2-yl)pyridin-2-ylamino)ethyl)-3-(5-(trifluoromethyl)pyridin-2-yl)urea $^1$H-NMR (DMSO-d6) δ: 9.70 (1H, s), 8.52 (1H, s), 8.45 (1H, s), 8.03-7.97 (2H, m), 7.61 (1H, d, J=9.09 Hz), 7.49 (1H, t, J=5.05 Hz), 5.92 (1H, t, J=6.06 Hz), 4.67 (2H, d, J=6.06 Hz), 3.61 (2H, br), 3.45 (2H, br). LC/MS (M+1): 458.

I-61: 39% yield as a white solid

1-(2-(3-chloro-5-(5-(hydroxymethyl)-1,3,4-oxadiazol-2-yl)pyridin-2-ylamino)ethyl)-3-(3-methyl-4-(trifluoromethyl)phenyl)urea $^1$H-NMR (DMSO-d6) δ: 8.86 (1H, s), 8.58 (1H, s), 8.06 (1H, s), 7.49 (1H, d, J=8.08 Hz), 7.44-7.40 (3H, m), 6.46 (1H, br), 5.93 (1H, t, J=6.06 Hz), 4.68 (2H, d, J=6.06 Hz), 3.56 (2H, br), 3.35 (2H, br), 2.36 (3H, s). LC/MS (M+1): 471.

I-92: 49% yield as a white solid

N-(3-chloro-4-(trifluoromethyl)phenyl)-4-(3-chloro-5-(5-(hydroxymethyl)-1,3,4-oxadiazol-2-yl)pyridin-2-yl)piperazine-1-carboxamide $^1$H-NMR (DMSO-d6) δ: 9.19 (1H, s), 8.77 (1H, s), 8.27 (1H, s), 7.92 (1H, s), 7.72 (1H, d, J=8.59 Hz), 7.63 (1H, d, J=8.59 Hz), 5.98 (1H, br), 4.72 (2H, d, J=5.56 Hz), 3.66 (4H, br), 3.55 (4H, br). LC/MS (M+1): 517.

I-93: 44% yield as a white solid

4-(3-chloro-5-(5-(hydroxymethyl)-1,3,4-oxadiazol-2-yl)pyridin-2-yl)-N-(5-(trifluoromethyl)pyridin-2-yl)piperazine-1-carboxamide $^1$H-NMR (DMSO-d6) δ: 9.87 (1H, s), 8.77 (1H, s), 8.63 (1H, s), 8.26 (1H, s), 8.07 (1H, d, J=8.08 Hz), 7.98 (1H, d, J=8.08 Hz), 5.98 (1H, t, J=5.56 Hz), 4.72 (2H, d, J=5.56 Hz), 3.68 (4H, br), 3.53 (4H, br). LC/MS (M+1): 484.

I-94: 38% yield as a white solid

4-(3-chloro-5-(5-(hydroxymethyl)-1,3,4-oxadiazol-2-yl)pyridin-2-yl)-N-(3-methyl-4-(trifluoromethyl)phenyl)piperazine-1-carboxamide $^1$H-NMR (DMSO-d6) δ: 8.93 (1H, s), 8.78 (1H, s), 8.27 (1H, s), 7.54-7.53 (3H, m), 5.98 (1H, t, J=6.06 Hz), 4.72 (2H, d, J=6.06 Hz), 3.64 (4H, br), 3.54 (4H, br), 2.38 (3H, s). LC/MS (M+1): 497.

I-95: 84% yield as a white solid

4-(3-chloro-5-(3-(hydroxymethyl)-1,2,4-oxadiazol-5-yl)pyridin-2-yl)-N-(5-(trifluoromethyl)pyridin-2-yl)piperazine-1-carboxamide $^1$H-NMR (DMSO-d6) δ: 9.87 (1H, s), 8.87 (1H, s), 8.62 (1H, s), 8.35 (1H, s), 8.07 (1H, d, J=9.09 Hz), 7.98 (1H, d, J=9.09 Hz), 5.78 (1H, t, J=6.06 Hz), 4.62 (2H, d, J=6.06 Hz), 3.67 (4H, br), 3.60 (4H, br). LC/MS (M+1): 484.

I-96: 88% yield as a white solid

4-(3-chloro-5-(3-(hydroxymethyl)-1,2,4-oxadiazol-5-yl)pyridin-2-yl)-N-(3-methyl-4-(trifluoromethyl)phenyl)piperazine-1-carboxamide $^1$H-NMR (DMSO-d6) δ: 8.93 (1H, s), 8.87 (1H, s), 8.34 (1H, s), 7.54-7.52 (3H, m), 5.78 (1H, t, J=6.06 Hz), 4.62 (2H, d, J=6.06 Hz), 3.64 (4H, br), 3.61 (4H, br), 2.38 (3H, s). LC/MS (M+1): 497.

Example 5
The following compounds were obtained in similar manner to Example 1, Step 5.
I-65
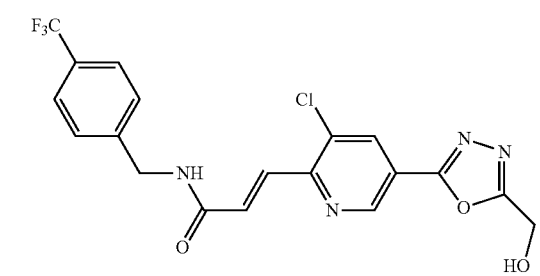
I-66
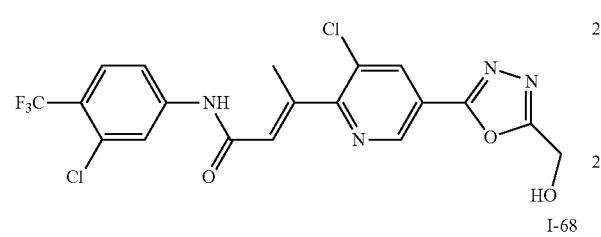
I-68
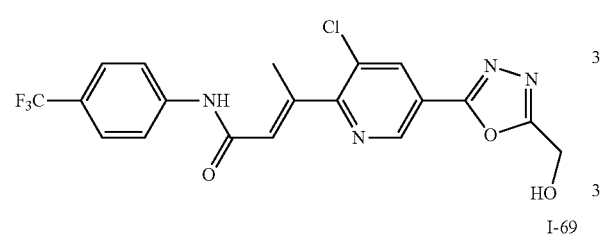
I-69
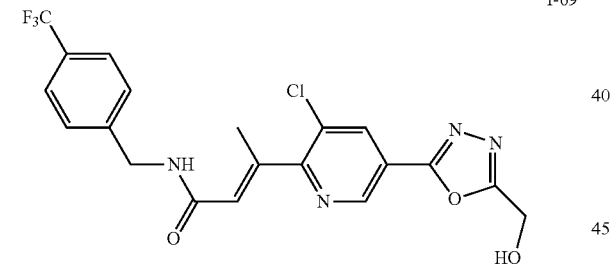
I-83
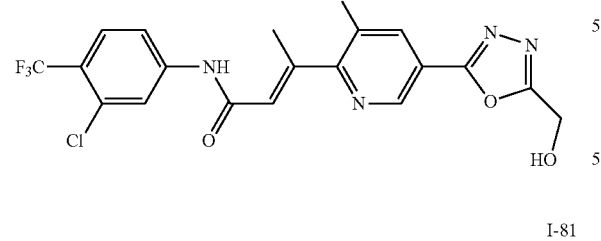
I-81
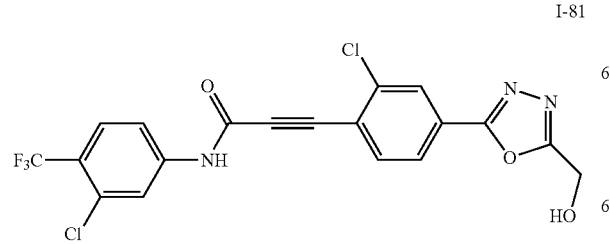
I-67
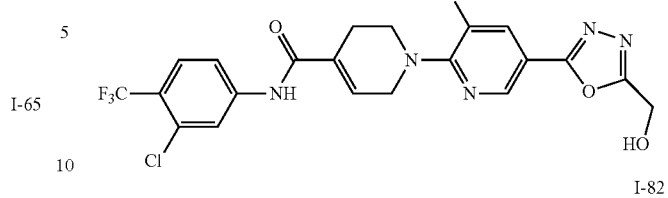
I-82
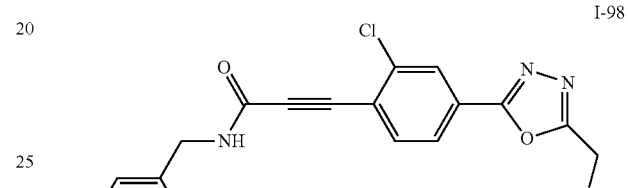
I-98
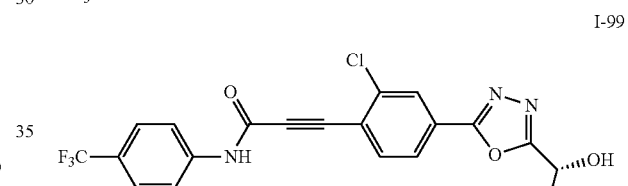
I-99
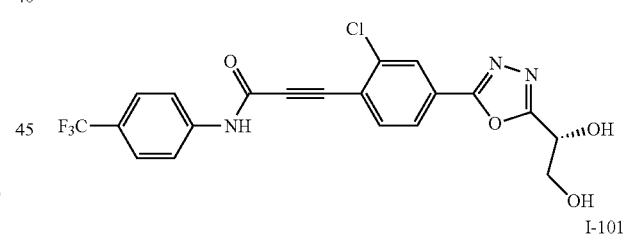
I-100
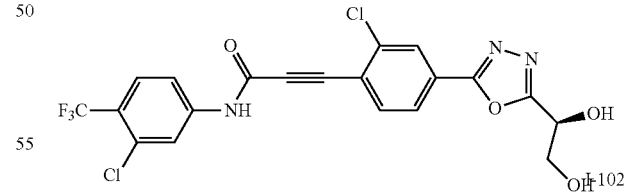
I-101
I-102
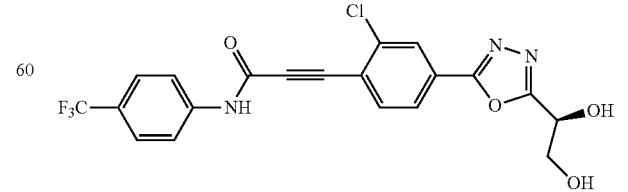
I-65: 5% yield as a brown solid

(E)-3-(3-chloro-5-(5-(hydroxymethyl)-1,3,4-oxadiazol-2-yl)pyridin-2-yl)-N-(4-(trifluoromethyl)benzyl)acrylamide ¹H-NMR (DMSO-d6) δ: 9.14 (2H, s), 8.50 (1H, s), 7.89 (1H, d, J=14.65 Hz), 7.71 (2H, d, J=8.08 Hz), 7.53 (2H, d, J=8.08 Hz), 7.42 (1H, d, J=14.65 Hz), 6.03 (1H, t, J=5.56 Hz), 4.76 (2H, d, J=5.56 Hz), 4.53 (2H, d, J=5.05 Hz). LC/MS (M+1): 439.

I-66: 25% yield as a yellow solid

(E)-N-(3-chloro-4-(trifluoromethyl)phenyl)-3-(3-chloro-5-(5-(hydroxymethyl)-1,3,4-oxadiazol-2-yl)pyridin-2-yl)but-2-enamide ¹H-NMR (DMSO-d6) δ: 10.78 (1H, s), 9.15 (1H, s), 8.55 (1H, s), 8.12 (1H, s), 7.82 (1H, d, J=8.59 Hz), 7.70 (1H, d, J=8.59 Hz), 6.38 (1H, s), 6.06 (1H, t, J=6.06 Hz), 4.77 (2H, d, J=6.06 Hz), 2.55 (3H, s). LC/MS (M+1): 473.

I-68: 15% yield as a yellow solid

(E)-3-(3-chloro-5-(5-(hydroxymethyl)-1,3,4-oxadiazol-2-yl)pyridin-2-yl)-N-(4-(trifluoromethyl)phenyl)but-2-enamide ¹H-NMR (DMSO-d6) δ: 10.61 (1H, s), 9.15 (1H, s), 8.56 (1H, s), 7.89 (2H, d, J=8.59 Hz), 7.71 (2H, d, J=8.59 Hz), 6.40 (1H, s), 6.05 (1H, t, J=5.56 Hz), 4.77 (2H, d, J=5.56 Hz), 2.55 (3H, s). LC/MS (M+1): 439.

I-69: 16% yield as a yellow solid

(E)-3-(3-chloro-5-(5-(hydroxymethyl)-1,3,4-oxadiazol-2-yl)pyridin-2-yl)-N-(4-(trifluoromethyl)benzyl)but-2-enamide ¹H-NMR (DMSO-d6) δ: 9.12 (1H, s), 8.83 (1H, br), 8.51 (1H, s), 7.71 (2H, d, J=7.58 Hz), 7.52 (2H, d, J=7.58 Hz), 6.22 (1H, s), 6.04 (1H, t, J=5.56 Hz), 4.76 (2H, d, J=5.56 Hz), 4.45 (2H, brs), 2.48 (3H, s). LC/MS (M+1): 453.

I-83: 7% yield as a white solid

(E)-3-(2-chloro-4-(5-(hydroxymethyl)-1,3,4-oxadiazol-2-yl)phenyl)-N-(3-chloro-4-(trifluoromethyl)phenyl)but-2-enamide ¹H-NMR (DMSO-d6) δ: 10.67 (1H, s), 8.11 (1H, s), 8.08 (1H, s), 8.02 (1H, d, J=8.08 Hz), 7.82 (1H, d, J=8.08 Hz), 7.68 (1H, d, J=8.08 Hz), 7.63 (1H, d, J=8.08 Hz), 6.11 (1H, s), 6.01 (1H, t, J=6.06 Hz), 4.75 (2H, d, J=6.06 Hz). LC/MS (M+1): 472.

I-81: 39% yield as a yellow solid

3-(2-chloro-4-(5-(hydroxymethyl)-1,3,4-oxadiazol-2-yl)phenyl)-N-(3-chloro-4-(trifluoromethyl)phenyl)propiolamide ¹H-NMR (DMSO-d6) δ: 11.54 (1H, s), 8.20 (1H, s), 8.08 (1H, d, J=8.59 Hz), 8.02 (1H, s), 8.01 (1H, d, J=8.59 Hz), 7.88 (1H, d, J=8.08 Hz), 7.76 (1H, d, J=8.08 Hz), 6.02 (1H, t, J=6.06 Hz), 4.75 (2H, d, J=6.06 Hz). LC/MS (M+1): 456.

I-82: 3-(2-chloro-4-(5-(hydroxymethyl)-1,3,4-oxadiazol-2-yl)phenyl)-N-(4-(trifluoromethyl)phenyl)propiolamide 27% yield as a white solid ¹H-NMR (DMSO-d6) δ: 11.39 (1H, s), 8.19 (1H, s), 8.07 (1H, d, J=7.58 Hz), 8.00 (1H, d, J=7.58 Hz), 7.87 (2H, d, J=8.08 Hz), 7.75 (2H, d, J=8.08 Hz), 6.03 (1H, t, J=6.06 Hz), 4.75 (2H, d, J=6.06 Hz). LC/MS (M+1): 422.

I-98: 55% yield as a white solid

3-(2-chloro-4-(5-(hydroxymethyl)-1,3,4-oxadiazol-2-yl)phenyl)-N-(4-(trifluoromethyl)benzyl)propiolamide ¹H-NMR (DMSO-d6) δ: 9.60 (1H, t, J=5.56 Hz), 8.16 (1H, s), 8.03 (1H, d, J=7.58 Hz), 7.93 (1H, d, J=7.58 Hz), 7.73 (2H, d, J=8.08 Hz), 7.53 (2H, d, J=8.08 Hz), 6.01 (1H, t, J=6.06 Hz), 4.74 (2H, d, J=6.06 Hz), 4.47 (2H, d, J=5.56 Hz). LC/MS (M+1): 436.

I-99: 46% yield as a yellow solid

(R)-3-(2-chloro-4-(5-(1,2-dihydroxyethyl)-1,3,4-oxadiazol-2-yl)phenyl)-N-(3-chloro-4-(trifluoromethyl)phenyl)propiolamide ¹H-NMR (DMSO-d6) δ: 11.54 (1H, s), 8.21 (1H, s), 8.09 (1H, d, J=8.59 Hz), 8.02 (1H, s), 8.01 (1H, d, J=8.59 Hz), 7.88 (1H, d, J=8.08 Hz), 7.76 (1H, d, J=8.08 Hz), 6.22 (1H, d, J=5.56 Hz), 5.08 (1H, t, J=6.06 Hz), 4.88 (1H, dt, J=6.06, 5.56 Hz), 3.79 (2H, dd, J=6.06, 5.56 Hz). LC/MS (M+1): 486.

I-100: 58% yield as a white solid

(R)-3-(2-chloro-4-(5-(1,2-dihydroxyethyl)-1,3,4-oxadiazol-2-yl)phenyl)-N-(4-(trifluoromethyl)phenyl)propiolamide ¹H-NMR (DMSO-d6) δ: 11.39 (1H, s), 8.21 (1H, s), 8.09 (1H, d, J=8.08 Hz), 8.01 (1H, d, J=8.08 Hz), 7.87 (2H, d, J=8.59 Hz), 7.75 (2H, d, J=8.59 Hz), 6.21 (1H, d, J=5.56 Hz), 5.07 (1H, t, J=6.06 Hz), 4.88 (1H, dt, J=6.06, 5.56 Hz), 3.79 (2H, dd, J=6.06, 5.56 Hz). LC/MS (M+1): 452.

I-101: 19% yield as a yellow solid

(S)-3-(2-chloro-4-(5-(1,2-dihydroxyethyl)-1,3,4-oxadiazol-2-yl)phenyl)-N-(3-chloro-4-(trifluoromethyl)phenyl)propiolamide ¹H-NMR (DMSO-d6) δ: 11.54 (1H, s), 8.21 (1H, s), 8.09 (1H, d, J=8.59 Hz), 8.02 (1H, s), 8.01 (1H, d, J=8.59 Hz), 7.88 (1H, d, J=8.08 Hz), 7.76 (1H, d, J=8.08 Hz), 6.21 (1H, d, J=6.06 Hz), 5.07 (1H, t, J=5.56 Hz), 4.88 (1H, dt, J=6.06, 5.65 Hz), 3.79 (2H, d, J=5.56 Hz). LC/MS (M+1): 486.

I-102: 21% yield as a yellow solid

(S)-3-(2-chloro-4-(5-(1,2-dihydroxyethyl)-1,3,4-oxadiazol-2-yl)phenyl)-N-(4-(trifluoromethyl)phenyl)propiolamide ¹H-NMR (DMSO-d6) δ: 11.39 (1H, s), 8.21 (1H, s), 8.09 (1H, d, J=8.08 Hz), 8.01 (1H, d, J=8.08 Hz), 7.87 (2H, d, J=8.59 Hz), 7.75 (2H, d, J=8.59 Hz), 6.21 (1H, d, J=5.56 Hz), 5.07 (1H, t, J=6.06 Hz), 4.88 (1H, dt, J=6.06, 5.56 Hz), 3.79 (2H, dd, J=6.06, 5.56 Hz). LC/MS (M+1): 452.

I-67: 6% yield as a yellow solid

N-(3-chloro-4-(thloro-5-(5-(hydroxymethyl)-1,3,4-oxadiazol-2-yl)pyridin-2-yl)-1,2,3,6-terifluoromethyl)phenyl)-1-(3-ctrahydropyridine-4-carboxamide ¹H-NMR (DMSO-d6) δ: 10.26 (1H, s), 8.76 (1H, s), 8.26 (1H, s), 8.12 (1H, s), 7.86-7.80 (2H, m), 6.89 (1H, br), 5.98

(1H, t, J=6.06 Hz), 4.72 (2H, d, J=6.06 Hz), 4.24 (2H, br), 3.69 (2H, br), 2.62 (2H, br). LC/MS (M+1): 514.

Example 6

Step 1

(E)-N-(4-bromo-2-fluorobenzyl)-3-(4-(trifluoromethyl)phenyl)acrylamide

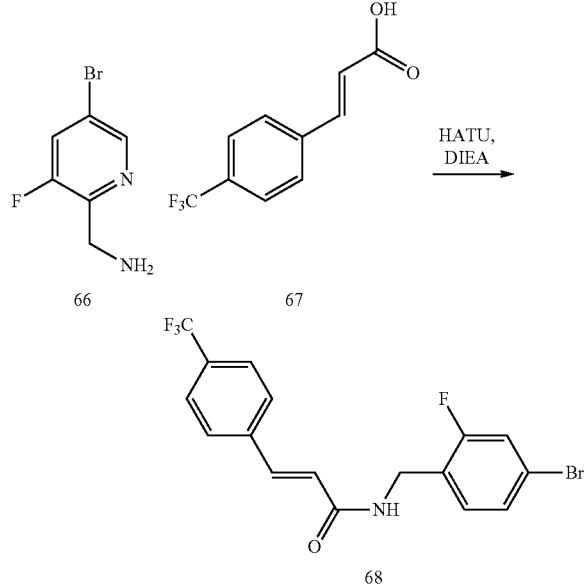

To a solution of (E)-3-(4-(trifluoromethyl)phenyl)acrylic acid (67) (500 mg, 2.31 mmol) (4-bromo-2-fluorophenyl)methanamine (66) (519 mg, 2.54 mmol) in DMF (5 ml) was added HATU (924 mg, 2.43 mmol) and DIEA (0.81 ml, 4.63 mmol) at 0° C. under nitrogen. After being stirred overnight at room temperature, the reaction mixture was quenched with 10% citric acid and diluted with ethyl acetate. The resulting organic layer was separated and the aqueous layer was extracted with ethyl acetate. The combined organic layers were washed with brine, dried over Na$_2$SO$_4$ and concentrated in vacuo. The crude product was chromatographed on silica gel eluting with a gradient of hexane/ethyl acetate (20-40%) to afford 460 mg of the desired product (68) in 91% yield as a white solid. $^1$H-NMR (DMSO-d6) δ: 8.74 (1H, t, J=5.05 Hz), 7.79 (4H, s), 7.56-7.52 (2H, m), 7.42 (1H, d, J=8.34 Hz), 7.33 (1H, d, J=8.34 Hz), 6.81 (1H, d, J=15.66 Hz), 4.41 (2H, d, J=5.05 Hz). LC/MS (M+1): 404.

Step 2

(E)-N-(2-fluoro-4-(5-(hydroxymethyl)-1,2,4-oxadiazol-3-yl)benzyl)-3-(4-(trifluoromethyl)phenyl)acrylamide

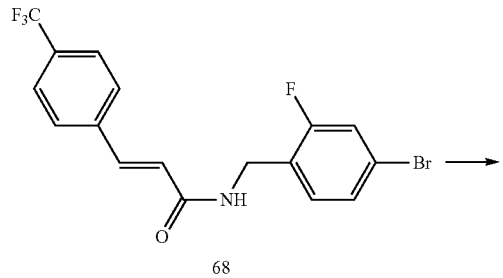

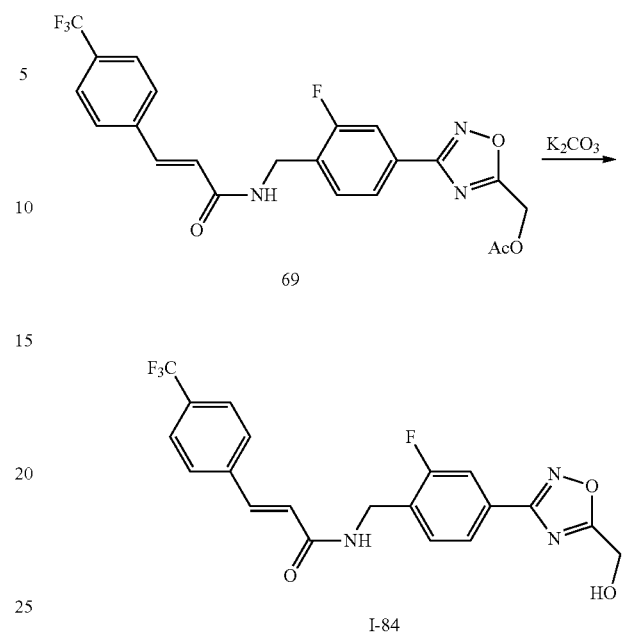

The compound (69) was obtained using the procedure shown in Reference Example 2, Steps 1 and 2. The residue was used for the next reaction without further purification.

To a solution of (59) (359 mg, 0.788 mmol) in THF (3 ml) and EtOH (3 ml) was added K$_2$CO$_3$ (108 mg, 0.764 mmol) in H$_2$O (0.5 ml) at 0° C. After being stirred overnight at room temperature, the reaction mixture was quenched with H$_2$O and extracted with ethyl acetate. The resulting organic layer was washed with brine, dried over Na$_2$SO$_4$ and concentrated in vacuo. The crude product was chromatographed on silica gel eluting with a gradient of CHCl$_3$/MeOH (0-5%) to afford 65 mg of the desired product (I-84) in 40% yield as a white solid. $^1$H-NMR (DMSO-d6) δ: 8.83 (1H, br), 7.86 (1H, d, J=7.58 Hz), 7.79-7.74 (5H, m), 7.58-7.54 (2H, m), 6.85 (1H, d, J=15.66 Hz), 6.10 (1H, t, J=6.06 Hz), 4.81 (2H, d, J=6.06 Hz), 4.52 (2H, brs). LC/MS (M+1): 422.

Example 7

Step 1

(5-((tert-butyldimethylsilyloxy)methyl)-1,3,4-oxadiazol-2-yl)(5,6-dichloropyridin-3-yl)methanone (68)

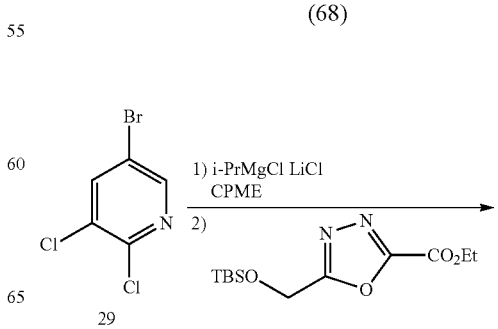

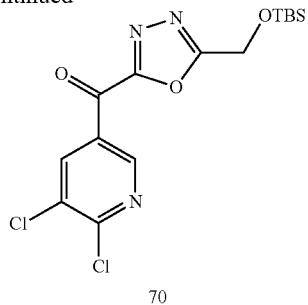

70

Under nitrogen atmosphere, to a 12 mL cyclopentyl methyl ether solution of 5-bromo-2,3-dichloropyridine (29) (1.72 g, 7.58 mmol) at −10° C. was dropwise added i-PrMgCl LiCl complex (1.3 M in tetrahydrofuran) (6.41 mL, 8.34 mmol) while maintaining the temperature of the mixture below −5° C. After finishing the addition, the mixture was stirred at −10° C. for 10 min and 5.2 mL of a cyclopentyl methyl ether solution of ethyl 5-((tert-butyldimethylsilyloxy)methyl)-1,3,4-oxadiazole-2-carboxylate (3.26 g, 11.37 mmol) was added over 5 min. The resulting mixture was stirred at −10° C. for 0.5 hrs. Saturated NH₄Cl was added to the reaction flask and the mixture was extracted with ethyl acetate (50 mL×2). The resulting organic layer was washed with H₂O, brine, dried over anhydrous sodium sulfate, and concentrated in vacuo. The crude product was chromatographed on silica gel eluting with a gradient of ethyl acetate (3-15%)/hexanes to afford 1.75 g of the product (70) (59%).

¹H-NMR (CDCl₃) δ: 9.42 (1H, d, J=2.1 Hz), 8.95 (1H, d, J=2.1 Hz), 5.01 (2H, s), 0.94 (9H, s), 0.18 (6H, s).

Step 2

(5-((tert-butyldimethylsilyloxy)methyl)-1,3,4-oxadiazol-2-yl)(5,6-dichloropyridin-3-yl)methanol (71)

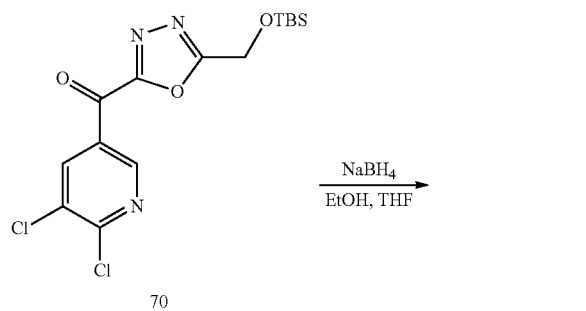

To a solution of (5-((tert-butyldimethylsilyloxy)methyl)-1,3,4-oxadiazol-2-yl)(5,6-dichloropyridin-3-yl)methanone (70) (1.75 g, 4.51 mmol) in tetrahydrofuran (8.8 mL) and ethanol (8.8 mL) was added sodium tetrahydroborate (0.085 g, 2.25 mmol) at 0° C. under nitrogen atmosphere. The resulting mixture was stirred at 0° C. for 15 min. AcOH was added to the reaction flask and the mixture was extracted with ethyl acetate (50 mL×2). The resulting organic layer was washed with H₂O, brine, dried over anhydrous sodium sulfate, and concentrated in vacuo to afford 1.79 g of the product (71) as a pale yellow oil (quant.).

¹H-NMR (CDCl₃) δ: 8.42 (1H, dd, J=2.2, 0.5 Hz), 7.98 (1H, d, J=2.2 Hz), 6.12 (1H, s), 4.84 (2H, s), 0.87 (9H, s), 0.09 (6H, s).

Step 3

O-(5-((tert-butyldimethylsilyloxy)methyl)-1,3,4-oxadiazol-2-yl)(5,6-dichloropyridin-3-yl)methyl O-phenyl carbonothioate (72)

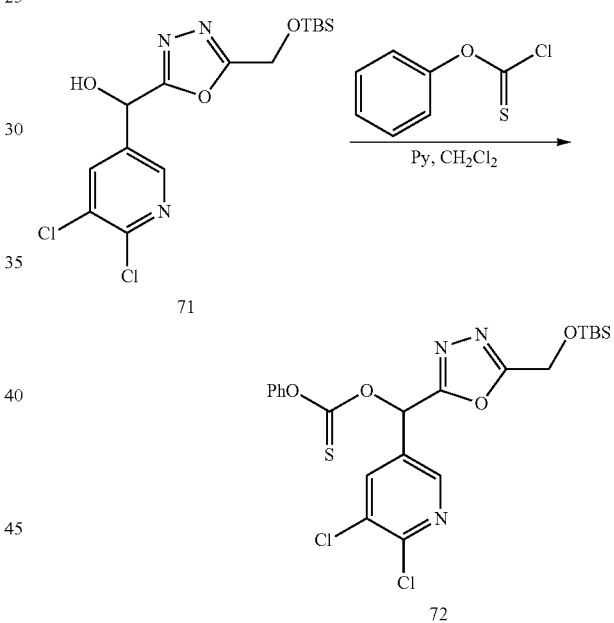

To a solution of (5-((tert-butyldimethylsilyloxy)methyl)-1,3,4-oxadiazol-2-yl)(5,6-dichloropyridin-3-yl)methanol (71) (1.77 g, 4.53 mmol) in dichloromethane (12.4 mL) and pyridine (12.4 mL) was added phenyl chlorothionoformate (1.17 g, 6.80 mmol) at 0° C. under nitrogen atmosphere. The resulting mixture was stirred at room temperature for 2.5 hrs. Saturated NaHCO₃ was added to the reaction flask and the mixture was extracted with ethyl acetate (50 mL×2). The resulting organic layer was washed with H₂O, brine, dried over anhydrous sodium sulfate, and concentrated in vacuo. The crude product was chromatographed on silica gel eluting with a gradient of ethyl acetate (5-20%)/hexanes to afford 1.79 g of the product (72) as a pale yellow oil (75%).

¹H-NMR (CDCl₃) δ: 8.53 (1H, d, J=2.3 Hz), 8.07 (1H, d, J=2.3 Hz), 7.50 (1H, s), 7.45-7.39 (2H, m), 7.33-7.30 (1H, m), 7.11-7.08 (2H, m), 4.90 (2H, s), 0.90 (9H, s), 0.13 (6H, s).

Step 5

2-((tert-butyldimethylsilyloxy)methyl)-5-(5,6-dichloropyridin-3-yl)methyl)-1,3,4-oxadiazole (73)

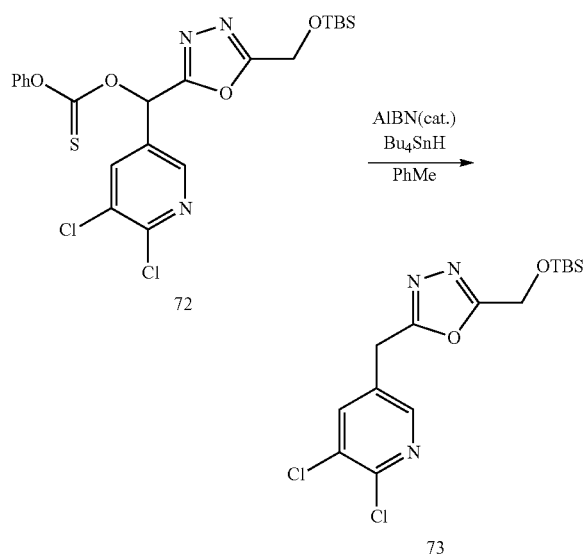

Under nitrogen atmosphere, to a 18 mL toluene solution of O-(5-((tert-butyldimethylsilyloxy)methyl)-1,3,4-oxadiazol-2-yl)(5,6-dichloropyridin-3-yl)methyl O-phenyl carbonothioate (72) (1.75 g, 3.32 mmol) were added AIBN (0.027 g, 0.166 mmol) and tributylstannane (1.16 g, 3.99 mmol) at room temperature The mixture was stirred at 80° C. for 3 hrs.

The reaction mixture was diluted with 20% KFaq. (20 mL) and stirred for 30 min, and then extracted with ethyl acetate (50 mL×2). The organic layer was washed with H₂O, brine, dried over anhydrous sodium sulfate, and concentrated in vacuo. The crude product was chromatographed on silica gel eluting with a gradient of ethyl acetate (20-50%)/hexanes to afford 1.13 g of the product (73) as a colorless oil (91%).

$^1$H-NMR (CDCl$_3$) δ: 8.29 (1H, d, J=2.4 Hz), 7.79 (1H, d, J=2.4 Hz), 4.83 (2H, s), 4.21 (2H, s), 0.88 (9H, s), 0.10 (6H, s).

Step 6 tert-butyl 4-(5-((5-((tert-butyldimethylsilyloxy)methyl)-1,3,4-oxadiazol-2-yl)methyl)-3-chloropyridin-2-yl)-5,6-dihydropyridine-1(2H)-carboxylate (74)

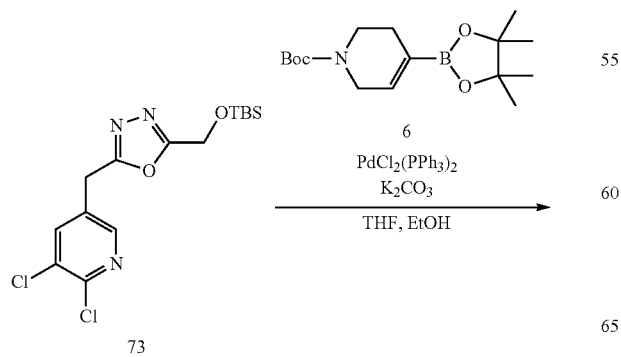

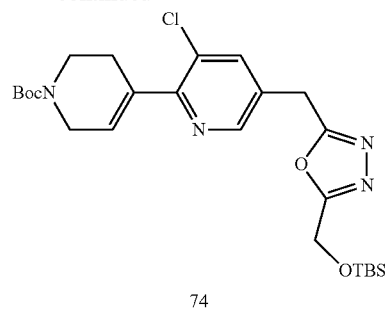

The compound (74) was obtained using the procedure shown in Example 1, Step 3. (yield 89%)

$^1$H-NMR (CDCl$_3$) δ: 8.43 (1H, d, J=2.0 Hz), 7.69 (1H, d, J=2.0 Hz), 6.10 (1H, br), 4.83 (2H, s), 4.20 (3H, s), 4.10 (2H, br), 3.64 (2H, t, J=5.4 Hz), 2.56 (2H, br), 1.49 (9H, s), 0.87 (9H, s), 0.10 (6H, s).

Step 7

(5-((5-chloro-6-(1,2,3,6-tetrahydropyridin-4-yl)pyridin-3-yl)methyl)-1,3,4-oxadiazol-2-yl)methanol hydrochloride (75)

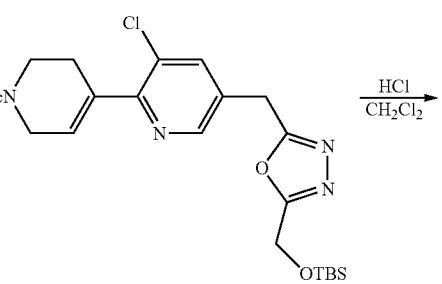

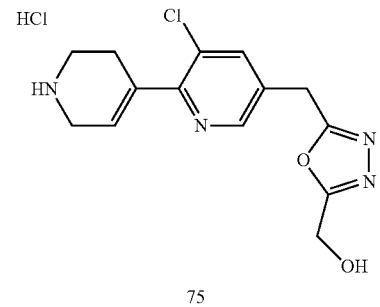

The compound (75) was obtained using the procedure shown in Example 1, Step 4. (yield 98%)

Step 8

4-(3-chloro-5-((5-(hydroxymethyl)-1,3,4-oxadiazol-2-yl)methyl)pyridin-2-yl)-N-(5-(trifluoromethyl)pyridin-2-yl)-5,6-dihydropyridine-1(2H)-carboxamide

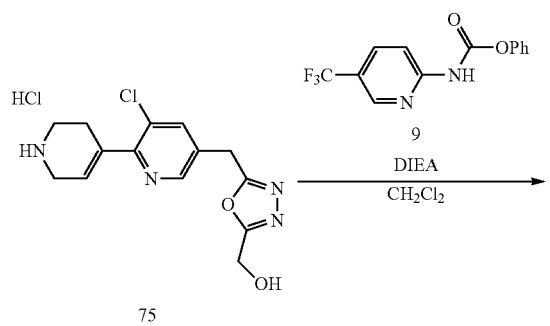

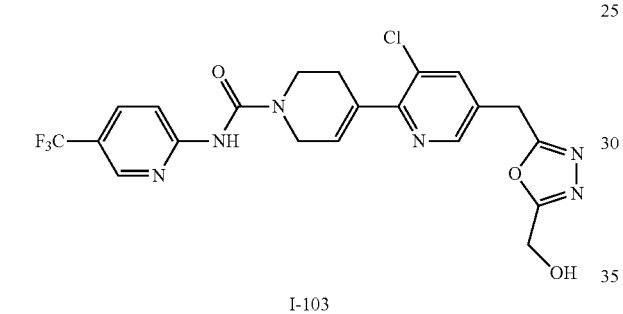

The compound I-103 was obtained using the procedure shown in Example 1, Step 5. (yield 98%.)

¹H-NMR (CDCl₃) δ: 8.45 (2H, d, J=2.0 Hz), 8.20 (1H, d, J=8.8 Hz), 7.87 (1H, dd, J=8.8, 2.0 Hz), 7.72 (1H, d, J=2.0 Hz), 7.46 (1H, s), 6.23-6.21 (1H, m), 4.85 (2H, d, J=6.6 Hz), 4.28-4.22 (4H, m), 3.79 (2H, t, J=5.6 Hz), 2.71-2.71 (2H, m), 2.49 (1H, t, J=6.6 Hz).

Example 8

4-(3-chloro-5-(oxazol-2-ylmethyl)pyridin-2-yl)-N-(5-(trifluoromethyl)pyridin-2-yl)-5,6-dihydropyridine-1(2H)-carboxamide

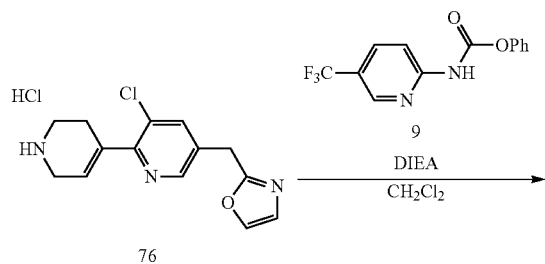

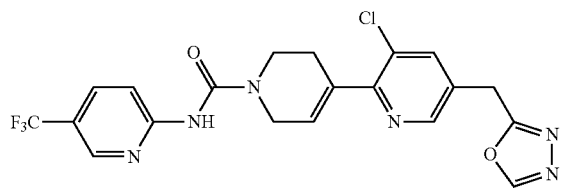

The compound I-104 was obtained using the procedure shown in Example 1, Step 5. (yield 68%)

¹H-NMR (CDCl₃) δ: 8.47-8.43 (2H, m), 8.21 (1H, d, J=8.9 Hz), 7.87 (1H, dd, J=8.9, 2.4 Hz), 7.70 (1H, d, J=2.4 Hz), 7.62 (1H, s), 7.40 (1H, s), 7.08 (1H, s), 6.21-6.19 (1H, m), 4.26 (2H, q, J=2.9 Hz), 4.13 (2H, s), 3.79 (2H, t, J=5.6 Hz).

Example 9

N-(3-chloro-4-(trifluoromethyl)phenyl)-4-(3-chloro-5-(oxazol-2-ylmethyl)pyridin-2-yl)-5,6-dihydropyridine-1(2H)-carboxamide

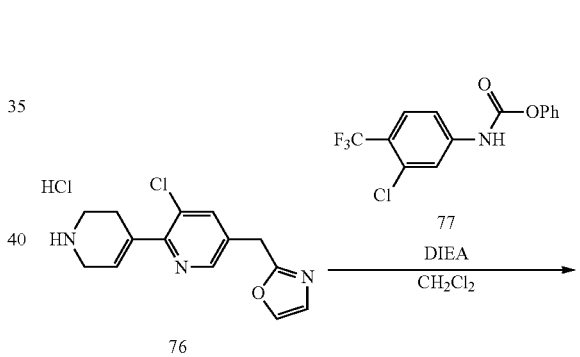

The compound I-79 was obtained using the procedure shown in Example 1, Step 5. (yield 70%)

¹H-NMR (CDCl₃) δ: 8.48 (1H, d, J=1.8 Hz), 7.74 (2H, dd, J=4.6, 1.8 Hz), 7.64 (2H, dd, J=11.7, 4.6 Hz), 7.41 (1H, dd, J=8.3, 1.8 Hz), 7.13 (1H, s), 6.58 (1H, s), 6.25-6.23 (1H, m), 4.27 (2H, q, J=2.8 Hz), 4.18 (2H, s), 3.80 (2H, t, J=5.5 Hz), 2.77-2.74 (2H, m).

Example 10

4-(3-chloro-5-(oxazol-2-ylmethyl)pyridin-2-yl)-N-(3-methyl-4-(trifluoromethyl)phenyl)-5,6-dihydropyridine-1(2H)-carboxamide

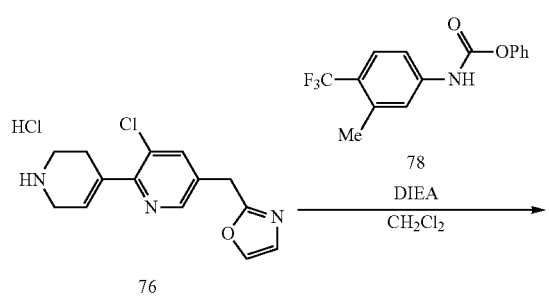

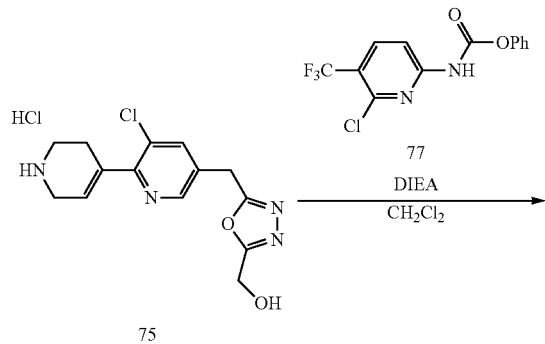

The compound I-80 was obtained using the procedure shown in Example 1, Step 5. (yield 65%)

$^1$H-NMR (CDCl$_3$) δ: 8.44 (1H, d, J=2.0 Hz), 7.70 (1H, d, J=2.0 Hz), 7.62 (1H, d, J=1.0 Hz), 7.51 (1H, d, J=8.7 Hz), 7.38-7.28 (2H, m), 7.08 (1H, d, J=0.8 Hz), 6.44 (1H, s), 6.20-6.18 (1H, m), 4.22 (2H, q, J=2.8 Hz), 4.13 (2H, s), 3.76 (2H, t, J=5.6 Hz), 2.70-2.69 (2H, m), 2.45 (3H, s).

Example 11

N-(3-chloro-4-(trifluoromethyl)phenyl)-4-(3-chloro-5-((5-(hydroxymethyl)-1,3,4-oxadiazol-2-yl)methyl)pyridin-2-yl)-5,6-dihydropyridine-1(2H)-carboxamide

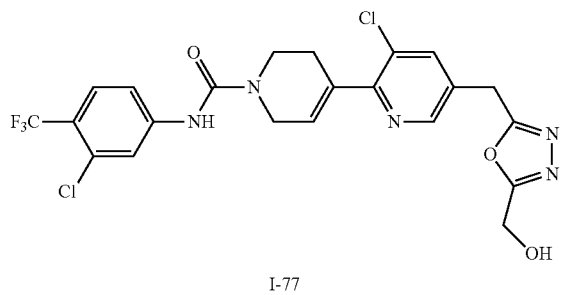

The compound I-77 was obtained using the procedure shown in Example 1, Step 5. (yield 36%.)

$^1$H-NMR (CDCl$_3$) δ: 8.46 (1H, d, J=2.0 Hz), 7.73 (1H, d, J=2.0 Hz), 7.68 (1H, d, J=2.0 Hz), 7.58 (1H, d, J=8.9 Hz), 7.36 (1H, dd, J=8.9, 2.0 Hz), 6.52 (1H, s), 6.23-6.21 (1H, m), 4.85 (2H, d, J=6.7 Hz), 4.24-4.23 (4H, m), 3.76 (2H, t, J=5.6 Hz), 2.72-2.69 (2H, m), 2.22 (1H, br).

Example 12

4-(3-chloro-5-((5-(hydroxymethyl)-1,3,4-oxadiazol-2-yl)methyl)pyridin-2-yl)-N-(3-methyl-4-(trifluoromethyl)phenyl)-5,6-dihydropyridine-1(2H)-carboxamide

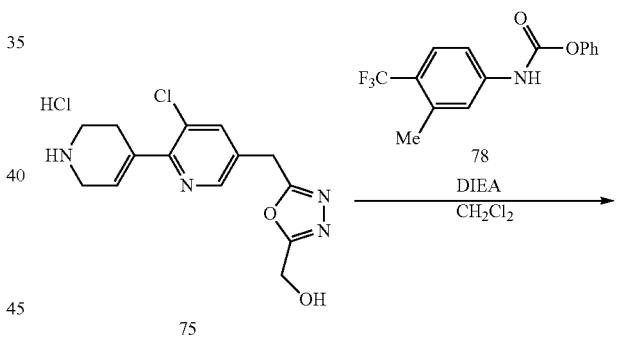

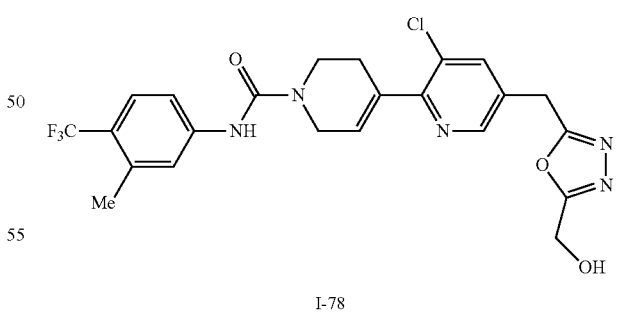

The compound I-78 was obtained using the procedure shown in Example 1, Step 5. (yield 40%)

$^1$H-NMR (CDCl$_3$) δ: 8.46 (1H, d, J=2.0 Hz), 7.73 (1H, d, J=2.0 Hz), 7.52 (1H, d, J=8.7 Hz), 7.38-7.29 (2H, m), 6.47 (1H, s), 6.23-6.21 (1H, m), 4.86 (2H, d, J=6.7 Hz), 4.25-4.23 (4H, m), 3.77 (2H, t, J=5.6 Hz), 2.71-2.71 (2H, m), 2.46-2.40 (4H, m).

Example 13

4-(3-chloro-5-(hydroxy(5-(hydroxymethyl)-1,3,4-oxadiazol-2-yl)methyl)pyridin-2-yl)-N-(3-methyl-4-(trifluoromethyl)phenyl)-5,6-dihydropyridine-1(2H)-carboxamide

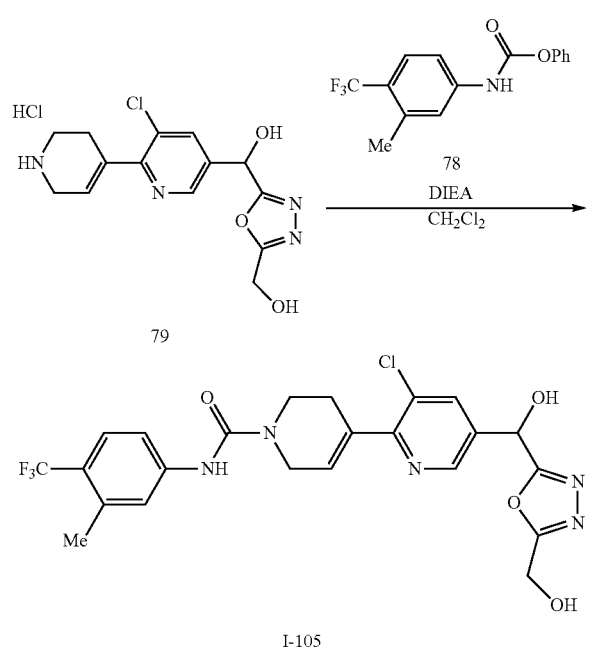

The compound I-105 was obtained using the procedure shown in Example 1, Step 5. (yield 30%)

$^1$H-NMR (DMSO-d6) δ: 8.90 (1H, s), 8.62 (1H, s), 8.01 (1H, s), 7.56-7.53 (3H, m), 6.26-6.17 (2H, m), 4.64 (2H, s), 4.20 (2H, s), 3.71-3.69 (2H, m), 2.60-2.57 (2H, m), 2.38 (3H, s).

Example 14

N-(3-chloro-4-(trifluoromethyl)phenyl)-4-(3-chloro-5-(hydroxy(5-(hydroxymethyl)-1,3,4-oxadiazol-2-yl)methyl)pyridin-2-yl)-5,6-dihydropyridine-1(2H)-carboxamide

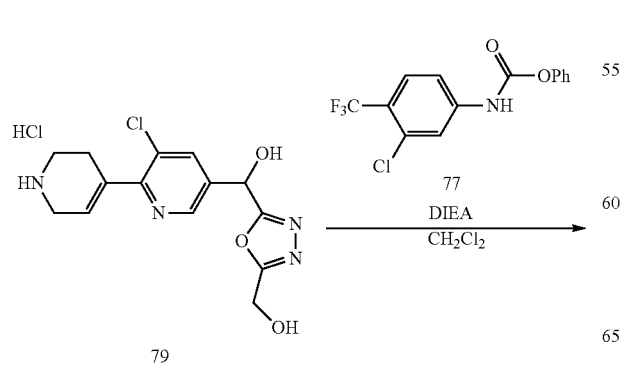

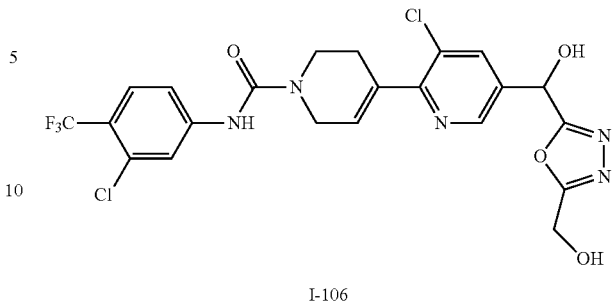

The compound I-106 was obtained using the procedure shown in Example 1, Step 5. (yield 20%)

$^1$H-NMR (DMSO-d6) δ: 9.15 (1H, s), 8.62 (1H, s), 8.01 (1H, s), 7.94 (1H, s), 7.72 (1H, d, J=8.6 Hz), 7.65 (1H, d, J=8.6 Hz), 6.28-6.25 (1H, m), 6.17 (1H, s), 4.64 (2H, s), 4.23-4.20 (2H, m), 3.72-3.70 (2H, m), 2.60-2.58 (2H, m).

Example 15

4-(3-chloro-5-(hydroxy(5-(hydroxymethyl)-1,3,4-oxadiazol-2-yl)methyl)pyridin-2-yl)-N-(5-(trifluoromethyl)pyridin-2-yl)-5,6-dihydropyridine-1(2H)-carboxamide

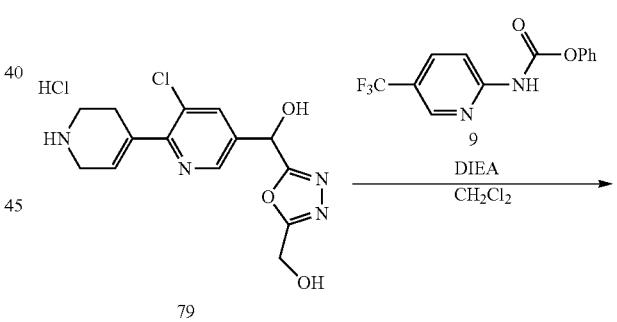

The compound I-107 was obtained using the procedure shown in Example 1, Step 5. (yield 22%)

¹H-NMR (DMSO-d6) δ: 9.84 (1H, s), 8.62 (2H, s), 8.06-8.00 (3H, m), 6.24-6.17 (2H, m), 4.64 (2H, s), 4.24-4.22 (2H, m), 3.74-3.71 (2H, m), 2.59 (2H, s).

Example 16

N-(3-chloro-4-(trifluoromethyl)phenyl)-4-(3-chloro-5-(furan-2-yl(hydroxy)methyl)pyridin-2-yl)-5,6-dihydropyridine-1(2H)-carboxamide

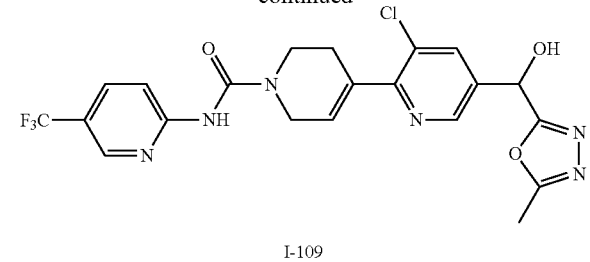

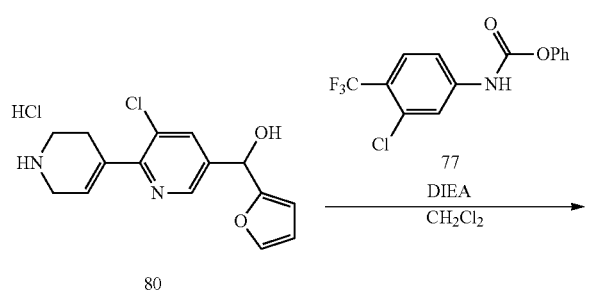

The compound I-108 was obtained using the procedure shown in Example 1, Step 5. (yield 6%)

¹H-NMR (DMSO-d6) δ: 9.16 (1H, s), 8.53 (1H, s), 7.92 (2H, d, J=22.0 Hz), 7.72-7.61 (3H, m), 6.41 (1H, d, J=1.8 Hz), 6.29 (1H, d, J=1.8 Hz), 6.25-6.23 (1H, m), 5.84 (1H, s), 4.22-4.20 (2H, m), 3.72-3.69 (2H, m), 2.60-2.57 (2H, m).

Example 17

4-(3-chloro-5-(hydroxy(5-methyl-1,3,4-oxadiazol-2-yl)methyl)pyridin-2-yl)-N-(5-(trifluoromethyl)pyridin-2-yl)-5,6-dihydropyridine-1(2H)-carboxamide

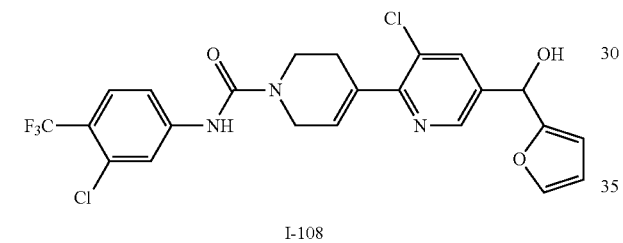

-continued

The compound I-109 was obtained using the procedure shown in Example 1, Step 5. (yield 33%)

¹H-NMR (CDCl₃) δ: 8.57 (1H, dd, J=1.9, 0.5 Hz), 8.45 (1H, s), 8.20 (1H, d, J=9.0 Hz), 7.89-7.86 (2H, m), 7.45 (1H, s), 6.25-6.21 (1H, m), 6.08 (1H, d, J=3.4 Hz), 4.27-4.26 (2H, m), 3.79 (2H, t, J=5.6 Hz), 2.73-2.70 (2H, m), 2.55 (3H, s).

Example 18

N-(3-chloro-4-(trifluoromethyl)phenyl)-4-(3-chloro-5-(hydroxy(5-methyl-1,3,4-oxadiazol-2-yl)methyl)pyridin-2-yl)-5,6-dihydropyridine-1(2H)-carboxamide

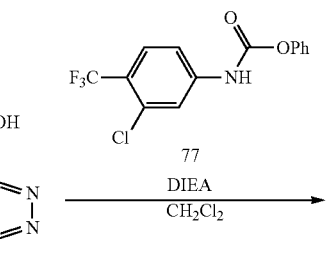

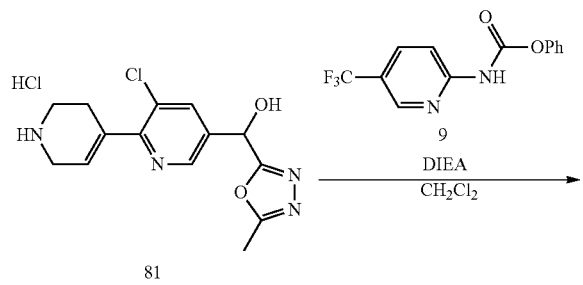

The compound I-110 was obtained using the procedure shown in Example 1, Step 5. (yield 38%)

¹H-NMR (CDCl₃) δ: 8.57 (1H, dd, J=2.0, 0.6 Hz), 7.91 (1H, dd, J=2.0, 0.6 Hz), 7.68 (1H, d, J=2.0 Hz), 7.58 (1H, d, J=8.7 Hz), 7.37 (1H, dd, J=8.7, 2.0 Hz), 6.58 (1H, s), 6.25-6.23 (1H, m), 6.08 (1H, d, J=4.5 Hz), 4.24-4.23 (2H, m), 3.76 (2H, t, J=5.6 Hz), 3.48 (1H, br), 2.72-2.71 (2H, m), 2.55 (3H, s).

Example 19

4-(3-chloro-5-(hydroxy(5-methyl-1,3,4-oxadiazol-2-yl)methyl)pyridin-2-yl)-N-(3-methyl-4-(trifluoromethyl)phenyl)-5,6-dihydropyridine-1(2H)-carboxamide

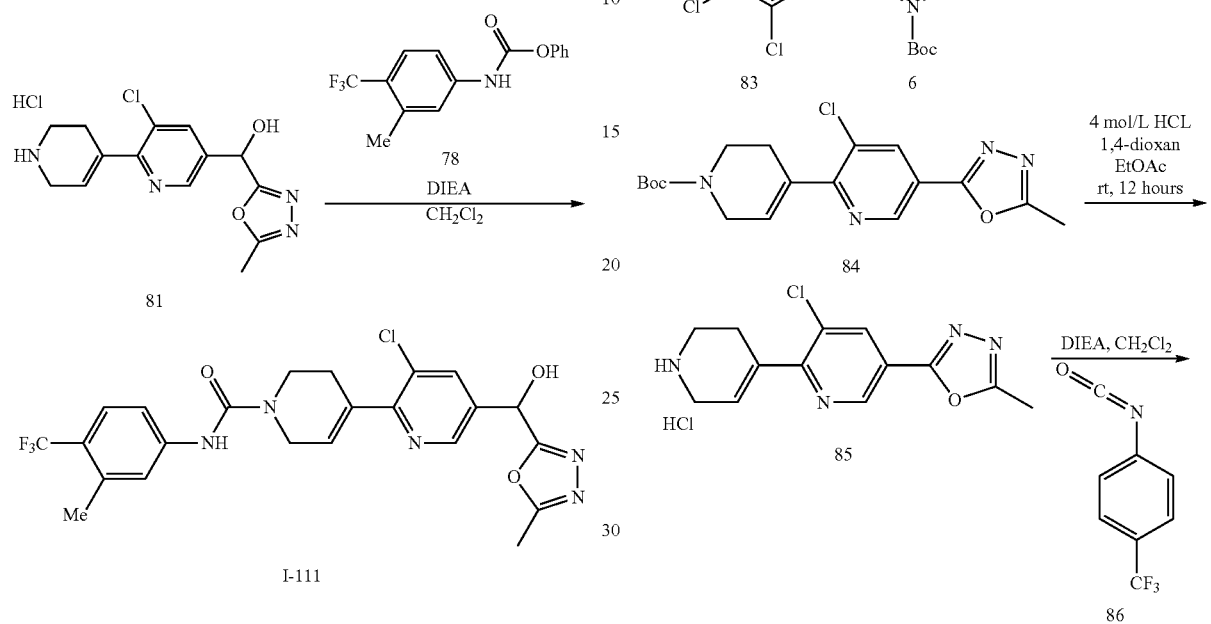

The compound I-111 was obtained using the procedure shown in Example 1, Step 5. (yield 43%)

$^1$H-NMR (CDCl$_3$) δ: 8.57 (1H, d, J=2.0 Hz), 7.90 (1H, dd, J=2.0, 0.5 Hz), 7.52 (1H, d, J=8.6 Hz), 7.35-7.31 (2H, m), 6.46 (1H, s), 6.25-6.23 (1H, m), 6.08 (1H, d, J=5.5 Hz), 4.23-4.23 (2H, m), 3.76 (2H, t, J=5.5 Hz), 3.39 (1H, d, J=5.5 Hz), 2.71-2.71 (2H, m), 2.55 (3H, s), 2.46-2.45 (3H, m).

Example 20

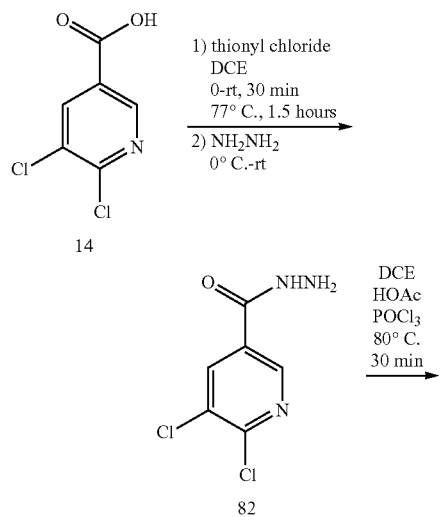

To a round bottom flask was added 14(1 g, 5.2 mmol), DCE (20 ml) and thionyl chloride (0.852 ml) at 0° C. with stir. The resulting mixture was heated at 77° C. oil bath for 5 hours, and extra thionyl chloride and solvent were removed under reduced pressure on rotary evaporator. The residue was diluted with DCM (20 ml) and cooled to 0° C. To this mixture, a solution of hydrazine (0.333 ml, 10 mmol) in DCM (1 ml) was added via syringe. The resulting mixture was allowed to warm to room temperature and stirred for 30 min. The reaction was then diluted with EtOAc (50 ml) and washed with sodium bicarbonate solution twice. The aqueous was extracted with EtOAc (50 ml) and the combined organic portions were dried over Na$_2$SO$_4$, filtered and concentrated on rotary evaporator to obtain the crude 82 (540 mg, 2.6 mmol) and was used without further purification. The crude 82 was dissolved in DCE (10 ml), to which was added acetic acid (1 ml), POCl$_3$(1 ml, 6.4 mmol) at room temperature, and the resulting viscous mixture was heated at 81° C. oil bath for 30 min. The reaction mixture was cooled and poured to ice water and adjusted to pH 7 with Na$_2$CO$_3$ at 0° C. The resulting mixture was extracted with EtOAc (3×50 ml) and the combined organic portions were dried over Na$_2$SO$_4$, filtered and concentrated. The residue was purified via silica chromatography (0~100% EtOAc/Hexane) to obtain 83(435 mg, 1.9 mmol). To a reaction vessel was added 83(435 mg, 1.9 mmol), 6(734 mg, 2.37 mmol), K$_2$CO$_3$(524 mg, 3.8 mmol), PdCl$_2$(PPh$_3$)$_2$(107 mg, 0.15 mmol), DME (4 ml), EtOH(2 ml) and water (4 ml). The vessel was then blanked with Argon, sealed and heated at 95° C. oil bath for 30 min. After cooled to room temperature, the mixture was extracted with EtOAc (3×50 ml) and the combined organic was dried over Na$_2$SO$_4$, filtered, and concentrated. The residue was purified via silica gel chromatography (5-10% MeOH/DCM) to obtain 84. To a solution of 84 in EtOAc (10 ml) was added 4 mol/L HCl in 1,4-dioxane (2 ml) at room temperature and stirred for 12 hours. The mixture was then concentrated on rotary evaporator to remove solvent, and the residue was diluted with Et$_2$O. The precipitate was filtered and collected to give 85(580 mg, 1.6 mmol as 2HCl salt). To a vial was added 85(100 mg, 0.28 mmol), polymer supported DIEA (0.5 g, 1.92 mmol) and DCM (2 ml). To this suspension at 0° C. was added 86(52 mg, 0.28 mmol) and the reaction mixture was allowed to warm to room temperature and stirred for 30 min. The clear solution was transferred to silica gel column and purified via chromatography (5-10% MeOH/DCM) to obtain I-1 (36 mg). $^1$HNMR (CD$_3$OD, δ, ppm): 8.98 (d, 1H, J=1.6 Hz), 8.37 (d, 1H, J=1.6 Hz), 7.50 (m, 4H), 6.29 (m, 1H), 4.20 (m, 2H), 3.71 (t, 2H, J=5.6 Hz), 2.63 (m, 2H), 2.56 (s, 3H). MS: 464(M+1).

Example 21

The following compounds were obtained in similar manner to Example 20.

I-2: $^1$HNMR (CD$_3$OD, δ, ppm): 8.98 (d, 1H, J=1.6 Hz), 8.37 (d, 1H, J=1.6 Hz), 7.3.9 (m, 2H), 7.09 (d, 2H, J=9.2 Hz), 6.29 (m, 1H), 4.18 (m, 2H), 3.69 (t, 2H, J=5.6 Hz), 2.62 (m, 2H), 2.56 (s, 3H). MS: 480(M+1).

I-5: $^1$HNMR (CDCl$_3$, δ, ppm): 9.02 (d, 1H, J=2 Hz), 8.41 (m, 1H), 8.29 (1H, J=2 Hz), 8.15 (d, 1H, J=8.8 Hz), 7.81 (dd, 1H, J=2.4, 8.8 Hz), 7.36 (s, NH, 1H), 6.34 (m, 1H), 4.24 (m, 2H), 3.75 (t, 2H, J=5.6 Hz), 2.71 (m, 2H), 2.60 (s, 3H). MS: 465(M+1).

I-7: $^1$HNMR (CDCl$_3$, δ, ppm): 9.02 (d, 1H, J=2 Hz), 8.28 (1H, J=2 Hz), 7.25 (m, 4H), 6.31 (m, 1H), 6.24 (m, NH, 1H), 4.19 (m, 2H), 3.71 (t, 2H, J=6 Hz), 2.69 (m, 2H), 2.60 (s, 3H), 1.24 (s, 9H). MS: 452(M+1).

Example 22

To a solution of 85(40 mg, 0.11 mmol), DIEA (0.1 ml, 0.55 mmol), DMC(1 ml) at 0° C. was added 87(34 mg, 0.13 mmol). The resulting mixture was allowed to warm to room temperature and stirred for 2 hours. The reaction mixture was concentrated on rotary evaporator and the residue was purified via prep-TLC (10% MeOH/DCM to obtain I-8 (13 mg).

$^1$HNMR (CD$_3$OD, δ, ppm): 9.09 (d, 1H, J=2 Hz), 8.47 (d, 1H, J=1.6 Hz), 7.37 (m, 1H), 7.31 (d, 1H, J=8 Hz), 7.13 (dd, 1H, J=2, 8 Hz), 6.41 (m, 1H), 4.40 (m, 2H), 3.91 (m, 2H), 2.71 (m, 2H), 2.67 (s, 3H). MS: 470(M+1).

Example 23

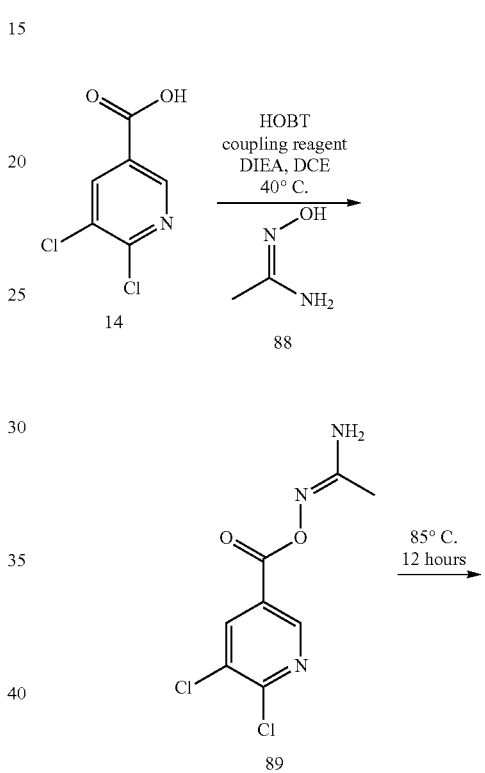

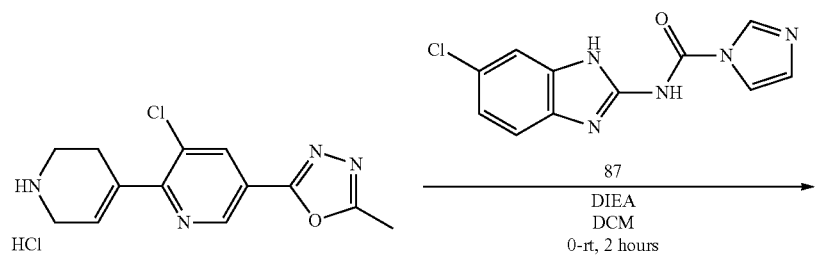

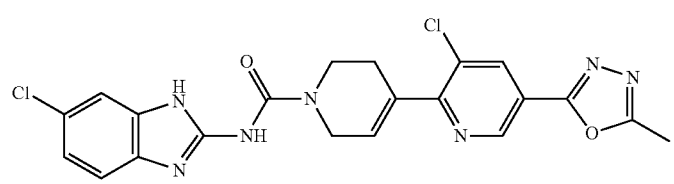

I-8

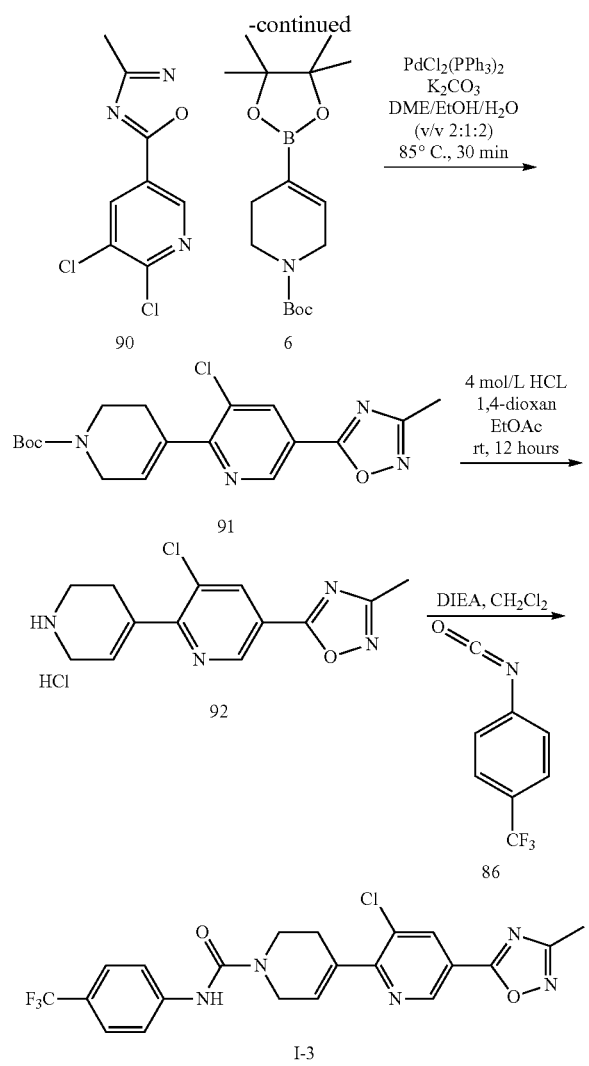

fied on silica gel chromatograph (5-15% EtOAc/Hexane to obtain 91 which was dissolved in EtOAc (3 ml) and treated with 4 mol/L HCl in 1,4-dioxane (1 ml) at room temperature for 12 hours. After removal of solvent on rotary evaporator, the residue was washed with Et₂O and 92 was obtained as white solid (70 mg). To a suspension of 92 (30 mg, 0.096 mmol), polymer supported DIEA (100 mg, 0.38 mmol) in DCM (1 ml) at room temperature was added 86(19 mg, 0.096 mmol) and the resulting mixture was stirred for 30 min. The mixture was purified via silica gel chromatograph (50% EtOAc/Hexane) and then prepTLC to obtain I-3(24 mg).

$^1$HNMR (CDCl$_3$, δ, ppm): 9.11 (d, 1H, J=2 Hz), 8.35 (1H, J=2 Hz), 7.47 (m, 4H), 6.47 (s, NH, 1H), 6.35 (m, 1H), 4.22 (m, 2H), 3.73 (t, 2H, J=6 Hz), 2.72 (m, 2H), 2.44 (s, 3H). MS: 464(M+1).

Example 24

I-4 was obtained in similar manner to Example 23.

$^1$HNMR (CDCl$_3$, δ, ppm): 9.11 (d, 1H, J=2 Hz), 8.35 (1H, J=2 Hz), 7.35 (m, 2H), 7.10 (d, 2H, J=8 Hz), 6.34 (m, NH, 1H), 6.34 (m, 1H), 4.21 (m, 2H), 3.72 (t, 2H, J=6 Hz), 2.71 (m, 2H), 2.44 (s, 3H). MS: 480(M+1).

Example 25

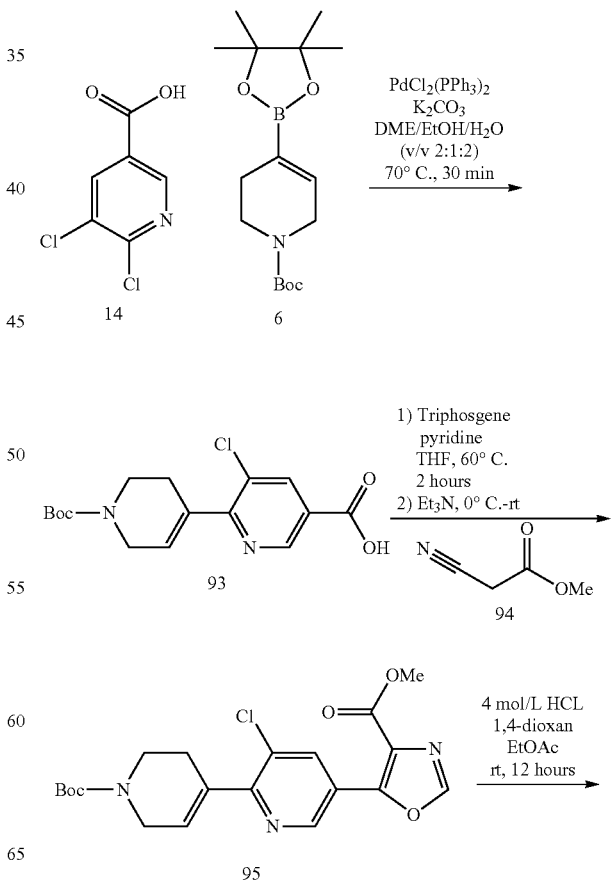

coupling reagent: N-(3-dimethylaminopropyl)-N'-ethyl-cabodiimide hydrochloride

A suspension of 14(500 mg, 2.6 mmol), N-(3-dimethylethylaminopropyl)-N' ethylcarbodiimide hydrochloride (599 mg, 3.12 mmol), HOBT (421 mg, 3.12 mmol), polymer supported DIEA (2 g, 7.8 mmol), 88(211 mg, 2.86 mmol) in DCE (20 ml) was heated at 40° C. for 12 hours. After cooled to room temperature, the crude was purified via silica gel chromatograph (50-100% EtOAC/Hexane) to obtain 89 (330 mg) as white solid. A solution of 89 (330 mg, 1.3 mmol) in a mixed solvents of DCE (10 ml) and acetonitrile (1 ml) was heated at 85° C. oil bath for 12 hours. After cooled to room temperature, the solvent was removed on rotary evaporator and the residue was purified via silica gel chromatograph (5-15% EtOAc/Hexane) to obtain 90(110 mg) as white solid. A vial containing a mixture of 90(110 mg, 0.48 mmol), 6(185 mg, 0.6 mmol), PdCl$_2$(PPh$_3$)$_2$(27 mg, 0.04 mmol), K$_2$CO$_3$(132 mg, 0.96 mmol) in a mixed solvents of DME (2 ml), EtOH(1 ml) and water (2 ml) was blanked with Argon, sealed and heated at 85° C. in oil bath fro 30 min. After cooled to room temperature, the mixture was extracted with EtOAc (3×20 ml) and the combined organic was dried over Na$_2$SO$_4$, filtered and concentrated on rotary evaporator. The residue was puri-

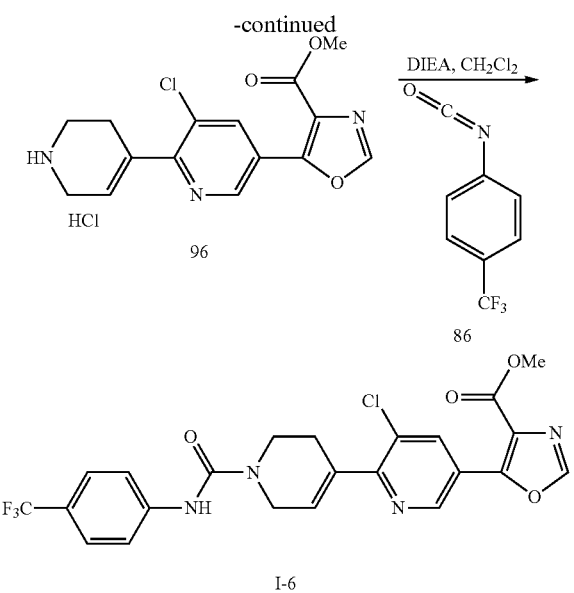

A reaction vessel containing a mixture of 14(1 g, 5.2 mmol), 6(1.9 g, 6.2 mmol), PdCl$_2$(PPh$_3$)$_2$(292 mg, 0.4 mmol), K$_2$CO$_3$(1.4 g, 10.4 mmol) in a mixed solvents of DME (4 ml), EtOH(2 ml) and water (4 ml) was blanked with Argon, sealed and heated at 70° C. oil bath for 30 min. After cooled to room temperature, the mixture was extracted with EtOAc (50 ml). The organic was washed with aqueous K$_2$CO$_3$ solution (50 ml). The combined aqueous solution was neutralized with dilute HCL solution at 0° C. to pH7 and freeze dried. The solid material was stirred with 5% MeOH/DMC(50 ml×3). After 10 min stirring, each time the suspension was filtered and the combined filtrate was concentrated to obtain 93(1.5 g). To a solution of 6(52 mg, 0.22 mmol) in THF (2 ml) was added pyridine (70 mg, 0.88 mmol), triphosgene (65 mg, 0.22 mmol) at room temperature. The resulting solution was heated at 60° C. for 2 hours. To this solution at 0° C. was added a solution of 94(33 μl, 0.33 mmol), Et$_3$N (0.1 ml, 0.66 mmol) in THF (0.5). The resulting solution was allowed to warm to room temperature, and stirred for 3 hours. The crude was purified via silica gel chromatograph (20-50% EtOAc/Hexane) to obtain 95 which was treated with 2 N HCl in Et$_2$O at room temperature for 10 min to obtain 96. To a suspension of the crude 96 in DCM (2 ml) at 0° C. was added DIEA (121 μl, 0.66 mmol) and 86(31 μl, 0.22 mmol). The resulting mixture was allowed to warm to room temperature and stirred for 30 min. The crude mixture was purified via silica gel chromatograph (50-100% EtOAc/Hexane), then prep-TLC to obtain I-6(9 mg) as brown solid.

$^1$HNMR (CDCl$_3$, δ, ppm): 9.05 (d, 1H, J=2 Hz), 8.57 (1H, J=2 Hz), 7.94 (s, 1H), 7.47 (m, 4H), 6.46 (m, NH, 1H), 6.32 (m, 1H), 4.21 (m, 2H), 3.93 (s, 3H), 3.73 (m, 2H), 2.71 (m, 2H). MS: 407(M+1).

Example 26

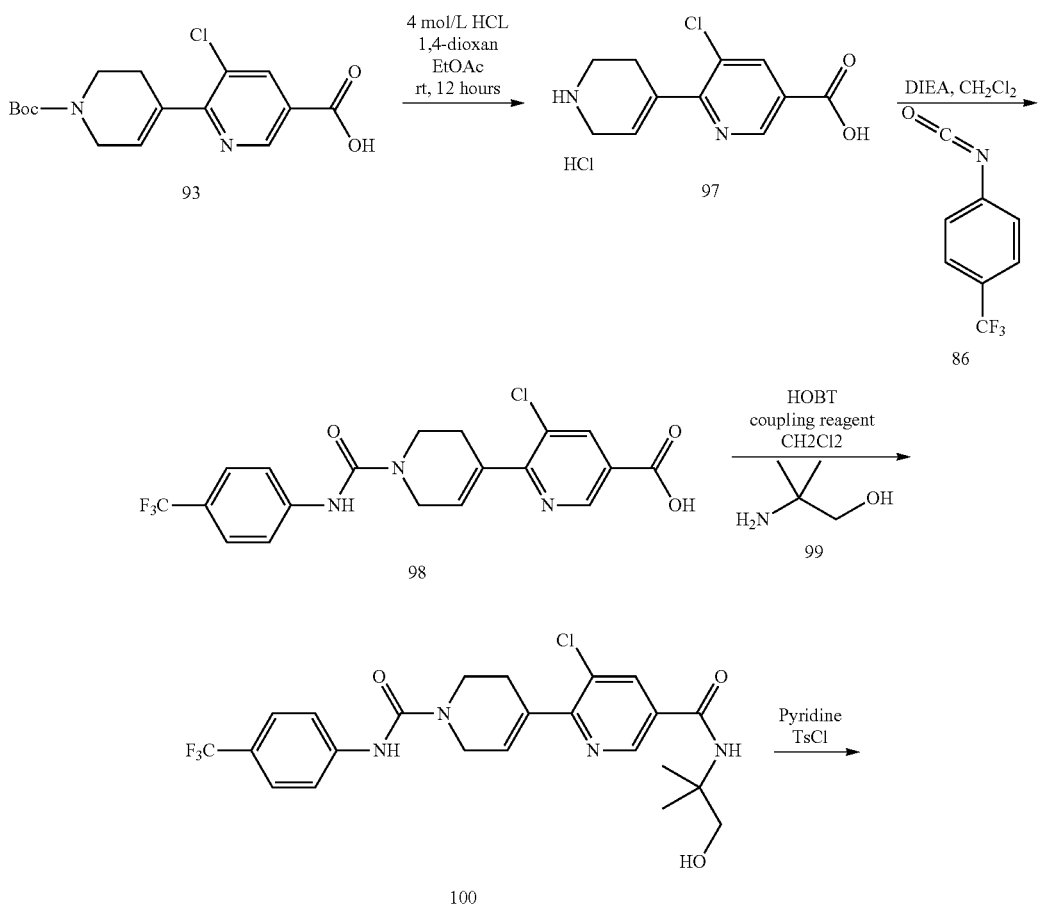

-continued

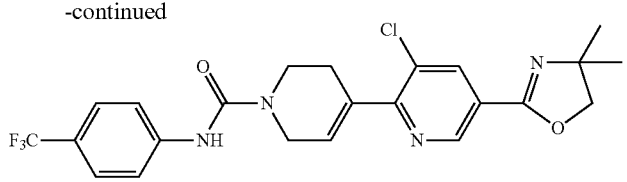

I-70 coupling reagent: N-(3-dimethylaminopropyl)-N′-ethylcabodiimide hydrochloride

A solution of 93(800 mg, 2.3 mmol) in 4 mol/L HCl in 1,4-dioxane (2 ml) was stirred at room temperature for 12 hours. After removal of solvent on rotary evaporator, the residue was suspended in DCM (4 ml). To the suspension was added DIEA (1.7 ml, 9.6 mmol), followed by 7(462 µl, 3.2 mmol) at 0° C. The resulting mixture was allowed to warm to room temperature and stirred for 30 min. The reaction mixture was diluted with DCM (20 ml) and washed with aqueous NaHCO$_3$ solution. The organic was dried with Na$_2$SO$_4$, filtered and concentrated on rotary evaporator. The residue was purified via silica gel chromatograph (10-30% MeOH/DCM) to obtain 98(665 mg) as white solid. To a suspension of 98(70 mg, 0.16 mmol) in DCM (1 ml) at 0° C. was added N-3-dimethylamoniumpropyl)-N'-ethylcarbodiimide hydrochloride (31 mg, 0.16 mmol), HOBT (22 mg, 0.16 mmol) and 99(14 mg, 0.16 mmol). The resulting solution was allowed to warm to room temperature and stirred for 2 hours. The crude was purified via silica gel chromatograph (10% MeOH/DCM) to obtain 100. To a solution of crude 21 in pyridine (2 ml) was added p-toluenesulfonyl chloride (156 mg, 0.48 mmol) and heated at 40° C. for 1 hour. The crude mixture was purified via silica gel chromatograph (0-15% MeOH/DCM) to obtain I-70 (23 mg).

$^1$HNMR (CDCl$_3$, δ, ppm): 8.88 (d, 1H, J=2 Hz), 8.19 (1H, J=2 Hz), 7.46 (m, 4H), 6.44 (m, NH, 1H), 6.21 (m, 1H), 4.19 (m, 2H), 4.07 (s, 2H), 3.71 (t, 2H, J=5.6 Hz), 2.67 (m, 2H), 1.32 (s, 6H). MS: 479(M+1).

TABLE I

| No. | Structure |
|-----|-----------|
| I-1 | 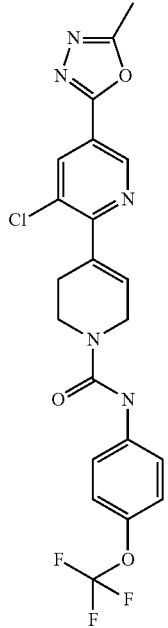 [SMILES: Cc1nnc(-c2cnc(C3=CCN(C(=O)Nc4ccc(OC(F)(F)F)cc4)CC3)c(Cl)c2)o1] |
| I-2 | 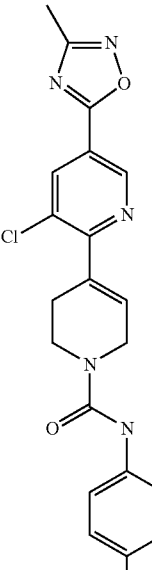 |
| I-3 | 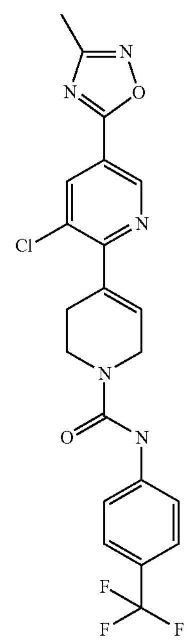 [SMILES: Cc1noc(-c2cnc(C3=CCN(C(=O)Nc4ccc(C(F)(F)F)cc4)CC3)c(Cl)c2)n1] |

TABLE I-continued
| No. | Structure |
|-----|-----------|
| I-4 | 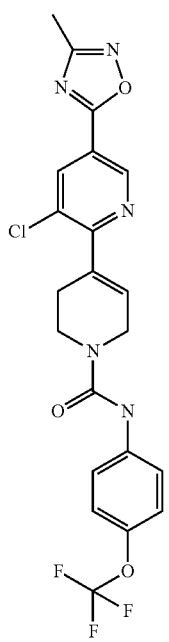 [SMILES: Cc1noc(-c2cnc(C3=CCN(C(=O)Nc4ccc(OC(F)(F)F)cc4)CC3)c(Cl)c2)n1] |
| I-5 | 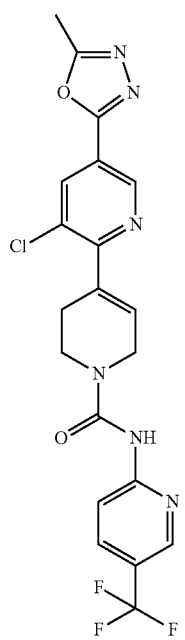 [SMILES: Cc1nnc(-c2cnc(C3=CCN(C(=O)Nc4ccc(C(F)(F)F)cn4)CC3)c(Cl)c2)o1] |
TABLE I-continued
| No. | Structure |
|-----|-----------|
| I-6 | 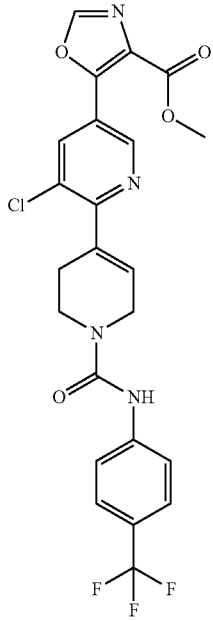 [SMILES: COC(=O)c1ncoc1-c1cnc(C2=CCN(C(=O)Nc3ccc(C(F)(F)F)cc3)CC2)c(Cl)c1] |
| I-7 | 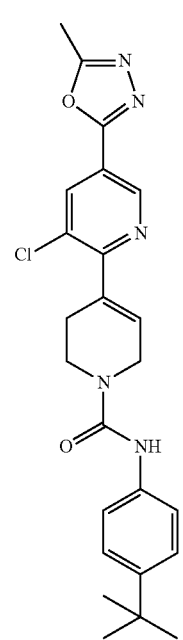 [SMILES: Cc1nnc(-c2cnc(C3=CCN(C(=O)Nc4ccc(C(C)(C)C)cc4)CC3)c(Cl)c2)o1] |

TABLE I-continued
| No. | Structure |
|---|---|
| I-8 | 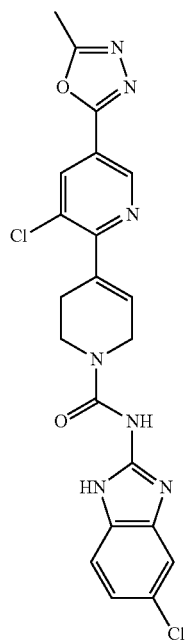 [SMILES: Cc1nnc(-c2cnc(C3=CCN(C(=O)Nc4nc5cc(Cl)ccc5[nH]4)CC3)c(Cl)c2)o1] |
| I-9 | 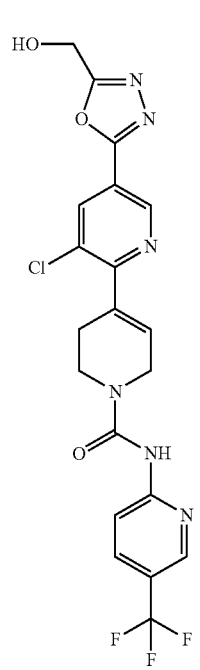 [SMILES: O=C(Nc1ccc(C(F)(F)F)cn1)N1CC=C(c2ncc(-c3nnc(CO)o3)cc2Cl)CC1] |
| I-10 | 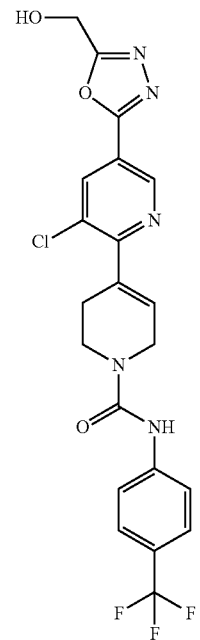 [SMILES: O=C(Nc1ccc(C(F)(F)F)cc1)N1CC=C(c2ncc(-c3nnc(CO)o3)cc2Cl)CC1] |
| I-11 | 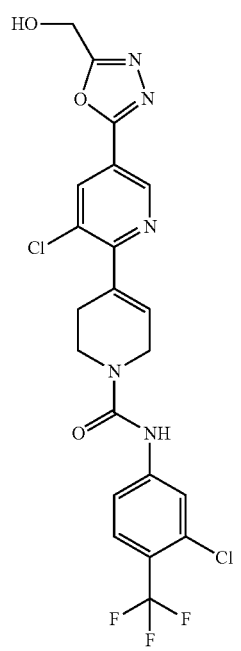 [SMILES: O=C(Nc1ccc(C(F)(F)F)c(Cl)c1)N1CC=C(c2ncc(-c3nnc(CO)o3)cc2Cl)CC1] |

TABLE I-continued
| No. | Structure |
| --- | --- |
| I-12 | 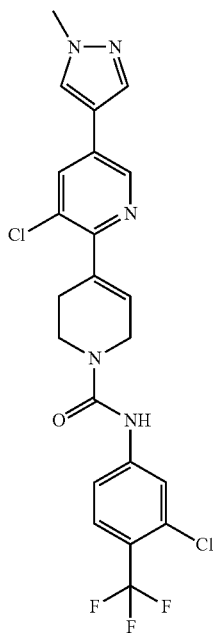 [SMILES: Cn1cc(-c2cnc(C3=CCN(C(=O)Nc4ccc(C(F)(F)F)c(Cl)c4)CC3)c(Cl)c2)cn1] |
| I-13 | 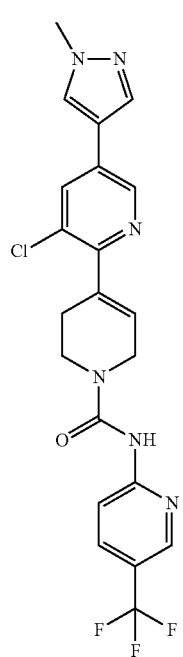 [SMILES: Cn1cc(-c2cnc(C3=CCN(C(=O)Nc4ccc(C(F)(F)F)cn4)CC3)c(Cl)c2)cn1] |
TABLE I-continued
| No. | Structure |
| --- | --- |
| I-14 | 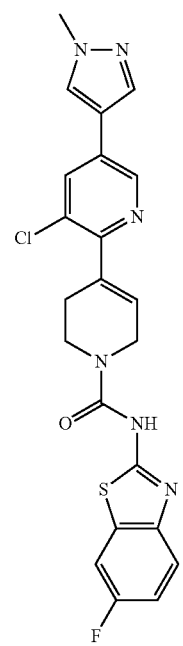 [SMILES: Cn1cc(-c2cnc(C3=CCN(C(=O)Nc4nc5ccc(F)cc5s4)CC3)c(Cl)c2)cn1] |
| I-15 | 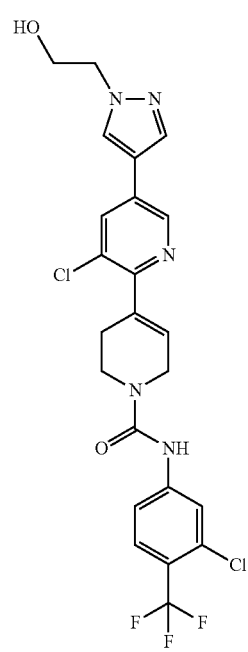 [SMILES: O=C(Nc1ccc(C(F)(F)F)c(Cl)c1)N1CC=C(c2ncc(-c3cnn(CCO)c3)cc2Cl)CC1] |

TABLE I-continued
| No. | Structure |
|---|---|
| I-16 | 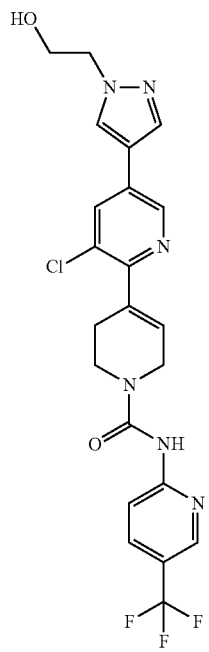 [SMILES: O=C(Nc1ccc(C(F)(F)F)cn1)N1CC=C(c2ncc(-c3cnn(CCO)c3)cc2Cl)CC1] |
| I-17 | 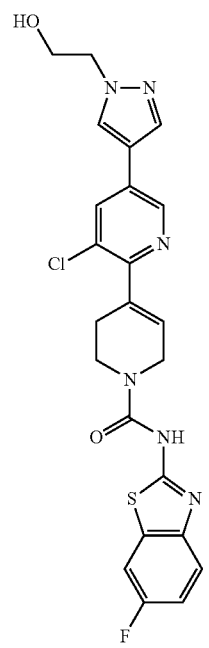 [SMILES: O=C(Nc1nc2ccc(F)cc2s1)N1CC=C(c2ncc(-c3cnn(CCO)c3)cc2Cl)CC1] |
TABLE I-continued
| No. | Structure |
|---|---|
| I-18 | 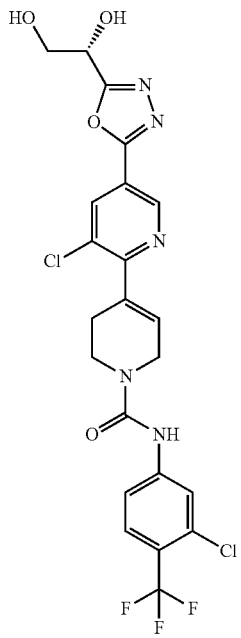 [SMILES: O=C(Nc1ccc(C(F)(F)F)c(Cl)c1)N1CC=C(c2ncc(-c3nnc([C@@H](O)CO)o3)cc2Cl)CC1] |
| I-19 | 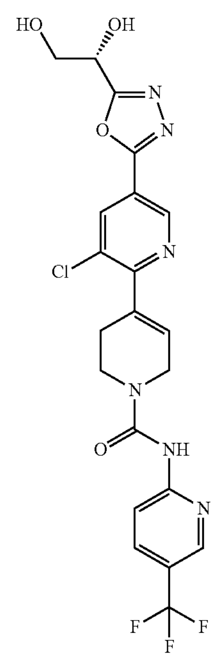 [SMILES: O=C(Nc1ccc(C(F)(F)F)cn1)N1CC=C(c2ncc(-c3nnc([C@@H](O)CO)o3)cc2Cl)CC1] |

TABLE I-continued
| No. | Structure |
|-----|-----------|
| I-20 | 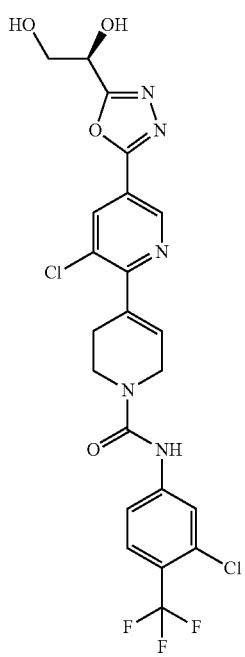 [SMILES: O=C(Nc1ccc(C(F)(F)F)c(Cl)c1)N1CC=C(c2ncc(-c3nnc([C@H](O)CO)o3)cc2Cl)CC1] |
| I-21 | 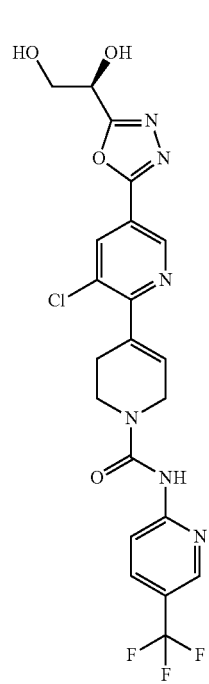 [SMILES: O=C(Nc1ccc(C(F)(F)F)cn1)N1CC=C(c2ncc(-c3nnc([C@H](O)CO)o3)cc2Cl)CC1] |
| I-22 | 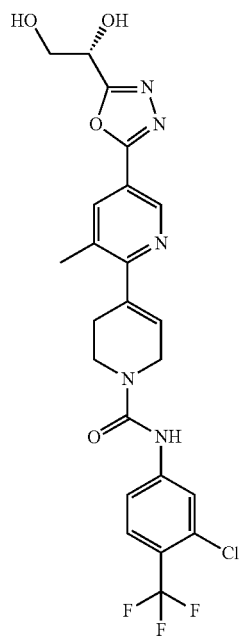 [SMILES: Cc1cc(-c2nnc([C@@H](O)CO)o2)cnc1C1=CCN(C(=O)Nc2ccc(C(F)(F)F)c(Cl)c2)CC1] |
| I-23 | 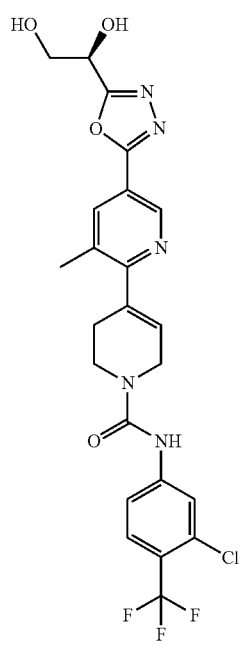 |

TABLE I-continued
| No. | Structure |
|-----|-----------|
| I-24 | 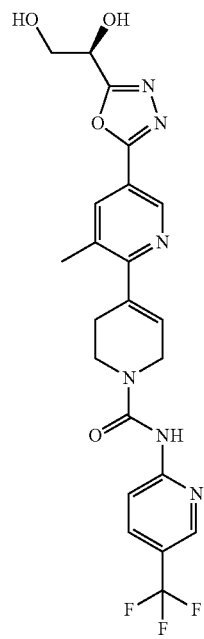 |
| I-25 | 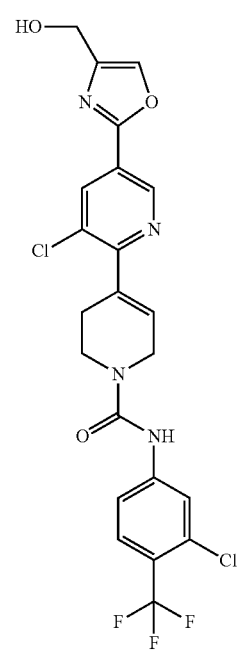 [SMILES: O=C(Nc1ccc(C(F)(F)F)c(Cl)c1)N1CC=C(c2ncc(-c3nc(CO)co3)cc2Cl)CC1] |
TABLE I-continued
| No. | Structure |
|-----|-----------|
| I-26 | 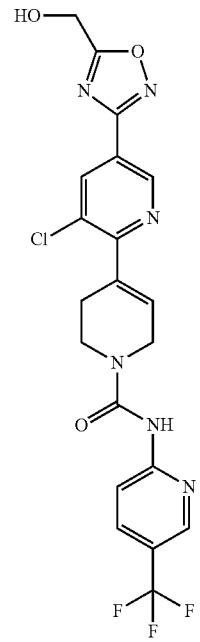 |
| I-27 | 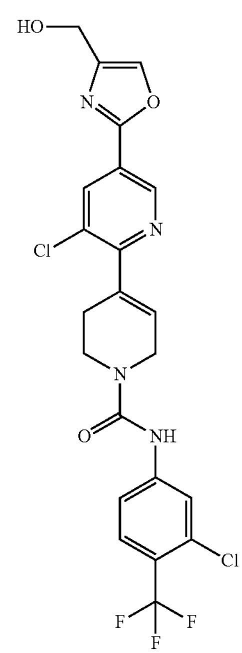 |

TABLE I-continued
| No. | Structure |
|-----|-----------|
| I-28 | 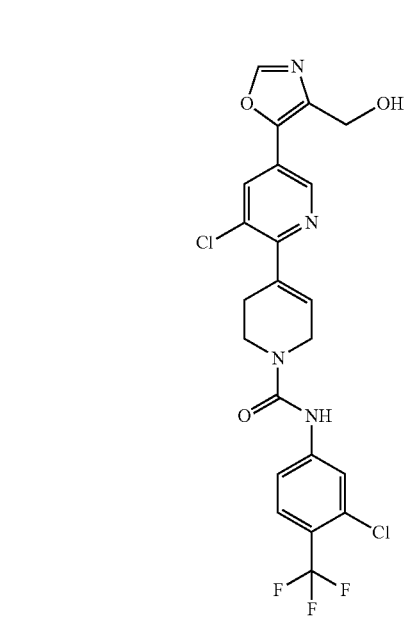 [SMILES: O=C(Nc1ccc(C(F)(F)F)c(Cl)c1)N1CC=C(c2ncc(-c3ocnc3CO)cc2Cl)CC1] |
| I-29 | 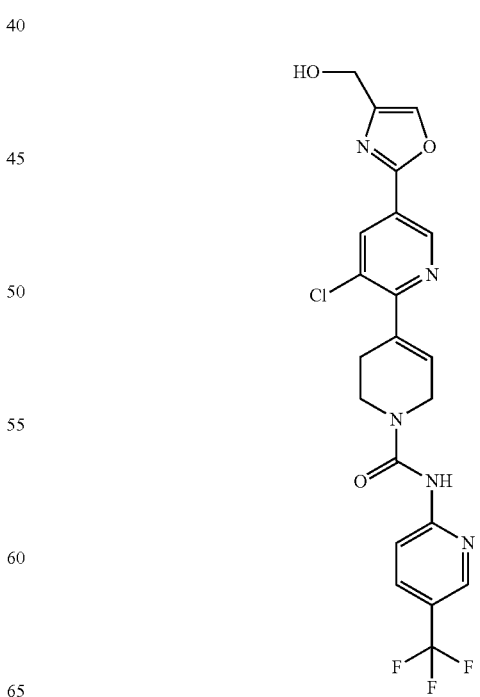 |
TABLE I-continued
| No. | Structure |
|-----|-----------|
| I-30 | 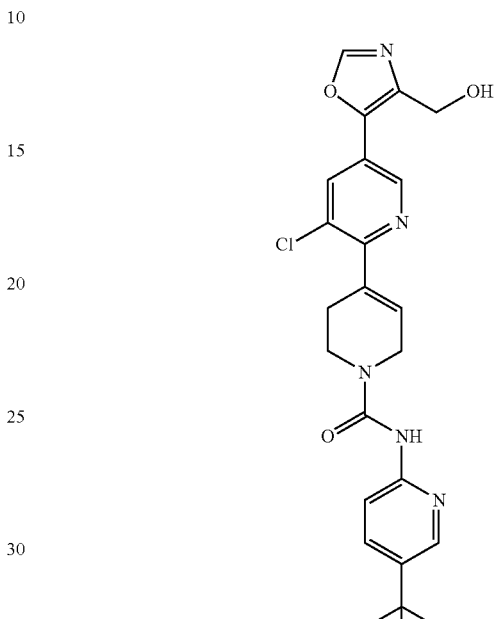 |
| I-31 | 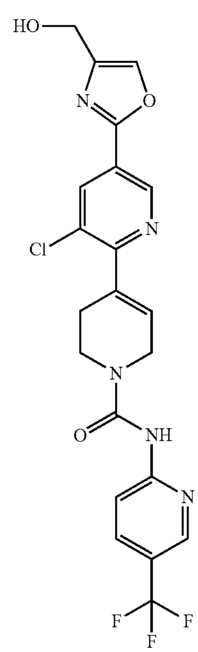 [SMILES: O=C(Nc1ccc(C(F)(F)F)cn1)N1CC=C(c2ncc(-c3nc(CO)co3)cc2Cl)CC1] |

TABLE I-continued
| No. | Structure |
|---|---|
| I-32 | 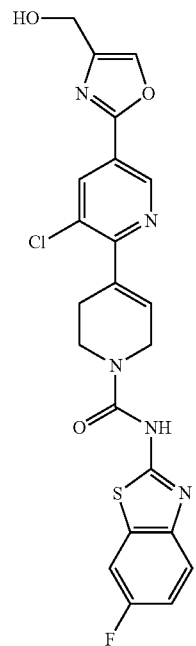 [SMILES: O=C(Nc1nc2ccc(F)cc2s1)N1CC=C(c2ncc(-c3nc(CO)co3)cc2Cl)CC1] |
| I-33 | 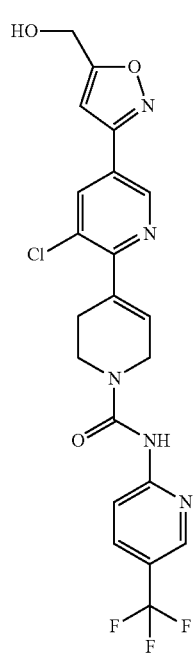 [SMILES: O=C(Nc1ccc(C(F)(F)F)cn1)N1CC=C(c2ncc(-c3cc(CO)on3)cc2Cl)CC1] |
| I-34 | 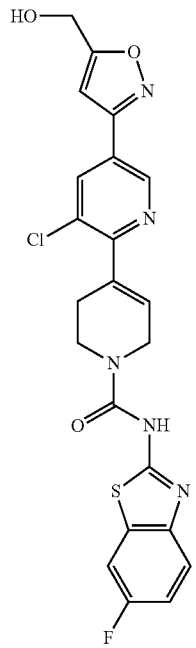 [SMILES: O=C(Nc1nc2ccc(F)cc2s1)N1CC=C(c2ncc(-c3cc(CO)on3)cc2Cl)CC1] |
| I-35 | 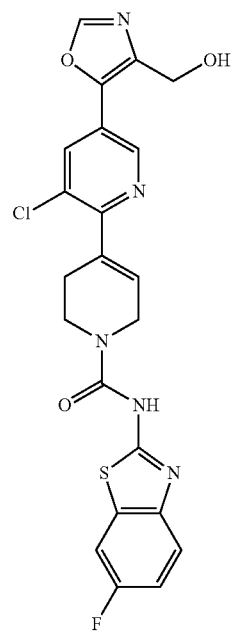 [SMILES: O=C(Nc1nc2ccc(F)cc2s1)N1CC=C(c2ncc(-c3ocnc3CO)cc2Cl)CC1] |

TABLE I-continued
| No. | Structure |
|---|---|
| I-36 | 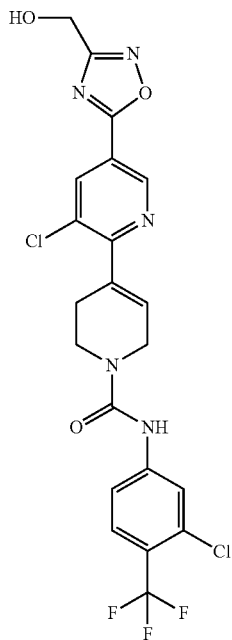 [SMILES: O=C(Nc1ccc(C(F)(F)F)c(Cl)c1)N1CC=C(c2ncc(-c3nc(CO)no3)cc2Cl)CC1] |
| I-37 | 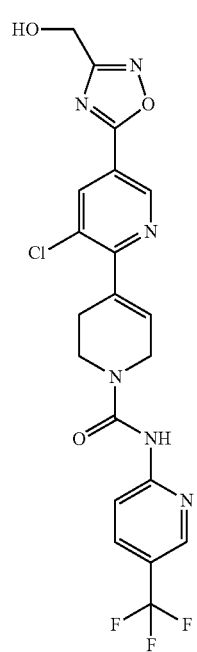 [SMILES: O=C(Nc1ccc(C(F)(F)F)cn1)N1CC=C(c2ncc(-c3nc(CO)no3)cc2Cl)CC1] |
TABLE I-continued
| No. | Structure |
|---|---|
| I-38 | 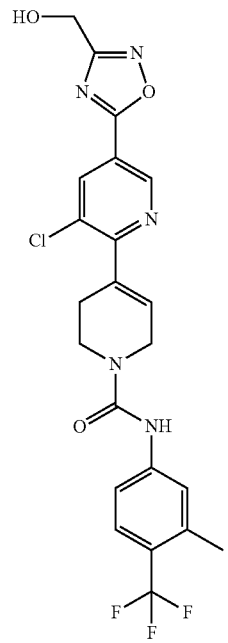 |
| I-39 | 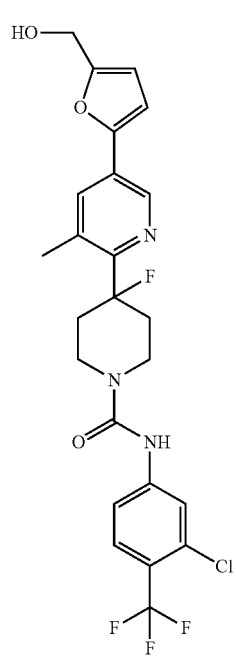 [SMILES: Cc1cc(-c2ccc(CO)o2)cnc1C1(F)CCN(C(=O)Nc2ccc(C(F)(F)F)c(Cl)c2)CC1] |

TABLE I-continued
| No. | Structure |
|---|---|
| I-40 | 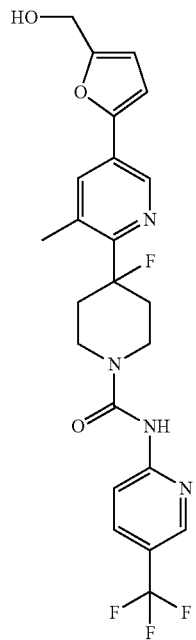 [SMILES: Cc1cc(-c2ccc(CO)o2)cnc1C1(F)CCN(C(=O)Nc2ccc(C(F)(F)F)cn2)CC1] |
| I-41 | 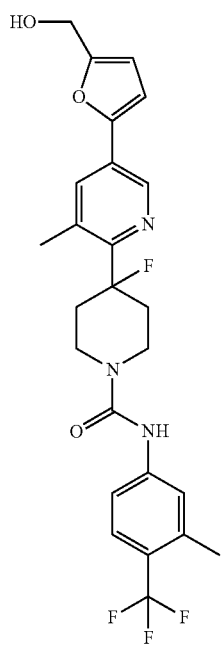 [SMILES: Cc1cc(NC(=O)N2CCC(F)(c3ncc(-c4ccc(CO)o4)cc3C)CC2)ccc1C(F)(F)F] |
TABLE I-continued
| No. | Structure |
|---|---|
| I-42 | 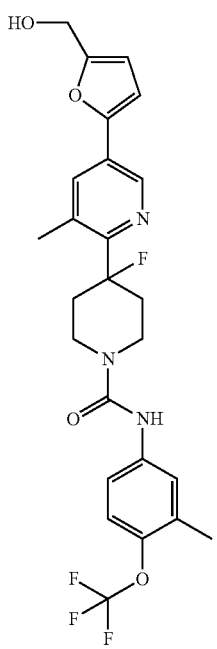 [SMILES: Cc1cc(NC(=O)N2CCC(F)(c3ncc(-c4ccc(CO)o4)cc3C)CC2)ccc1OC(F)(F)F] |
| I-43 | 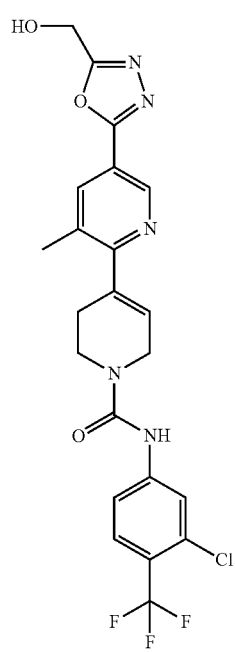 [SMILES: Cc1cc(-c2nnc(CO)o2)cnc1C1=CCN(C(=O)Nc2ccc(C(F)(F)F)c(Cl)c2)CC1] |

TABLE I-continued
| No. | Structure |
|---|---|
| I-44 | 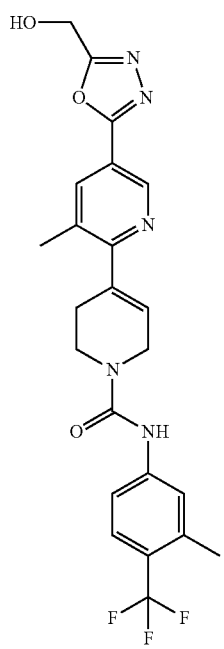 [SMILES: Cc1cc(NC(=O)N2CC=C(c3ncc(-c4nnc(CO)o4)cc3C)CC2)ccc1C(F)(F)F] |
| I-45 | 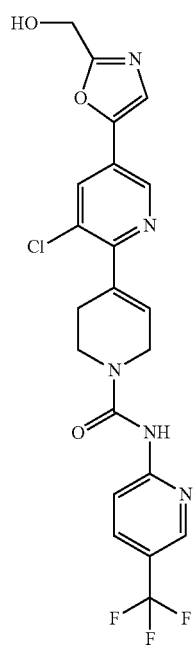 |
TABLE I-continued
| No. | Structure |
|---|---|
| I-46 | 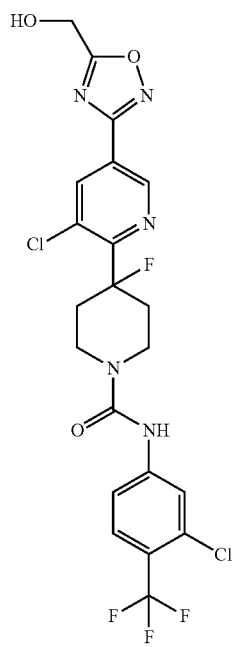 [SMILES: O=C(Nc1ccc(C(F)(F)F)c(Cl)c1)N1CCC(F)(c2ncc(-c3noc(CO)n3)cc2Cl)CC1] |
| I-47 | 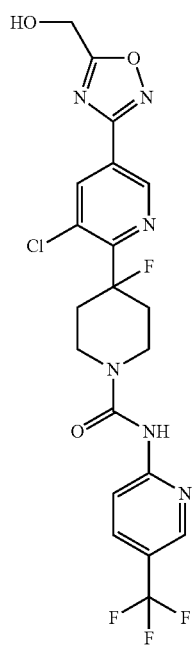 |

TABLE I-continued
| No. | Structure |
|---|---|
| I-48 | 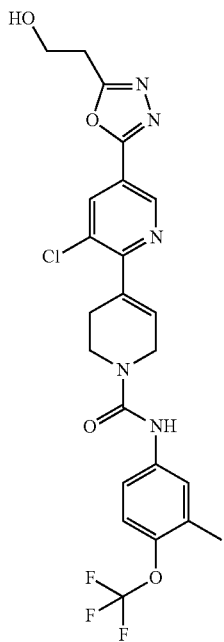 [SMILES: Cc1cc(NC(=O)N2CC=C(c3ncc(-c4nnc(CCO)o4)cc3Cl)CC2)ccc1OC(F)(F)F] |
| I-49 | 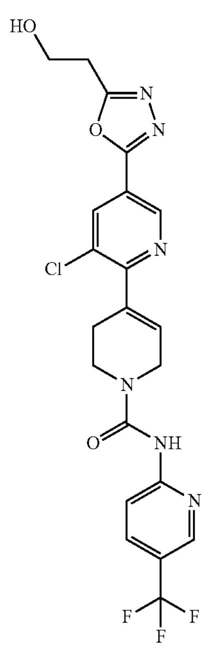 |
| I-50 | 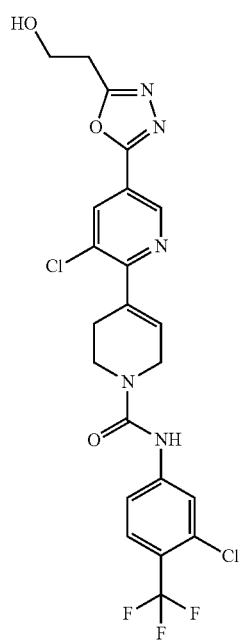 [SMILES: O=C(Nc1ccc(C(F)(F)F)c(Cl)c1)N1CC=C(c2ncc(-c3nnc(CCO)o3)cc2Cl)CC1] |
| I-51 | 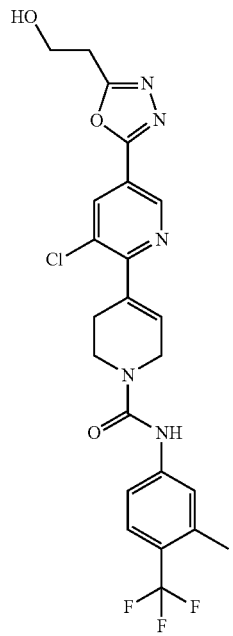 [SMILES: Cc1cc(NC(=O)N2CC=C(c3ncc(-c4nnc(CCO)o4)cc3Cl)CC2)ccc1C(F)(F)F] |

TABLE I-continued
| No. | Structure |
|---|---|
| I-52 | 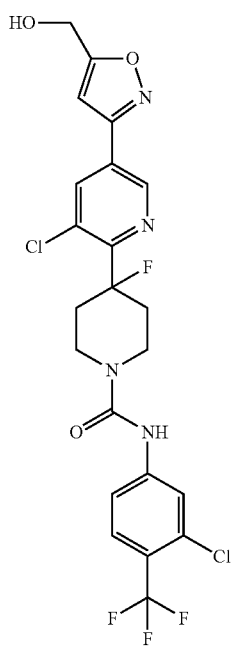 [SMILES: O=C(Nc1ccc(C(F)(F)F)c(Cl)c1)N1CCC(F)(c2ncc(-c3cc(CO)on3)cc2Cl)CC1] |
| I-53 | 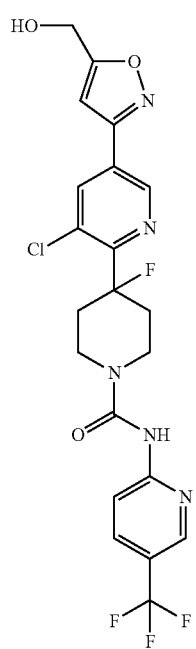 [SMILES: O=C(Nc1ccc(C(F)(F)F)cn1)N1CCC(F)(c2ncc(-c3cc(CO)on3)cc2Cl)CC1] |
| I-54 | 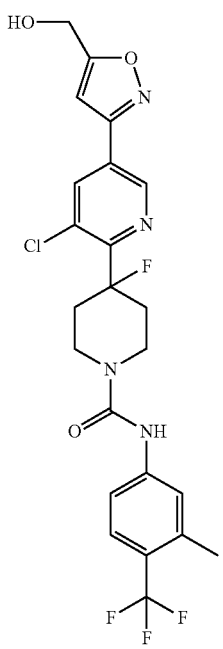 [SMILES: Cc1cc(NC(=O)N2CCC(F)(c3ncc(-c4cc(CO)on4)cc3Cl)CC2)ccc1C(F)(F)F] |
| I-55 | 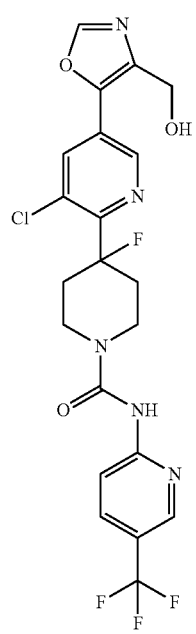 [SMILES: O=C(Nc1ccc(C(F)(F)F)cn1)N1CCC(F)(c2ncc(-c3ocnc3CO)cc2Cl)CC1] |

TABLE I-continued
| No. | Structure |
|---|---|
| I-56 | 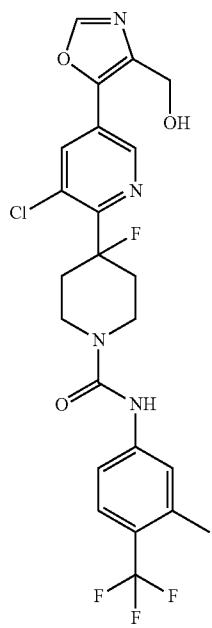 [SMILES: Cc1cc(NC(=O)N2CCC(F)(c3ncc(-c4ocnc4CO)cc3Cl)CC2)ccc1C(F)(F)F] |
| I-57 | 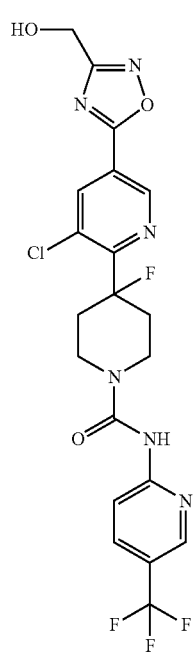 [SMILES: O=C(Nc1ccc(C(F)(F)F)cn1)N1CCC(F)(c2ncc(-c3nc(CO)no3)cc2Cl)CC1] |
| I-58 | 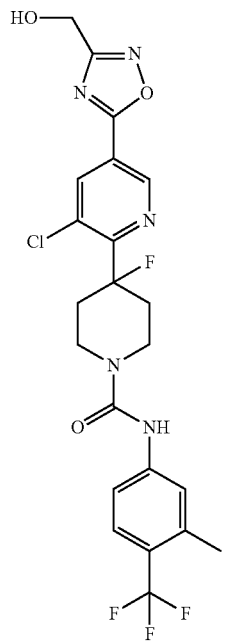 [SMILES: Cc1cc(NC(=O)N2CCC(F)(c3ncc(-c4nc(CO)no4)cc3Cl)CC2)ccc1C(F)(F)F] |
| I-59 | 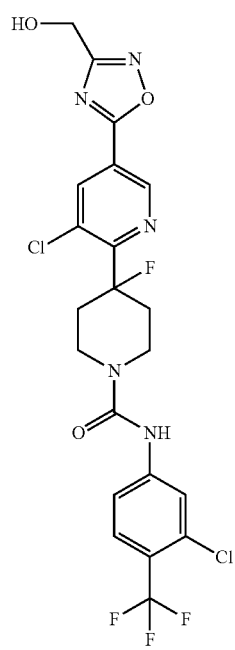 [SMILES: O=C(Nc1ccc(C(F)(F)F)c(Cl)c1)N1CCC(F)(c2ncc(-c3nc(CO)no3)cc2Cl)CC1] |

TABLE I-continued
| No. | Structure |
|---|---|
| I-60 | 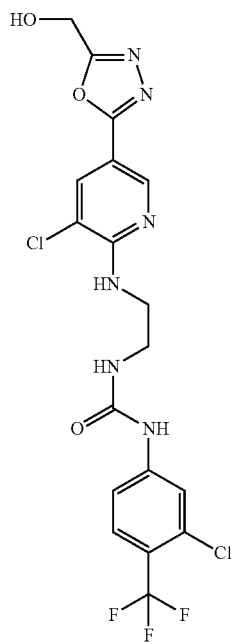 [SMILES: O=C(NCCNc1ncc(-c2nnc(CO)o2)cc1Cl)Nc1ccc(C(F)(F)F)c(Cl)c1] |
| I-61 | 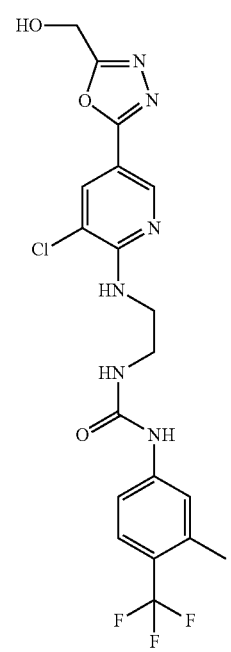 [SMILES: Cc1cc(NC(=O)NCCNc2ncc(-c3nnc(CO)o3)cc2Cl)ccc1C(F)(F)F] |
| I-62 | 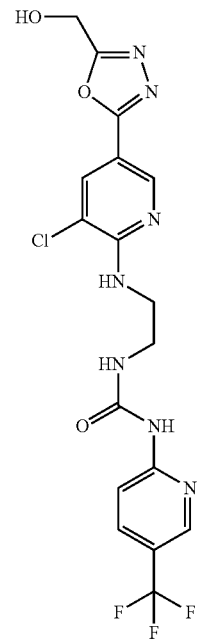 [SMILES: O=C(NCCNc1ncc(-c2nnc(CO)o2)cc1Cl)Nc1ccc(C(F)(F)F)cn1] |
| I-63 | 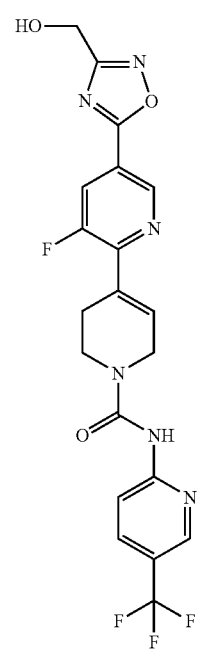 |

TABLE I-continued
| No. | Structure |
|---|---|
| I-64 | 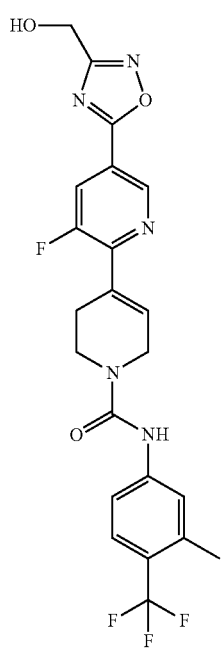 [SMILES: Cc1cc(NC(=O)N2CC=C(c3ncc(-c4nc(CO)no4)cc3F)CC2)ccc1C(F)(F)F] |
| I-65 | 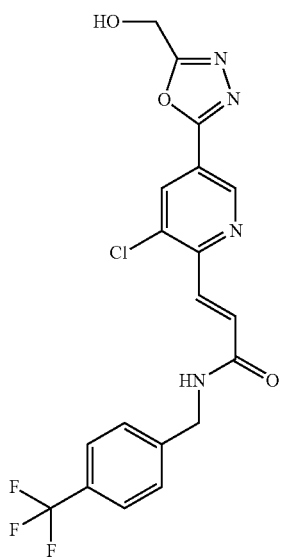 [SMILES: O=C(/C=C/c1ncc(-c2nnc(CO)o2)cc1Cl)NCc1ccc(C(F)(F)F)cc1] |
| I-66 | 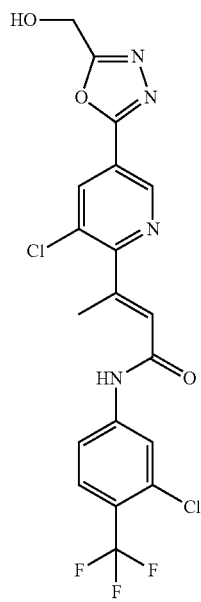 [SMILES: C/C(=C\C(=O)Nc1ccc(C(F)(F)F)c(Cl)c1)c1ncc(-c2nnc(CO)o2)cc1Cl] |
| I-67 | 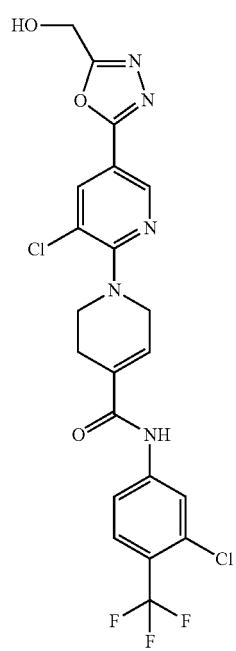 [SMILES: O=C(Nc1ccc(C(F)(F)F)c(Cl)c1)C1=CCN(c2ncc(-c3nnc(CO)o3)cc2Cl)CC1] |

TABLE I-continued
| No. | Structure |
|-----|-----------|
| I-68 | 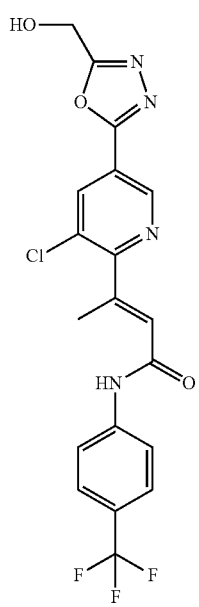 [SMILES: C/C(=C\C(=O)Nc1ccc(C(F)(F)F)cc1)c1ncc(-c2nnc(CO)o2)cc1Cl] |
| I-69 | 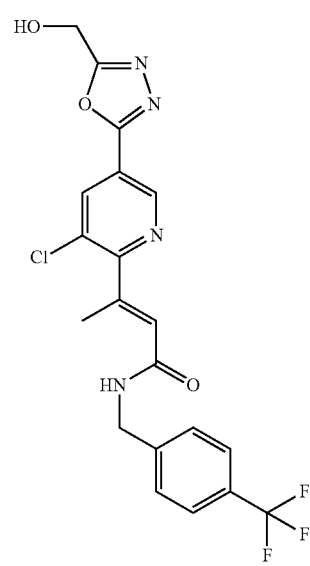 [SMILES: C/C(=C\C(=O)NCc1ccc(C(F)(F)F)cc1)c1ncc(-c2nnc(CO)o2)cc1Cl] |
| I-70 | 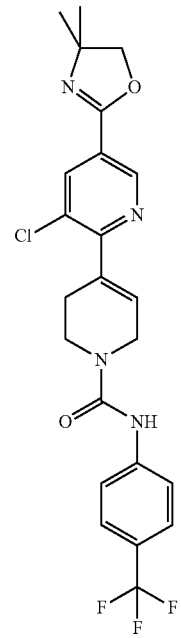 [SMILES: CC1(C)COC(c2cnc(C3=CCN(C(=O)Nc4ccc(C(F)(F)F)cc4)CC3)c(Cl)c2)=N1] |
| I-71 | 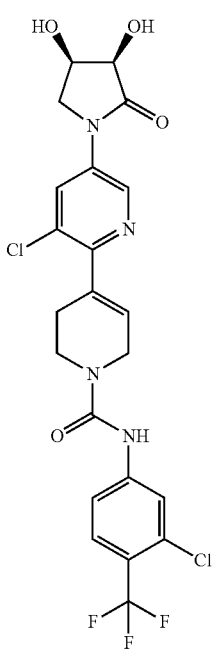 [SMILES: O=C(Nc1ccc(C(F)(F)F)c(Cl)c1)N1CC=C(c2ncc(N3C[C@@H](O)[C@@H](O)C3=O)cc2Cl)CC1] |

| No. | Structure |
|---|---|
| I-72 | 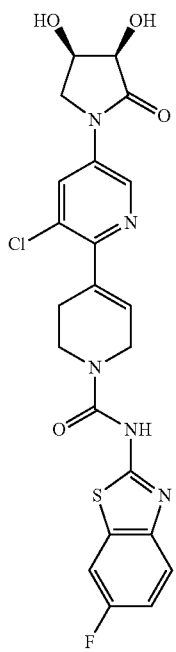 [SMILES: O=C(Nc1nc2ccc(F)cc2s1)N1CC=C(c2ncc(N3C[C@@H](O)[C@@H](O)C3=O)cc2Cl)CC1] |
| I-73 | |
| No. | Structure |
|---|---|
| I-74 | 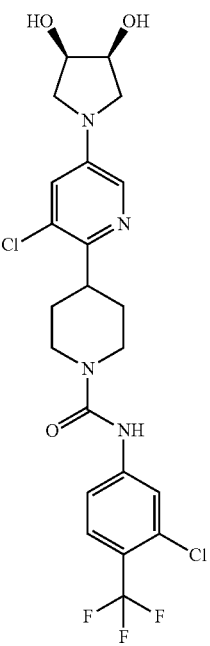 [SMILES: O=C(Nc1ccc(C(F)(F)F)c(Cl)c1)N1CCC(c2ncc(N3C[C@@H](O)[C@@H](O)C3)cc2Cl)CC1] |
| I-75 | 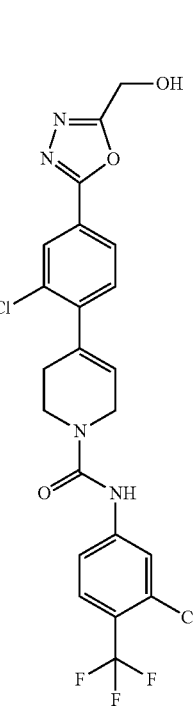 |

TABLE I-continued
| No. | Structure |
|---|---|
| I-76 | 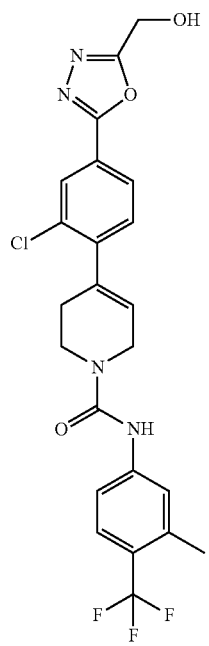 [SMILES: Cc1cc(NC(=O)N2CC=C(c3ccc(-c4nnc(CO)o4)cc3Cl)CC2)ccc1C(F)(F)F] |
| I-77 | 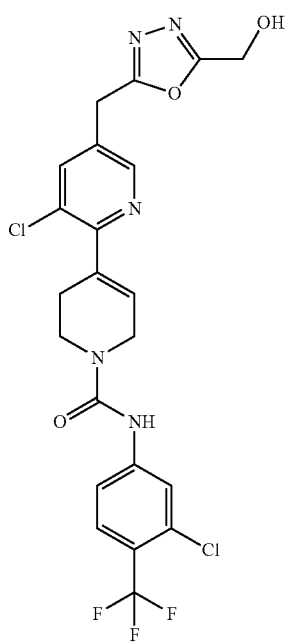 [SMILES: O=C(Nc1ccc(C(F)(F)F)c(Cl)c1)N1CC=C(c2ncc(Cc3nnc(CO)o3)cc2Cl)CC1] |
TABLE I-continued
| No. | Structure |
|---|---|
| I-78 | 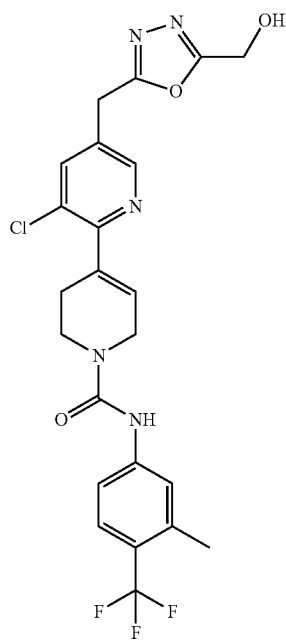 [SMILES: Cc1cc(NC(=O)N2CC=C(c3ncc(Cc4nnc(CO)o4)cc3Cl)CC2)ccc1C(F)(F)F] |
| I-79 | 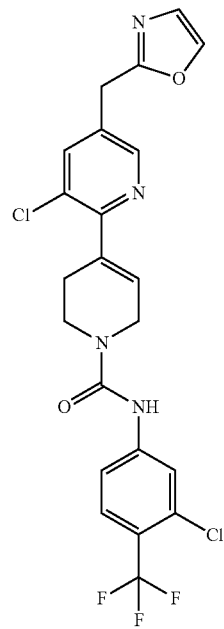 [SMILES: O=C(Nc1ccc(C(F)(F)F)c(Cl)c1)N1CC=C(c2ncc(Cc3ncco3)cc2Cl)CC1] |

TABLE I-continued
| No. | Structure |
|---|---|
| I-80 | 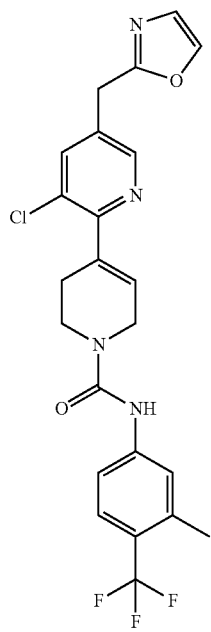 [SMILES: Cc1cc(NC(=O)N2CC=C(c3ncc(Cc4ncco4)cc3Cl)CC2)ccc1C(F)(F)F] |
| I-81 | 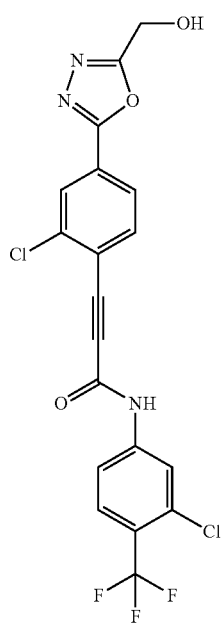 [SMILES: O=C(C#Cc1ccc(-c2nnc(CO)o2)cc1Cl)Nc1ccc(C(F)(F)F)c(Cl)c1] |
TABLE I-continued
| No. | Structure |
|---|---|
| I-82 | 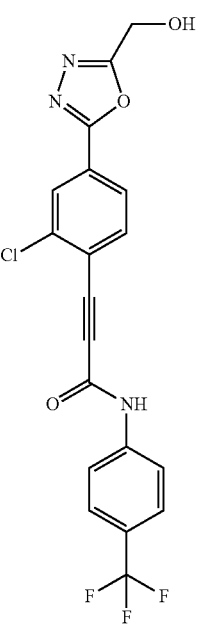 [SMILES: O=C(C#Cc1ccc(-c2nnc(CO)o2)cc1Cl)Nc1ccc(C(F)(F)F)cc1] |
| I-83 | 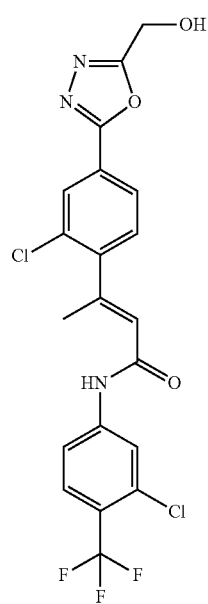 [SMILES: C/C(=C\C(=O)Nc1ccc(C(F)(F)F)c(Cl)c1)c1ccc(-c2nnc(CO)o2)cc1Cl] |

TABLE I-continued
| No. | Structure |
|---|---|
| I-84 | 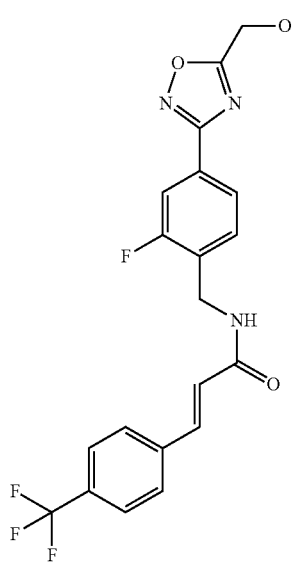 |
| I-85 | 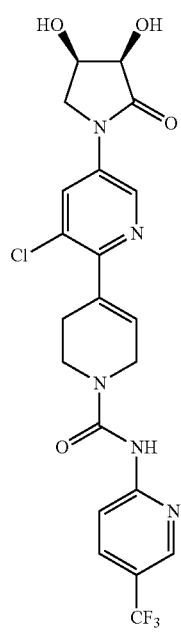 [SMILES: O=C(Nc1ccc(C(F)(F)F)cn1)N1CC=C(c2ncc(N3C[C@@H](O)[C@@H](O)C3=O)cc2Cl)CC1] |
TABLE I-continued
| No. | Structure |
|---|---|
| I-86 | 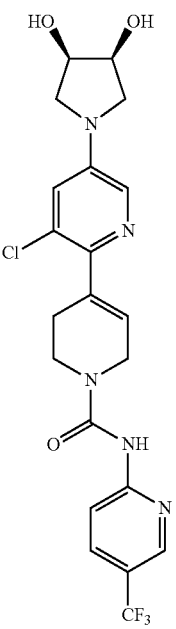 [SMILES: O=C(Nc1ccc(C(F)(F)F)cn1)N1CC=C(c2ncc(N3C[C@@H](O)[C@@H](O)C3)cc2Cl)CC1] |
| I-89 | 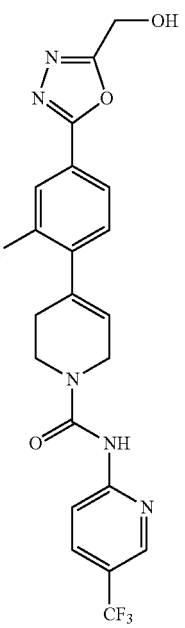 |

TABLE I-continued
| No. | Structure |
|-----|-----------|
| I-92 | 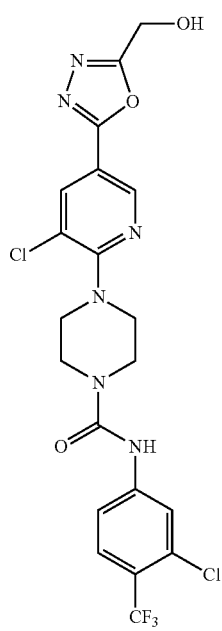 [SMILES: O=C(Nc1ccc(C(F)(F)F)c(Cl)c1)N1CCN(c2ncc(-c3nnc(CO)o3)cc2Cl)CC1] |
| I-93 | 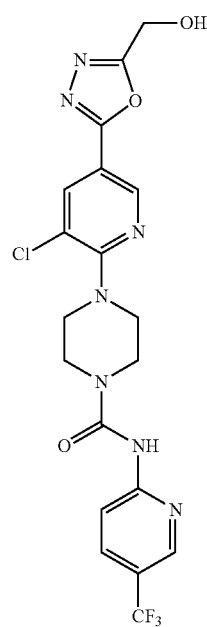 [SMILES: O=C(Nc1ccc(C(F)(F)F)cn1)N1CCN(c2ncc(-c3nnc(CO)o3)cc2Cl)CC1] |
TABLE I-continued
| No. | Structure |
|-----|-----------|
| I-94 | 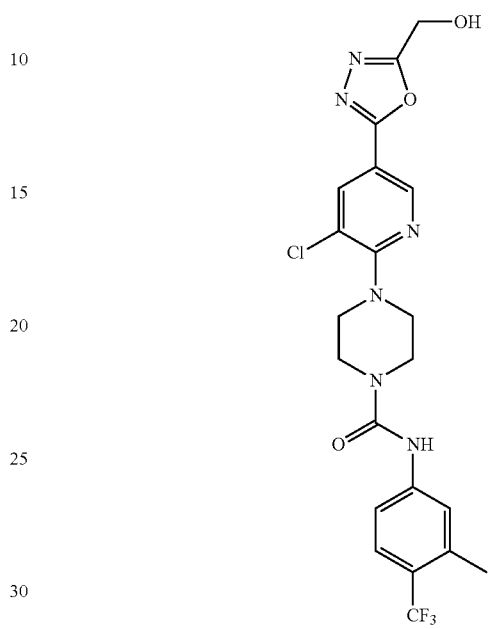 |
| I-95 | 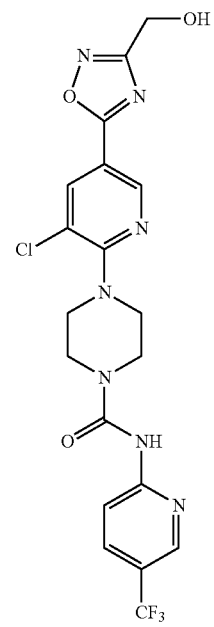 [SMILES: O=C(Nc1ccc(C(F)(F)F)cn1)N1CCN(c2ncc(-c3nc(CO)no3)cc2Cl)CC1] |

TABLE I-continued
| No. | Structure |
|-----|-----------|
| I-96 | 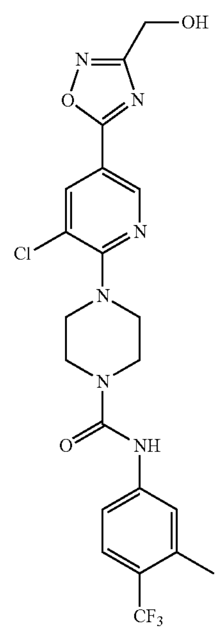 [SMILES: Cc1cc(NC(=O)N2CCN(c3ncc(-c4nc(CO)no4)cc3Cl)CC2)ccc1C(F)(F)F] |
| I-98 | 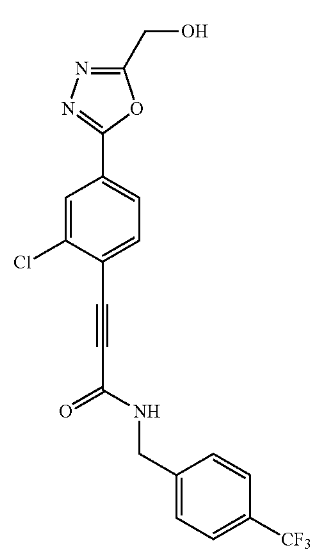 [SMILES: O=C(C#Cc1ccc(-c2nnc(CO)o2)cc1Cl)NCc1ccc(C(F)(F)F)cc1] |
| I-99 | 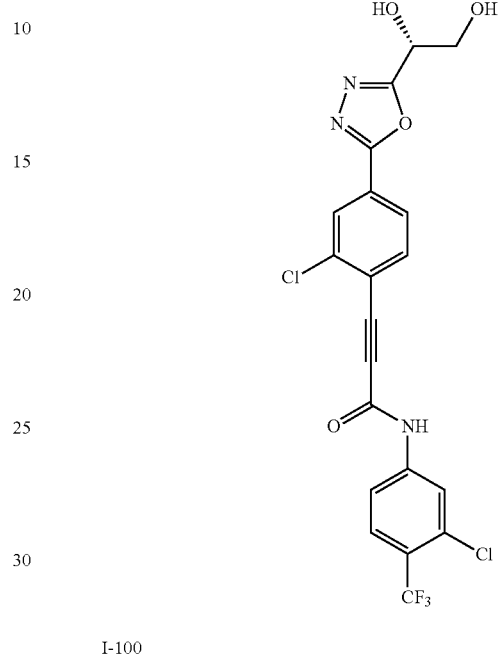 |
| I-100 | 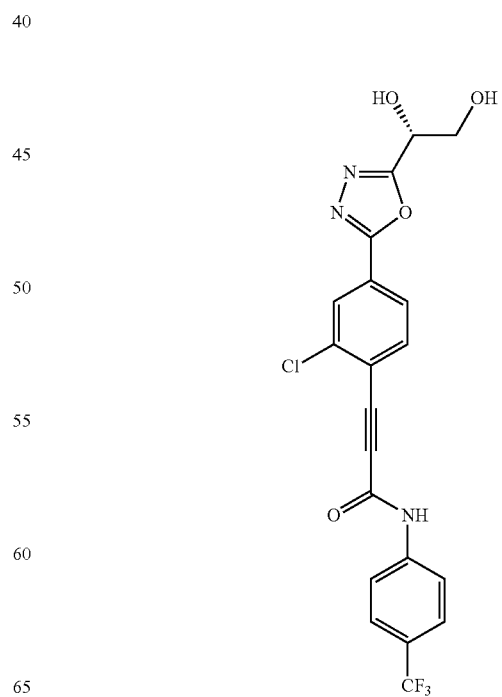 |

TABLE I-continued
| No. | Structure |
|---|---|
| I-101 | 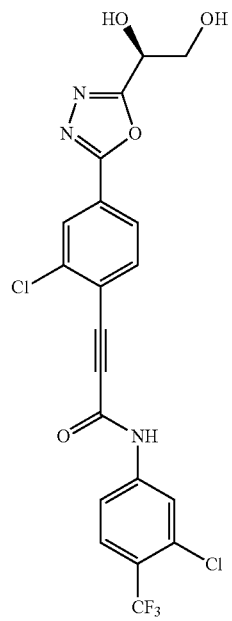 [SMILES: O=C(C#Cc1ccc(-c2nnc([C@@H](O)CO)o2)cc1Cl)Nc1ccc(C(F)(F)F)c(Cl)c1] |
| I-102 | 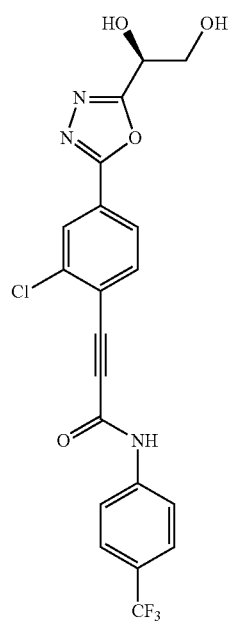 [SMILES: O=C(C#Cc1ccc(-c2nnc([C@@H](O)CO)o2)cc1Cl)Nc1ccc(C(F)(F)F)cc1] |
| I-103 | 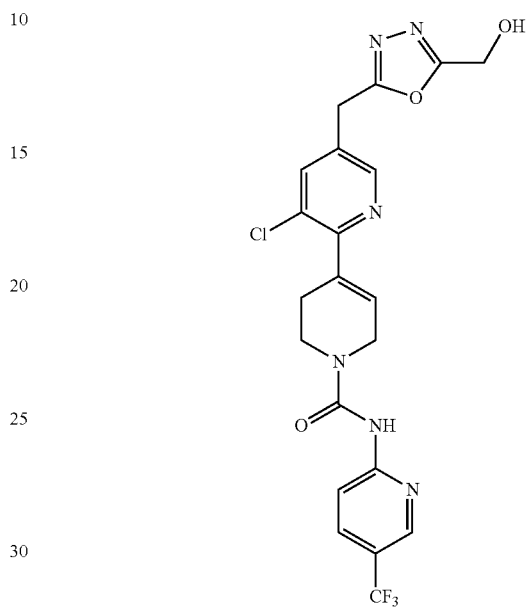 |
| I-104 | 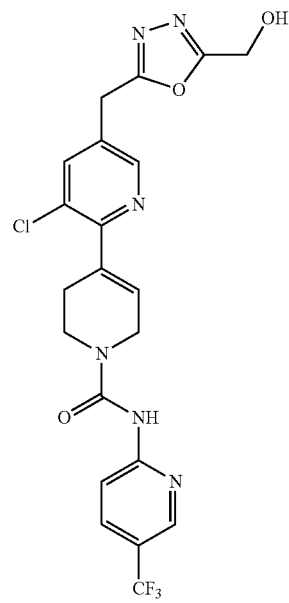 [SMILES: O=C(Nc1ccc(C(F)(F)F)cn1)N1CC=C(c2ncc(Cc3nnc(CO)o3)cc2Cl)CC1] |

TABLE I-continued
| No. | Structure |
|-----|-----------|
| I-105 | 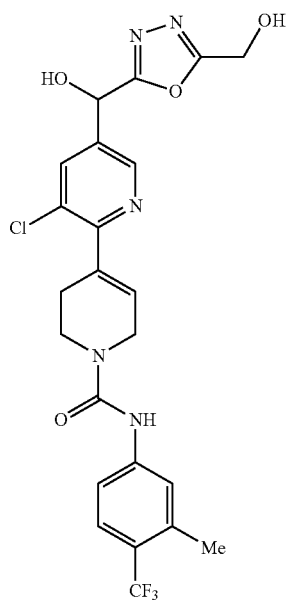 [SMILES: Cc1cc(NC(=O)N2CC=C(c3ncc(C(O)c4nnc(CO)o4)cc3Cl)CC2)ccc1C(F)(F)F] |
| I-106 | 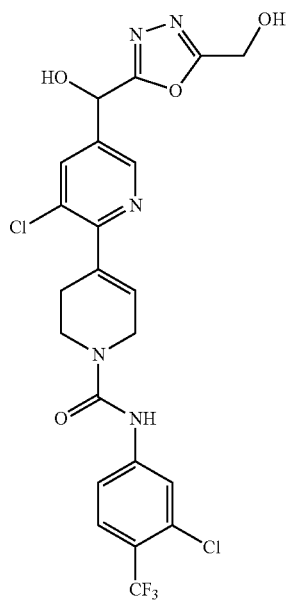 [SMILES: O=C(Nc1ccc(C(F)(F)F)c(Cl)c1)N1CC=C(c2ncc(C(O)c3nnc(CO)o3)cc2Cl)CC1] |
TABLE I-continued
| No. | Structure |
|-----|-----------|
| I-107 | 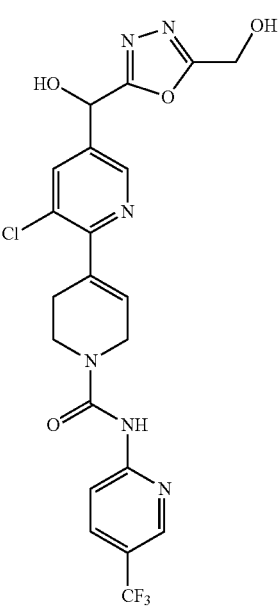 [SMILES: O=C(Nc1ccc(C(F)(F)F)cn1)N1CC=C(c2ncc(C(O)c3nnc(CO)o3)cc2Cl)CC1] |
| I-108 | 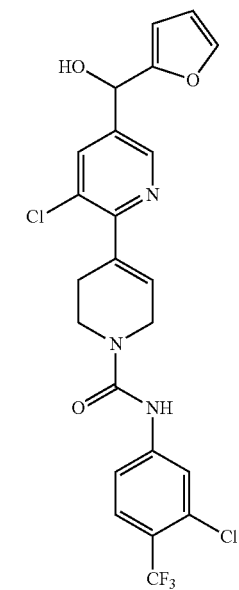 [SMILES: O=C(Nc1ccc(C(F)(F)F)c(Cl)c1)N1CC=C(c2ncc(C(O)c3ccco3)cc2Cl)CC1] |

TABLE I-continued

| No. | Structure |
|---|---|
| I-109 | (structure: 5-chloro-6-(1,2,3,6-tetrahydropyridin-4-yl)pyridine with HO-CH-(5-methyl-1,3,4-oxadiazol-2-yl) substituent; N-carboxamide linked to 5-(trifluoromethyl)pyridin-2-yl) |
| I-110 | (structure: analogous compound with N-(3-chloro-4-(trifluoromethyl)phenyl) carboxamide) |
| I-111 | (structure: analogous compound with N-(3-methyl-4-(trifluoromethyl)phenyl) carboxamide) |

Example 27

Solubility Test

The solubility of each compound is determined under 1% DMSO addition conditions. A 10 mM solution of the compound is prepared with DMSO, and 64 of the compound solution is added to 594 μL of an artificial intestinal juice (water and 118 mL of 0.2 mol/L NaOH reagent are added to 250 mL of 0.2 mol/L potassium dihydrogen phosphate reagent to reach 1000 mL) with a pH of 6.8. The mixture is left standing for 16 hours at 25° C., and the mixture is vacuum-filtered. The filtrate is two-fold diluted with methanol/water=1/1, and the compound concentration in the filtrate is measured with HPLC or LC/MS/MS by the absolute calibration method.

Example 28

Measurement of Body Temperature Increase

Test Animals:

Selection of rats (Crl/SD rats, 7 weeks, male) for this study is based on rectal body temperature measured during the morning of the day of dosing. In addition, animals selected for this study are acclimated to both the rectal measurement procedure and to being handled and dosed to minimize spontaneous, stress-induced, increases in body temperature. The study is conducted in the animal care laboratories where the room temperature and humidity are kept. The rats are free to move and food and water during the study. Each rat is numbered with color line on the tail, housed in each cage and permittted the normal range of movement. Immediately before each body temperature is measured, they transferred to a single cage at each measurement. To reduce stress which affected the body temperature, the rats are covered with towels at the measurement. The thermistor probe is then carefully inserted into the rectum of each rat and left in place until the value on the digital display had stabilized.

Assays:

On the day before dosing, rectal body temperatures are measured at 9:00, 10:00, 11:00, 12:30, 13:30, 14:30 and 15:30 to familiarize the animals with the measurement procedure prior to administration of the test or control treatments. The rats are also dosed by oral gavage without vehicle at 12:30 to acclimate and familiarized the animals with the handling and dosing procedure.

On the day of dosing, only rats whose rectal body temperatures are within the range of 37.0° C. to 37.7° C. are selected for this study. Rectal body temperatures are measured at 9:00, 10:00 and 11:00. Rats whose rectal body temperatures are over 37.9° C. at 10:00, and are outside the range of 37.0° C. to 37.7° C. at 11:00 are excluded from the study. The selected rats are divided to several groups based on their rectal body temperatures at 11:00. Rectal body temperatures of the selected rats are measured again at 12:30, and any rats whose rectal body temperature is 38.0° C. or greater are excluded from the study.

Following the group assignment, test compounds or vehicle is administrated to the rats. Each test compound is dissolved in 0.5% methylcellulose and the final concentration of the compound is adjusted to 1 mg/mL. Test compound is orally administrated in a volume 10 mL/kg once. 10 mL/kg of vehicle (0.5% methylcellulose) is administered to the vehicle group. The rectal body temperatures are measured 0.5, 1 and 2 hrs after the administration. The study is conducted in the animal care laboratories where the room temperature and humidity are kept.

Body temperature increase (ΔTb) is calculated from the difference from an average of the vehicle group at each time point. The body temperature increases (ΔTb) of Compounds I-20, I-25, I-26, I-28, I-29, I-33, I-34, I-36, I-37, I-63 and I-64 were less than 0.3° C.

Example 29

In Vivo Assays for Prevention or Treatment of Pain

Test Animals:

Each experiment uses rats weighing between 200-260 g at the start of the experiment. The rats are group-housed and have free access to food and water at all times, except prior to oral administration of a compound of Formula I when food is removed for 16 hours before dosing. A control group acts as a comparison to rats treated with a compound of Formula I. The control group is administered the carrier for the compound of Formula I. The volume of carrier administered to the control group is the same as the volume of carrier and compound of Formula I administered to the test group.

Acute Pain:

To assess the actions of the compounds of Formula I on the treatment or prevention of acute pain the rat tail flick test can be used. Rats are gently restrained by hand and the tail exposed to a focused beam of radiant heat at a point 5 cm from the tip using a tail flick unit (Model 7360, commercially available from Ugo Basile of Italy). Tail flick latencies are as defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a compound of Formula I. Data are expressed as tail flick latency(s) and the percentage of the maximal possible effect (% MPE), i.e., 20 seconds, is calculated as follows:

$$\% \ MPE = \frac{[(\text{post administration latency}) - (\text{pre-administration latency})]}{(20 \ \text{s pre-administration latency})} \times 100$$

The rat tail flick test is described in F. E. D'Amour et al., "A Method for Determining Loss of Pain Sensation," *J. Pharmacol. Exp. Ther.* 72:74-79 (1941).

Acute pain can also be assessed by measuring the animal's response to noxious mechanical stimuli by determining the paw withdrawal threshold ("PWT"), as described below.

Inflammatory Pain:

To assess the actions of the compounds of Formula I on the treatment or prevention of inflammatory pain the Freund's complete adjuvant ("FCA") model of inflammatory pain is used. FCA-induced inflammation of the rat hind paw is associated with the development of persistent inflammatory mechanical and thermal hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacol.* 342:666-670 (1990)). The left hind paw of each animal is administered a 50 μL intraplantar injection of 50% FCA. 24 hour post injection, the animal is assessed for response to noxious mechanical stimuli by determining the PWT, or to noxious thermal stimuli by determining the PWL, as described below. Rats are then administered a single injection of 1, 3, 10 or 30 mg/Kg of either a compound of Formula I; 30 mg/Kg of a control selected from Celebrex, indomethacin or naproxen; or carrier. Responses to noxious mechanical or thermal stimuli are then determined 1, 3, 5 and 24 hours post administration. Percentage reversal of hyperalgesia for each animal is defined as:

$$\% \ \text{Reversal} = \frac{[(\text{post administration} \ PWT \ \text{or} \ PWL) - (\text{pre-administration} \ PWT \ \text{or} \ PWL)]}{[(\text{baseline} \ PWT \ \text{or} \ PWL) - (\text{pre-administration} \ PWT \ \text{or} \ PWL)]} \times 100$$

Neuropathic Pain:

To assess the actions of the compounds of Formula I for the treatment or prevention of neuropathic pain either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anaesthesia. Following induction of anaesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anaesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration for rear paw of the animal. Percentage reversal of neuropathic hyperalgesia is defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anaesthesia. Animals are then be returned to their home cages until behavioral testing begins. The animals are assessed for response to noxious mechanical stimuli by determining PWT, as described below, prior to surgery (baseline), then immediately prior to and 1, 3, and 5 hours after being administered a compound of Formula I for the left rear paw of the animal. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia:

The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455 (1988). The maximum weight that can be applied to the hind paw is set at 250 g and the end point is taken as complete withdrawal of the paw. PWT is determined once for each rat at each time point and only the affected (ipsilateral) paw is tested.

Response to Thermal Stimuli as an Assessment of Thermal Hyperalgesia:

The plantar test can be used to assess thermal hyperalgesia. For this test, hind paw withdrawal latencies (PWL) to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Only the affected (ipsilateral) paw is tested.

Assessment of Tactile Allodynia:

To assess tactile allodynia, rats are placed in clear, Plexiglas compartments with a wire mesh floor and allowed to habituate for a period of at least 15 minutes. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

Capsaicin-Induced Eye Wipe Test:

To assess the effect of compounds of Formula I on TRPV1 receptor-mediated pain, the capsaicin-induced eye wipe test is used (N. R. Gavva et al., "AMG 9810 [(E)-3-(4-t-Butylphenyl)-N-(2,3-dihydrobenzo[b][1,4]dioxin-6-yl)acrylamide], a Novel Vanilloid Receptor 1 (TRPV1) Antagonist with Antihyperalgesic Properties", *J. Pharmacol. Exp. Ther.* 313:474-484 (2005)). The eye wipe test is a reliable high-throughput test of the effect of TRPV1 antagonists. Rats are given a single injection of 1, 3, 10 or 30 mg/kg of either a compound of Formula I; 30 mg/kg of a control selected from Celebrex, indomethacin or naproxen; or carrier. At 1, 3 or 5 hours after drug administration, 34 of a 100 µM capsaicin solution (in 10% EtOH/PBS) is instilled in one eye of each animal with a pipette. The number of forelimb movements (touching or wiping of the capsaicin-treated eye) are counted during a 2 minute period following instillation of capsaicin into the eye.

Example 30

Binding of Compounds of Formula I to TRPV1

Methods for assaying compounds capable of inhibiting TRPV1 are known in the art, for example, those methods disclosed in U.S. Pat. No. 6,239,267 to Duckworth et al.; U.S. Pat. No. 6,406,908 to Mc Intyre et al.; or U.S. Pat. No. 6,335,180 to Julius et al. The results of these assays will demonstrate that compounds of Formula I bind to and modulate the activity of TRPV1.

Protocol 1

Human TRPV1 Cloning:

Human spinal cord RNA (commercially available from Clontech, Palo Alto, Calif.) is used. Reverse transcription is conducted on 1.0 µg total RNA using Thermoscript Reverse Transcriptase (commercially available from Invitrogen, Carlsbad, Calif.) and oligo dT primers as detailed in its product description. Reverse transcription reactions are incubated at 55° C. for 1 h, heat-inactivated at 85° C. for 5 min, and RNase H-treated at 37° C. for 20 min.

Human TRPV1 cDNA sequence is obtained by comparison of the human genomic sequence, prior to annotation, to the published rat sequence. Intron sequences are removed and flanking exonic sequences are joined to generate the hypothetical human cDNA. Primers flanking the coding region of human TRPV1 are designed as follows: forward primer, GAAGATCTTCGCTGGTTGCACACTGGGCCACA (SEQ ID No: 1); and reverse primer, GAAGATCTTCGGGGA-CAGTGACGGTTGGATGT (SEQ ID No: 2).

Using these primers, PCR of TRPV1 is performed on one tenth of the Reverse transcription reaction mixture using Expand Long Template Polymerase and Expand Buffer 2 in a final volume of 50 μL according to the manufacturer's instructions (Roche Applied Sciences, Indianapolis, Ind.). After denaturation at 94° C. for 2 min PCR amplification is performed for 25 cycles at 94° C. for 15 sec, 58° C. for 30 sec, and 68° C. for 3 min followed by a final incubation at 72° C. for 7 min to complete the amplification. The PCR product of about 2.8 kb is gel-isolated using a 1.0% agarose, Tris-Acetate gel containing 1.6 μg/mL of crystal violet and purified with a S.N.A.P. UV-Free Gel Purification Kit (commercially available from Invitrogen). The TRPV1 PCR product is cloned into the pIND/V5-His-TOPO vector (commercially available from Invitrogen) according to the manufacturer's instructions to result in the TRPV1-pIND construct. DNA preparations, restriction enzyme digestions, and preliminary DNA sequencing are performed according to standard protocols. Full-length sequencing confirms the identity of the human TRPV1.

Generation of Inducible Cell Lines:

Unless noted otherwise, cell culture reagents are purchased from Life

Technologies of Rockville, Md. HEK293-EcR cells expressing the ecdysone receptor (commercially available from Invitrogen) are cultured in Growth Medium (Dulbecco's Modified Eagles Medium containing 10% fetal bovine serum (commercially available from HYCLONE, Logan, Utah), 1× penicillin/streptomycin, 1× glutamine, 1 mM sodium pyruvate and 400 μg/mL Zeocin (commercially available from Invitrogen)). The TRPV1-pIND constructs are transfected into the HEK293-EcR cell line using Fugene transfection reagent (commercially available from Roche Applied Sciences, Basel, Switzerland). After 48 h, cells are transferred to Selection Medium (Growth Medium containing 300 μg/mL G418 (commercially available from Invitrogen)). Approximately 3 weeks later individual Zeocin/G418 resistant colonies are isolated and expanded. To identify functional clones, multiple colonies are plated into 96-well plates and expression is induced for 48 h using Selection Medium supplemented with 5 μM ponasterone A ("PonA") (commercially available from Invitrogen). On the day of assay, cells are loaded with Fluo-4 (a calcium-sensitive dye that is commercially available from Molecular Probes, Eugene, Oreg.) and CAP-mediated calcium influx is measured using a Fluorescence Imaging Plate Reader ("FLIPR") as described below. Functional clones are re-assayed, expanded, and cryopreserved.

pH-Based Assay:

Two days prior to performing this assay, cells are seeded on poly-D-lysine-coated 96-well clear-bottom black plates (commercially available from Becton-Dickinson) at 75,000 cells/well in growth media containing 5 μM PonA (commercially available from Invitrogen) to induce expression of TRPV1. On the day of the assay, the plates are washed with 0.2 mL 1× Hank's Balanced Salt Solution (commercially available from Life Technologies) containing 1.6 mM $CaCl_2$ and 20 mM HEPES, pH 7.4 ("wash buffer"), and loaded using 0.1 mL of wash buffer containing Fluo-4 (3 μM final concentration, commercially available from Molecular Probes). After 1 h, the cells are washed twice with 0.2 mL wash buffer and resuspended in 0.05 mL 1× Hank's Balanced Salt Solution (commercially available from Life Technologies) containing 3.5 mM $CaCl_2$ and 10 mM Citrate, pH 7.4 ("assay buffer"). Plates are then transferred to a FLIPR for assay. The test compound is diluted in assay buffer, and 50 μL of the resultant solution is added to the cell plates and the solution is monitored for two minutes. The final concentration of the test compound is adjusted to range from about 50 picoM to about 3 μM. Agonist buffer (wash buffer titrated with 1N HCl to provide a solution having a pH of 5.5 when mixed 1:1 with assay buffer) (0.1 mL) is then added to each well, and the plates are incubated for 1 additional minute. Data are collected over the entire time course and analyzed using Excel and Graph Pad Prism to determine the $IC_{50}$.

Capsaicin-Based Assay:

Two days prior to performing this assay, cells are seeded in poly-D-lysine-coated 96-well clear-bottom black plates (50,000 cells/well) in growth media containing 5 μM PonA (commercially available from Invitrogen) to induce expression of TRPV1. On the day of the assay, the plates are washed with 0.2 mL 1× Hank's Balanced Salt Solution (commercially available from Life Technologies) containing 1 mM $CaCl_2$ and 20 mM HEPES, pH 7.4, and cells are loaded using 0.1 mL of wash buffer containing Fluo-4 (3 μM final). After one hour, the cells are washed twice with 0.2 mL of wash buffer and resuspended in 0.1 mL of wash buffer. The plates are transferred to a FLIPR for assay. 50 μL of test compound diluted with assay buffer (1× Hank's Balanced Salt Solution containing 1 mM $CaCl_2$ and 20 mM HEPES, pH 7.4) are added to the cell plates and incubated for 2 min. The final concentration of the compound is adjusted to range from about 50 picoM to about 3 μM. Human TRPV1 is activated by the addition of 50 μL of capsaicin (400 nM), and the plates are incubated for an additional 3 min. Data is collected over the entire time course and analyzed using Excel and GraphPad Prism to determine the $IC_{50}$.

Protocol 2

For Protocol 2, a Chinese Hamster Ovary cell line (CHO) that has been engineered to constitutively express human recombinant TRPV1 was used (TRPV1/CHO cells). The TRPV1/CHO cell line was generated as described below.

Human TRPV1 Cloning:

A cDNA for the human TRPV1 receptor (hTRPV1) was amplified by PCR (KOD-Plus DNA polymerase, ToYoBo, Japan) from a human brain cDNA library (BioChain) using primers designed surrounding the complete hTRPV1 open reading frame (forward 5'-GGATCCAGCAAGGATGAA-GAAATGG (SEQ ID NO:3), and reverse 5'-TGTCTGCGT-GACGTCCTCACTTCT (SEQ ID NO:4)). The resulting PCR products were purified from agarose gels using Gel Band Purification Kit (GE Healthcare Bioscience) and were subcloned into pCR-Blunt vector (Invitrogen). The cloned cDNA was fully sequenced using a fluorescent dye-terminator reagent (BigDye Terminator ver3.1 Cycle Sequencing Kit, Applied Biosystems) and ABI Prism 3100 genetic analyzer (Applied Biosystems). The pCR-Blunt vector containing the hTRPV1 cDNA was subjected to restriction digestion with EcoR1. The restriction fragment was subcloned into expression vector pcDNA3.1(−) (Invitrogen) and named pcDNA3.1 (−)-hVR1 plasmid. The sequence of the cDNA encoding TRPV1 is available at GenBank accession number AJ277028.

Generation of the TRPV1/CHO Cell Line:

CHO-K1 cells were maintained in growth medium consisting of α-MEM, 10% FBS (Hyclone), and 100 IU/mL of penicillin −100 μg/mL of streptomycin mixed solution (Nacalai Tesque, Japan) at 37° C. in an environment of humidified 95% air and 5% $CO_2$. The cells were transfected with the pcDNA3.1(−)-hVR1 plasmid using FuGENE6 (Roche) according to the manufacturer's protocol. 24 hr after transfection, neomycin-resistant cells were selected using 1 mg/mL G418 (Nacalai Tesque). After 2 weeks, individual colonies were picked, expanded, and screened for the expression of hTRPV1 in the capsaicin-induced $Ca^{2+}$ influx assay (see below) with a FLIPR (Molecular Devices). A clone with the largest $Ca^{2+}$ response to capsaicin was selected and re-cloned by the same procedure. The cells expressing hTRPV1 were cultured in the growth medium supplemented with 1 mg/mL G418. Approximately 1 month later, stable expression of functional TRPV1 receptors in the selected cell line was confirmed by validating $Ca^{2+}$ responses with or without capsazepine (Sigma, at 1 nM-10 µM) in capsaicin assay.

Capsaicin-Induced $Ca^{2+}$ Influx Assay for Cell Selection:

The following assay was performed to identify cells with hTRPV1 expression. CHO-K1 cells transfected with pcDNA3.1(−)-hVR1 plasmid were seeded in 384-well black-wall clear-bottom plates (Corning) and cultivated in growth medium (see above) for 1 day. On the day of experiment, culture medium was exchanged to assay buffer (20 mM HEPES, 137 mM NaCl, 2.7 mM KCl, 0.9 mM $MgCl_2$, 5.0 mM $CaCl_2$, 5.6 mM D-glucose, 2.5 mM probenecid, pH 7.4) containing 4 µM Fluo-3-AM (Dojin, Japan). After the incubation at 37° C. for 1 hr, each well was washed 3 times with assay buffer using an EMBLA 384 plate washer (Molecular Devices) and refilled with assay buffer. The plates were incubated at a temperature of about 25° C. for 10 min. Subsequently, the plates were inserted into a FLIPR, and 1.5 µM capsaicin (Sigma) solution prepared in assay buffer was added to each well (final concentration was 500 nM). Cellular responses were monitored for 5 min.

Cell Culture:

1. Cell Culture Media
1. Alpha-MEM (Gibco, CAT: 12561-056, LOT: 1285752): 450 mL.
2. Fetal Bovine Serum (FBS), heat inactivated (Gibco, CAT: 16140-071, LOT: 1276457): 50 mL.
3. HEPES Buffer Solution, 1M stock (Gibco, CAT: 15630-080): 10 mL (final 20 mM).
4. Geneticin, 50 mg/mL stock (Gibco, CAT: 10135-035): 10 mL (final 1 mg/mL).
5. Antimicotic Antibiotic Mixed Solution, 100× stock (Nacalai Tesque, Japan, CAT: 02892-54): 5 mL.

Components 1-5 above were combined at the indicated amounts and stored at 4° C. The cell culture media were brought to about 37° C. before use. Optionally, component 5 can be replaced by penicillin-streptomycin solution (for example, Gibco 15140-122 or Sigma P-0781).

2. Thawing the Cells

TRPV1/CHO cells were frozen in Cellbanker™ (Juji-Field INC, Japan, CAT: BLC-1) and stored at −80° C. Optimized cryopreservation solution containing dimethyl sulphoxide and FBS was used.

Vials containing the TRPV1/CHO cells were stored at −80° C. After removal from −80° C., the vial was immediately transferred to a 37° C. water bath to thaw for ca. 1-2 minutes. Once completely thawed, the contents of the vial (1 mL/vial) was transferred to a sterile 15 mL test tube and 9 mL warm culture media were slowly added. The test tube was subsequently centrifuged at 1000 rpm for 4 min at a temperature of about 25° C. The supernatant was removed and the pellet resuspended in 10 mL of culture media. The cell suspension was transferred to a sterile 75 $cm^2$ plastic flask and incubated at humidified 5% $CO_2$/95% air at 37° C. To monitor viability, the cells were visually inspected and/or counted, beginning at approximately 1 hr after incubation.

3. Passaging the Cells

The cells in a flask were close to confluence at the time of passaging. Cell culture media were removed from the culture flask and 10 mL of sterile PBS (−) added and the flask gently shaken. The PBS was removed from the flask and 2 mL of trypsin/EDTA solution (0.05% trypsin with EDTA-4Na; Gibco, CAT: 25300-054) was added and the flask gently shaken. The flask was incubated at 37° C. for about 2 min. 8 mL cell culture media were subsequently added to the flask and the flask shaken to ensure that all cells were in solution. The cell suspension was then transferred to a sterile 15 mL or 50 mL plastic tube, centrifuged at 1,000 rpm for 4 min at a temperature of about 25° C. The supernatant was removed and the pellet resuspended in ca. 5 mL of culture media. The cell count was measured using the Burker-Turk hemocytometer.

The cells were seeded into a sterile 75 $cm^2$ plastic flask in ca. $0.8\times10^5$ cells/mL for 72 hr and incubated in humidified 5% $CO_2$/95% air at 37° C.

4. Freezing the Cells

The procedure up to the measurement of the cell count was the same as in the section Passaging the Cells above. Subsequently, the cell suspension was centrifuged at 1,000 rpm for 4 min at a temperature of about 25° C. The supernatant was removed and the pellet resuspended in Cellbanker™ solution to get a final concentration of from $5\times10^5$ to $5\times10^6$ cells/mL. The cell suspension was transferred into appropriately labeled 1 mL cryovials and then placed into the −80° C. freezer.

pH-Based Assay:

The following assay was conducted to determine the concentration of sulfuric acid that would give rise to a pH that induces a $Ca^{\mathit{l\hspace{-0.1em}f}}$ response optimal to test compounds for their effect on TRPV1.

1. Cells

TRPV1/CHO cells were seeded in the 96-well clear-bottom black-wall plate (Nunc) at densities of $1-2\times10^4$ cells/well and grown in 100 µL of culture medium (alpha-MEM supplemented with 10% FBS, 20 mM HEPES, 1 mg/mL geneticin and 1% antibiotic-antimycotic mixed stock solution) for 1-2 days before the experiment.

2. Determination of pH Sensitivity and Agonist Dose 2.1. Agonist Solution

Different agonist solutions with sulfuric acid concentrations of from 15 mM to 18 mM (see FIG. 1) were prepared by diluting 1M sulfuric acid with measuring buffer. The different sulfuric acid concentrations in the agonist solutions were selected such that a 1:4 dilution would result in a final sulfuric acid concentration of between 3.0 mM to 3.6 mM, respectively, as indicated in FIG. 1.

2.2. Assay pH dependent $Ca^{2+}$ responses in TRPV1/CHO cells cultured in a 96-well plate are shown in FIG. 2. In particular, $Ca^{2+}$ influx into TRPV1/CHO cells in response to low pH as measured by Fura-2 AM fluorescence is indicated in FIG. 2. The cells were stimulated using 3.0 mM (well number B1-6), 3.1 mM (C1-6), 3.2 mM (D1-6), 3.3 mM (E1-6), 3.4 mM (F1-6), 3.5 mM (G1-6), or 3.6 mM (H1-6) $H_2SO_4$ or pH 7.2 measuring buffer without $H_2SO_4$ (A1-6) (FIG. 2).

(1) Culture medium was removed using an 8-channel-pipette (Rainin, USA) from the 96-well plate and the wells were refilled with 100 µL of loading buffer (20 mM HEPES, 115 mM NaCl, 5.4 mM KCl, 0.8 mM $MgCl_2$, 1.8 mM $CaCl_2$, 13.8 mM D-glucose, 2.5 mM probenecid, pH 7.4) containing 5 µM Fura-2 AM (Dojin, Japan).

(2) The 96-well plate was incubated at 37° C. for 45 min.

(3) The loading buffer was removed from each well. The cells were subsequently washed twice with 150 µL of measuring buffer (20 mM HEPES, 115 mM NaCl, 5.4 mM KCl, 0.8 mM $MgCl_2$, 5.0 mM $CaCl_2$, 13.8 mM D-glucose, 0.1% BSA, pH 7.4) (no probenecid). The wells were then refilled with 80 µL of measuring buffer.

(4) After an incubation at 4° C. for 15 min, the 96-well plate was transferred to FDSS-3000 (Hamamatsu Photonics, Japan).

(5) The Fura-2 fluorescent intensity was monitored at a wavelength of 340 nm and at 380 nm, respectively, at a rate of 0.5 Hz for a total of 240 seconds. After 16 time points (32 sec)

of baseline detection, 20 µL of agonist solution was added to each well. The final volume was 100 µL/well.

(6) Fluorescence intensity ratio refers to the fluorescence intensity at 340 nm over the fluorescence intensity at 380 nm at a particular time point. The baseline was set as the average of the fluorescent intensity ratios for the first 16 time points before the addition of agonist solution. The maximum response was the highest fluorescent intensity ratio during the 60 time points following addition of agonist solution.

(7) Maximal signal ratios from each well were calculated as output data using the FDSS-3000 analysis program. Data were analyzed using Excel (Microsoft) and XLfit (idbs) software.

2.3. pH Determination

After the observation of $Ca^{2+}$ responses, the buffer of each lane (50 µL/well, 8-20 wells/plate) was collected well by well and the pH values were measured using a portable pH meter (Shindengen, Japan).

As shown in FIG. 2, the $Ca^{2+}$ responses in lanes D and E were intermediate and therefore optimal for testing the effects of compounds on the TRPV1 calcium channel. The final sulfuric acid concentrations in the wells of these lanes were 3.2 mM and 3.3 mM, respectively. These final sulfuric acid concentrations were obtained using agonist solutions with 16.0 mM and 16.5 mM sulfuric acid concentrations, respectively (lanes D and E in FIG. 1). The pH obtained using these sulfuric acid concentrations was ca. 5.0-5.1.

Thus, agonist solutions with 16.0 mM and 16.5 mM sulfuric acid concentrations, respectively, (lanes D and E in FIG. 1) were selected for the experiments described below in section 3.

3. pH Assay 3.1. Agonist

Two different agonist solutions with different $H_2SO_4$ concentrations were used for the pH assay (FIG. 3A). For one half of a 96-well plate one agonist solution was used, for the other half the other agonist solution. The agonist solutions were obtained by diluting sulfuric acid ($H_2SO_4$, 1 M) with measuring buffer. The concentrations for the two agonist solutions were determined as described above in Section 2 of Protocol 2.

The sulfuric acid concentrations between the two agonist solutions differed by 0.5 mM. In the experiment described in Section 2 of Protocol 2, the sulfuric acid concentrations in the agonist solutions were determined to be 16 mM and 16.5 mM, respectively. After 1:4 dilution of the agonist solutions, the final sulfuric acid concentration was 3.2 mM and 3.3 mM, respectively. The resulting pH value for the pH assay was 5.0 to 5.1.

3.2. Test Compounds

Test compounds were dissolved in DMSO to yield 1 mM stock solutions. The stock solutions were further diluted using DMSO in 1:3 serial dilution steps with 6 points (1000 µM, 250 µM, 62.5 µM, 15.625 µM, 3.9062 µM and 0.977 µM). The thereby-obtained solutions were further diluted in measuring buffer (1:100) as 10× stock serial dilutions with a DMSO concentration of 1%. 10 µL of a 10× stock was added into each well at step 3.3.(4) of Protocol 2. Thus, the final concentrations of antagonists ranged from 1000-0.977 nM containing 0.1% DMSO (FIG. 3B).

3.3. Assay

Steps (1) and (2) of this Assay were the same as steps 2.2.(1) and 2.2.(2) of Protocol 2, respectively.

(3) The cells were washed twice with 150 µL of measuring buffer (mentioned in 2.2.(3) of Protocol 2, no probenecid). The wells were subsequently refilled with 70 µL of measuring buffer.

(4) Either 10 µL of measuring buffer or 10 µL of 10× stock serial dilution of test compound (described in 3.2. above) were applied to each well. Usually, only one test compound was tested per 96-well plate. The number of replicates per 96-well plate for a particular antagonist at a particular concentration was 7×2 since two different sulfuric acid concentrations were used per 96-well plate (N=7×2)(FIG. 3).

Step (5) was the same as 2.2.(4) above.

(6) Fura-2 fluorescent intensity was monitored as described in 2.2.(5) above. After 16 time points of baseline detection, 20 µL of agonist solution (measuring buffer titrated with $H_2SO_4$ to yield pH 5.0-5.1 when mixed 1:4 with the measuring buffer containing test compound) was added to each well (final volume 100 µL/well).

Steps (7) and (8) were as described in 2.2.(6) and 2.2.(7) above, respectively.

3.4. pH Check (1) The pH values of the buffer in the wells of A1→H1 and A7→H7 (longitudinally; FIG. 3) were measured one by one using a portable pH meter.

(2) When a well was confirmed as pH 5.0 or 5.1, the next five wells to its right were checked one after another.

(3) For $IC_{50}$ calculation, only the data from wells with pH values of 5.0-5.1 were used.

The number of wells tested for their pH varied among plates (about 16-60 wells/plate). The number depended on the results of 3.4.(1) above and the $Ca^{2+}$ responses.

Capsaicin-Based Assay:

One day prior to assay, TRPV1/CHO cells were seeded in 96-well clear-bottom black plates (20,000 cells/well) in growth media. On the day of the experiment, the cells were washed with 0.2 mL 1× Hank's Balanced Salt Solution (Life Technologies) containing 1.6 mM $CaCl_2$ and 20 mM HEPES, pH 7.4 ("wash buffer"). Subsequently, the cells were loaded by incubation in 0.1 mL of wash buffer containing Fluo-4 at 3 µM final concentration. After 1 hour, the cells were washed twice with 0.2 mL wash buffer and resuspended in 0.1 mL wash buffer. The plates were then transferred to a Fluorescence Imaging Plate Reader (Molecular Devices). Fluorescence intensity was monitored for 15 seconds to establish a baseline. Subsequently, test compounds diluted in assay buffer (1× Hank's Balanced Salt Solution containing 1 mM $CaCl_2$ and 20 mM HEPES, pH 7.4) containing 1% DMSO were added to the cell plate and fluorescence was monitored for 2 minutes. The final concentration of the compound was adjusted to range from 100 µM to 1.5625 µM. If the test compound was an especially potent antagonist, the final concentration of the compound was adjusted to range from 10 µM to 1.5625 nM. Human TRPV1 was then activated by the addition of 50 µL capsaicin (100 nM final concentration) and plates incubated for an additional 3 min. Data were collected over the entire time course and analyzed using Excel and the curve-fitting formula GraphPad Prism.

The results of the assays of Protocol 2 are shown in Tables II and III.

TABLE II

| TRPV1 $IC_{50}$ Potency | |
|---|---|
| Compound | pH-Based Assay $IC_{50}$ (nM) |
| I-7 | 0.5 |
| I-34 | 33.6 |
| I-44 | 1 |
| I-50 | 60.8 |
| I-73 | 160.1 |
| I-76 | 2.1 |
| I-81 | 12.8 |

The following compounds had an $IC_{50}$ value of 100 nM or less by the pH-Based Assay:

Compounds I-1, I-2, I-3, I-4, I-5, I-9, I-10, I-11, I-25, I-26, I-28, I-29, I-33, I-36, I-37, I-38, I-43, I-45, I-46, I-47, I-48, I-51, I-52, I-53, I-54, I-58, I-59, I-64, I-67, I-75, I-82, I-89, I-92, I-93, I-94, I-95 and I-96.

TABLE III

TRPV1 IC$_{50}$ Potency

| Compound | Capsaicin-Based Assay IC$_{50}$ (nM) |
|---|---|
| I-20 | 146.9 |
| I-39 | 342.2 |
| I-57 | 16.6 |
| I-60 | 357.3 |
| I-71 | 322.2 |
| I-77 | 38.8 |
| I-80 | 223.4 |

The following compounds had an IC$_{50}$ value of 100 nM or less by the Capsaicin-Based Assay:

Compounds I-1, I-2, I-5, I-7, I-9, I-10, I-11, I-25, I-26, I-33, I-36, I-37, I-38, I-43, I-44, I-45, I-46, I-47, I-52, I-53, I-54, I-56, I-58, I-59, I-63, I-64, I-67, I-75, I-76, I-81, I-82, I-89, I-92, I-93, I-94, I-95 and I-96.

Formulation Examples

The following Formulation Examples are only exemplified and not intended to limit the scope of the present invention.

Formulation Example 1

Tablet

| | |
|---|---|
| Compound of the present invention | 15 mg |
| Lactose | 15 mg |
| Calcium stearate | 3 mg |

All of the above ingredients except for calcium stearate are uniformly mixed. Then the mixture is crushed, granulated and dried to obtain a suitable size of granules. Then, calcium stearate is added to the granules. Finally, tableting is performed under a compression force.

Formulation Example 2

Capsules

| | |
|---|---|
| Compound of the present invention | 10 mg |
| Magnesium stearate | 10 mg |
| Lactose | 80 mg |

The above ingredients are mixed uniformly to obtain powders or fine granules, and then the obtained mixture is filled in capsules.

Formulation Example 3

Granules

| | |
|---|---|
| Compound of the present invention | 30 g |
| Lactose | 265 g |
| Magnesium stearate | 5 g |

After the above ingredients are mixed uniformly, the mixture is compressed. The compressed matters are crushed, granulated and sieved to obtain suitable size of granules.

The invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

What is claimed:

1. A compound of Formula I:

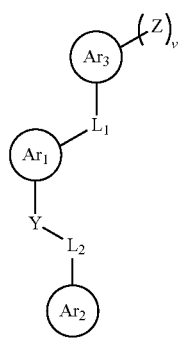

(I)

or a pharmaceutically acceptable derivative thereof, wherein $Ar_1$ is

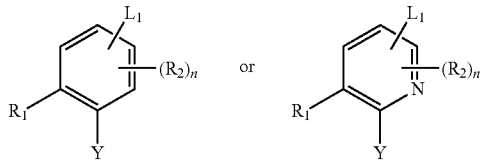

Y is

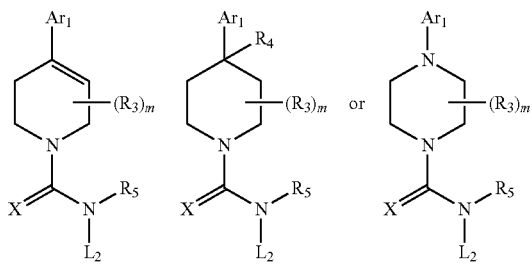

$Ar_2$ is

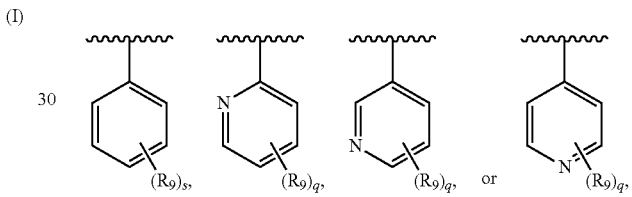

$Ar_3$ is oxadiazole, isoxazole, oxazole, furan or pyrazole, each of which is unsubstituted or substituted with 1 or 2 independently selected $R_6$ groups;

Z is
- (a) —$(C_1$-$C_6)$alkyl which is unsubstituted or substituted with 1 or 2 —$OR_{12}$ groups,
- (b) —$(C_2$-$C_6)$alkenyl which is unsubstituted or substituted with 1 or 2 —$OR_{12}$ groups,
- (c) —$OR_{12}$, or
- (d) —$C(O)OR_7$;

$L_1$ and $L_2$ are each independently a bond;

$R_1$ is —H, -halo, —$NO_2$, —CN, —$OR_7$, —$N(R_7)_2$, —$(C_1$-$C_4)$alkyl, —$C(halo)_3$, —$CH(halo)_2$, $CH_2(halo)$, —$OC(halo)_3$, —$OCH(halo)_2$, or —$OC_{H2}(halo)$;

each $R_2$ is independently -halo, —$OR_7$, —CN, —$NO_2$, —$N(R_7)_2$, —$(C_1$-$C_{10})$alkyl, —$(C_2$-$C_{10})$alkenyl, —$(C_2$-$C_{10})$alkynyl, or -phenyl;

X is O;

each $R_3$ is independently:
- (a) —$(C_1$-$C_6)$alkyl, —$(C_1$-$C_6)$alkyl-OR13, —$C(O)R_{13}$, —$C(O)OR_{13}$, —$N(R_{13})C(O)R_{13}$, or —$C(O)N(R_{13})_2$;
- (b) two $R_3$ groups together form =O;
- (c) two $R_3$ groups together form a $(C_2$-$C_6)$ bridge, which is unsubstituted or substituted with 1, 2 or 3 independently selected $R_{13}$ groups, and which bridge optionally contains —HC=CH— within the $(C_2$-$C_6)$ bridge; or (d) two R₃ groups together form

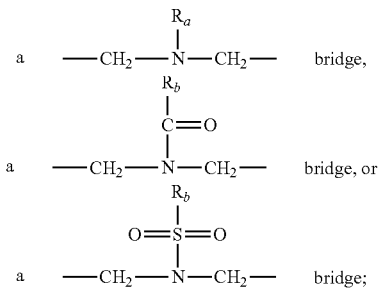

R₄ is —H -halo, —(C₁-C₆)alkyl, —CH₂OR₇, —CH₂(halo), —CH(halo)₂, —C(halo)₃, —OC(halo)₃, —OR₇, —SR₇, —C(O)OR₇, —C(O)R₇, —OC(O)R₇, —OC(O)N(R₈)₂, —NR₇C(O)R₁₃, —C(O)N(R₈)₂, —S(O)₂R₇, or —NO₂;

R₅ is —H, —(C₁-C₆)alkyl, —(C₃-C₈)cycloalkyl, —(C₁-C₆)alkyl-OC(O)R₇, —C(O)R₇, or —C(O)N(R₈)₂;

each R₆ is independently —(C₁-C₆)alkyl or two R₆ groups together form =O;

each R₇ is independently —H or —(C₁-C₆)alkyl;

each R₈ is independently —H, —(C₁-C₆)alkyl, —(C₂-C₆)alkenyl, —(C₂-C₆)alkynyl, —(C₃-C₈)cycloalkyl, or phenyl;

each R₉ is independently —(C₁-C₆)alkyl, —(C₂-C₆)alkenyl, —(C₂-C₆)alkynyl, —(C₃-C₈)cycloalkyl, —(C₅-C₈)cycloalkenyl, -phenyl, -(3- to 7-membered)heterocycle, —(C₁-C₆)haloalkyl, —(C₂-C₆)haloalkenyl, —(C₂-C₆)haloalkynyl, —(C₁-C₆)hydroxyalkyl, —(C₂-C₆)hydroxyalkenyl, —(C₂-C₆)hydroxyalkynyl, —(C₁-C₆)alkoxy(C₁-C₆)alkyl, —(C₁-C₆)alkoxy(C₂-C₆)alkenyl, —(C₁-C₆)alkoxy(C₂-C₆)alkynyl, —CN, -halo, —N₃, —NO₂, —CH=NR₁₃, —N(R₁₃)₂, —NR₁₃OR₁₃, —OR₁₃, —SR₁₃, —O(CH₂)ᵦOR₁₃, —O(CH₂)ᵦSR₁₃, —O(CH₂)ᵦN(R₁₃)₂, —N(R₁₃)(CH₂)ᵦOR₁₃, —N(R₁₃)(CH₂)ᵦSR₁₃, —N(R₁₃)(CH₂)ᵦN(R₁₃)₂, —N(R₁₃)C(O)R₁₃, —C(O)R₁₃, —C(O)OR₁₃, —OC(O)R₁₃, —OC(O)OR₁₃, —S(O)R₁₃, —S(O)₂R₁₃, —S(O)₂N(R₁₃)₂, —S(O)₂-(3- to 7-membered)heterocycle, —C(O)₂N(R₁₃)₂, —(C₁-C₆)alkyl-C=N—OR₁₃, —(C₁-C₆)alkyl-C(O)N(R₁₃)₂, —(C₁-C₆)alkyl-NHS(O)₂N(R₁₃)₂, or —(C₁-C₆)alkylC(=NH)—N(R₁₃)₂, each of which -phenyl, -(3- to 7-membered)heterocycle, or —(C₃-C₆)cycloalkyl is unsubstituted or substituted with 1, 2 or 3 independently selected R₁₃ groups;

each R₁₀ is independently:
(a) —(C₁-C₆)alkyl, —(C₂-C₆)alkenyl, —(C₂-C₆)alkynyl, —(C₃-C₈)cycloalkyl, —(C₅-C₈)cycloalkenyl, or -phenyl, each of which is unsubstituted or substituted with 1 or 2 —OH groups;
(b) —CH₂CH₂(halo), —CH₂CH(halo)₂, —CH₂C(halo)₃, —C(halo)₃, —CH(halo)₂, —CH2(halo), —CN, -halo, —N₃, —NO₂, —CH=NR₁₃, —N(R₁₃)₂—NR₁₃OR₁₃, —OR₁₃, —C(O)R₁₃, —C(O)OR₁₃, —OC(O)R₁₃, —OC(O)OR₁₃, —SR₁₃, —S(O)R₁₃, or —S(O)₂R₁₃; or
(c) two R₁₀ groups on adjacent carbon atoms together form a (C₁-C₂)alkylenedioxy bridge, which is unsubstituted or substituted 1, 2 or 3 independently selected R₁₃ groups;

each R₁₂ is independently —H, —(C₁-C₆)alkyl, —(C₃-C₈)cycloalkyl, —C(O)R₁₃, C(O)OR₁₃, or —C(O)N(R₁₃)₂;

each R₁₃ is independently —H, —(C₁-C₆)alkyl, —(C₂-C₆)alkenyl, —(C₂-C₆)alkynyl, —(C₃-C₈)cycloalkyl, —(C₅-C₈)cycloalkenyl, -phenyl, -benzyl, —(C₁-C₆)haloalkyl, —(C₁-C₆)hydroxyalkyl, —(C₁-C₆)alkoxy(C₁-C₆)alkyl, —(C₁-C₆)alkyl-N(R₈)₂ or —C(O)N(R₈)₂;

Rₐ is —H, —(C₁-C₆)alkyl, —(C₃-C₈)cycloalkyl, —CH₂—C(O)Rᶜ, —(CH₂)—C(O)ORᶜ, (CH₂)—C(O)N(Rᶜ)₂, —(CH₂)₂—ORᶜ, —(CH₂)₂—S(O)₂N(Rᶜ)₂, or —(CH₂)₂—N(Rᶜ)S(O)₂Rᶜ;

Rb is
(a) —H, —(C₁-C₆)alkyl, —(C₃-C₈)cycloalkyl, -(3- to 7-membered)heterocycle, —N(Rᶜ)₂, —N(Rᶜ)—(C₃-C₈)cycloalkyl, or —N(Rᶜ)-(3- to 7 membered)heterocycle, each of which -(3- to 7-membered)heterocycle or —(C₃-C₈)cycloalkyl is unsubstituted or substituted with 1, 2 or 3 independently selected R₁₃ groups; or
(b) -phenyl, -(5- or 6-membered)heteroaryl, —N(Rᶜ)-phenyl, or —N(Rᶜ)-(5- to 10-membered)heteroaryl, each of which is unsubstituted or substituted with 1, 2 or 3 independently selected R₁₃ groups;

each Rᶜ is independently —H or —(C₁-C₄)alkyl each R₁₄ is independently —H, —(C₁-C₆)alkyl, —C(O)R₁₃, —S(O)R₁₃, —S(O)₂R₁₃,

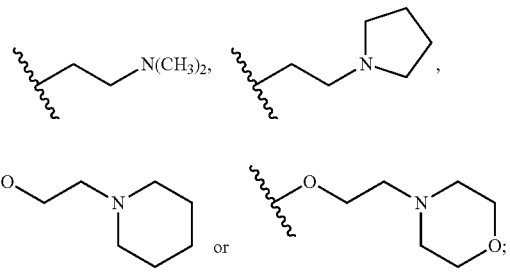

each halo is independently —F, —Cl, —Br, or —I;

n is the integer 0, 1, or 2;

m is the integer 0, 1, or 2;

q is the integer 0, 1, 2, 3, or 4;

s is the integer 0, 1, 2, 3, 4, or 5;

u is the integer 0, 1, 2 or 3;

v is the integer 0, 1, 2 or 3;

b is the integer 1 or 2; and provided that when Ar₁ is

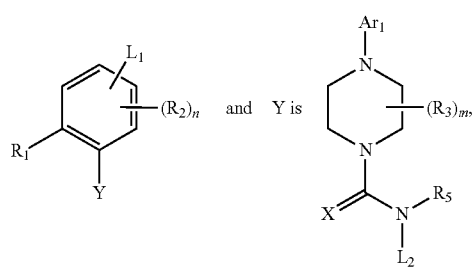

then Ar₂ is not

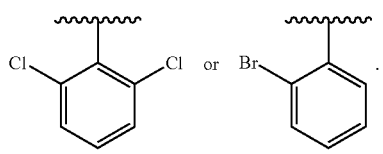 [SMILES: *c1c(Cl)cccc1Cl ; *c1ccccc1Br]

2. The compound according to claim 1 or a pharmaceutically acceptable derivative thereof, wherein Z is
  (a) —($C_1$-$C_3$)alkyl substituted with 1 or 2 —OH groups, or
  (c) —OH; and V is 1, 2 or 3.

3. The compound according to claim 1 or a pharmaceutically acceptable derivative thereof, wherein Z is —($C_1$-$C_3$)alkyl substituted with 1 or 2 —OH groups, V is 1, 2 or 3, and $Ar_1$ is

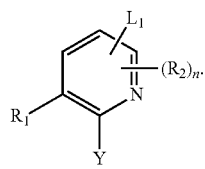

4. The compound according to claim 1 or a pharmaceutically acceptable derivative thereof, wherein $Ar_1$ is

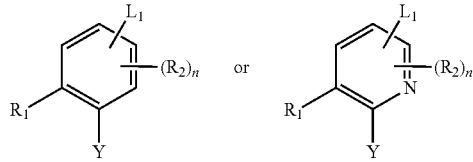

Y is

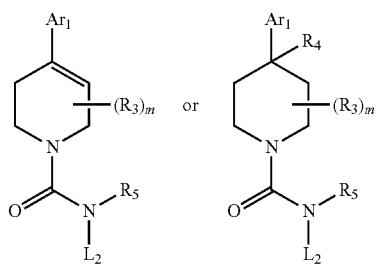

$L_1$ and $L_2$ are each independently a bond.

5. The compound according to claim 1 or a pharmaceutically acceptable derivative thereof, wherein $Ar_1$ is

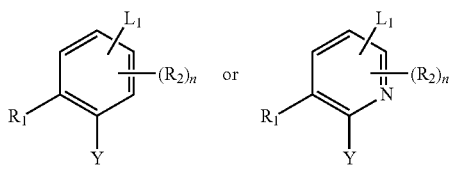

Y is $Ar_3$ is oxadiazole, isoxazole, oxazole, furan or pyrazole, each of which is unsubstituted or substituted with 1 or 2 independently selected $R_6$ groups;

Z is
  (a) —($C_1$-$C_2$)alkyl substituted with 1 or 2 —OH groups, or
  (c) —OH

V is 1, 2 or 3; and $L_1$ and $L_2$ are each independently a bond.

6. The compound according to claim 1 or a pharmaceutically acceptable derivative thereof, wherein $Ar_1$ is Y is

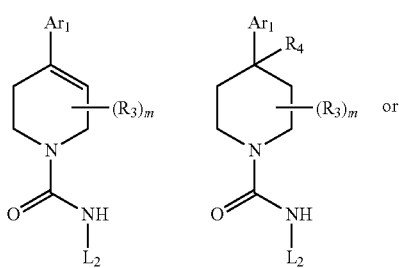

-continued

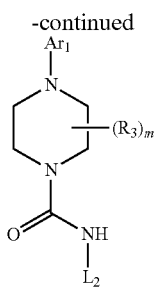

Ar₂ is

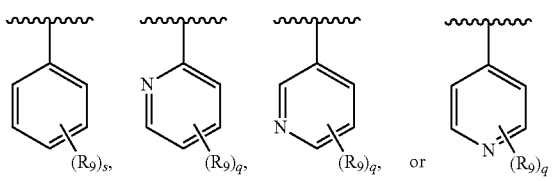

Ar₃ is oxadiazole, isoxazole, oxazole, furan or pyrazole, each of which is unsubstituted or substituted with 1 or 2 independently selected R₆ groups;

Z is
(a) —($C_1$-$C_6$)alkyl substituted with 1 or 2 —OH groups, or
(c) —OH v is 1, 2 or 3;
$L_1$ is a bond;
$L_2$ is a bond; and
X is O.

7. The compound according to claim 1 or a pharmaceutically acceptable derivative thereof, wherein
Ar₁ is

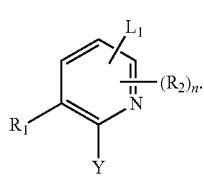

8. The compound according to claim 1 or a pharmaceutically acceptable derivative thereof, wherein
Y is

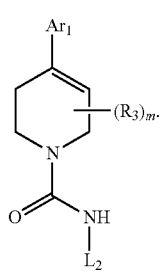

9. The compound according to claim 1 or a pharmaceutically acceptable derivative thereof, wherein
Y is

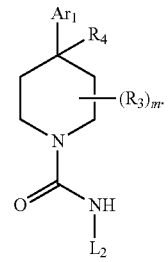

10. The compound according to claim 1 or a pharmaceutically acceptable derivative thereof, wherein
Y is

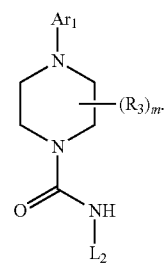

11. The compound according to claim 1 or a pharmaceutically acceptable derivative thereof, wherein Z is —OH, —($C_1$-$C_3$)alkyl substituted with 1 or 2 —OH groups, or —($C_2$-$C_4$)alkenyl substituted with 1 or 2 —OH groups; and v is 1 or 2.

12. The compound according to claim 1 or a pharmaceutically acceptable derivative thereof, wherein Z is —OH or —($C_1$-$C_3$)alkyl substituted with 1 or 2 —OH groups; and v is 1 or 2.

13. The compound according to claim 1 or a pharmaceutically acceptable derivative thereof, wherein Z is —($C_2$-$C_3$) alkyl substituted with 2 —OH groups; and v is 1 or 2.

14. The compound according to claim 1 or a pharmaceutically acceptable derivative thereof, wherein Z is —OH and v is 1 or 2.

15. The compound according to claim 1 or a pharmaceutically acceptable derivative thereof, wherein Z is $CH_2OH$ and v is 1 or 2.

16. The compound according to claim 1 or a pharmaceutically acceptable derivative thereof, wherein Z is —$CH_2CH_2OH$ and v is 1 or 2.

17. The compound according to claim 1 or a pharmaceutically acceptable derivative thereof, wherein Z is —CH(OH)CH(OH) and v is 1 or 2.

18. The compound according to claim 1 or a pharmaceutically acceptable derivative thereof, wherein Z is —OH or —($C_1$-$C_3$)alkyl substituted with 1 or 2 —OH groups; and v is 1 or 2.

19. The compound according to claim 1 or a pharmaceutically acceptable derivative thereof, wherein $R_1$ is -methyl, -halo or —C(halo)₃.

20. The compound according to claim 1 or a pharmaceutically acceptable derivative thereof, wherein $R_4$ is —H or -halo.

21. The compound according to claim 1 or a pharmaceutically acceptable derivative thereof, wherein each $R_9$ is independently selected from -halo, —C(halo)$_3$,)alkyl, —(C$_1$-C$_6$)alkoxy, —OC(halo)$_3$, and S(O)$_2$C(halo)$_3$.

22. The compound according to claim 1 or a pharmaceutically acceptable derivative thereof, wherein Ar$_2$ is

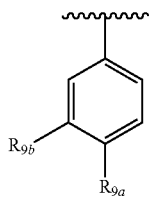

R$_{9a}$ is —C(halo)$_3$ or —OC(halo)$_3$; and
R$_{9b}$ is —H, -halo, -methyl, or —OCH$_3$.

23. The compound according to claim 1 or a pharmaceutically acceptable derivative thereof, wherein Ar$_2$ is

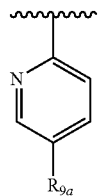

R$_{9a}$ is —C(halo)$_3$ or —OC(halo)$_3$.

24. The compound according to claim 1 or a pharmaceutically acceptable derivative thereof, wherein n or p=0.

25. The compound according to claim 1 or a pharmaceutically acceptable derivative thereof, wherein m=0.

26. The compound according to claim 1 or a pharmaceutically acceptable derivative thereof wherein the pharmaceutically acceptable derivative is a pharmaceutically acceptable salt.

27. A composition comprising a compound of claim 1 or a pharmaceutically acceptable derivative thereof and a pharmaceutically acceptable carrier or excipient.

28. A composition for treating pain, UI, IBD, or BS in an animal comprising a compound of claim 1 or a pharmaceutically acceptable derivative thereof and a pharmaceutically acceptable carrier or excipient.

29. A composition for inhibiting TRPV1 function comprising a compound of claim 1 or a pharmaceutically acceptable derivative thereof and a pharmaceutically acceptable carrier or excipient.

30. A method for treating pain, UI, an ulcer, IBD, or IBS in an animal, comprising administering to an animal in need thereof, an effective amount of a compound of claim 1 or a pharmaceutically acceptable derivative thereof.

31. A method of inhibiting TRPVI function in a cell comprising contacting a cell capable of expressing TRPV 1 with an effective amount of a compound of claim 1 or a pharmaceutically acceptable derivative thereof.

* * * * *

UNITED STATES PATENT AND TRADEMARK OFFICE
CERTIFICATE OF CORRECTION

PATENT NO. : 9,156,830 B2
APPLICATION NO. : 14/118113
DATED : October 13, 2015
INVENTOR(S) : Noriyuki Kurose et al.

It is certified that error appears in the above-identified patent and that said Letters Patent is hereby corrected as shown below:

In the Claims

Claim 1, col. 235, lines 44-45, "-$C(O)_2N(R_{13})_2$," should read -- -$C(O)N(R_{13})_2$,--.

Claim 1, col. 235, line 48, "or -$(C_3-C_6)$cycloalkyl" should read --or -$(C_3-C_8)$cycloalkyl--.

Claim 21, col. 241, line 1, "selected from –halo, -C(halo)$_3$,)alkyl," should read --selected from –halo, -C(halo)$_3$, -$(C_1-C_6)$alkyl,--.

Claim 27, col. 242, line 14, "UI, IBD, or BS" should read --UI, IBD, or IBS--.

Signed and Sealed this
Twenty-second Day of March, 2016

Michelle K. Lee
*Director of the United States Patent and Trademark Office*

SEQUENCE LISTING

```
<160> NUMBER OF SEQ ID NOS: 4

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaagatcttc gctggttgca cactgggcca ca                                    32

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gaagatcttc ggggacagtg acggttggat gt                                    32

<210> SEQ ID NO 3
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggatccagca aggatgaaga aatgg                                             25

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgtctgcgtg acgtcctcac ttct                                              24
```